(12) United States Patent
Bandarage et al.

(10) Patent No.: US 6,593,347 B2
(45) Date of Patent: Jul. 15, 2003

(54) NITROSATED AND NITROSYLATED NONSTEROIDAL ANTIINFLAMMATORY COMPOUNDS, COMPOSITIONS AND METHODS OF USE

(75) Inventors: Upul K. Bandarage, Newton, MA (US); Qing Dong, Cambridge, MA (US); Xinqin Fang, Chestnut Hill, MA (US); David S. Garvey, Dover, MA (US); Gregory J. Mercer, Stoughton, MA (US); Stewart K. Richardson, Tolland, CT (US); Joseph D. Schroeder, Dedham, MA (US); Tiansheng Wang, Concord, MA (US)

(73) Assignee: NitroMed, Inc., Bedford, MA (US)

( * ) Notice: Subject to any disclaimer, the term of this patent is extended or adjusted under 35 U.S.C. 154(b) by 0 days.

(21) Appl. No.: 09/938,560

(22) Filed: Aug. 27, 2001

(65) Prior Publication Data

US 2002/0016322 A1 Feb. 7, 2002

Related U.S. Application Data

(60) Division of application No. 09/429,019, filed on Oct. 29, 1999, now Pat. No. 6,297,260, which is a continuation-in-part of application No. 09/182,433, filed on Oct. 30, 1998, now abandoned.

(51) Int. Cl.$^7$ .............................................. A61K 31/445
(52) U.S. Cl. ................... 514/327; 514/226.2; 514/291; 514/365; 514/374; 514/375; 514/378; 514/393; 514/404; 514/406; 514/411; 514/416; 514/419; 514/423; 514/427; 514/428; 514/431; 514/448; 514/450; 514/532; 514/539; 514/545; 514/621; 514/640; 514/658; 514/676; 514/709; 514/719
(58) Field of Search ................................. 514/327, 532, 514/539, 545; 546/221; 560/10, 19, 47, 48, 51, 52, 74, 100, 102, 110

(56) References Cited

U.S. PATENT DOCUMENTS

| | | | |
|---|---|---|---|
| 3,591,584 A | 7/1971 | Lombardino | 260/243 |
| 4,556,672 A | 12/1985 | Kadin | 514/414 |
| 5,004,742 A | 4/1991 | Satoh et al. | 514/226.5 |
| 5,081,118 A | 1/1992 | Braisted et al. | 514/226.5 |
| 5,132,304 A | 7/1992 | Ribalta-Baro et al. | 514/226.5 |
| 5,344,929 A | 9/1994 | Dean et al. | 544/48 |
| 5,473,067 A | 12/1995 | Dean et al. | 544/48 |
| 5,474,985 A | 12/1995 | Polansky et al. | 514/26 |
| 5,527,796 A | 6/1996 | Binder et al. | 514/226.5 |
| 5,538,966 A | 7/1996 | May et al. | 514/226.5 |

(List continued on next page.)

FOREIGN PATENT DOCUMENTS

| | | |
|---|---|---|
| EP | 0 759 899 | 9/1999 |
| EP | 0 871 606 | 6/2000 |
| WO | 9309806 | 5/1993 |
| WO | 9404484 | 3/1994 |
| WO | 9412463 A1 | 6/1994 |
| WO | 9509831 | 4/1995 |
| WO | 0658559 | 6/1995 |
| WO | 9530641 | 11/1995 |
| WO | 9412463 | 12/1995 |
| WO | 9632946 | 10/1996 |
| WO | 9716405 | 5/1997 |
| WO | 9731654 | 9/1997 |
| WO | 9809948 | 3/1998 |
| WO | WO00/44705 | 8/2000 |
| WO | WO00/51988 | 9/2000 |
| WO | WO00/72838 | 12/2000 |
| WO | WO01/10814 | 2/2001 |

OTHER PUBLICATIONS

Reuter et al, *Life Sciences*, 55(1):1–8 (1994).
Reuter et al, *Gastroenterology*, 106(4), A759 (1994).
Cuzzolin et al, *Pharmacological Research*, 29(1):89–97 (1994).
Rachmilewitz et al, *Gut*, 35:1394–1397 (1994).
Conforti et al, *Agents Action*, 40(3):176–180 (1993).
Carty et al, *Agents Action*, 39:157–165 (1993).
Chemical Abstracts 66:64987, vol. 66 (1967).
Chemical Abstracts 87:151928, vol. 87 (1977).
Chemical Abstracts 87:39546, vol. 87 (1977).
Chemical Abstracts 121:255784, vol. 121 (1994).
Chemical Abstracts 114:600, vol. 114 (1991).
Chemical Abstracts 114:158969, vol. 114 (1991).
Wallace et al, *Trends Pharmacol. Sci.*, 15(11):405–406 (1994).
Wallace et al, *Journal of Gastroenterology and Hepatology*, 9:S40–S44 (1944).
Wallace et al, *Novel Molecular Approaches to Anti–Inflammatory Theory*, 121–129 (1995).
Wallace et al, *Gastroenterology*, 106(4), Part 2, A208 (1994). (Abstract).
Wallace et al, *European Journal of Pharmacology*, 257:249–255 (1994).
Wallace et al, *Gastroenterology*, 107:173–179 (1994).

*Primary Examiner*—Richard L. Raymond
(74) *Attorney, Agent, or Firm*—Hale and Dorr LLP

(57) ABSTRACT

The present invention describes novel nitrosated and/or nitrosylated nonsteroidal antiinflammatory compounds, and novel compositions comprising at least one nitrosated and/or nitrosylated nonsteroidal antiinflammatory compound, and, optionally, at least one compound that donates, transfers or releases nitric oxide, elevates endogenous levels of endothelium-derived relaxing factor, stimulates endogenous synthesis of nitric oxide or is a substrate for nitric oxide synthase. The present invention also provides methods for treating, preventing and/or reducing inflammation, pain, and fever; decreasing or reversing the gastrointestinal, renal and other toxicities resulting from the use of nonsteroidal anti-inflammatory drugs; treating and/or preventing gastrointestinal disorders; treating inflammatory disease states and disorders; and treating and/or preventing ophthalmic diseases or disorders.

28 Claims, No Drawings

U.S. PATENT DOCUMENTS

| | | |
|---|---|---|
| 5,599,535 A | 2/1997 | Polansky et al. ......... 424/78.04 |
| 5,621,000 A | 4/1997 | Arena et al. ................. 514/411 |
| 5,674,888 A | 10/1997 | Polansky et al. ............ 514/418 |
| 5,700,947 A | 12/1997 | Soldato ....................... 548/491 |
| 5,703,073 A | 12/1997 | Garvey et al. ............ 514/226.5 |
| 5,780,495 A | 7/1998 | Del Soldato ................ 514/413 |
| 5,814,655 A | 9/1998 | Patel et al. ................. 514/413 |
| 5,854,415 A | 12/1998 | Nguyen et al. ............. 536/23.5 |
| 5,861,426 A | 1/1999 | Del Soldato et al. ....... 514/313 |
| 5,861,497 A | 1/1999 | Nguyen et al. ............. 536/23.5 |
| 6,040,341 A | 3/2000 | Del Soldato et al. ........ 514/509 |
| 6,043,232 A | 3/2000 | Garvey et al. ............... 514/159 |
| 6,043,233 A | 3/2000 | Garvey et al. ............... 514/159 |
| 6,048,858 A | 4/2000 | Garvey et al. ........... 514/226.5 |
| 6,051,588 A | 4/2000 | Garvey et al. ............... 514/364 |
| 6,057,347 A | 5/2000 | Garvey et al. ............... 514/364 |
| 6,083,515 A | 7/2000 | Garvey et al. ............... 424/400 |
| 6,143,734 A | 11/2000 | Garvey et al. ............... 514/159 |

NITROSATED AND NITROSYLATED NONSTEROIDAL ANTIINFLAMMATORY COMPOUNDS, COMPOSITIONS AND METHODS OF USE

RELATED APPLICATIONS

This application is a divisional of U.S. application Ser. No. 09/429,019, filed Oct. 29, 1999, now U.S. Pat. No. 6,297,260, which is a continuation-in-part of U.S. application Ser. No. 09/182,433 filed Oct. 30, 1998, now abandoned.

FIELD OF INVENTION

The present invention describes novel nitrosated and/or nitrosylated nonsteroidal antiinflammatory drugs, and novel compositions comprising at least one nitrosated and/or nitrosylated nonsteroidal antiinflammatory drug, and, optionally, at least one compound that donates, transfers or releases nitric oxide, elevates endogenous levels of endothelium-derived relaxing factor, stimulates endogenous synthesis of nitric oxide or is a substrate for nitric oxide synthase. The present invention also provides methods for treating, preventing and/or reducing inflammation, pain, and fever; decreasing or reversing the gastrointestinal, renal and other toxicities resulting from the use of nonsteroidal antiinflanmatory compounds; treating and/or preventing gastrointestinal disorders; treating inflammatory disease states and disorders; and treating and/or preventing ophthalmic diseases or disorders.

BACKGROUND OF THE INVENTION

The chemistry and pharmacology of nitroxybutylester $((CH_2)_4—ONO_2)$ derivatives of several aryl propionic acid nonsteroidal antiinflammatory compounds, including ketoprofen, flurbiprofen, suprofen, indobufen and etodolac, was described in PCT Application No. WO 94/12463. Studies on nitroxybutylester derivatives of flurbiprofen and ketoprofen are also reported in Wallace et al, *Gastroenterology*, 107:173–179 (1994). See, also, Cuzzolin et al, *Pharmacol. Res.*, 29(1):89–97 (1994); Reuter et al, *Life Sci.* (USA), 55/1(PL1–PL8) (1994); Reuter et al, *Gastroenterology*, 106(4):Suppl. A759 (1994); Wallace et al, *Eur. J. Pharmacol.*, 257(3):249–255 (1994); Wallace et al, *Gastroenterology*, 106(4):Suppl. A208 (1994); and Conforti et al, *Agents-Actions*, 40(3–4): 176–180 (1993). These publications uniformly examine and rely upon the use of indirectly linked nitrogen dioxide substitutions. U.S. Pat. No. 5,703,073 describes nonsteroidal antiinflammatory compounds containing a nitrogen monoxide group indirectly linked to the nonsteroidal antiinflammatory compound and their protection against gastrointestinal, renal and other toxicities normally induced by nonsteroidal antiinflammatory compounds. The compounds described in U.S. Pat. No. 5,703,073 all contain a heteroatom flanked by a carbonyl group in the form of an ester, amide or thioester in the main chain of the linker.

The use of nonsteroidal antiinflammatory compounds for the treatment and/or prevention of ophthalmic diseases or disorders such as glaucoma, inflammations of the eye and elevation of intraocular pressure has been described. For example, U.S. Pat. No. 5,474,985 describes the use of nonsteroidal antiinflammatory compounds to treat or prevent non-inflammatory induced, elevated intraocular pressure associated with the administration of corticosteroids; U.S. Pat. Nos. 5,674,888 and 5,599,535 describe the use of nonsteroidal antiinflammatory compounds to treat loss of trabecular meshwork resulting from aging, exposure to toxic substances, environmental stresses, such as oxidative or phagocytic injury, or glucocorticoid exposure; U.S. Pat. No. 5,814,655 describes topical ophthalmic compositions comprising nonsteroidal antiinflammatory compounds; Wiederholt et al., *Invest. Opthalmol. Vis. Sci.*, 2515–2520 (1994) describes the use of nitric oxide donors to relax trabecular meshwork and ciliary muscle; Behar-Cohen et al., *Invest. Opthalmol. Vis. Sci.*, describes the use of nitric oxide donors to decrease intraocular pressure.

There is a need in the art for nonsteroidal antiinflammatory compounds that do not have the adverse side effects associated with prior art compounds. There is also a need for new and improved treatments of inflammatory disease states and disorders; and ophthalmic diseases and disorders. The present invention is directed to these, as well as other important ends.

SUMMARY OF THE INVENTION

The present invention is based on the discovery that it is possible to link a nitrogen monoxide group (NO), and/or a nitrogen dioxide group ($NO_2$) (i.e., nitrosylated and/or nitrosated group, respectively) to a nonsteroidal antiinflammatory compound and that the resulting compounds have good bioavailibility, possess potent analgesic and antiinflammatory properties and have an unexpectedly reduced potential for producing gastrointestinal lesions (ulcers). The novel compounds also have unexpected properties in the treatment and/or prevention of ophthalmic diseases and disorders.

The present invention is also based on the discovery that it is possible to administer at least one nitrosated and/or nitrosylated nonsteroidal antiinflammatory compound (NSAID) and at least one nitric oxide donor to prevent, reduce, or reverse gastrointestinal, renal, and other toxicities induced by the NSAID. NSAIDs are antiinflammatory, analgesic and antipyretic compounds that act at cyclooxygenase, the enzyme responsible for the biosyntheses of the prostaglandins and certain autocoid inhibitors, including inhibitors of the various isozymes of cyclooxygenase (including but not limited to cyclooxygenase-1 and -2) and as inhibitors of both cyclooxygenase and lipoxygenase. A nitric oxide donor is a compound that contains a nitric oxide moiety and which releases or chemically transfers nitric oxide to another molecule. Nitric oxide donors include, for example, S-nitrosothiols, nitrites, N-oxo-N-nitrosamines, and substrates of the various isozymes of nitric oxide synthase.

One aspect of the present invention provides novel nitrosated and/or nitrosylated nonsteroidal antiinflammatory compounds. The nonsteroidal antiinflammatory compound can be nitrosated and/or nitrosylated through one or more sites such as oxygen (hydroxyl condensation), sulfur (sulfhydryl condensation), carbon and/or nitrogen. The nonsteroidal antiinflammatory compound can be, for example, an aryl propionic acid, an aryl acetic acid or an enolic anilide. The present invention also provides compositions comprising such compounds in a pharmaceutically acceptable carrier.

Another aspect of the invention provides compositions comprising a therapeutically effective amount of at least one nitrosated and/or nitrosylated nonsteroidal antiinflammatory compound and at least one compound that donates, transfers or releases nitrogen monoxide as a charged species, i.e., nitrosonium ($NO^+$) or nitroxyl (NO–), or as the neutral species, nitric oxide (NO·), and/or stimulates endogenous production of nitric oxide or endothelium-derived relaxing factor (EDRF) in vivo and/or is a substrate for nitric oxide synthase. The nitrosated and/or nitrosylated nonsteroidal antiinflammatory compounds can be, for example, aryl propionic acids, aryl acetic acids, or enolic anilides. The invention also provides for such compositions in a pharmaceutically acceptable carrier.

Yet another aspect of the present invention provides kits comprising at least one nitrosated and/or nitrosylated nonsteroidal antiinflammatory compound, and, optionally, at least one compound that donates, transfers or releases nitrogen monoxide as a charged species, i.e., nitrosonium ($NO^+$) or nitroxyl (NO−), or as the neutral species, nitric oxide (NO·), and/or stimulates endogenous production of nitric oxide or EDRF in vivo and/or is a substrate for nitric oxide synthase. The nitrosated and/or nitrosylated NSAID and the nitric oxide donor can be separate components in the kit or can be in the form of a composition.

The present invention also provides methods for treating and/or preventing inflammation, pain and fever; decreasing and/or reversing gastrointestinal, renal and other toxicities resulting from the use of nonsteroidal antiinflammatory compounds; and treating and/or preventing gastrointestinal disorders in a patient in need thereof which comprises administering to the patient a therapeutically effective amount of at least one nitrosated and/or nitrosylated nonsteroidal antiinflammatory compound, and, optionally, at least one compound that donates, transfers or releases nitrogen monoxide as a charged species, i.e., nitrosonium ($NO^+$) or nitroxyl (NO−), or as the neutral species, nitric oxide (NO·), and/or stimulates endogenous production of nitric oxide or endothelium-derived relaxing factor (EDRF) in vivo and/or is a substrate for nitric oxide synthase. The nitrosated and/or nitrosylated NSAID and nitric oxide donor can be administered separately or as components of the same composition.

The present invention also provides methods to treat inflammatory disease states and disorders by administering to a patient in need thereof a therapeutically effective amount of at least one nitrosated and/or nitrosylated nonsteroidal antiinflammatory compound, and, optionally, at least one nitric oxide donor. The nitrosated and/or nitrosylated NSAID and nitric oxide donor can be administered separately or as components of the same composition. Such inflammatory disease states and disorders include, for example, reperfusion injury to an ischemic organ (e.g., reperfusion injury to the ischemic myocardium), myocardial infarction, inflammatory bowel disease, rheumatoid arthritis, osteoarthritis, hypertension, psoriasis, organ transplant rejection, organ preservation, a female or male sexual dysfunctions, radiation-induced injury, asthma, atherosclerosis, thrombosis, platelet aggregation, restenosis, metastasis, influenza, incontinence, stroke, burn, trauma, acute pancreatitis, pyelonephritis, hepatitis, an autoimmune disease, an immunological disorder, senile dementia, insulin-dependent diabetes mellitus, disseminated intravascular coagulation, fatty embolism, Alzheimer's disease, adult or infantile respiratory disease, carcinogenesis or a hemorrhage in a neonate.

The present invention also provides methods to treat and/or prevent ophthalmic diseases and disorders by administering to a patient in need thereof a therapeutically effective amount of at least one nitrosated and/or nitrosylated nonsteroidal antiinflammatory compound, and, optionally, at least one nitric oxide donor. The ophthalmic diseases and disorders include glaucoma, inflammation of the eye and elevation of intraocular pressure. The nitrosated and/or nitrosylated NSAID and nitric oxide donor can be administered separately or as components of the same composition.

These and other aspects of the present invention are explained in detail below.

DETAILED DESCRIPTION OF THE INVENTION

As used throughout the disclosure, the following terms, unless otherwise indicated, shall be understood to have the following meanings.

"Gastrointestinal disorder" refers to any disease or disorder of the upper gastrointestinal tract of a patient including, for example, peptic ulcers, stress ulcers, gastric hyperacidity, dyspepsia, gastroparesis, Zollinger-Ellison syndrome, gastroesophageal reflux disease, short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns.

"Upper gastrointestinal tract" refers to the esophagus, the stomach, the duodenum and the jejunum.

"Ulcers" refers to lesions of the upper gastrointestinal tract lining that are characterized by loss of tissue. Such ulcers include gastric ulcers, duodenal ulcers and gastritis.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase.

"Patient" refers to animals, preferably mammals, more preferably humans.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, NO·), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, NO−, NO·), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, an alkenyl group, an alkynyl group, a bridged cycloalkyl group, a cycloalkyl group or a heterocyclic ring, as defined herein.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Haloalkyl" refers to a lower alkyl group, an alkenyl group, an alkynyl group, a bridged cycloalkyl group, a cydoalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2-C_{10}$ hydrocarbon (preferably a $C_2-C_8$ hydrocarbon, more preferably a $C_2-C_6$ hydrocarbon) which can comprise one or more carbon—carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Alkynyl" refers to an unsaturated acyclic $C_2-C_{10}$ hydrocarbon (preferably a $C_2-C_8$ hydrocarbon, more preferably a $C_2-C_6$ hydrocarbon) which can comprise one or more carbon—carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6 -dioxabicyclo[3.3.0] octane, 7-oxabycyclo[2.2.1]heptyl, 8-azabicyclo[3,2,1]oct-2-enyl and the like.

"Cycloalkyl" refers to a saturated or unsaturated cyclic hydrocarbon comprising from about 3 to about 8 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo and nitro. Exemplary cycloalkyl groups include cyclopropyl, cyclobutyl, cyclopentyl, cyclohexyl, cyclohexenyl, cyclohepta,1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. The heterocyclic ring or group can be fused to an aromatic hydrocarbon group. Heterocyclic groups can be unsubstituted or substituted with one, two or three substituents independently selected from alkyl, alkoxy, amino, alkylamino, dialkylamino, arylamino, diarylamino, alkylarylamino, hydroxy, oxo, halo, carboxyl, carboxylic ester, alkylcarboxylic acid, alkylcarboxylic ester, aryl, amnidyl, ester, carboxamido, alkylcarboxamido, arylcarboxamido, sulfonyl and nitro. Exemplary heterocyclic groups include pyrrolyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, 2-pyrrolinyl, 3-pyrrolinyl, pyrrolindinyl, oxazolindinyl 1,3-dioxolanyl, 2-imidazonlinyl, imidazolindinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4 H-pyranyl, piperidinyl, 1,4-dioxanyl, morpholinyl, 1,4-dithianyl, thiomorpholinyl, pyrazinyl, piperazinyl, 1,3,5-triazinyl, 1,3, 5-trithianyl, benzo(b)thiophenyl, benzimidazolyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicylic aryl groups) can be unsubstituted or substituted with one, two or three substituents independently selected from alkyl, alkoxy, amino, alkylamino, dialkylamino, arylamino, diarylamino, alkylarylamino, hydroxy, carboxyl, alkylcarboxylic acid, alkylcarboxylic ester, aryl, amidyl, ester, carboxamido, alkylcarboxamido and nitro. Exemplary substituted aryl groups include tetrafluorophenyl, pentafluorophenyl, sulfonamide, alkylsulfonyl, arylsulfonyl, and the like.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein.

"Cycloalkylalkyl" refers to a cycloalkyl radical, as defined herein, attached to an alkyl radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkoxy" refers to $R_{50}O$—, wherein $R_{50}$ is an alkyl group, as defined herein. Exemplary alkoxy groups include methoxy, ethoxy, t-butoxy, cyclopentyloxy, and the like.

"Arylalkoxy or alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O—$, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Haloalkoxy" refers to a haloalkyl group, as defined herein, to which is appended an alkoxy group, as defined herein. Exemplary haloalkyl groups include 1,1,1-trichloroethoxy, 2-bromobutoxy, and the like.

"Hydroxy" refers to —OH.

"Oxo" refers to =O.

"Oxy" refers to —O⁻$R_{77}^+$ wherein $R_{77}$ is an organic or inorganic cation.

"Hydroxyalkyl" refers to a hydroxy group, as defined herein, appended to an alkyl group, as defined herein.

"Amino" refers to —NH₂.

"Nitrate" refers to —O—NO₂.

"Nitrite" refers to —O—NO.

"Thionitrate" refers to —S—NO₂.

"Thionitrite" and "nitrosothiol" refer to —S—NO.

"Nitro" refers to the group —NO₂ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Alkylamino" refers to $R_{50}NH—$, wherein $R_{50}$ is an alkyl group, as defined herein. Exemplary alkylamino groups include methylamino, ethylamino, butylamino, cyclohexylamino, and the like.

"Arylamino" refers to $R_{55}NH—$, wherein $R_{55}$ is an aryl group, as defined herein.

"Dialkylamino" refers to $R_{52}R_{53}N—$, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{56}N—$, wherein $R_{55}$ and $R_{60}$ are each independently an aryl group, as defined herein.

"Alkylarylamino" refers to $R_{52}R_{55}N—$, wherein $R_{52}$ is an alkyl group, as defined herein, and $R_{55}$ is an aryl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein.

"Aminoaryl" refers to an amino group, an alkylamino group, a dialkylamino group, an arylamino group, a diarylamino group, an alkylarylamino group or a heterocyclic ring, as defined herein, to which is appended an aryl group, as defined herein.

"Sulfinyl" refers to —S(O)—.

"Sulfonyl" refers to —S(O)₂O$R_{58}$, wherein $R_{58}$ is an alkyl group, an aryl group, an alkylaryl group or an aryl heterocyclic ring, as defined herein.

"Sulfonic acid" refers to —S(O)₂O$R_{76}$, wherein $R_{76}$ is a hydrogen, an organic cation or an inorganic cation.

"Alkylsulfonic acid" refers to a sulfonic acid group, as defined herein, appended to an alkyl group, as defined herein.

"Arylsulfonic acid" refers to an sulfonic acid group, as defined herein, appended to an aryl group, as defined herein "Sulfonic ester" refers to —S(O)₂O$R_{58}$, wherein $R_{58}$ is an alkyl group, an aryl group, an alkylaryl group or an aryl heterocyclic ring, as defined herein.

"Sulfonamido" refers to —S(O)₂—N($R_{51}$)($R_{57}$), wherein $R_{51}$ and $R_{57}$ are each independently a hydrogen atom, an alkyl group, an aryl group, an alkylaryl group, or an arylheterocyclic ring, as defined herein, and $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to $R_{50}S—$, wherein $R_{50}$ is an alkyl group, as defined herein.

"Arylthio" refers to $R_{55}S—$, wherein $R_{55}$ is an aryl group, as defined herein.

"Alkylsulfinyl" refers to $R_{50}—S(O)—$, wherein $R_{50}$ is an alkyl group, as defined herein.

"Alkylsulfonyl" refers to $R_{50}—S(O)_2—$, wherein $R_{50}$ is an alkyl group, as defined herein.

"Arylsulfinyl" refers to $R_{55}—S(O)—$, wherein $R_{55}$ is an aryl group, as defined herein.

"Arylsulfonyl" refers to $R_{55}—S(O)_2—$, wherein $R_{55}$ is an aryl group, as defined herein.

"Amidyl" refers to $R_{51}C(O)N(R_{57})—$ wherein $R_{51}$ and $R_{57}$ are each independently a hydrogen atom, an alkyl group, an aryl group, an alkylaryl group, or an arylheterocyclic ring, as defined herein.

"Ester" refers to $R_{51}C(O)O—$ wherein $R_{51}$ is a hydrogen atom, an alkyl group, an aryl group, an alkylaryl group, or an arylheterocyclic ring, as defined herein.

"Carbamoyl" refers to —O—C(O)N($R_{51}$)($R_{57}$), wherein $R_{51}$ and $R_{57}$ are each independently a hydrogen atom, an alkyl group, an aryl group, an alkylaryl group or an aryl-heterocyclic ring, as defined herein, or $R_{51}$ and $R_{57}$ taken together are a heterocyclic ring, a cycloalkyl group or a bridged cycloalkyl group, as defined herein.

"Carboxyl" refers to —C(O)O$R_{76}$ wherein $R_{76}$ is a hydrogen, an organic cation or an inorganic cation.

"Carbonyl" refers to —C(O)—.

"Methanthial" refers to —C(S)—.

"Thial" refers to =S.

"Carboxylic ester" refers to —C(O)O$R_{58}$, wherein $R_{58}$ is an alkyl group, an aryl group, an alkylaryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" refers to an aryl group, as defined herein, appended to a carboxylic ester group, as defined herein.

"Carboxamido" refers to —C(O)N($R_{51}$)($R_{57}$), wherein $R_{51}$ and $R_{57}$ are each independently a hydrogen atom, an alkyl group, an aryl group, an alkylaryl group or an arylheterocyclic ring, as defined herein, and $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to —N($R_{58}$)—C(O)N($R_{51}$)($R_{57}$) wherein $R_{51}$, $R_{57}$, and $R_{58}$ are each independently a hydrogen atom, an alkyl group, an aryl group, an alkylaryl group, or an arylheterocyclic ring, as defined herein, or $R_{51}$ and $R_{57}$ taken together are a heterocyclic ring, a cycloalkyl group or a bridged cycloalkyl group, as defined herein.

"Phosphoryl" refers to —P($R_{70}$)($R_{71}$)($R_{72}$), wherein $R_{70}$ is a lone pair of electrons, thial or oxo, and $R_{71}$ and $R_{72}$ are each independently a covalent bond, a hydrogen, a lower alkyl, an alkoxy, an alkylamino, a hydroxy, an oxy or an aryl, as defined herein.

"Silyl" refers to —Si($R_{73}$)($R_{74}$)($R_{75}$), wherein $R_{73}$, $R_{74}$ and $R_{75}$ are each independently a covalent bond, a lower alkyl, an alkoxy, an aryl or an arylalkoxy, as defined herein.

The NSAIDs that are nitrosated and/or nitrosylated in accordance with the invention and/or are included in the compositions of the invention can be any of those known in the art, including those exemplified below.

Despite the introduction of many new drugs, aspirin (acetylsalicylic acid) is still the most widely prescribed antiinflammatory, analgesic and antipyretic compound and is a standard for the comparison and evaluation of all other NSAIDs. Salicylic acid itself is so irritating that it can only be used externally. However, derivatives, particularly salicylate esters and salts, have been prepared which provide ingestible forms of the salicylates which have the desired antiinflammatory and other properties. In addition to aspirin, which is the acetate ester of salicylic acid, are the diflurophenyl derivative (diflunisal) and salicylsalicylic acid (salsalate). Also available are the salts of salicylic acid, principally sodium salicylate. Sodium salicylate and aspirin are the two most commonly used preparations for systemic treatment. Other salicylates include salicylamide, sodium thiosalicylate, choline salicylate and magnesium salicylate. Also available are combinations of choline and magnesium salicylates. Also contemplated for use in the present invention are 5-aminosalicylic acid (mesalamine), salicylazosulfapyridine (sulfasalazine) and methylsalicylate.

Another group of NSAIDs are the pyrazolon derivatives, which include, for example, phenylbutazone, oxyphenbutazone, antipyrine, aminopyrine, dipyrone and apazone (azapropazone).

Another group of NSAIDs are the para-aminophenol derivatives, which are the so-called "coal tar" analgesics, including, for example, phenacetin and its active metabolite acetaminophen.

Another group of compounds for use in the present invention include indomethacin, a methylated indole derivative, and the structurally related compound sulindac.

Also contemplated is a group of compounds referred to as the fenamates which are derivatives of N-phenylanthranilic acid. The most well known of these compounds is mefenamic, meclofenamic, flufenamic, tolfenamic and etofenamnic acids. They are used either as the acid or as pharmaceutically acceptable salts.

Another contemplated NSAID is tolmetin which, like the other NSAIDs discussed herein, causes gastric erosion and prolonged bleeding time.

Another group of NSAIDs are the propionic acid derivatives. Principal members of this group are, for example, ibuprofen, naproxen, flurbiprofen, fenoprofen and ketoprofen. Other members of this group, in use or study in countries outside the U.S., include, for example, fenbufen, pirprofen, oxaprozin, indoprofen and tiaprofenic acid.

Also contemplated for use in the present invention are piroxicam and ampiroxicam, oxicam derivatives which are a class of antiinflammatory enolic acids. The other related compounds, tenoxicam and tenidap, can also be used. Another compound that is particularly preferred in the present invention is diclofenac, one of the series of phenylacetic acid derivatives that have been developed as antiinflammatory compounds. Other NSAIDs which are contemplated as suitable in the present invention include etodolac and nabumentone.

Each of the above NSAIDs is described more fully in the literature, such as in Goodman and Gilman, The Pharmacological Basis of Therapeutics (9th Edition), McGraw-Hill, 1995, Pgs. 617–657; the Merck Index on CD-ROM, Twelfth Edition, Version 12:1, 1996.

In one embodiment, the present invention describes nitrosated and/or nitrosylated NSAIDs of Formula (I):

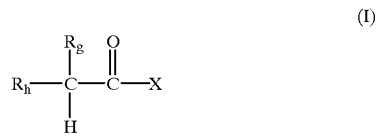

(I)

wherein $R_g$ is a hydrogen atom or a lower alkyl group;

$R_h$ is:

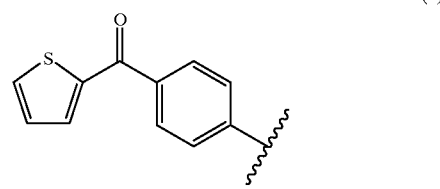

(1)

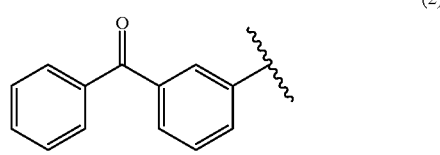

(2)

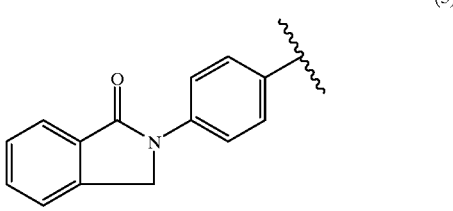

(3)

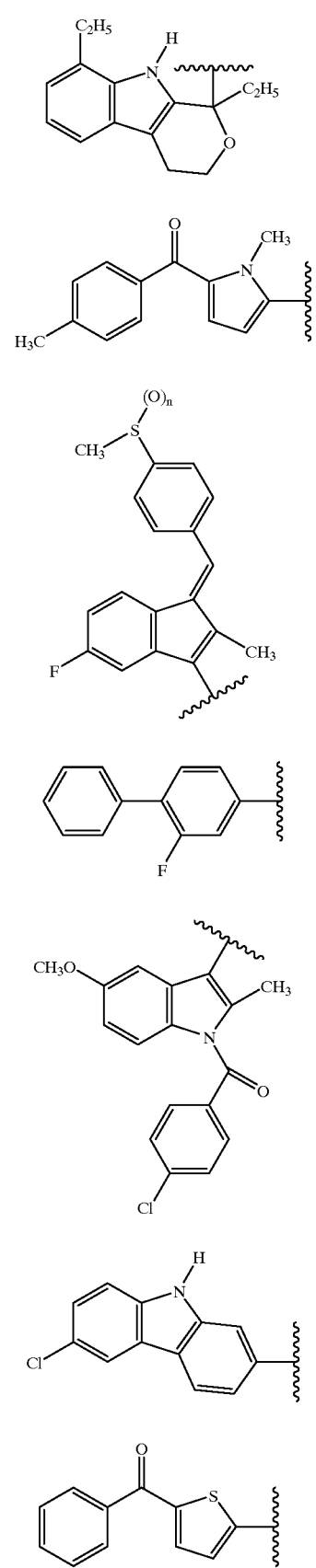
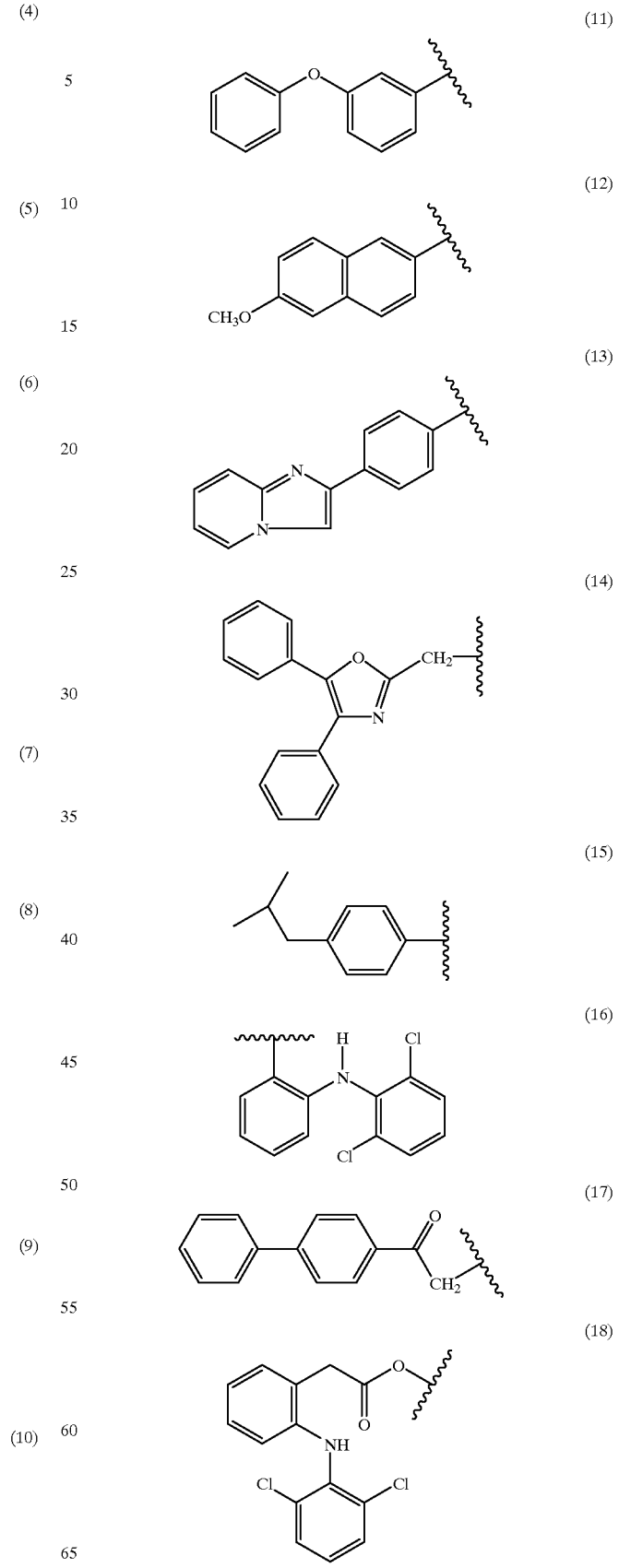

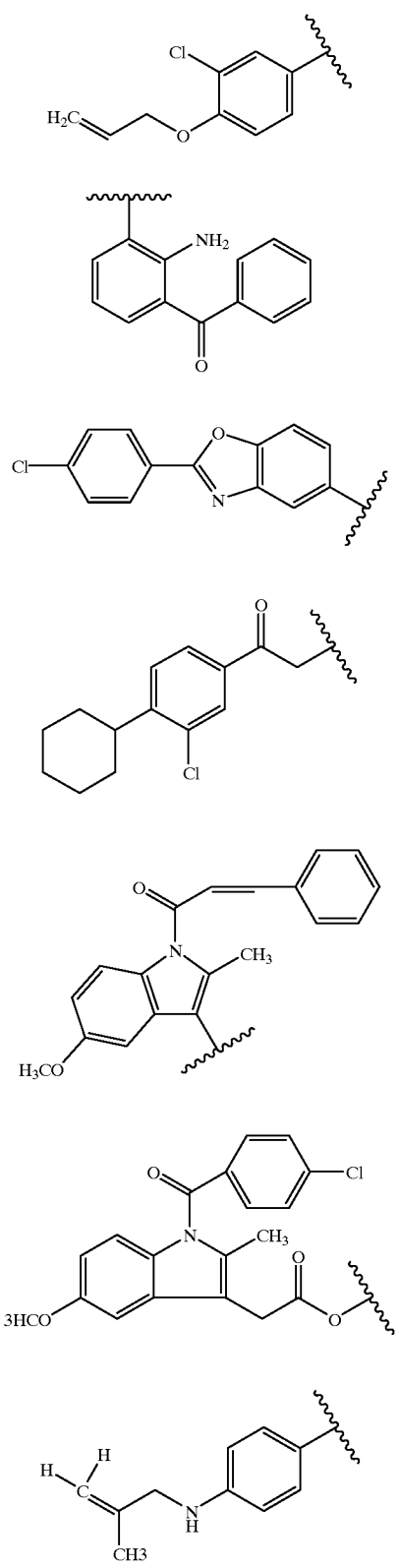
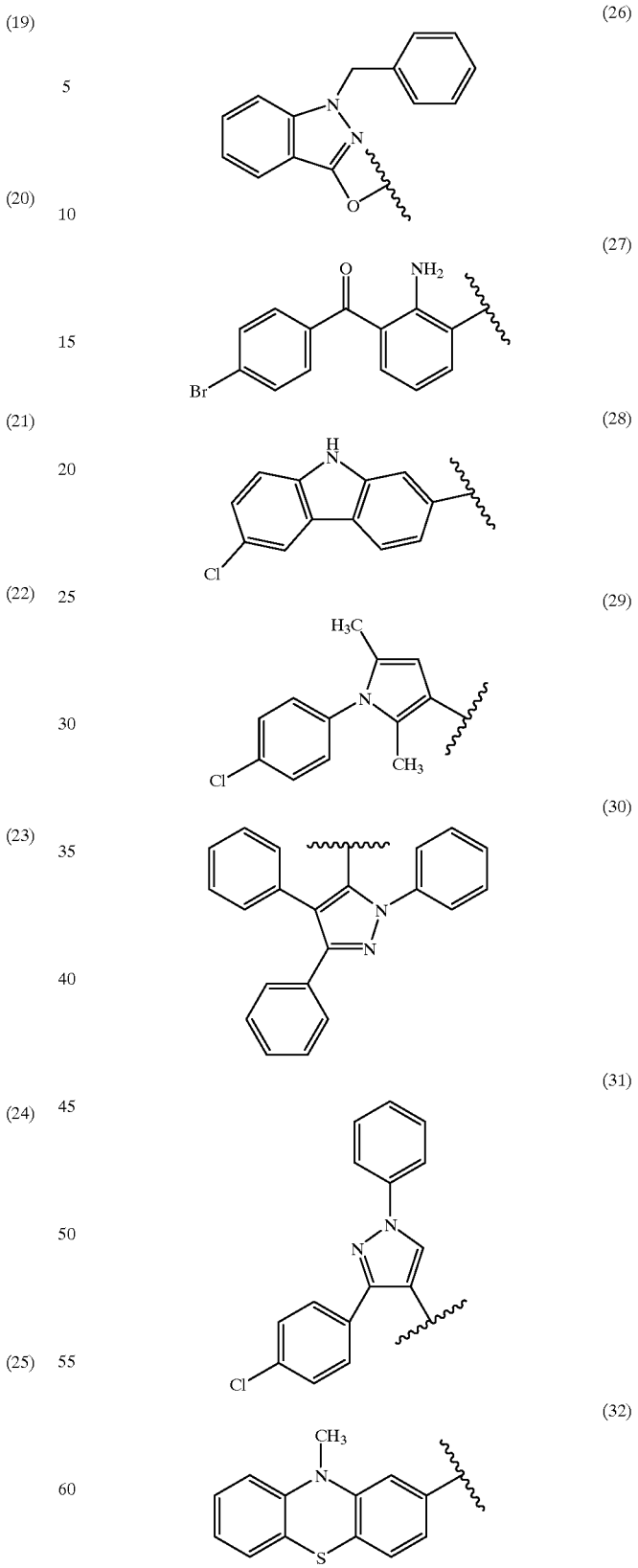

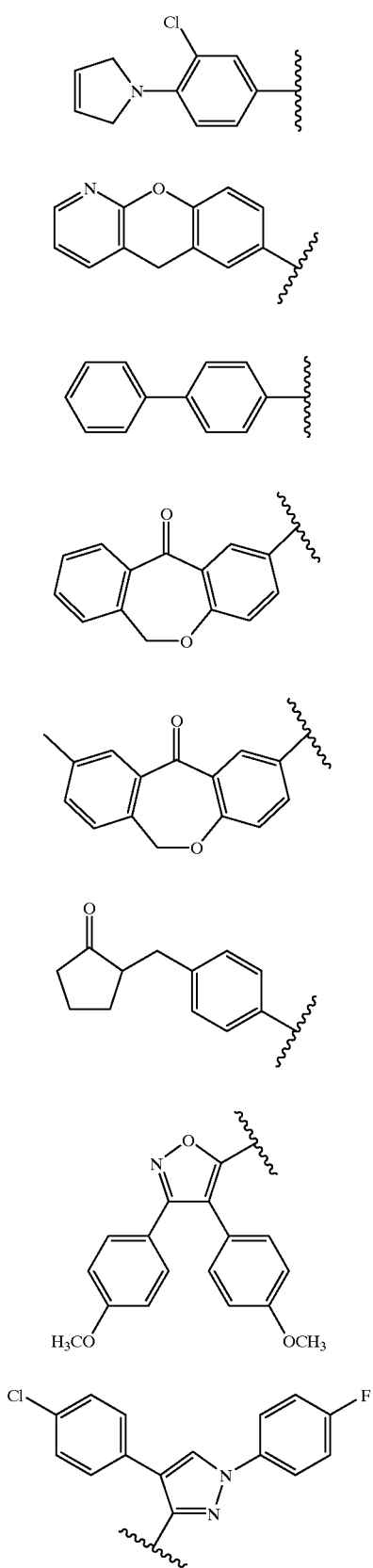
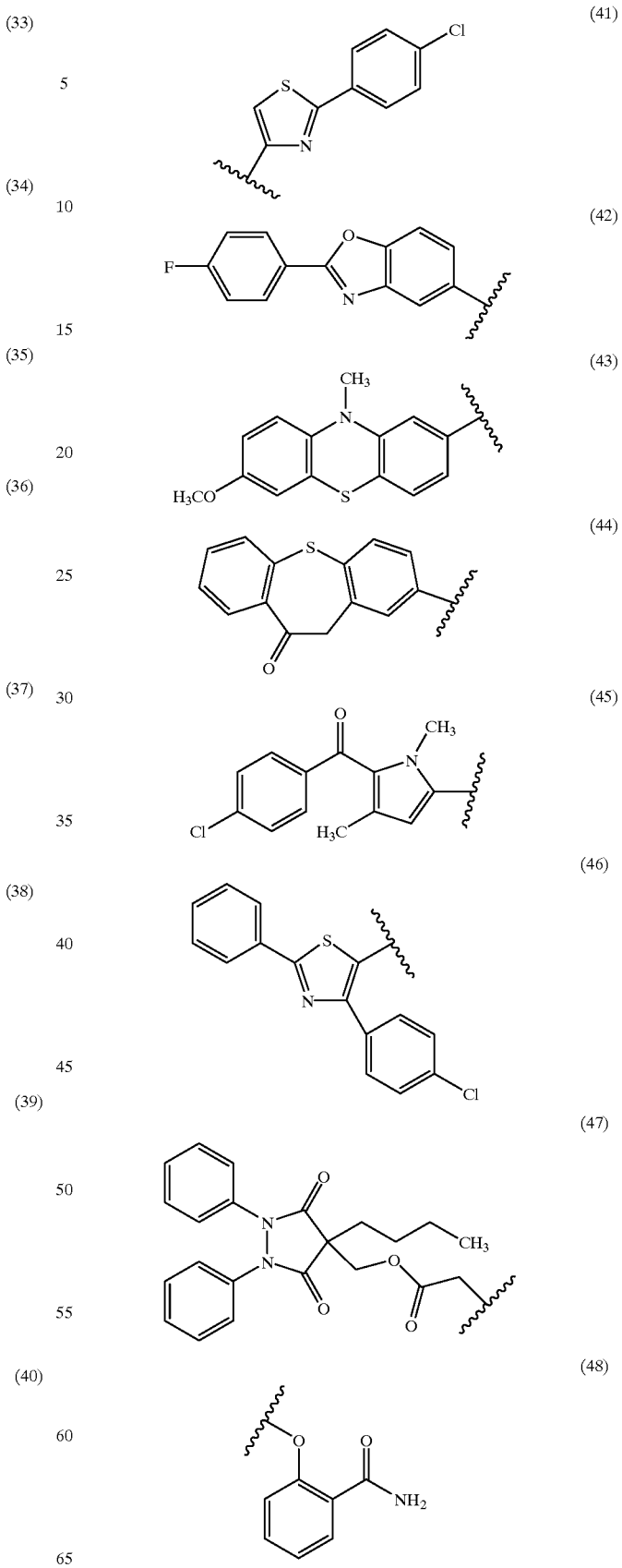

(49)
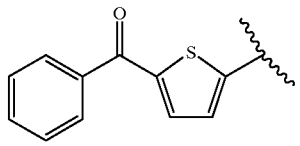

(50)
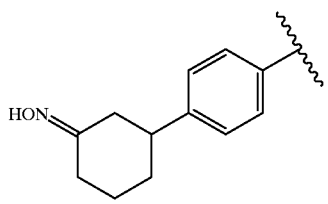

(51)
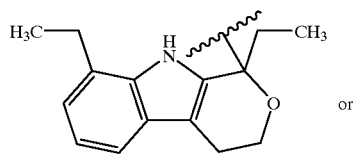 or

(52)
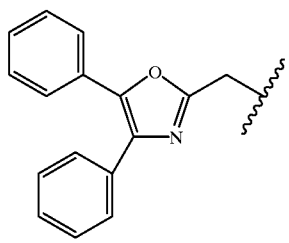

n is an integer of 0 or 1;
X is:
(i) -T-$B_f$—W—$B_t$-T-$NO_s$;
(ii) -T-$B_f$-$L_y$-$B_x$-T-$NO_s$;
(iii) -T-$B_f$-W-$B_t$-$W_x$-$B_k$-T-$NO_s$;
(iv) -T-$B_f$-(C($R_b$)($R_c$))$_p$-$E_x$-T-$NO_s$;
(v) -T-$B_f$-G-$B_t$-$W_z$-$B_k$-$G_x$-$B_r$-T-$NO_s$;
(vi) -T-$B_f$-J-$E_x$-T-$NO_s$; or
(vii) -T-$B_f$—C($R_e$)=N-$E_z$-T-$NO_s$;
wherein
s is an integer of 1 or 2;
T at each occurrence is independently a covalent bond, a carbonyl, an oxygen, —S(O)$_{o\text{— or }N(Ra)}$($R_i$)—;
o is an integer from 0 to 2;
$R_a$ is a lone pair of electrons, a hydrogen or an alkyl group;
$R_i$ is a hydrogen, an alkyl group, an aryl group, an alkylcarboxylic acid group, an aryl carboxylic acid group, an alkylcarboxylic ester group, an arylcarboxylic ester group, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$—C—(T-Q)($R_e$)($R_f$), or —($N_2O_2$—)$^-\cdot M^+$, wherein $M^+$ is an organic or inorganic cation,
L at each occurrence is independently —C(O)—, —C(S)—, -T-, a heterocyclic ring, an aryl group, an alkenyl group, an alkynyl group, an arylheterocyclic ring, or —(CH$_2$CH$_2$O)$_q$;
q is an integer from 1 to 5;
B at each occurrence is independently an alkyl group, an aryl group, —(C($R_e$)($R_f$))$_p$—, a heterocyclic ring, an aryl heterocyclic ring, or —(CH$_2$CH$_2$O)$_q$;

p is an integer from 1 to 10;
$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, -T-$NO_s$, or (C($R_e$)($R_f$))$_k$-T-$NOR_s$, or $R_e$ and $R_f$ taken together with the carbon atoms to which they are attached are a heterocyclic ring, a cycloalkyl group or a bridged cycloalkyl group;
$R_b$ and $R_c$ are each independently a haloalkyl, an alkenyl group, an alkynyl group, a bridged cycloalkyl group, a heterocyclic ring, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an arylalkyl, an alkylaryl, a carboxamido, an alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, -T-$NO_s$, or (C($R_e$)($R_f$))$_k$-T-$NO_s$, or $R_b$ and $R_c$ taken together with the carbon atoms to which they are attached are a carbonyl, a methanthial, a heterocyclic ring, a cloalkyl group or a bridged cycloalkyl group;
G is a covalent bond, -T-C(O)—, —C(O)-T- or T;
J is a carbonyl, a phosphoryl or a silyl;
k, l, t and z are each independently an integer from 1 to 3;
y is an integer from 1 to 3;
x and r are each independently an integer from 0 to 3;
E at each occurrence is independently —C(O)—, —C(S)—, -T-, —(C($R_e$)($R_f$))$_p$—, an alkyl group, an aryl group, a heterocyclic ring, arylheterocyclic ring, or —(CH$_2$CH$_2$O)$_q$;
W is oxygen, —S(O)$_o$—, —N($R_a$)($R_i$)—, carbonyl, or methanthial;
with the proviso that when $R_i$ is —CH$_2$—C(T-$NO_s$)($R_e$)($R_f$) or —($N_2O_2$)$^-\cdot M^+$, or $R_b$, $R_c$, $R_e$ or $R_f$ are T-$NO_s$ or (C($R_e$)($R_f$))$_k$-T-$NO_s$, then the "-T-$NO_s$" subgroup designated in X can be a hydrogen, an alkyl, an alkoxy, an alkoxyalkyl, an aminoalkyl, a hydroxy, a heterocyclic ring or an aryl group.
In cases where multiple designations of variables which reside in sequence are chosen as a "covalent bond" or the integer chosen is 0, the intent is to denote a single covalent bond connecting one radical to another. For example, $B_0$ would denote a covalent bond, while $B_2$ denotes (B—B) and (C($R_e$)($R_f$))$_2$ denotes —C($R_e$)($R_f$)—C($R_e$)($R_f$)—.
Another embodiment of the present invention describes nitrosated and/or nitrosylated NSAIDs of Formula (II):

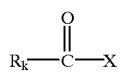
(II)
wherein
R_k is:
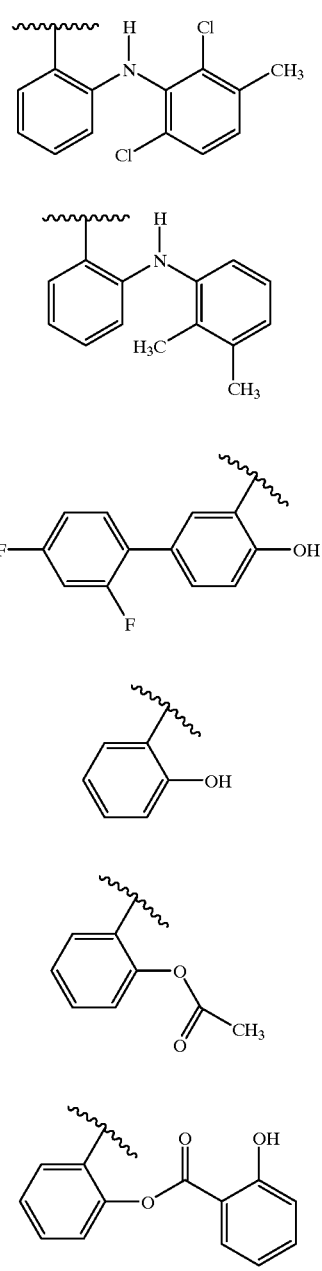
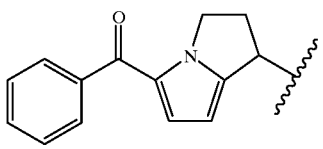
(7)
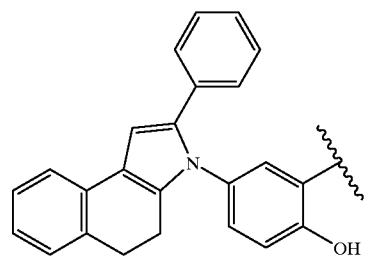
(8)
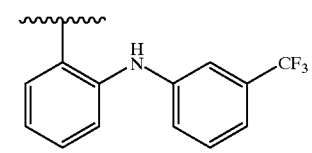
(9)
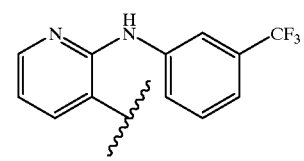
(10)
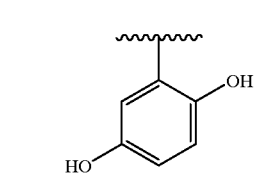
(11)
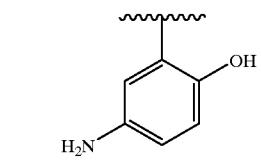
(12)
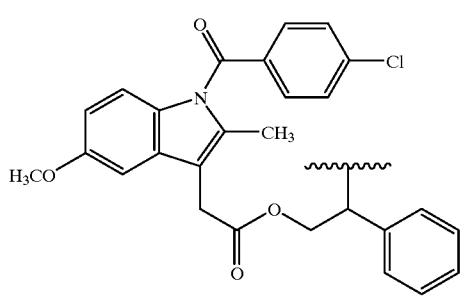
(13)

(14)

(15)

(16)

(17)

(18)

(19)

and X is as defined herein.

Another embodiment of the present invention describes nitrosated and/or nitrosylated NSAIDs of Formula (III)

(III)

wherein
X is as defined herein;

$R_i$ at each occurrence is independently $R_i$, wherein $R_i$ is as defined herein;

Z is an aryl group; and $A_1$, $A_2$ and $A_3$ comprise the other subunits of a 5- or 6-membered monocyclic aromatic ring and each of $A_1$, $A_2$ and $A_3$ is independently:

(1) C—$R_o$, wherein $R_o$ at each occurrence is independently a hydrogen, an alkyl, an alkoxyalkyl, a halogen or a nitro group;

(2) N—$R_p$, wherein $R_p$ at each occurrence is independently a covalent bond to an adjacent ring atom in order to render the ring aromatic, a hydrogen, an alkyl, an arylalkyl, an aryl or a heteroaryl group;

(3) a sulfur atom;

(4) an oxygen atom; or (5) $B_a$=$B_b$, wherein $B_a$ and $B_b$ are each independently a nitrogen atom or C—$R_o$ wherein $R_o$ is as defined herein.

Another embodiment of the present invention describes nitrosated and/or nitrosylated NSAIDs of Formula (IV):

(IV)

wherein $R_m$ is an alkyl group or an aryl group; and X, Z, $A_1$, $A_2$ and $A_3$ are as defined herein.

Compounds of the present invention which have one or more asymmetric carbon atoms can exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof.

Another aspect of the present invention provides processes for making the novel compounds of the invention and to the intermediates useful in such processes. The compounds of the present invention for Formulas (I), (II), (III) and (IV) can be synthesized by one skilled in the art following the methods and examples described herein. The reactions are performed in solvents appropriate to the reagents and materials used are suitable for the transformations being effected. It is understood by one skilled in the art of organic synthesis that the functionality present in the compound must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known in the art for protecting thiol and alcohol groups against undesirable reactions during a synthetic procedure and many such protecting groups are known, such as those described by T. H. Greene and P. G. M. Wuts, *Protective Groups in Organic Synthesis*, John Wiley & Sons, New York (1991), the disclosure of which is incorporated by reference herein in its entirety.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Nitroso compounds of Formula (I), wherein $R_g$ and $R_h$ are as defined herein, and an O-nitrosylated NSAID ester in which 2{4-[2-(nitrosooxy)ethyl]piperazinyl} ethan-1-ol is representative of the X group as defined herein may be prepared as described below. An appropriate acid (i.e., Formula (I) where X is substituted with hydroxyl) is converted into the ester by reaction with an appropriate monoprotected diol. Preferred methods for the preparation of esters are initially forming the mixed anhydride via reaction of the acid with a chloroformate such as isobutylchloroformate in the presence of a non-nucleophilic base such as triethylamine in an anhydrous inert solvent such as dichloromethane, diethylether or THF. The mixed anhydride is then reacted with the monoprotected alcohol preferably in the presence of a condensation catalyst such as 4-dimethylamine pyridine. Alternatively, the acid may first be converted to the acid chloride by treatment with oxalyl chloride in the presence of a catalytic amount of DMF. The acid chloride is then reacted with the monoprotected alcohol preferably in the presence of a condensation catalyst such as 4-dimethylamine pyridine and a tertiary amine base such as triethyl amine to produce the ester. Alternatively, the acid and monoprotected diol may be coupled to produce the ester by treatment with a dehydration agent such as DCC. Alternatively, the acid may first be converted into an alkali metal salt such as the sodium, potassium or lithium salt, and reacted with an alkyl halide that also contains a protected hydroxyl group in a polar solvent such as DMF to produce the ester. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite or nitrosium tetrafluoroborate in a suitable anhydrous solvent such as dichlormethane, THF, DMF or acetonitrile produces the compound of Formula (I).

Nitroso compounds of Formula (I), where $R_g$ and $R_h$ are as defined herein, and a S-nitrosylated NSAID ester in which 2-{methyl[2-methyl-2-(nitrosothiol) propyl]amino}ethan-1-ol is representative of the X group as defined herein may be synthesized as described below. An appropriate acid (i.e., Formula (I) where X is substituted with hydroxyl) is converted into the ester by reaction with an appropriate protected thiol containing alcohol. Preferred methods for the preparation of esters are initially forming the mixed anhydride via reaction of the acid with a chloroformate such as isobutylchloroformate in the presence of a non-nucelophilic base such as triethylamine in an anhydrous inert solvent such as diethylether or THF. The mixed anhydride is then reacted with the protected thiol-containing alcohol preferably in the presence of a condensation catalyst such as 4-dimethylamnine pyridine. Alternatively, the acid may first be converted to the acid chloride by treatment with oxalyl chloride in the presence of a catalytic amount of DMF. The acid chloride is then reacted with the protected thiol containing alcohol preferably in the presence of a condensation catalyst such as 4-dimethylamine pyridine and a tertiary amine base such as triethyl amine to produce an ester. Alternatively, the appropriate acid and protected thiol-containing alcohol may be coupled to produce the ester by treatment with a dehydration agent such as DCC. Alternatively, the acid may first be converted into an alkali metal salt such as the sodium, potassium or lithium salt, which is then reacted with an alkyl halide which also contains a protected thiol group in a polar solvent such as DMF to produce the ester. Preferred protecting groups for the thiol moiety are as a thioester such as thioacetate or thiobenzoate, as a disulfide, as a thiocarbamate such as N-methoxymethyl thiocarbamate, or as a thioether such as paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF or acetonitrile produces the compound of Formula (I). Alternatively, a stoichiometric quantity of sodium nitrite in aqueous acid produces the compound of Formula (I).

Nitroso compounds of Formula (II), where $R_k$ is defined herein and a S-nitrosylated NSAID ester in which 2-{methyl [2-methyl-2-(nitrosothiol)propyl] amino}ethan-1-ol is representative of the X group as defined herein may be synthesized as described below. An appropriate acid (i.e., Formula (II) where X is substituted with hydroxyl) is converted into the ester by reaction with an appropriate protected thiol containing alcohol. Preferred methods for the preparation of esters are initially forming the mixed anhydride via reaction of the acid with a chloroformate such as isobutylchloroformate in the presence of a non-nucelophilic base such as triethylamine in an anhydrous inert solvent such as diethylether or THF. The mixed anhydride is then reacted with the protected thiol-containing alcohol preferably in the presence of a condensation catalyst such as 4-dimethylamine pyridine. Alternatively, the acid may first be converted to the acid chloride by treatment with oxalyl chloride in the presence of a catalytic amount of DMF. The acid chloride is then reacted with the protected thiol containing alcohol preferably in the presence of a condensation catalyst such as 4-dimethylamine pyridine and a tertiary amine base such as triethyl amine to produce an ester. Alternatively, the appropriate acid and protected thiol-containing alcohol may be coupled to produce the ester by treatment with a dehydration agent such as DCC. Alternatively, the acid may first be converted into an alkali metal salt such as the sodium, potassium or lithium salt, which is then reacted with an alkyl halide which also contains a protected thiol group in a polar solvent such as DMF to produce the ester. Preferred protecting groups for the thiol moiety are as a thioester such as thioacetate or thiobenzoate, as a disulfide, as a thiocarbamate such as N-methoxymethyl thiocarbamate, or as a thioether such as paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF or acetonitrile produces the compound of Formula (II). Alternatively, a stoichiometric quantity of sodium nitrite in aqueous acid produces the compound of Formula (II).

Nitroso compounds of Formula (II) where $R_k$ is as defined herein and an O-nitrosylated NSAID ester in which 2{4-[2-(nitrosooxy)ethyl]piperazinyl}ethan-1-ol is representative of the X group as defined herein may be prepared as described below. An appropriate acid (i.e., Formula (II) where X is substituted with hydroxyl) is converted into the ester by reaction with an appropriate monoprotected diol. Preferred methods for the preparation of esters are initially forming the mixed anhydride via reaction of the acid with a chloroformate such as isobutylchloroformate in the presence of a non-nucleophilic base such as triethylamine in an anhydrous inert solvent such as dichloromethane, diethylether or THF. The mixed anhydride is then reacted with the monoprotected alcohol preferably in the presence of a condensation catalyst such as 4-dimethylamine pyridine. Alternatively, the acid may first be converted to the acid chloride with oxalyl chloride in the presence of a catalytic amount of DMF. The acid chloride is then reacted with the monoprotected alcohol preferably in the presence of a condensation catalyst such as 4-dimethylamine pyridine and a tertiary amine base such as triethyl amine to produce the ester. Alternatively, the acid and monoprotected diol may be coupled to produce the ester by treatment with a dehydration agent such as DCC. Alternatively, the acid may first be converted into an alkali metal salt such as the sodium, potassium or lithium salt, and reacted with an alkyl halide that also contains a protected hydroxyl group in a polar solvent such as DMF to produce the ester. Preferred protecting groups for the alcohol moiety are silyl ethers such as trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF or acetonitrile produces the compound of Formula (II).

Nitroso compounds of Formula (III) wherein $A_1$, $A_2$, $A_3$, $R_i$ and Z are as defined herein and an S-nitrosylated enol ester in which 2-{methyl[2-methyl-2-nitrosothiol)propyl]amino} acetyl is representative of the X group as defined herein may be prepared as described below. The enolic form of the β-keto amide of Formula (III) where X is substituted with hydrogen is converted to the ester by reaction with an appropriate protected thiol containing activated acylating agent. Preferred methods for the formation of an enol ester are reacting the enol with the preformed acid chloride or symmetrical anhydride of the protected thiol-containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF or acetonitrile with or without an amine base such as pyridine or triethylamine acid produces the compound of Formula (III). Alternatively, a stoichimetric quantity of sodium nitrite in aqueous acid produces the compound of Formula (III).

Nitroso compounds of Formula (III) wherein $A_1$, $A_2$, $A_3$, $R_i$ and Z are as defined herein and an O-nitrosylated enol ester in which 2-{methyl[2-methyl-2-nitrosooxy)ethyl]amino}acetyl is representative of the X group as defined herein may be prepared as described below. The enolic form of the β-keto amide of Formula (III) where X is substituted by hydrogen is converted to the ester by reaction with an appropriate protected alcohol containing activated acylating agent. Preferred methods for the formation of enol ester are reacting the enol with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF or acetonitrile with or without an amine base such as pyridine or triethylamnine produces the compound of Formula (III).

Nitroso compounds of Formula (IV) wherein $A_1$, $A_2$, $A_3$, $R_m$ and Z are as defined herein and an S-nitrosylated enol ester in which 2-{methyl[2-methyl-2-nitrosothiol)propyl]amino}acetyl is representative of the Y group as defined herein may be prepared as described below. The enolic form of the β-keto amide of Formula (IV) where X is substituted with hydrogen is converted to the ester by reaction with an appropriate protected thiol-containing alcohol activated acylating agent. Preferred methods for the formation of an enol ester are reacting the enol with the preformed acid chloride or symmetrical anhydride of the protected thiol-containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF or acetonitrile with or without an amine base such as pyridine or triethylamine acid produces the compound of Formula (IV). Alternatively, a stoichiometric quantity of sodium nitrite in aqueous acid produces the compound of Formula (IV).

Nitroso compounds of Formula (IV) wherein $A_1$, $A_2$, $A_3$, $R_m$ and Z are as defined herein and an O-nitrosylated enol ester in which 2-{methyl[2-methyl-2-nitrosooxy)ethyl] amino}acetyl is representative of the X group as defined herein may be prepared as described below. The enolic form of the β-keto amide of Formula (IV) where X is substituted by hydrogen is converted to the ester by reaction with an appropriate protected alcohol containing activated acylating agent. Preferred methods for the formation of enol ester are reacting the enol with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF or acetonitrile with or without an amine base such as pyridine or triethylamine produces the compound of Formula (IV).

The compounds of the present invention include NSAIDs, including those described herein, which have been nitrosated and/or nitrosylated through one or more sites such as oxygen (hydroxyl condensation), sulfur (sulfhydryl condensation), carbon and/or nitrogen. The nitrosated and/or nitrosylated NSAIDs of the present invention donate, transfer or release a biologically active form of nitrogen monoxide (i.e., nitric oxide).

Nitrogen monoxide can exist in three forms: NO– (nitroxyl), NO· (uncharged nitric oxide) and NO$^+$ (nitrosonium). NO· is a highly reactive short-lived species that is potentially toxic to cells. This is critical because the pharmacological efficacy of NO depends upon the form in which it is delivered. In contrast to the nitric oxide radical (NO·), nitrosonium (NO$^+$) does not react with $O_2$ or $O_2^-$ species, and functionalities capable of transferring and/or releasing NO$^+$ and NO– are also resistant to decomposition in the presence of many redox metals. Consequently, administration of charged NO equivalents (positive and/or negative) is a more effective means of delivering a biologically active NO to the desired site of action.

Compounds contemplated for use in the present invention (e.g., nitrosated and/or nitrosylated NSAIDs) are, optionally, used in combination with nitric oxide and compounds that release nitric oxide or otherwise directly or indirectly deliver or transfer a biologically active form of nitrogen monoxide to a site of its intended activity, such as on a cell membrane in vivo.

The term "nitric oxide" encompasses uncharged nitric oxide (NO) and charged nitrogen monoxide species, preferably charged nitrogen monoxide species, such as nitrosonium ion (NO$^+$) and nitroxyl ion (NO–). The reactive form of nitric oxide can be provided by gaseous nitric oxide. The nitrogen monoxide releasing, delivering or transferring compounds have the structure F-NO, wherein F is a nitrogen monoxide releasing, delivering or transferring moiety, and include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines (NONOates), (E)-alkyl-2-[(E)-hydroxyimino]-5-nitro-3-hexene amines or amnides, nitrosoamines, furoxans as well as substrates for the endogenous enzymes which synthesize nitric oxide. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3):165–198 (1983), the disclosures of each of which are incorporated by reference herein in their entirety.

Another embodiment of the present invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine and S-nitroso-glutathione.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS(C(R_e)(R_f))_m SNO$;

(ii) $ONS(C(R_e)(R_f))_m R_e$; and (iii) $H_2N—CH(CO_2H)-(CH_2)_m—C(O)NH—CH(CH_2SNO)—C(O)NH—CH_2—CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, or -T-Q; or $R_e$ and $R_f$ taken together are a carbonyl, a methanthial, a heterocyclic ring, a cycloalkyl group or a bridged cycloalkyl group; Q is —NO or —NO$_2$; and T is independently a covalent bond, a carbonyl, an oxygen, —S(O)$_o$— or —N($R_a$)$R_f$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —$CH_2$—C(T-Q)($R_e$)($R_f$), or —($N_2O_2$—)⁻·M⁺, wherein M⁺ is an organic or inorganic cation; with the proviso that when $R_i$ is —$CH_2$—C(T-Q)($R_e$)($R_f$) or —($N_2O_2$—)·M⁺; then "-T-Q" can be a hydrogen, an alkyl group, an alkoxyalkyl group, an aminoalkyl group, a hydroxy group or an aryl group.

In cases where $R_e$ and $R_f$ are a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetraflurorborate in an inert solvent.

Another group of NO adducts for use in the present invention include nitrates that donate, transfer or release nitric oxide, such as compounds comprising at least one $O_2N$—O—, $O_2N$—N—, $O_2N$—S— or $O_2N$—C— group. Preferred among these compounds are $O_2N$—O—, $O_2N$—N—, $O_2N$—S— or $O_2N$—C— polypeptides (the term "polypeptide" includes proteins and also polyamino acids that do not possess an ascertained biological function, and derivatives thereof); $O_2N$—O—, $O_2N$—N—, $O_2N$—S— or $O_2N$—C— amino acids (including natural and synthetic amino acids and their stereoisomers and racemic mixtures); $O_2N$—O—, $O_2N$—N—, $O_2N$—S— or $O_2N$—C-sugars; $O_2N$—O—, $O_2N$—N—, $O_2N$—S— or $O_2N$—C— modified and unmodified oligonucleotides (comprising at least 5 nucleotides, preferably 5–200 nucleotides); $O_2N$—O—, $O_2N$—N—, $O_2N$—S— or $O_2N$—C— straight or branched, saturated or unsaturated, aliphatic or aromatic, substituted or unsubstituted hydrocarbons; and $O_2N$—O—, $O_2N$—N—, $O_2N$—S— or $O_2N$—C— heterocyclic compounds. Preferred examples of compounds comprising at least one $O_2N$—O—, $O_2N$—N—, $O_2N$—S— or $O_2N$—C— group include isosorbide dinitrate, isosorbide mononitrate, clonitrate, erythrityltetranitrate, mannitol hexanitrate, nitroglycerin, pentaerythritoltetranitrate, pentrinitrol and proparylnitrate.

Another group of NO adducts are N-oxo-N-nitrosoamines that donate, transfer or release nitric oxide and are represented by the formula: $R^1R^2$—N(O-M⁺)—NO, where $R^1$ and $R^2$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where M⁺ is an organic or inorganic cation, such as, for example, an alkyl substituted ammonium cation or a Group I metal cation.

Another group of NO adducts are thionitrates that donate, transfer or release nitric oxide and are represented by the formula: $R^1$—(S)—$NO_2$, where $R^1$ is a polypeptide, an amino acid, a sugar, a modified or unmodified oligonucleotide, a straight or branched, saturated or unsaturated, aliphatic or aromatic, substituted or unsubstituted hydrocarbon, or a heterocyclic group. Preferred are those compounds where $R^1$ is a polypeptide or hydrocarbon with a pair or pairs of thiols that are sufficiently structurally proximate, i.e., vicinal, that the pair of thiols will be reduced to a disulfide. Compounds which form disulfide species release nitroxyl ion (NO–) and uncharged nitric oxide (NO·). Compounds where the thiol groups are not sufficiently close to form disulfide bridges generally provide nitric oxide as the NO– form and not as the uncharged NO· form.

The present invention is also directed to compounds that stimulate endogenous NO or elevate levels of endogenous endothelium-derived relaxing factor (EDRF) in vivo or are substrates for nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine or glutamine, inhibitors of the enzyme arginase (e.g., N-hydroxy-L-arginine and 2(S)-amino-6-boronohexanoic acid) and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature*, 327:524–526 (1987); Ignarro et al, *Proc. Natl. Acad. Sci. USA*, 84:9265–9269 (1987)).

The present invention is also based on the discovery that the administration of a therapeutically effective amount of the compounds and compositions described herein is effective for treating inflammation, pain and fever. For example, the patient can be administered a therapeutically effective amount of at least one nitrosated and/or nitrosylated NSAID of the present invention. In another embodiment, the patient can be administered a therapeutically effective amount of at least one nitrosated and/or nitrosylated NSAID, and, at least one compound that donates, transfers or releases nitric oxide, or elevates levels of endogenous EDRF or nitric oxide, or is a substrate for nitric oxide synthase. The compounds can be administered separately or in the form of a composition.

Another aspect of the invention provides methods to decrease or reverse gastrointestinal, renal and other toxicity (such as, for example, kidney toxicity) resulting from the use of nonsteroidal antiinflammatory drugs by administering to a patient in need thereof a therapeutically effective amount of the compounds and/or compositions described herein. For example, the patient can be administered a therapeutically effective amount of at least one nitrosated and/or nitrosylated NSAID, and, optionally, at least one compound that donates, transfers or releases nitric oxide, or elevates levels of endogenous EDRF or nitric oxide, or is a substrate for nitric oxide synthase. The nitrosated and/or nitrosylated NSAID and nitric oxide donor can be administered separately or as components of the same composition.

Another aspect of the invention provides methods for decreasing and/or preventing gastrointestinal disorders by administering to the patient in need thereof a therapeutically effective amount of the compounds and/or compositions described herein. For example, the patient can be administered a therapeutically effective amount of at least one nitrosated and/or nitrosylated NSAID, and, optionally, at least one compound that donates, transfers or releases nitric oxide, or elevates levels of endogenous EDRF or nitric oxide, or is a substrate for nitric oxide synthase. The nitrosated and/or nitrosylated NSAID and nitric oxide donor can be administered separately or as components of the same composition. Such gastrointestinal disorders include, for example, peptic ulcers, stress ulcers, gastric hyperacidity, dyspepsia, gastroparesis, Zollinger-Ellison syndrome, gastroesophageal reflux disease, short-bowel (anastomosis) syndrome, hypersecretory states associated with systemic mastocytosis or basophilic leukemia and hyperhistaminemia, and bleeding peptic ulcers that result, for example, from neurosurgery, head injury, severe body trauma or burns.

Another aspect of the invention provides methods for treating inflammatory disease states and disorders by administering to the patient in need thereof a therapeutically effective amount of at least one nitrosated and/or nitrosylated nonsteroidal antiinflammatory compound, and, optionally, at least one nitric oxide donor. Such inflammatory disease states and disorders include, for example, reperfusion injury to an ischemic organ (e.g., reperfusion injury to the ischemic myocardium), myocardial infarction, inflammatory bowel disease, rheumatoid arthritis, osteoarthritis, hypertension, psoriasis, organ transplant rejection, organ preservation, a female or male sexual dysfunction, radiation-induced injury, asthma, atherosclerosis, thrombosis, platelet aggregation, restenosis, metastasis, influenza, incontinence, stroke, bur, trauma, acute pancreatitis, pyelonephritis, hepatitis, an autoimmune diseases, an immunological disorder, senile dementia, insulin-dependent diabetes mellitus, disseminated intravascular coagulation, fatty embolism, Alzheimer's disease, adult or infantile respiratory disease, carcinogenesis or a hemorrhage in a neonate. The compounds and compositions of the present invention can also be administered in combination with other medications used for the treatment of these disorders.

Another aspect of the invention provides methods for treating and/or preventing ophthalmic diseases and disorders in a patient by administering to the patient a therapeutically effect amount of at least one nitrosated and/or nitrosylated nonsteroidal antiinflammatory compound, and optionally at least one nitric oxide donor. For example, the patient can be administered a therapeutically effective amount of at least one nitrosated and/or nitrosylated NSAID, and, optionally, at least one compound that donates, transfers or releases nitric oxide, or elevates levels of endogenous EDRF or nitric oxide, or is a substrate for nitric oxide synthase. The nitrosated and/or nitrosylated NSAID and nitric oxide donor can be administered separately or as components of the same composition. Such ophthalmic diseases and disorders include, for example, glaucoma, inflammation of the eye and elevation of intraocular pressure.

When administered in vivo, the compounds and compositions of the present invention can be administered in combination with pharmaceutically acceptable carriers and in dosages described herein. When the compounds and compositions of the present invention are administered as a mixture of at least one nitrosated and/or nitrosylated NSAID and at least one nitric oxide donor, they can also be used in combination with one or more additional compounds which are known to be effective against the specific disease state targeted for treatment. The nitric oxide donors and/or other additional compounds can be administered simultaneously with, subsequently to, or prior to administration of the nitrosated and/or nitrosylated NSAID.

The compounds and compositions of the present invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the present invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention, such as for treating pediatric fever and the like, can be prepared by mixing the compounds or compositions with a suitable nonirritating excipient such as cocoa butter and polyethylene glycols which are solid at room temperature but liquid at rectal temperature, such that they will melt in the rectum and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, pentoethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the present invention, including, for example, encapsulation in liposomes, microbubbles, emulsions, microparticles, microcapsules and the like.

The bioavailabilty of the compositions can be enhanced by micronization of the formulations using conventional techniques such as grinding, milling, spray drying and the like in the presence of suitable excipients or agents such as phospholipids or surfactants.

The compounds and compositions of the present invention can be formulated as neutral or pharmaceutically acceptable salt forms. Pharmaceutically acceptable salts include, for example, those formed with free amino groups such as those derived from hydrochloric, hydrobromic, phosphoric, sulfuric, acetic, citric, benzoic, fumaric, glutamic, lactic, malic, maleic, nitric, succinic, tartaric p-toluene-sulfonic, methanesulfonic, acids, gluconic acid, and the like, and those formed with free carboxyl groups such as those derived from sodium, potassium, ammonium, calcium, ferric hydroxides, isopropylamine, triethylamine, 2-ethylamino ethanol, histidine, procaine, and the like.

"Therapeutically effective amount" refers to the amount of the nitrosated and/or nitrosylated NSAID and nitric oxide donor that is effective to achieve its intended purpose. While individual patient needs may vary, determination of optimal ranges for effective amounts of each of the compounds and compositions is within the skill of the art. Generally, the dosage required to provide an effective amount of the composition, and which can be adjusted by one of ordinary skill in the art will vary, depending on the age, health, physical condition, sex, weight, extent of the dysfunction of the recipient, frequency of treatment and the nature and scope of the dysfunction or disease.

The amount of a given nitrosated and/or nitrosylated NSAID which will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The amount of nitric oxide donor in a pharmaceutical composition can be in amounts of about 0.1 to about 10 times the molar equivalent of the NSAID. The usual daily doses of NSAIDs are about 3 to about 40 mg/kg of body weight and the doses of nitric oxide donors in the pharmaceutical composition can be in amounts of about 1 to about 500 mg/kg of body weight daily, preferably about 1 to about 50 mg/kg of body weight daily. Effective doses may be extrapolated from dose-response curves derived from in vitro or animal model test systems and are in the same ranges or less than as described for the commercially available compounds in the Physician's Desk Reference, supra.

The present invention also provides pharmaceutical kits comprising one or more containers filled with one or more of the ingredients of the pharmaceutical compositions of the present invention, including, at least, one or more of the nitrosated and/or nitrosylated NSAIDs described herein and one or more of the NO donors described herein. Associated with such kits can be a notice in the form prescribed by a governmental agency regulating the manufacture, use or sale of pharmaceuticals or biological products, which notice reflects approval by the agency of manufacture, use or sale for human administration.

EXAMPLES

The following non-limiting examples further describe and enable one of ordinary skill in the art to make and use the present invention. In each of the examples, flash chromatography was performed on 40 micron silica gel (Baker).

Example 1

2-[4-Methyl-4-(nitrosothio)piperidyl]ethyl 2-{2-[(2, 6-dichlorophenyl)amino]phenyl}acetate hydrochloride 1a. Phenylmethyl 2-(4-oxopiperidyl)acetate To a stirred suspension of 4-piperidone (10.0 g, 65.0 mmol) and bromobenzyl acetate (14.9 g, 65.2 mmol) in acetone (100 ml) was added $K_2CO_3$ (9.0 g) and $Et_3N$ (9.1 ml, 65.2 mmol). The reaction mixture was stirred at room temperature for two days, and then the solvent was evaporated. The residue was partitioned between EtOAc and water. The aqueous layer was extracted with EtOAc. The organic extracts were combined and dried over $Na_2SO_4$. The solvent was evaporated to afford the title compound (13.3 g, 53.8 mmol, 83%) as a thick oil. $^1$H NMR (300 MHz, $CDCl_3$) δ 7.33–7.37 (m, 5H), 5.18 (s, 2H), 3.42 (s, 2H), 2.91 (t, J=6.1 Hz, 4H), 2.50 (t, J=6.1 Hz, 4H).

1b. Phenylmethyl 2-(6-aza-1-oxaspiro[2.5]oct-6-yl)acetate

Sodium hydride (1.6 g, 66.7 mmol) was suspended in dimethylsulfoxide (80 ml). Trimethylsulfoxonium iodide (14.7 g, 66.8 mmol) was added in several portions at room temperature. After stirring for 20–30 minutes, the mixture became homogeneous. The product of Example 1a (12.7 g, 51.4 mmol) in dimethylsulfoxide (40 ml) was then added and the reaction mixture was heated to 60° C. for one hour. The reaction mixture was then cooled to room temperature, poured into water, and extracted with EtOAc. The organic extracts were combined and dried over $Na_2SO_4$. The solvent was evaporated to give the title compound (13.1 g, 50.1 mmol, 97%) as a thick oil. $^1$H NMR (300 MHz, $CDCl_3$) δ 7.33–7.38 (m, 5H), 5.18 (s, 2H), 3.32 (s, 2H), 2.74–2.80 (m, 2H), 2.66 (s, 2H), 2.61–2.70 (m, 2H), 1.88–1.96 (m, 2H), 1.52–1.59 (m, 2H).

1c. Phenylmethyl 2-(6-aza-1-thiaspiro[2.5]oct-6-yl)acetate

%p The product of Example 1b (5.35 g, 20.5 mmol) was dissolved in methanol (70 ml). Thiourea (1.72 g, 22.6 mmol) was added and the mixture was stirred at 40° C. for three hours and then overnight at room temperature. The solvent was evaporated and the residue was dissolved in EtOAc and washed twice with water. The EtOAc layer was dried over $Na_2SO_4$. The solvent was evaporated to give the title compound which was used without further purification (5.6 g, 20.2 mmol, 98%). 1H NMR (300 MHz, $CDCl_3$) δ 7.30–7.38 (m, 5H), 5.17 (s, 2H), 3.34 (s, 2H), 2.88–2.91 (m, 2H), 2.55–2.62 (m, 2H), 2.44 (s, 2H), 2.21–2.28 (m, 2H), 1.52–1.57 (m, 2 H).

1d. 2-(4-Methyl-4-sulfanylpiperidyl)ethan-1-ol

To an ice-cooled solution of $LiAlH_4$ (24.0 ml in 1M tetrahydrofuran, 24.0 mmol) was added dropwise a solution of the product of Example 1c (5.32 g, 19.2 mmol) in 20 ml tetrahydrofuran. The solution was stirred cold for half an hour after the addition was complete. Water was added dropwise to quench the reaction. 5% methanol/dichloromethane solution was added and the mixture was filtered through Celite. The filtrate was concentrated to give an oil, which was dissolved in ether (20 ml). HCl in ether was added to precipitate the salt, which was filtered and washed thoroughly with ether to remove the last trace of benzyl alcohol. The amine was liberated by adding 10% ammonium hydroxide solution followed by extraction with EtOAc. The organic extracts were combined and dried over $Na_2SO_4$. The solvent was evaporated to afford the title compound (2.1 g, 12.0 mmol, 62%) as a clear oil. $^1$H NMR (300 MHz, $CDCl_3$) δ 3.60 (t, J=5.4 Hz, 2H), 2.45–2.67 (m, 4H), 2.57 (t, J=5.4 Hz, 2H), 1.64–1.76 (m, 4H), 1.46 (s, 3H).

1e. 2-(4-Methyl-4-sulfanylpiperidyl)ethyl 2-{2-[(2,6-dichlorophenyl)amino]phenyl}acetate To a mixture of the product of Example 1d (362 mg, 2.07 mmol), (2-((2,6-dichlorophenyl)amino)benzene)acetic acid (797 mg, 2.69 mmol) and dimethylaminopyridine (126 mg, 1.03 mmol) in dichloromethane (20 ml) was added dicyclohexylcarbodiimide (555 mg, 2.69 mmol) all at once. A white precipitate started to form after about five minutes. The reaction was stirred for three hours. Ether was added to the mixture, and the solid was filtered off. The solvent was evaporated. The residue was chromatographed on silica gel eluting with 1:1 EtOAc/hexanes to afford the title compound (287 mg, 0.63 mmol, 31%) as a clear oil. $^1$H NMR (300 MHz, $CDCl_3$, free base) δ 7.33–7.35 (m, 2H), 7.21–7.26 (m, 1H), 7.09–7.14 (m, 1H), 6.89–7.00 (m, 3H), 6.53–6.56 (m, 1H), 4.27 (t, J=5.9 Hz, 2H), 3.82 (s, 2H), 2.67 (t, J=5.9 Hz, 2H), 2.56–2.62 (m, 2H), 2.39–2.48 (m, 2H), 1.64–1.67 (m, 4H), 1.60 (s, 1H), 1.39 (s, 3H).

1f. 2-[4-Methyl-4-(nitrosothio)piperidyl]ethyl 2-{2-[(2,6-dichlorophenyl)amino]phenyl}acetate The product of Example 1e (287 mg, 0.63 mmol) was dissolved in ether and HCl in ether was added dropwise. The white solid thus formed was collected and washed thoroughly with ether and vacuum dried to give the HCl salt (270 mg, 0.55 mmol) as a white solid. The salt (200 mg, 0.41 mmol) was dissolved in dichloromethane (4 ml). The solution was cooled to −78° C. t-Butyl nitrite (54 μL, 0.41 mmol) was added. The cold bath was then removed. Ten minutes later, the solvent was evaporated to give a green solid, which was converted to the free amine by treatment with saturated aqueous $K_2CO_3$ and then extracted with EtOAc. The EtOAc extracts were combined and dried over $Na_2SO_4$. The solvent was evaporated and the crude product was chromatographed on silica gel eluting with 1:1 EtOAc/hexanes to give the title compound (135 mg, 0.28 mmol, 69%) as a thick oil. $^1$H NMR (300 MHz, $CDCl_3$) δ 7.33–7.36 (m, 2H), 7.21–7.24 (m, 1H), 7.08–7.14 (m, 1H), 6.88–7.01 (m, 3H), 6.53–6.56 (m, 1H), 4.29 (t, J=5.8 Hz, 2H), 3.82 (s, 2H), 2.66–2.76 (m, 2H), 2.68 (t, J=5.8 Hz, 2H), 2.33–2.40 (m, 2H), 2.08–2.17 (m, 2H), 1.94 (s, 3H).

1g. 2-[4-Methyl-4-(nitrosothio)piperidyl]ethyl 2-{2-[(2,6-dichlorophenyl)amino]phenyl}acetate hydrochloride The product of Example 1f (130 mg, 0.27 mmol) was dissolved in ether and HCl in ether was added dropwise. The green solid thus formed was collected on a Buchner funnel and washed thoroughly with ether. The solid was vacuum dried to furnish the title compound (127 mg, 0.24 mmol) as a green solid. $^1$H NMR (300 MHz, $CDCl_3$) δ 7.36–7.43 (m, 2H), 7.16–7.19 (m, 1H), 7.00–7.08 (m, 2H), 6.83–6.87 (m, 1H), 6.41–6.44 (m, 1H), 4.72–4.75 (m, 2H), 3.86 (s, 2H), 3.38–3.47 (m, 2H), 3.20–3.22 (m, 2H), 2.92–3.03 (m, 2H), 2.45–2.66 (m, 4H), 2.03 (s, 2H).

Example 2

2-(Methyl{[(nitrosothio)cyclohexyl]methyl}amino) ethyl 2-{2-[(2,6-dichlorophenyl)amino] phenyl}acetate hydrochloride 2a. 1-[(Formylcyclohexyl)disulfanyl]cyclohexanecarbaldehyde To a stirred solution of cyclohexanecarboxaldehyde (100 g, 89 mmol) in carbon tetrachloride (100 ml) was added sulfur monochloride (36.4 ml, 91 mmol) dropwise at 50° C. After a short lag phase (15 min), evolution of HCl gas began. After the gas evolution had ceased, the mixture was stirred at 55° C. for 1 hour and then cooled to room temperature. The $CCl_4$ was evaporated to produce a yellow solid and the solid was placed in a sintered glass funnel and washed with hexane (3×100 ml) to give the title compound as a white solid (114 g, 89%). mp. 85–88° C.; $^1$H NMR (300 MHz, $CDCl_3$) δ 1.24–1.33 (m, 6 H), 1.42–1.46 (m, 6 H), 1.62–1.69 (m, 4 H), 1.94–1.99 (m, 4 H), 8.94 (s, 2 H); $^{13}$C NMR (75 MHz, $CDCl_3$) δ 23.0, 25.1, 30.3, 60.8, 194.3. Anal. Calcd for $C_{14}H_{22}O_2S_2$: C, 58.70; H, 7.74; S, 22.38. Found: C, 58.74; H, 7.69; S, 22.18.

2b. 2-[({[({[(2-Hydroxyethyl)amino]methyl}cyclohexyl) disulfanyl]cyclohexyl}methyl)amino]ethan-1-ol A mixture of the product of Example 2a (10 g, 34.91 mmol), ethanol amine (4.26 g, 69.82 mmol) and $MgSO_4$ (10 g) in dry $CHCl_3$ (100 ml) was heated under reflux for 8 hours. The solid was filtered and the solvent was evaporated under reduced pressure to yield a viscous yellow liquid. The crude product was dissolved in methanol (125 ml) and $NaBH_4$ (3.3 g, 87.25 mmol) was added portionwise over 10 mm. The resulting solution was stirred at room temperature for 1 hour. Methanol was evaporated and the crude material was partitioned between a mixture of water (200 ml) and ethyl acetate (100 ml). The organic layer was separated and the aqueous layer was extracted with ethyl acetate (100 ml). The combined organic layers were dried over $Na_2SO_4$ and evaporated under reduced pressure to give a colorless viscous liquid. This product was then further purified by dissolving in ether (50 ml) followed by the dropwise addition of HCl in ether to form a white salt. The salt was washed with ether (2×50 ml) and then the solid was dissolved in water (100 ml). The aqueous layer was washed with ether (100 ml) and the ether layer was discarded. The aqueous layer was basified with 15% ammonium hydroxide (10 ml) to form a white suspension which was extracted with ethyl acetate (2×50 ml). The organic layer was dried over $Na_2SO_4$ and concentrated under reduced pressure to give the title compound (12.2 g, 93%) as a viscous liquid. $^1H$ NMR (300 MHz, $CDCl_3$) δ 1.20–1.95 (in, 20 H), 2.66 (s, 4 H), 2.78 (t, J=5.2 Hz, 4 H), 3.61 (t, J=5.2 Hz, 4 H); 13C NM (75 MHz, $CDCl_3$) δ 22.7, 25.8, 34.3, 51.5, 54.7, 60.6, 68.2.

2c. 2-[({[({[(2-Hydroxyethyl)methylamino]methyl}cyclohexyl)disulfanyl]cyclohexyl}methyl)methylamino]ethan-1-ol A mixture of the product of Example 2b (12.2 g, 32.4 mmol), 38% formaldehyde (35 ml) and methanol (70 ml) was stirred at room temperature under nitrogen for 12 hours. The solution was diluted with water (100 ml) and extracted with ethyl acetate (3×100 ml). The organic layer was dried over $Na_2SO_4$ and concentrated under reduced pressure to give an oil. The crude product was dissolved in methanol (120 ml) and $NaBH_4$ (3.05 g, 80.6 mmol) was added portionwise over 10 min. The resulting solution was stirred at room temperature for 1 hour. Methanol was evaporated and the crude material was dissolved in a mixture of water (200 ml) and ethyl acetate (100 ml). The organic layer was separated and the aqueous layer was extracted with ethyl acetate (2×100 ml). The combined organic layers were dried over $Na_2SO_4$ and evaporated under reduced pressure to give the title compound (11.6 g, 88.5%) as a colorless viscous liquid. The product solidified on standing. mp. 65–70° C.; $^1H$ NMR (300 MHz, $CDCl_3$) δ 1.23–1.65 (m, 20 H), 2.34 (s, 6 H), 2.59 (s, 4 H), 2.65 (t, J=5.3 Hz, 4 H), 3.60 (t, J=5.3 Hz, 4 H), $^{13}C$ NMR (100 MHz, $CDCl_3$) δ 22.3, 25.6, 33.4, 44.2, 55.9, 59.2, 61.7, 67.4; Anal. Calcd for $C_{20}H_{40}N_2O_2S_2$: C, 59.36; H, 9.96; N, 6.92; S, 15.84 Found: C, 59.05; H, 9.71; N, 6.61; S, 15.88.

2d. 2-{Methyl[(sulfanylcyclohexyl)methyl]amino}ethan-1-ol

To a stirred solution of the product of Example 2c (11.6 g, 28.66 mmol) in dry tetrahydrofuran (100 ml) was added 1M tetrahydrofuran solution of lithium aluminium hydride (43 ml, 43 mmol) dropwise at room temperature under nitrogen. The resulting clear solution was stirred at room temperature for 1 hour. The excess lithium aluminium hydride was destroyed carefully by dropwise addition of water (5 ml) and dry $NH_4Cl$ (2 g). Ethyl acetate (100 ml) was added and the precipitate was filtered. The white precipitate was washed with 10% methanol in dichloromethane (2×50 ml). The combined filtrate was dried over $Na_2SO_4$ and concentrated under reduced pressure to give the title compound (9.2 g, 79%) as a viscous liquid. $^1H$ NMR (300 MHz, $CDCl_3$) δ 1.05–1.25 (m, 2 H), 1.45–1.85 (m, 8 H), 2.34 (s, 3 H), 2.50 (s, 2 H), 2.64 (t, J=5.4 Hz, 2 H), 3.56 (t, J=5.4 Hz, 2 H), $^{13}C$ NMR (75 MHz, $CDCl_3$)δ 22.2, 25.9, 38.2, 44.8, 52.2, 59.4, 62.1, 72.2.

2e. 2-{Methyl[(sulfanylcyclohexyl)methyl]amino}ethyl-2-{2-[(2,6-dichlorophenyl) amino]phenyl}acetate Dicyclohexylcarbodiimide (1.21 g, 5.89 mmol) in $CH_2Cl_2$ (40 ml) was added dropwise to a stirred solution of the product of Example 2d (1.0 g, 4.91 mmol) and 2-((2,6-dichlorophenyl)amino)benzeneacetic acid (1.45 g, 4.91 mmol), in dry $CH_2Cl_2$ (50 ml) over 1 hour. The suspension was then stirred at room temperature for 2 hours. The precipitate was filtered and washed with $CH_2Cl_2$ (2×20 ml) and the filtrate was concentrated. The crude material was triturated with hexane (2×25 ml) and hexane was evaporated to give viscous oil. The crude product was dissolved in $CH_2Cl_2$ (5 ml) and chromatographed on silica gel column packed in hexane eluting with 5% ethyl acetate in hexane to give the title compound (1.35 g, 57%). TLC $R_f$=0.35 (hexane/ethylacetate, 9:1; $KMnO_4$ brown); $^1H$ NMR (300 MHz, $CDCl_3$) δ 1.15–1.18 (m, 1H), 1.29–1.80 (m, 9 H), 2.12 (bs, 1 H), 2.42 (s, 3 H), 2.52 (s, 2 H), 2.86 (t, J=5.9 Hz, 2 H), 3.84 (s, 2 H), 4.28 (t, J=5.9 Hz, 2 H), 6.56 (d, J=7.9 Hz, 1 H), 6.93–7.00 (m, 3 H), 7.14 (t, J=6.7 Hz, 1 H), 7.23 (d, J=6.7 Hz, 1 H), 7.34 (d, J=8.0 Hz, 2 H), $^{13}C$ NMR (75 MHz, $CDCl_3$) δ 22.3, 25.9, 37.6, 38.6, 45.2, 52.2, 58.5, 60.2, 63.1, 72.1, 118.1, 121.9, 123.9, 124.1, 127.8, 128.7, 129.3, 130.8, 137.7, 142.6, 172.2; mass spectrum (EI) 510 ($M^+$), 172 (100).

2f. 2-{Methyl[(sulfanylcyclohexyl)methyl]amino}ethyl-2-{2-[(2,6-dichlorophenyl) amino]phenyl}acetate hydrochloride HCl in ether was added dropwise to a solution of the product of Example 2e in dry ether (30 ml) to form an insoluble white sticky product. The ether was evaporated under reduced pressure to give a white foam which was triturated with hexane (25 ml) to afford a white suspension. The hexane was evaporated under reduced pressure and the material was dried in vacuo for 12 hours to give the title compound (2.1 g) as a white powder. mp. 113° C; $^1H$ NMR (300 MHz, $CDCl_3$) δ 1.14–1.30 (m, 1 H), 1.34–2.00 (m, 9 H), 2.95–3.01 (m, 1 H), 2.96 (d, J=4.2 Hz, 3 H), 3.30 (d, J=13.5 Hz, 1 H), 3.43–3.60 (m, 3 H), 3.86 (s, 2 H), 4.66–4.82 (m, 2 H), 6.51–6.54 (m, 2 H), 6.94 (t, J=7.4 Hz, 1 H), 7.02 (t, J=8.0 Hz, 1 H), 7.06–7.16 (m, 1 H), 7.20 (d, J=7.4 Hz, 1 H), 7.35 (d, J=8.0 Hz, 2 H), 11.66 (bs, 1 H).

2g. 2-(Methyl{[(nitrosothio)cyclohexyl]methyl}amino)ethyl-2-{2-[(2,6 dichlorophenyl)amino]phenyl}acetate Tert-butyl nitrite (0.46 g, 4.42 mmol) was added to a stirred solution of the product of Example 2f (2.28 g, 4.42 mmol) in $CH_2Cl_2$ (50 ml) at −78° C. The cooling bath was removed and the green solution was stirred for 10 min and then concentrated under reduced pressure to give a green foam. The green foam was dissolved in ethyl acetate (25 ml) and washed with saturated $K_2CO_3$ (10 ml) and then with water (25 ml). The organic layer was dried over $Na_2SO_4$ and concentrated under reduced pressure to give a green viscous oil. The crude product was purified by flash chromatography on silica gel eluting with 5% ethyl acetate in hexane to give the title compound (1.92 g, 85.2%) as a green colored viscous oil. TLC $R_f$=0.47 (hexane/ethylacetate, 9:1; green); $^1H$ NMR (300 MHz, $CDCl_3$) δ 1.25–1.70 (m, 6 H), 2.05–2.14 (m, 2 H), 2.35–2.44 (m, 2 H), 2.37 (s, 3 H), 2.81 (t, J=5.9 Hz, 2 H), 3.19 (s, 2 H), 3.80 (s, 2 H), 4.21 (t, J=5.9 Hz, 2 H), 6.54 (d, J=8.0 Hz, 1 H), 6.90–6.99 (m, 3 H), 7.08–7.13 (m, 1 H), 7.20 (d, J=7.4 Hz, 1 H), 7.32 (d, J=8.0 Hz, 2 H); $^{13}C$ NMR (75 MHz, $CDCl_3$) δ 22.2, 25.6, 34.0, 38.6, 45.0, 58.4, 63.0, 64.4, 69.0, 118.2, 122.0, 124.0, 124.2, 128.0, 128.8, 129.4, 130.9, 137.8, 142.7, 172.2.

2h. 2-(Methyl{[(nitrosothio)cyclohexyl]methyl}amino)ethyl-2-{2-[(2,6-dichlorophenyl) amino]phenyl}acetate hydrochloride HCl in ether was added dropwise to a solution of the product of Example 2 g (1.8 g) in dry ether (30 ml) to form an insoluble green sticky product. The ether was evaporated under reduced pressure to give a green foam which was triturated with hexane (25 ml) to afford a green color suspension. The hexane was evaporated under reduced pressure and material was dried in a vacuo for 12 hours to give the title compound (1.86 g) as a green powder. mp. 105–107° C. dec; $^1$H NMR (300 MHz, CDCl$_3$) δ 1.50–1.90 (m, 6 H), 2.52 (bs, 2 H), 2.88 (s, 3 H), 3.35–3.52 (m, 2 H), 3.80–4.20 (m, 2 H), 3.82 (s, 2 H), 4.72 (bs, 2 H), 6.52 (d, J=7.6 Hz, 2 H), 6.92 (t, J=7.3 Hz, 1 H), 7.01 (t, J=7.7 Hz, 1 H), 7.09–7.22 (m, 2 H), 7.34 (d, J=8.0 Hz, 2 H), 12.61 (bs, 1 H); Anal. Calcd for C$_{24}$H$_{30}$N$_3$O$_3$SlCl$_3$: C, 52.89; H, 5.58; N, 7.76; S, 5.86 Found: C, 53.48; H,6.04; N, 6.55; S, 6.35.

Example 3

2-(Methyl{[(nitrosothio)cyclohexyl]methyl}amino) ethyl (2S)-2-(6-methoxy(2-naphthyl))propanoate hydrochloride 3a. 2-{Methyl[(sulfanylcyclohexyl)methyl]amino}ethyl (2S)-2-(6-methoxy(2-naphthyl))propanoate Dicyclohexylcarbodimide (1.26 g, 20.28 mmol) was added to a stirred solution of the product of Example 2d (1.0 g, 4.91 mmol), (S)-6-methoxy-α-methyl-2-naphthaleneacetic acid (1.41 g, 6.14 mmol) and dimethylaminopyridine (0.3 g, 2.45 mmol) in dry CH$_2$Cl$_2$ (150 ml). The suspension was then stirred at room temperature for 3 hours. The precipitate was filtered and washed with CH$_2$Cl$_2$ (2×50 ml). The filtrate was concentrated. The crude material was chromatographed on silica gel eluting with 10% ethyl acetate in hexane to give the title compound (1.2 g, 59%). TLC R$_f$=0.34 (hexane/ethylacetate, 9:1; KMNO$_4$ brown); $^1$H NMR (300 MHz, CDCl$_3$) δ 1.05–1.70 (m, 10 H), 1.59 (d, J=7.1 Hz, 3 H), 2.05 (bs, 1 H), 2.33 (s, 3 H), 2.43 (s, 2 H), 2.77 (t, J=5.7 Hz, 2 H), 3.82–3.95 (m, 1 H), 3.90 (s, 3 H), 4.11–4.24 (m, 2 H), 7.11–7.15 (m, 2 H), 7.41 (d, J=8.4 Hz, 1 H), 7.67–7.71 (m, 3 H); $^{13}$C NMR (75 MHz, CDCl$_3$) δ 18.46, 22.32, 25.93, 37.59, 45.05, 45.45, 52.19, 55.20, 58.33, 62.71, 72.00, 105.51, 118.87, 125.91, 126.17, 127.07, 128.86, 129.19, 133.63, 135.57, 157.54, 174.55

3b. 2-{Methyl[(sulfanylcyclohexyl)methyl]amino}ethyl (2S)-2-(6-methoxy(2-naphthyl))propanoate hydrochloride HCl in ether was added dropwise to a solution of the product of Example 3a (1.2 g) in dry ether (20 ml) to form an insoluble white sticky product. The ether was evaporated under reduced pressure to give a white foam which was triturated with hexane (25 ml) to afford a white suspension. The hexane was evaporated under reduced pressure and the material was dried in vacuo for 12 hours to give the title compound (1.28 g) as a white powder; $^1$H NMR (300 MHz, CDCl$_3$) δ 0.94–1.80 (m, 10 H), 1.58 (d, J=7.1 Hz, 3 H), 2.73 (dd, J=4.5, 12.0 Hz, 3 H), 2.98 (t, J=12.1 Hz, 3 H), 3.25–3.26 (m, 2 H), 3.90–4.00 (m, 1 H), 3.90 (s, 3 H), 4.40–4.80 (m, 2 H), 7.08–7.18 (m, 2 H), 7.30–7.37 (m, 1 H), 7.60–7.80 (m, 3 H).

3c. 2-(Methyl{[(nitrosothio)cyclohexyl]methyl}amino) ethyl(2S)-2-(6-methoxy(2-naphthyl))propanoate Tert-butyl nitrite (0.46 g, 4.42 mmol) was added to a stirred solution of the product of Example 3b (0.82 g, 1.81 mmol) in CH$_2$Cl$_2$ (10 ml) at room temperature under nitrogen and allowed to stir 30 minutes at room temperature. The solvent was evaporated under reduced pressure to give a green foam which was dissolved in ethyl acetate (25 ml) and washed with saturated K$_2$CO$_3$ (10 ml) and then with water (25 ml). The organic layer was dried over Na$_2$SO$_4$ and concentrated under reduced pressure to give a green viscous oil. The crude product was purified by flash chromatography on silica gel eluting with 10% ethyl acetate in hexane to afford the title compound (0.774 g, 96%) as a green colored viscous oil. TLC R$_f$=0.34 (hexane/ethylacetate, 9:1; green); $^1$H NMR (300 MHz, CDCl$_3$) δ 1.25–1.66 (m, 6 H), 1.55 (d, J=7.1 Hz, 3 H), 2.05–2.14 (m, 2H), 1.92–2.02 (m, 2 H), 2.25–2.35 (m, 2 H), 2.27 (s, 3 H), 2.70 (t, J=5.8 Hz, 2 H), 3.06 (dd, J=14.6, 17.19 Hz, 2 H), 3.78–3.90 (m, 1 H), 3.85 (s, 3 H), 4.07–4.16 (m, 2 H), 7.05–7.13 (m, 2 H), 7.37 (dd, J=1.6, 8.4 Hz, 1 H), 7.63–7.68 (m, 3 H); $^{13}$C NMR (75 MHz, CDCl$_3$) δ 18.4, 22.0, 25.4, 32.4, 44.7, 45.3, 55.0, 58.0, 62.4, 64.3, 68.5, 105.4, 118.8, 125.8, 126.0, 127.0, 128.8, 129.1, 133.6, 135.8, 157.5, 174.4.

3d. 2-(Methyl{[(nitrosothio)cyclohexyl]methyl}amino) ethyl(2S)-2-(6-methoxy(2-naphthyl))propanoate hydrochloride HCl in ether was added dropwise to a solution of the product of Example 3c (0.4 g) in a mixture of dry ether (9 ml) and CH$_2$Cl$_2$ (1 ml) to form a insoluble green suspension. The solvent was evaporated under reduced pressure to give green foam which was triturated with hexane (10 ml) to afford a green color precipitate. The hexane was evaporated under reduced pressure and the material was dried in vacuo for 12 hours to give the title compound (0.403 g) as a green powder. mp. 85–88° C., 110° C. dec; $^1$H NMR (300 MHz, CDCl$_3$) δ 1.17–1.81 (m, 6 H), 1.54 (d, J=7.1, 3 H), 2.02–2.82 (m, 4 H), 2.66 (s, 3 H), 3.31–4.00 (bm, 5 H), 3.90 (s, 3 H), 4.52–4.63 (bm, 2 H), 7.07–7.15 (m, 2 H), 7.25–7.33 (m, 1 H), 7.56–7.66 (m, 3 H), 12.04 (bs, 1 H).

Example 4

3-{Methyl{[(nitrosothio)cyclohexyl]methyl}amino) propyl 2-{2-[(2,6-dichlorophenyl)amino] phenyl}acetate 4a. 3-[({[({[(3-Hydroxypropyl)methylamino] methyl}cyclohexyl)disulfanyl]cyclohexyl}methyl) methylamino]propan-1-ol Propanolamine (15.7 g, 209 mnnol) in methanol (50 mL) was added to a stirred suspension of the product of Example 2a (30 g, 105 mmol) in methanol (150 mL) at room temperature. The reactants gradually dissolved to form a light brown solution over 45 min. The reaction was monitored by TLC and showed complete consumption of the starting material. Sodium borohydride (4 g, 105 mmol) was added portionwise over 10 min and the reaction mixture was stirred at room temperature for 1 hour. 38% formaldehyde (120 mL) was added and the resulting cloudy solution was stirred for 2 hours at room temperature. The flask was placed in a freezer (–20° C.) for 12 hours. The clear solution was decanted leaving a gummy precipitate. The residue was vigorously shaken with methanol (50 mL) to produce a solid. The solid was filtered, washed with methanol (50 mL), and dried in vacuo to give the title compound (34 g, 75.7%) as a white powder. mp. 65–66° C.; $^1$H-NMR (300 MHz, CDCl$_3$) 61.20–1.80 (mult, 24 H), 2.92 (s, 4 H), 3.06 (t, J=5.3 Hz, 4 H), 3.93 (t, J=5.2 Hz, 4 H), 4.39 (s, 2 H); $^{13}$C-NMR (75 MHz, CDCl$_3$) δ 22.1, 22.7, 25.6, 32.3, 52.6, 55.8, 60.9, 67.7, 86.9; Anal. Calcd for C$_{22}$H$_{40}$N$_2$O$_2$S$_2$: C, 61.64; H, 9.40; N, 6.53; S, 14.96. Found: C, 61.70; H, 9.62; N, 6.38; S, 14.64.

4b. 3-{Methyl[(sulfanylcyclohexyl)methyl]amino}propan-1-ol

To a stirred solution of lithium aluminum hydride (18 mL @ 1 M, 18 mmol) was added the product of Example 4a (5.00 g, 11.66 mmol) in THF (25 mL) dropwise at room temperature under nitrogen. The resulting clear solution was stirred at room temperature for 3 hours. The excess LiAlH$_4$ was destroyed by dropwise addition of water (1 mL). Ethyl acetate (100 mL) was added and the precipitate was filtered. The white precipitate was washed with 10% methanol in CH$_2$Cl$_2$ (2×50 mL). The combined filtrate was dried over Na$_2$SO$_4$ and concentrated under reduced pressure to give the title compound (4.9 g, 97%) as a viscous liquid. $^1$H-NMR (300 MHz, CDCl$_3$) d: 1.11–1.78 (mult, 12 H), 2.33 (s, 3 H), 2.46 (s, 2 H), 2.69 (t, J=6.3 Hz, 2 H), 3.75 (t, J=5.1 Hz, 2 H), $^{13}$C-NMR (75 MHz, CDCl$_3$) δ 22.1, 25.8, 37.8, 44.5, 51.5, 60.4, 63.5, 73.34.

4c. 3-{Methyl{[(nitrosothio)cyclohexyl]methyl}amino) propan-1-ol

HCl in ether was added dropwise to a solution of the product of Example 4b (4.9 g, free base) in dry ether (50 mL) to form an insoluble gummy material. The ether was decanted and residue was washed with ether (2×50 mL) and dried in vacuo for 12 hours to give a gummy solid (4.8 g). This solid was taken up in CH$_2$Cl$_2$ (50 mL) and added dropwise to a stirred solution of t-BuONO (2.43 g, 23.6 mmol) in CH$_2$Cl$_2$ (10 mL) at room temperature. The resulting green solution was stirred for 30 min at room temperature. The reaction mixture was washed with satd K$_2$CO$_3$ (10 mL) and then with water (50 mL). The organic layer was dried over Na$_2$SO$_4$ and concentrated under reduced pressure to give (4.2 g, 87%) of the title compound as a green viscous oil. TLC R$_f$=0.23 (Hexane/ethyl acetate, 1:1; green); $^1$H-NMR (300 MHz, CDCl$_3$) 81.45–1.80 (mult, 8 H), 2.09 (dd, J=11.0 and 13.6 Hz, 2H), 2.38 (s, 3 H), 2.53 (d, J=14 Hz, 2 H), 2.74 (t, J=5.8 Hz, 2H), 3.24 (s, 2 H), 3.77 (t, J=5.2 Hz, 2 H), $^{13}$C-NMR (75 MHz, CDCl$_3$) δ 21.9, 25.3, 28.7, 34.3, 44.2, 60.1, 63.1, 63.7, 69.7.

4d. 3-{Methyl{[(nitrosothio)cyclohexyl]methyl}amino) propyl 2-{2-[(2,6-dichlorophenyl)amino]phenyl}acetate Dicyclohexylcarbodiimide (4.4 g, 21.46 mmol) in CH$_2$Cl$_2$ (30 mL) was added dropwise over 15 min to a stirred solution of the product of Example 4c (4.2 g, 17.04 mmol), diclofenac (5.30 g, 17.89 mmol), and DMAP (0.15 g) in dry CH$_2$Cl$_2$ (30 mL) at 0° C. The suspension was then stirred at 0° C. for 30 min. The precipitate was filtered and washed with CH$_2$Cl$_2$ (25 mL). The filtrate was concentrated at 40° C. Hexane (100 mL) was added and the precipitate was filtered. The filtrate was concentrated under reduced pressure to give a green oil. The oil was dissolved in ethyl acetate (10 mL) and methanol (40 mL) was added. The solution was filtered and the filtrate was heated gently at 40° C. for 2 min and then left at −20° C. overnight (12 hours). The green crystals which formed were filtered and dried in vacuo pump for 6 hours to give (8.4 g, 94%) the title compound as green crystals. mp. 58–60° C.; TLC R$_f$=0.46 (Hexane/ethyl acetate, 9:1). $^1$H-NMR (300 MHz, CDCl$_3$) δ 1.40–1.77 (mult, 6H), 1.84 (p, J=6.8 Hz, 2 H), 2.08–2.18 (mult, 2 H), 2.35 (s, 3 H), 2.47 (d, J=13.9 Hz, 2 H), 2.58 (t, J=7.1 Hz, 2 H), 3.16 (s, 2 H), 3.85 (s, 2 H), 4.22 (t, J=6.4 Hz, 2 H), 6.61 (d, J=7.9 Hz, 1 H), 6.97–7.05 (mult, 3 H), 7.16 (t, J=5.0 Hz, 1 H), 7.28 (d, J=7.4 Hz, 1 H), 7.38 (d, J=8.0 Hz, 2 H); $^3$C-NMR (75 MHz, CDCl$_3$) δ 22.2, 25.5, 26.7, 34.2, 38.6, 44.5, 56.5, 63.2, 64.4, 68.9, 118.2, 121.9, 123.9, 124.3, 127.8, 128.8, 129.4, 130.8, 137.8, 142.7, 172.3. Anal. Calcd for C$_{25}$H$_{31}$N$_3$O$_3$S$_1$Cl$_2$: C, 57.25; H, 5.96; N, 8.01; S, 6.11; Cl, 13.52. Found: C, 57.42; H, 5.99; N, 7.73; S, 5.91; Cl, 13.20.

Example 5

4-({Methyl[2-methyl-2-(nitrosothio)propyl]amino}methyl)phenyl(2S)-2-(6-methoxy(2-naphthyl))propanoate hydrochloride 5a. 4-{[(2-Methyl-2-sulfanylpropyl)amino]methyl}phenol To a hot solution of 4-hydroxybenzaldehyde (8.90 g, 72.8 mmol) in CHCl$_3$ (250 mL) were added 1-amino-2-methyl-2-propanethiol hydrochloride (10.32 g, 72.8 mmol), K$_2$CO$_3$ (20.2 g, 146 mmol), and MgSO$_4$ (5 g). The mixture was stirred and refluxed under nitrogen atmosphere for 3 hours. After cooling, the mixture was filtered to remove inorganic solid, and the filter cake was washed through with MeOH (2×100 mL). Evaporation of the filtrate afforded the product 5a as a white solid (15 g, 98%). mp 85–87° C.; $^1$H NMR (CDCl$_3$, 300 MHz) δ 7.38 (d, J=8.5 Hz, 2H), 6.76 (d, J=8.5 Hz, 2H), 574 (s, 1 H), 3.25 (d, J=12.1 Hz, 1 H), 3.01 (d, J=12.1 Hz, 1 H), 1.59 (s, 3H), 1.58 (s, 3H).

5b. N-[(4-Hydroxyphenyl)methyl]methoxy-N-(2-methyl-2-sulfanylpropyl) carboxamide To a suspension of the product of Example 5a (700 mg, 3.35 mmol) in THF (80 mL) was added methyl choroformate (518 mL, 6.70 mmol), and solid NaHCO$_3$ (588 mg, 7.0 mmol). The mixture was stirred at ambient temperature for 2 hours at which time the reactants were completely consumed. The inorganic solid was removed from the mixture by filtration, and the filtrate was evaporated. The resulting crude product was purified by flash chromatography on silica gel, eluting with Hex:EtOAc 1:4 to yield the title compound (877 mg, 98%) as white snowflakes. mp 51° C.; $^1$H NMR (CDCl$_3$, 300 MHz) δ 7.49 (br, 1H), 7.19 (br, 2H), 6.70 (br, 2H), 6.14 (s, 1H), 4.1–4.0 (br, 1H), 3.66 (s, 3H), 3.58–3.53 (m, 1H), 1.47 (s, 3H), 1.46 (s, 3H).

5c. 4-{[Methyl(2-methyl-2-sulfanylpropyl)amino]methyl}phenol

To a stirred solution of the product of Example 5b (5.00 g, 18.7 mmol) in THF (150 mL) was added lithium aluminum hydride (37.4 mL @ 1 M, 37.4 mmol) in a dropwise fashion. After the addition, the reaction mixture was heated to reflux overnight. Upon cooling, the mixture was poured onto ice, and extracted with ethyl acetate (2×150 mL). The organic layers were dried over Na$_2$SO$_4$, filtered, and evaporated to afford the title compound (3.44 g, 83%) as a colorless oil. $^1$H NMR (CDCl$_3$, 300 MHz) δ 7.20 (d, J=8.4 Hz, 2H), 6.78 (d, J=8.4 Hz, 2H), 5.30 (br, 1H), 3.60 (s, 2H), 2.54 (s, 2H), 2.28 (s, 3H), 2.05 (s, 1H), 1.35 (s, 6H); $^{13}$C NMR (CDCl$_3$, 75 MHz) δ 154.8, 130.5, 129.8, 115.0, 70.5, 63.5, 46.2, 44.2, 30.2.

5d. 4-{[Methyl(2-methyl-2-sulfanylpropyl)amino]methyl}phenyl(2S)-2-(6-methoxy(2-naphthyl))propanoate To a stirred solution of the product of Example 5c (1.92 g, 7.18 mmol), (S)-6-Methoxy-a-methyl-2-naphthaleneacetic acid (1.65 g, 7.18 mmol), and DMAP (0.88 g, 7.18 mmol) in CH$_2$Cl$_2$ (80 mL) was added dicyclohexylcarbodiimide (1.48 g, 7.18 mmol). The reaction mixture was stirred at room temperature under nitrogen for 2 hours. The white solid formed during the reaction was removed by filtration, and the filtrate was concentrated in vacuo. The residue was purified by column chromatography on silica gel eluting with ethyl acetate:hexane 1:5 to furnish the title compound (2.90 g, 90%) as a glassy solid. 1H NMR (CDCl$_3$, 300 MHz) δ 7.72–6.91 (m, 10H), 4.02 (q, J=7.1 Hz, 1H), 3.74 (s, 3H), 3.51 (s, 2H), 2.42 (s, 2H), 2.16 (s, 3H), 2.06 (s, 1H), 1.63 (d, J=7.1 Hz, 3H), 1.26 (s, 6H); $^{13}$C NMR (CDCl$_3$, 75 MHz) δ 172.7, 157.3, 149.3, 137.0, 134.8, 133.4, 129.0, 128.9, 128.5, 127.0, 125.7, 125.7, 120.7, 118.7, 105.2, 70.8, 63.4, 54.8, 46.1, 45.1, 44.2, 30.0, 18.2.

5e. 4-({Methyl[2-methyl-2-(nitrosothio)propyl]amino}methyl)phenyl(2S)-2-(6-methoxy(2-naphthyl))propanoate hydrochloride The HCl salt of the product of Example 5d was prepared by treating the compound with HCl in Et$_2$O. To a stirred solution of the salt (1.34 g, 2.82 mmol) in CH$_2$Cl$_2$ (40 mL) was added t-BuONO (tech. 90%, 0.391 mL, 2.96 mmol).

The reaction mixture was stirred at ambient temperature for 15 min before being evaporated to dryness. The resulting green hydrochloride salt was converted into the free base by partitioning between ethyl acetate and 1M aq. $K_2CO_3$. The organic layer was washed with water, dried over $Na_2SO_4$, and evaporated. The residue was purified by flash chromatography on silica gel eluting with ethyl acetate:hexane 1:4. The purified free base was reconverted into its hydrochloride salt by treating with HCl-$Et_2O$. The HCl salt was triturated with hexane to give the title compound (1.18 g, 83%) as a green amorphous solid. $^1$H NMR (CDCl$_3$, 300 MHz) δ 7.75–6.90 (m, 10H), 4.07 (q, J=7.1 Hz, 1H), 3.89 (s, 3H), 3.59 (s, 2H), 3.11 (s, 2H), 2.23 (s, 3H), 1.85 (s, 6H), 1.67 (d, J=7.1 Hz, 3H); $^{13}$C NMR (CDCl$_3$, 75 MHz) δ 172.8, 157.3, 149.4, 134.8, 133.4, 129.1, 128.9, 128.6, 127.0, 125.5, 120.9, 120.8, 118.8, 105.2, 67.8, 63.4, 58.6, 55.0, 45.2, 44.3, 26.8, 25.9, 18.2.

Example 6

2-[4-(Nitrosothio)-4-piperdyl]ethyl 2-{2-[(2,6-dichlorophenyl)amino]phenyl}acetate hydrochloride 6a. Ethyl 2-{1-[(tert-butyl)oxycarbonyl]-4-piperidene}acetate A solution of triethylphosphonoacetate (8.9 mL, 45 mmol) in THF (50 mL) was cooled to −78° C. n-BuLi (18 mL @ 2.5 m, 45 mmol) was added in a rapid dropwise fashion and the mixture was stirred for 30 min. t-Butyl 4-oxo-1-piperidinecarboxylate (9 g, 45 mmol) in THF (50 mL) was added and the mixture was kept at −78° C. for 1 hour. The cold bath was removed and the reaction continued to stir for 2 hours. The reaction was diluted with $Et_2O$ (100 mL) and washed with NaHCO$_3$ (1×50 mL). The aqueous layer was back extracted with $Et_2O$ (50 mL). The combined organic phases were washed with $H_2O$ (1×30 mL), brine (1×50 mL), and dried over Na$_2$SO$_4$. Evaporation of solvent left the title compound (12 g, 99%) which crystallized on standing. mp 84–85° C. $^1$H NMR (300 MHz, CDCl$_3$) δ 5.69 (s, 1 H), 4.14 (q, J=7.1 Hz, 2 H), 3.44–3.50 (mult, 4 H), 2.92 (t, J=5.7 Hz, 2 H), 2.26 (t, J=5.8 Hz, 2 H), 1.46 (s, 9 H), 1.26 (t, J=7.1 Hz, 3 H). Anal Calcd for C$_{14}$H$_{23}$NO$_4$: C, 62.43; H, 8.61; N, 5.20. Found C, 61.92; H, 8.36; N, 5.89.

6b. Ethyl 2-{1-[(tert-butyl)oxycarbonyl]-4-(phenylmethylthio)-4-piperdyl}acetate The product of Example 6a (12 g, 45 mmol) and benzyl mercaptan (5.3 mL, 45 mmol) were dissolved in piperidine (20 mL) and heated to reflux for 5 hours. Toluene (100 mL) was added and the solvent was then removed under reduced pressure to leave a thick syrup. The residue was dissolved in $Et_2O$ (200 mL) and washed with 1 N HCl (1×50 mL), 0.5 N NaOH (1×50 mL), brine (1×50 mL), and dried over Na$_2$SO$_4$. Evaporation of the solvent afforded the title compound (18 g, 100%) as an oil. $^1$H NMR (300 MHz, CDCl$_3$) δ 7.23–7.32 (mult, 5 H), 4.14 (q, J=7.1 Hz, 2 H), 3.72 (s, 2 H), 3.70–3.80 mult, 2 h), 3.30 (t, J=12 Hz, 2 H), 2.65 (s, 2 H), 1.70–1.90 (mult, 4 H), 1.46 (s, 9 H), 1.26 (t, J=7.1 Hz, 3 H); $^{13}$C NMR (75 MHz, d$_6$-DMSO) δ 169.6, 153.8, 137.6, 128.9, 128.3, 126.8, 78.5, 59.7, 46.8, 44.9, 41.8, 34.4, 30.9, 14.0.

6c. tert-Butyl 4-(2-hydroxyethyl)-4-(phenylmethylthio)piperdinecarboxylate

The product of Example 6b (1 g, 2.5 mmol) in THF (10 mL) was cooled to 0° C. Dibal-H (5.5 mL @ 1 M, 5.5 mmol) was added and the reaction was stirred for 30 minutes. The cold bath was removed and the mixture stirred until the reaction was complete as determined by TLC. The reaction mixture was cooled to 0° C., 1 N HCl was added dropwise until the reaction become gelatinous, whereupon 1 N HCl was added more rapidly until the gel dissolved. The mixture was transferred to a separatory funnel with $Et_2O$ 1 N HCl was added as needed to obtain 2 homogeneous layers. The layers were separated, the aqueous layer was extracted with $Et_2O$ (2×10 mL). The combined organic layers were washed with 1 N HCl (1×10 mL), brine (1×10 mL), and dried over Na$_2$SO$_4$. Evaporation of the solvent and chromatography of the residue on silica gel eluting with hexane:ethyl acetate 1:1 gave the title compound (340 mg, 40%) as an oil. $^1$H NMR (300 MHz, CDCl$_3$) δ 7.23–7.32 (mult, 5 H), 3.76 (mult, 2 H), 3.69–3.76 (mult, 2 H), 3.69 (s, 2 H), 3.32 (t, J=11 Hz, 2 H), 2.20 (brs, 1 H), 1.88 (t, J=6.4 Hz, 2 H), 1.76 (d, J=14 Hz, 2 H), 1.52–1.61 (mult, 2 H), 1.46 (s, 9 H); $^{13}$C NMR (75 MHz, CDCl$_3$) δ 154.5, 137.3, 128.7, 128.3, 126.9, 79.3, 58.4, 47.7, 42.2, 39.0, 35.3, 31.5, 28.2.

6d. tert-Butyl 4-(2-hydroxyethyl)-4-sulfanylpiperdinecarboxylate

Ammonia (20 mL) was condensed into a 3-neck flask fitted with a dry ice condenser. The product of Example 4c (340 mg, 1 mmol) was added in ETOH (4 mL) followed by metallic sodium (76 mg, 3.3 mmol) until the blue color persisted. A small amount of NH$_4$Cl was added to discharge the blue color and the ammonia was allowed to evaporate under a stream of nitrogen. The residue was partitioned between $Et_2O$ and 1 N HCl. The aqueous layer was extracted with $Et_2O$ (1×20 mL). The combined organic layers were washed with brine (1×10 mL) and dried over Na$_2$SO$_4$. Evaporation of the solvent gave the title compound (210 mg, 80%) as an oil. $^1$H NMR (300 MHz, CDCl$_3$) δ 3.95 (t, J=6.7 Hz, 2 H), 3.80–3.90 (mult, 2 H), 3.20–3.35 (mult, 2 H), 1.95 (t, J=6.7 Hz, 2 H), 1.60–1.80 (mult, 4 H), 1.46 (s, 9 H).

6e. tert-Butyl 4-(2-hydroxyethyl)-4-(nitrosothio)piperdinecarboxylate

The product of Example 6d (2.5 g, 9.5 mmol) was dissolved in CH$_2$Cl$_2$ (50 mL) and cooled to 10° C. t-Butyl nitrite was added with continued stirring for 30 min. The solvent was evaporated and the green residue was chromatographed on silica gel eluting with hexane:ethyl acetate 1:1. This gave the title compound (1 g, 35%) as a green oil. $^1$H NMR (300 MHz, CDCl$_3$) δ 3.83 (d, J=12 Hz, 2H), 3.71 (t, J=6. Hz, 2 H), 2.99–3.12 (mult, 3 H), 2.40–2.50 (mult, 4 H), 2.06–2.16 (mult, 2 H), 1.36 (s, 9 H).

6f. 2-{1-[(tert-butyl)oxycarbonyl]-4-(nitrosothio)-4-piperdyl}ethyl 2-{2-[(2,6-dichlorophenyl)amino]phenyl}acetate To the product of Example 6e (1 g, 3.4 mmol) and (2-((2,6-dichlorophenyl)-amino)benzene)acetic acid (1.1 g, 3.4 mmol) in CH$_2$Cl$_2$ (10 mL) was added a mixture of dicyclohexylcarbodiimide (0.77 g, 4 mmol) and DMAP (10 mg, 0.08 mmol) in CH$_2$Cl$_2$ (10 mL). The mixture was allowed to stir at room temperature for 2 hours. The precipitate was removed by filtration and the filtrate was concentrated. The residue was chromatographed on silica gel eluting with hexane:ethyl acetate 4:1 to give the title compound (1.4 g, 72%) as a green oil. $^1$H NMR (300 MHz, CDCl$_3$) δ 7.33 (d, J=8 Hz, 2 H), 7.19 (d, J=7.4 Hz, 1H), 7.12 (t, J=7.5 Hz, 1 H), 6.92–6.99 (mult, 2 H), 6.78 (s, 1 H), 6.54 (d, J=7.9 Hz, 1 H), 4.36 (t, J=6.7 Hz, 2 H), 3.90 (brs, 2 H), 3.77 (s, 2 H), 2.69 (t, J=6.7 Hz, 2 H), 2.44 (t, J=15 Hz, 2 H), 2.05–2.15 (mult, 2 H), 1.47 (s, 9 H).

6g. 2-[4-(Nitrosothio)-4-piperdyl]ethyl 2-{2-[(2,6-dichlorophenyl)amino]phenyl}acetate hydrochloride The product of Example 6f was dissolved in a mixture of CH$_2$Cl$_2$ (2 mL) and $Et_2O$ (2 mL) saturated with HCl and then allowed to stand at room temperature for 1.5 hours. Addition of $Et_2O$ caused precipitation of a green material. The supernatant was discarded. The residue was dissolved in CH$_2$Cl$_2$ and precipitated with Et$_2$O. This was repeated 2 more times. The residue was then dried in vacuo to give product 6 g (0.95 g, 82%) as a green foam. $^1$H NMR (300 MHz, d6-DMSO) δ 9.25 (brs, 1 H), 7.52 (d, J=8 Hz, 2 H), 7.15–7.23 (mult, 2 H), 7.01–7.08 (mult, 2 H), 6.84 (t, J=7.4 Hz, 1 H), 6.23 (d, J=7.9 Hz, 1 H), 4.26 (t, J=6.5 Hz, 2 H), 3.77 (brs, 2 H), 2.93 (t, J=9 Hz, 2 H), 2.59–2.69 (mult, 2 H), 2.49–2.51 (mult, 4 H). Mass spectrum (API-ES) MH$^+$=468 Anal Cacld for C$_{21}$H$_{24}$Cl$_3$N$_3$O$_3$S: C, 49.96; H, 4.79; N, 8.32. Found: C, 48.98; H, 5.06; N, 7.99.

Example 7

2-[2-(2-{2-[(2,6-Dichlorophenyl)amino] phenyl}acetoxy)ethoxy]ethyl 3-(N-{[(nitrosothio) cyclohexyl]methyl}-N-benzylcarbamoyl)propanoate 7a. di{[Benzylamino]methyl}cyclohexyl disulfide The product of Example 2a (12.0 g, 41.89 mmol) and benzylamine (8.98 g, 83.8 mmol) in CHCl$_3$ (150 mL) were heated at reflux for 3 hours. After cooling to room temperature the solvent was evaporated using a rotary evaporator. The residue was dissolved in MeOH (150 mL) and NaBH$_4$ (3.17 g, 83.8 mmol) was added portionwise. After 1 h, the solvent was evaporated and the residue was partitioned between water (200 mL) and EtOAc (100 mL). The organic phase was separated and the aqueous phase was extracted with EtOAc (2×100 mL). The combined organic phases were dried over Na$_2$SO$_4$ and evaporated to give the title compound. $^1$H NMR (300 MHz, CDCl$_3$) δ 1.30–1.74 (mult, 20 H), 2.59 (s, 4 H), 3.45 (s, 2 H), 3.79 (s, 4 H), 7.22–7.32 (mult, 10 H); $^{13}$C NMR (75 MHz, CDCl$_3$) δ 22.23, 25.80, 34.36, 54.01, 54.63, 56.42, 126.78, 128.00, 128.25, 140.50.

7b. 1-{[Benzylamino]methyl}cyclohexane-1-thiol

The product of Example 7a was dissolved in THF (100 mL) and LiAlH$_4$ in THF (50 mL @ 1M, 50 mmol) was added. After stirring at room temperature for 2 hours the reaction was quenched using the following protocol, water (1.9 mL), 15% sodium hydroxide (1.9 mL) and water (5.8 mL). The precipitate was removed by filtration and the solvent was evaporated. The residue was purified by flash chromatography (SiO$_2$, 1:5 to 1:1 Et$_2$O/hexane) to give the title compound (11.05 g, 56%, 2 steps) and unreacted starting material (7.94 g, 40%). $^1$H NMR (300 MHz, CDCl$_3$) δ 1.20–1.75 (mult, 10 H), 2.64 (s, 2 H), 3.84 (s, 2 H), 7.04–7.33 (mult, 5 H); $^{13}$C NMR (75 MHz, CDCl$_3$) δ 22.23, 26.02, 38.08, 50.62, 54.15, 62.04, 126.78, 127.88, 128.26, 140.54.

7c. 3-(N-{[(Nitrosothio)cyclohexyl]methyl}-N-benzylcarbamoyl)propanoic acid

An ice-cooled solution of the product of 7b (2.98 g, 12.66 mmol) in CH$_2$Cl$_2$ (50 mL) and succinic anhydride (1.2 g, 12.6 mmol) was stirred at room temperature for 2 hours. The reaction was diluted with CH$_2$Cl$_2$ (50 mL) and washed with 2 N hydrogen chloride (50 mL) and brine (50 mL). The CH$_2$Cl$_2$ solution was dried over Na$_2$SO$_4$ and evaporated. The residue was taken up in CH$_2$Cl$_2$ (100 mL) To this solution was added t-BuONO (1.53 ml, 13.09 mmol). After 2 h, the solution was washed with brine and dried over Na$_2$SO$_4$. Evaporation of the solvent under reduced pressure gave the crude product which was triturated with EtOAc/hexane to afford the title compound (4.30 g, 93.2% over two steps) as a green solid. mp. 93–95° C. $^1$H NMR (300 MHz, CDCl$_3$) δ 1.43–1.73 (mult, 6 H), 2.13 (t, J=11 Hz, 2 H), 2.51 (d, J=14.2 Hz, 2H), 2.59–2.75 (mult, 4H), 4.08 and 4.24 (2 s, 2 H), 4.56 and 4.81 (2 s, 2 H), 7.04 and 7.12 (2 d, J=7.1 Hz, 2 H), 7.23–7.35 (mult, 3 H); $^{13}$C NMR (75 MHz, CDCl$_3$) δ 21.9, 25.3, 28.3, 29.3, 34.9, 53.4, 56.5, 64.1, 125.9, 127.7, 129.0, 136.1, 174.0, 177.9; mass spectrum (API-ES), m/z): 366 (M++1); Anal. Calcd for C$_{18}$H$_{24}$N$_2$O$_4$S: C, 59.32; H, 6.64; N, 7.69; S, 8.80. Found: C, 59.56; H, 6.83; N, 7.57; S, 8.77.

7d. 2-(2-Hydroxyethoxy)ethyl 2-{2-[(2,6-dichlorophenyl) amino]phenyl}acetate 1,1'-Carbonyldiimidazole (1.37 g, 6.75 mmol) was added portionwise to a stirred suspension of 2-[(2,6-dichlorophenyl)amino]benzeneacetic acid (2.0 g, 6.7 mmol) in dry CHCl$_3$ at room temperature. The resulting clear solution was stirred at room temperature for 30 min. Di(ethyleneglycol) (2.30 g, 22.3 mmol) in CHCl$_3$ (10 mL) was added and the solution was stirred at room temperature for 6 hours. The CHCl$_3$ was evaporated under reduced pressure and the crude material was flash chromatographed on silica gel eluting with ethyl acetate/hexane (1:2) to give the title compound (2.1 g, 81%) as a clear oil. TLC R$_f$=0.33 (EtOAc:Hex, 1:2); $^1$H NMR (300 MHz, CDCl$_3$) δ 2.71 (brs, 1 H), 3.44 (mult, 2 H), 3.57–3.63 (mult, 4 H), 3.76 (s, 2 H), 4.23 (t, J=4.8 Hz, 2 H), 6.46 (d, J=8.0 Hz, 1 H), 6.80–7.01 (mult, 1 H), 7.03 (mult, 1 H), 7.15 (dd, J=1.4 and 7.4 Hz, 2 H), 7.24 (d, J=8.0 Hz, 2 H); $^{13}$C NMR (75 MHz, CDCl$_3$) δ 38.4, 61.6, 64.2, 68.8, 72.3, 118.1, 121.9, 124.0, 127.9, 128.8, 129.4, 130.8, 137.6, 142.6, 172.3; mass spectrum (API-ES), m/z 384 (MH$^+$).

7e. 2-[2-(2-{2-[(2,6-Dichlorophenyl)amino] phenyl}acetoxy)ethoxy]ethyl 3-(N-{[(nitrosothio) cyclohexyl]methyl}-N-benzylcarbamoyl)propanoate To the product of Example 7c (0.41 g, 1.1 mmol), Example 7d (0.43 g, 1.1 mmol), and DMAP (0.025 g) in CH$_2$Cl$_2$ (10 mL) at room temperature was added dicyclohexylcarbodiimide (0.28 g, 1.3 mmol). The resulting suspension was stirred at room temperature for 1 hour. The precipitate was filtered and washed with CH$_2$Cl$_2$ (25 mL). The filtrate was concentrated and crude material was chromatographed on silica gel eluting with ethyl acetate/hexane (1:9) to give the title compound (0.55 g, 67%) as a green oil. TLC R$_f$=0.48, (EtOAc:Hex, 1:2); $^1$H NMR (300 MHz, CDCl$_3$) δ 1.45–1.56 (mult, 3 H), 1.70–1.74 (mult, 3 H), 2.10–2.18 (mult, 2 H), 2.50–2.69 (mult, 6 H), 3.66 (t, J=4.6 Hz, 2 H), 3.72 (t, J=4.6 Hz, 2 H), 3.86 (s, 2 H), 4.21–4.38 (mult, 6 H), 4.58 (s, 2 H), 6.55 (d, J=7.8 Hz, 1 H), 6.97–7.30 (mult, 12 H); $^{13}$C NMR (75 MHz, CDCl$_3$) δ 21.9, 25.3, 28.2, 29.2, 34.8, 38.4, 53.2, 56.2, 63.5, 64.2, 68.8, 68.9, 118.1, 121.9, 124.1, 125.1, 127.5, 127.9, 128.5, 128.7, 128.9, 129.3, 130.8, 136.2, 137.7, 142.6, 172.2, 172.7, 173.6; mass spectrum (API-ES), m/z 730 (MH$^+$), 700 (M$^+$–30, —NO).

Example 8

2-{4-[2-Methyl-2-(nitrosothio)propyl] piperazinyl}ethyl 2-{2-[(2,6-dichlorophenyl)amino] phenyl}acetate citrate 8a. 2,2-Dimethylthiirane A mixture of isobutylene epoxide (25.0 g, 346 mmol), water (50 ml), and KSCN (67.2 g, 692 mmol) was stirred at room temperature for 20 hours. The organic layer was separated and dried over Na$_2$SO$_4$. The solid was filtered off to give the title compound (26.4 g, 87%) as a clear oil. $^1$H NMR (300 MHz, CDCl$_3$) δ 2.41(s, 2H), 1.62 (s, 6H).

8b. 2-[4-(2-Methyl-2-sulfanylpropyl)piperazinyl]ethan-1-ol

The product of Example 8a (1.0 g, 11.3 mmol) and 1-(2-hydroxyethyl) piperizine (2.95 g, 22.7 mmol) were dissolved in benzene (1.5 ml) and heated to 80° C. for two hours. The mixture was cooled to room temperature and partitioned between EtOAc and water. The organic layer was dried over Na$_2$SO$_4$. The volatiles were evaporated to give the title compound (2.06 g, 83%) as a white solid. $^1$H NMR (300 MHz, CDCl$_3$) δ 3.61 (t, J=5.4, 2 H), 2.66–2.71 (m, 4 H), 2.52–2.56 (m, 6 H), 2.47 (s, 2 H), 1.31 (s, 6 H); $^{13}$C NMR (75 MHz, CDCl$_3$) δ 71.0, 59.2, 57.6, 55.5, 53.2, 46.4, 30.1.

8c. 2-{4-[2-Methyl-2-(nitrosothio)propyl] piperazinyl}ethan-1-ol

The product of Example 8b (5.9 g, 27.1 nmmol) in CH$_2$Cl$_2$ (100 ml) was treated with 1 N HCl—Et$_2$O (70 ml). The solvent was removed to give a white solid. The solid was dissolved in EtOH (30 ml) and water (20 ml) and added dropwise to a stirred solution of t-BuONO (6.2 g, 54.1 mmol) in EtOH (10 ml). The reaction was kept at room temperature for one hour after which the volatiles were evaporated. The residue was partitioned between satd NaHCO$_3$ and EtOAc. The aqueous layer was extracted with EtOAc. The organic extracts were combined and dried over Na$_2$SO$_4$. The volatiles were evaporated. The residue was chromatographed on silica gel eluting with MeOH:CH$_2$Cl$_2$ 1:19 to give the title compound (3.15 g, 47%) as a green oil. $^1$H NMR (300 MHz, CDCl$_3$) δ 3.67 (t, J=5.3, 2 H), 3.00 (s, 2 H), 2.62–2.67 (m, 4 H), 2.48–2,54 (m, 6 H), 1.88 (s, 6 H); $^{13}$C NMR (75 MHz, CDCl$_3$) δ 68.1, 59.1, 58.8, 57.6, 55.4, 53.0, 27.0; mass spectrum (m/e): 248 (MH$^+$).

8d. 2-{4-[2-methyl-2-(nitrosothio)propyl]piperazinyl}ethyl 2-{2-[(2,6 dichlorophenyl) amino]phenyl}acetate To a stirred solution of the product of Example 8c (1.52 g, 6.15 mmol) and 2-((2,6-dichlorophenyl)amino) benzeneacetic acid (2.19 g, 7.4 nunol) in CH$_2$Cl$_2$ (20 ml) was added 1M DCC in CH$_2$Cl$_2$ (7.4 ml, 7.4 mmol) dropwise over half an hour. The reaction was kept at room temperature for another hour. The precipitate was filtered off. The solvent was evaporated and the residue was chromatographed on silica gel eluting with 3:1 Hex:EtOAc to afford the title compound (3.07 g, 95%) as a green oil. $^1$H NMR (300 MHz, CDCl$_3$) δ 7.34 (d, J=8.0, 2 H), 7.21–7.26 (m, 2 H), 7.10–7.12 (m, 1 H), 6.94–7.01 (m, 2 H), 6.87 (brs., 1 H), 6.54 (d, J=8.0, 1H), 4.26 (t, J=5.8, 2 H), 3.82 (s, 2 H), 2.94 (s, 2 H), 2.56–2.65 (m, 6 H), 2.40–2.43 (m, 4 H), 1.86 (s, 6 H); $^{13}$C NMR (75 MHz, CDCl$_3$) δ 172.27, 142.7, 137.7, 130.9, 129.5, 128.9, 127.9, 124.2, 124.0, 121.9, 118.2, 68.1, 62.7, 58.8, 56.4, 55.2, 53.5, 38.6, 27.0. Mass Spectrum (m/e): 525.

8e. 2-{4-[2-methyl-2-(nitrosothio)propyl]piperazinyl}ethyl 2-{2-[(2,6-dichlorophenyl)amino]phenyl}acetate citrate The product of Example 8d (1.78 g, 3.39 mmol) in CH$_2$Cl$_2$ (10 ml) was mixed with citric acid (0.65 g, 3.38 mmol) in MeOH (5 ml). The solvents were evaporated and the residue was dissolved in MeGH (10 ml) and EtOAc (10 ml). The mixture was cooled to −20° C. to facilitate crystallization. The title compound (2.0 g, 82%) was collected on a funnel and dried in vacuc. $^1$H NMR (300 MHz, CDCl$_3$) δ 7.42 (d, J=8.1, 2 H), 7.23 (dd, J=7.5 and 1.2, 1 H), 7.03–7.14 (in, 2 H), 6.90 (dd, J=7.5 and 1.0, 1 H), 6.37 (d, J=8.0, 1 H), 4.44–4.47 (t, J=4.8, 2 H), 3.87 (s, 2 H), 3.29–3.31 (in, 1 H), 3.22 (t, J=4.8, 2 H), 3.06, (s, 2 H), 2.86–2.95 (in, 4 H), 2.70–2.81 (in, 8 H), 1.86 (s, 6 H); 13C NMR (75 MHz, CDCl) δ 170.4, 166.0, 164.4, 135.8, 130.3, 123.7, 123.3, 121.6, 117.8, 116.3, 114.0, 109.6, 65.8, 59.6, 52.6, 51.0, 48.0, 45.3, 45.0, 36.1, 30.2, 18.6.

Example 9

2-[2-(tert-Butyl)-5-(nitrosothio)-1,3-dioxan-5-yl] ethyl(2S)-2-(6-methoxy(2-naphthyl))propanoate 9a. 1,3-Bis(1,1,2,2-tetramethyl-1-silapropoxy)acetone Dihydroxy acetone dimer (7.5 g, 41.46 mmol) was added to a stirred solution of TBDMSCI (25.0 g, 166 mmol) in dry pyridine (100 mL). The resulting solution was stirred at room temperature for 12 hours. Ethyl acetate (100 mL) was added and the solution was washed with 10% HCl (3×50 mL) and water (200 mL). The organic phase was dried over Na$_2$SO$_4$ and evaporated to give the title compound (25.0 g, 94%) as a viscous oil. $^1$H NMR (300 MHz, CDCl$_3$) δ 4.45 (s, 4H), 0.94 (s, 18H), 0.11 (s, 12H).

9b. Ethyl (2E)-4-(1,1,2,2-tetramethyl-1-silapropoxy)-3-[(1, 1,2,2-tetramethyl-1-silapropoxy)methyl]but-2-enoate A solution of n-BuLi (2.5M in hexane, 15.0 mL, 37.5 mmol) was added to a stirred solution of triethyl phosphonoacetate (7.04 g, 31.4 mmol) in THF (50 mL) at −78° C. under N$_2$. The resulting brownish solution was stirred for 30 minutes and then a solution of the product of Example 9a (10.0 g, 31.4 mmol) in THF (10 mL) was added. The cold bath was removed and the mixture was stirred at room temperature for 12 hours. Water (250 mL) was added and the mixture was extracted with EtOAc (3×100 mL). The combined organic extracts were dried over Na$_2$SO$_4$. The solvent was evaporated to afford the title compound (11 g, 90%). $^1$H NMR (300 MHz, CDCl$_3$) δ 5.99–6.01 (mult, 1H), 4.88 (s, 2H), 4.45 (s, 2H), 4.16 (q, J=7.1 Hz, 2H), 1.29 (t, J=7.1 Hz, 3H), 0.95 (s, 9H), 0.91 (s, 9H), 0.10 (s, 6H), 0.08 (s, 6H).

9c 4-(Hydroxymethyl)-4-(phenylmethylthio)-3,4,5-trihydrofuran-2-one

The product of Example 9b (5.1 g, 13.1 mmol) and benzylmercaptan (1.53 mL, 13.1 mmol) in piperidine (50 mL) was heated at 100° C. for 4 hours and then cooled to room temperature. Water (50 mL) was added and the aqueous layer was extracted with EtOAc (3×50 mL). The combined organic layers were dried over Na$_2$SO$_4$. The solvent was evaporated and the residue was purified by chromatography on silica gel eluting with 5:95 EtOAc:hexane to afford the title compound (4.6 g, 68%) as a viscous liquid. The viscous liquid (10.0 g, 19.5 mmol) was dissolved in CH$_3$CN (10 mL) and 48% HF (10 mL) was added. The solution was stirred at room temperature for 2 hours. Satd NaHCO$_3$ (100 mL) was added. The solution was extracted with EtOAc (3×100 mL). The combined organics were dried over Na$_2$SO$_4$. The solvent was evaporated and the residue was chromatographed on silica gel eluting with 1:2 hexane:EtOAc to give the title compound (4.7 g, 95%). $^1$H NMR (300 MHz, CDCl$_3$) δ 7.22–7.30 (mult, 5H), 3.75 (s, 2H), (ABq, J=9.9 Hz, 2H), 3.60 (d, J=4.8 Hz, 2H), 2.04–2.08 (mult, 1H), (ABq, J=17.8 Hz, 2H).

9d. 2-(Hydroxymethyl)-2-(phenylmethylthio)butane-1,4-diol

A solution of lithium aluminum hydride (1M in THF, 14.9 mL, 14.9 mmol) was added to a stirred solution of the product of Example 9c (3.8 g, 14.94 mmol) in THF (50 mL) at 0° C. The cold bath was removed and the mixture was stirred at room temperature for 1 hour. Solid Na$_2$SO$_4$·10H$_2$O (3 g) was added portionwise with stirring until a thick precipitate formed. 10% MeOH in CH$_2$Cl$_2$ (50 mL) was added and the solid was removed by filtration. The solid was washed with additional 10% MeOH in CH$_2$Cl$_2$ (50 mL) and the solvent was evaporated. The residue was chromatographed on silica gel eluting with 4:1 EtOAc:hexane to give the title compound (2.4 g, 67%). $^1$H NMR (300 MHz, CDCl$_3$) δ 7.20–7.45 (mult, 5H), 4.00 (brs, 3H), 3.78 (t, J=5.5 Hz, 2H), 3.67 (s, 2H), 3.46 (s, 4H), 1.84 (t, J=5.5 Hz, 2H); $^{13}$C NMR (75 MHz, CDCl$_3$) 137.7, 128.9, 128.7, 127.3, 65.2, 58.2, 55.4, 35.7, 31.6.

9e. 2-[2-(tert-Butyl)-5-(phenylmethylthio)-1,3-dioxan-5-yl] ethan-1-ol

To stirred solution of the product of Example 9d (1.02 g, 4.2 mmol) and trimethylacetaldehyde (1.44 g, 16.8 rnmol) in $CH_2Cl_2$ (30 mL) was added $BF_3 \cdot OEt_2$ (6 drops). The clear solution was stirred at room temperature for 2 hours. The solvent was evaporated and the residue was chromatographed on silica gel eluting with 1:2 EtOAc:hexane to afford the title compound (0.84 g, 64%). $^1$H NMR (300 MHz, $CDCl_3$) δ 7.04–7.21 (mult, 5H), 3.98 (d, J=12.3 Hz, 2H), 3.91 (s, 1H), 3.85 (s, 2H), 3.60 (t, J=6.3 Hz, 2H), 3.51 (d, J=12.3 Hz, 2H), 1.38 (t, J=6.3 Hz, 2H), 0.78 (s, 9H); $^{13}$C NMR (75 MHz, $CDCl_3$) δ 138.0, 129.1, 128.5, 127.0, 108.2, 75.6, 58.3, 46.3, 37.4, 34.9, 33.8, 24.7.

9f. 2-[2-(tert-Butyl)-5-sulfanyl-1,3-dioxan-5-yl]ethan-1-ol

The product of Example 9e (0.8 g, 2.6 mmol) was dissolved in THF (10 mL) and cooled to –78° C. and liquid $NH_3$ (~25 mL) was added. Small pieces of sodium (1.3 g) were added until the blue color was persistent for 10 minutes. Solid $NH_4Cl$ (~1 g) was added to discharge the color, the cold bath was removed and $NH_3$ was allowed to evaporate (12 hours). Water (100 mL) was added and the mixture was extracted with EtOAc (3×50 mL). The organic layer was dried over $Na_2SO_4$, filtered, and concentrated to give the title compound (0.51 g, 90%) as a white solid. mp 68° C. $^1$H NMR (300 MHz, $CDCl_3$) δ 4.03–4.08 (mult, 13H), 3.88 (t, J=6.1 Hz, 2H), 3.56 (d, J=11.4 Hz, 2H), 2.15 (t, J=6.1 Hz, 2H), 1.39 (s, 1H), 0.84 (s, 9H); $^{13}$C NMR (75 MHz, $CDCl_3$), δ 76.9, 59.4, 42.2, 39.2, 34.7, 24.5 (3 C); mass spectrum (API-TIS) m/z 238 (M+$NH_4$)

9g. 2-[2-(tert-Butyl)-5-sulfanyl-1,3-dioxan-5-yl]ethyl(2S)-2-(6-methoxy(2-naphthyl))propanoate A solution of (2S)-2-(6-methoxy(2-naphthyl))propanoyl chloride (0.56 g, 2.27 mmol) and the product of Example 9f (0.5 g, 2.27 mmol) in $CH_2Cl_2$ (10 mL) were stirred at room temperature for 18 hours. The solvent was evaporated and the residue was chromatographed on silica gel eluting with 1:9 EtOAc:hexane to give the title compound (0.82 g, 83%) as a white solid. $^1$H NMR (300 MHz, $CDCl_3$) δ 7.52 (d, J=8.5 Hz, 3H), 7.26 (d, J=8.4 Hz, 1H), 6.94–6.99 (mult, 2H), 4.09–4.19 (mult, 2H), 3.85 (s, 1H), 3.65–3.75 (mult, 3H), 3.71 (s, 3H), 3.27 (d, J=4.1 Hz, 1H), 3.23 (d, J=4.2 Hz, 1H), 2.01–2.09 (mult, 2H), 1.43 (d, J=7.1 Hz, 3H), 0.99 (S, 1H), 0.74 (s, 9H); $^{13}$C NMR (75 MHz, $CDCl_3$) δ 174.3, 157.6, 135.0, 133.7, 129.2, 128.9, 127.1, 126.3, 126.0, 118.9, 107.7, 105.6, 76.4, 76.3, 61.5, 55.2, 45.5, 42.1, 34.7, 33.4, 24.5 (3 C), 18.3.

9h. 2-[2-(tert-Butyl)-5-(nitrosothio)-1,3-dioxan-5-yl]ethyl (2S)-2-(6-methoxy(2-naphthyl))propanoate To a stirred solution of the product of Example 9 g (0.5 g, 1.15 mmol) in $CH_2Cl_2$ (10 mL) was added t-BuONO (0.183 mL, 1.38 mmol) and the resulting green solution was stirred at room temperature for 1 hour. The reaction mixture was washed with water (10 mL), dried over $Na_2SO_4$, and concentrated to give the title compound (0.51 g, 96%) as a green oil. $^1$H NMR (300 MHz, $CDCl_3$) δ 7.64–7.72 (mult, 3H), 7.26–7.39 (mult, 1H), 7.11–7.16 (mult, 2H), 3.79–4.49 (mult, 7H), 3.99 (s, 1H), 3.92 (s, 3H), 2.84–2.86 (mult, 2H), 1.58 (d, J=7.2 Hz, 3H), 0.99 (s, 9H); $^{13}$C NMR (75 MHz, $CDCl_3$) δ 174.3, 157.6, 135.4, 133.7, 129.2, 128.8, 127.2, 126.2, 125.9, 118.9, 107.7, 105.6, 76.4, 76.3, 61.5, 55.2, 53.9, 45.4, 34.9, 32.4, 24.5 (3 C), 18.2.

Example 10

5-(Bis{[(nitrosothio)cyclohexyl]lmethyl}amino) pentyl (2S)-2-(6 -methoxy(2-naphthyl))propanoate 10a. 5-(16-Aza-7,8-dithiadispiro[5.2.5.3]heptadec-16-yl) pentan-1-ol 5-Amino-1-pentanol (1.9 g, 18.32 mmol) was added to a stirred solution of the product of Example 2a (5 g, 17.45 mmol) in $CH_2Cl_2$ (75 mL). The mixture was heated to reflux for 12 hours then cooled to room temperature. Sodium triacetoxyborohydride (7.4 g, 34.9 mmol) was added and the resulting suspension was stirred at room temperature for 24 hours. The solution was added to water (200 mL). The organic layer was separated and dried over $Na_2SO_4$. The solvent was evaporated and the residue was chromatographed on silica gel eluting with 1:1 EtOAc:hexane to give the title compound (2.8 g, 45%). TLC $R_f$ (0.45, EtOAc:hexane, 1:2); $^1$H NMR (300 MHz, $CDCl_3$) δ 3.66 (t, J=6.5 Hz, 2H), 2.84 (d, J=14 Hz, 2H), 2.56 (d, J=14 Hz, 2H), 2.35–2.70 (mult, 2H), 1.97–2.10 (mult, 2H), 1.10–1.80 (mult, 24H); $^{13}$C NMR (75 MHz, $CDCl_3$) δ 70.2, 62.6, 60.7, 55.5, 34.7, 33.6, 32.6, 28.1, 26.1, 23.3, 22.2, 21.8, 20.9; mass spectrum (API-TIS) m/z 358 (M+H).

10b. 5-(16-Aza-7,8-dithiadispiro[5.2.5.3]heptadec-16-yl) pentyl (2S)-2-(6-methoxy(2-naphthyl))propanoate DCC (1.8 g, 8.72 mmol) in $CH_2Cl_2$ (50 mL) was added dropwise to a stirred solution of the product of Example 10a (2.6 g, 7.3 mmol), (2S)-2-(6-methoxy(2-naphthyl)) propanoic acid (2.0 g, 8.7 mmol), and DMAP (0.106 g, 0.87 mmol) in $CH_2Cl_2$(50 mL) over 30 minutes at room temperature. The resulting suspension was stirred at room temperature for 2 hours. The precipitate was removed by filtration and washed with $CH_2Cl_2$ (25 mL). The filtrate was concentrated and the residue was chromatographed on silica gel eluting with 1:9 EtOAc:hexane to afford the title compound (3.6 g, 86.7%) as a viscous oil. TLC $R_f$ (0.43, EtOAc:hexane, 1:9); $^1$H NMR (300 MHz, $CDCl_3$) δ 7.66–7.80 (mult, 3H), 7.39 (d, J=8.4 Hz, 1H), 7.05–7.14 (mult, 2H), 4.06 (t, J=6.4 Hz, 2H), 3.90 (s, 3H), 3.80–3.90 (mult, 1H), 2.75 (d, J=13.8 Hz, 2H), 2.25–2.60 (mult, 4H), 1.56 (d, J=7.0 Hz, 3H), 1.05–2.10 (mult, 26H); $^{13}$C NMR (75 MHz, $CDCl_3$) δ 174.0, 157.5, 135.7, 133.6, 129.2, 128.8, 127.0, 126.2, 125.8, 118.9, 105.5, 70.3, 64.7, 60.6, 55.5, 55.2, 45.4, 34.8, 33.7, 28.5, 28.0, 26.2, 23.5, 22.3, 21.9, 18.5; mass spectrum (API-TIS) m/z 570 (M+H).

10c. 5-{bis[(Sulfanylcyclohexyl)methyl]amino}pentyl (2S)-2-(6-methoxy(2 -naphthyl))propanoate A mixture of the product of Example 10b (3.25 g, 5.70 mmol) and zinc powder (5 g) in HOAc (50 mL) were stirred at room temperature under $N_2$ for 24 hours. The inorganic solid was removed by filtration and washed with HOAc (25 mL). The filtrate was poured onto crushed ice, and the mixture was made basic with conc $NH_4OH$ (15 mL). The white precipitate was extracted into EtOAc (3×50 mL). The organic phase was dried over $Na_2SO_4$ and concentrated. The residue was chromatographed on silica gel eluting with 1:6 EtOAc:hexane then with 1:1 with EtOAc:hexane to afford the title compound (2.2 g, 68%) as a white foam. $^1$H NMR (300 MHz, $CDCl_3$) δ 7.65–7.75 (mult, 3H), 7.39 (d, J=8.4 Hz, 1H), 7.05–7.14 (mult, 2H), 4.08 (t, J=6.2 Hz, 2H), 3.89 (s, 3H), 3.80–3.89 (mult, 1H), 2.70–3.00 (mult, 4H), 2.52 (d, J=13.2 Hz, 2H), 1.56 (d, J=7.2 Hz, 3H), 1.05–2.05 (mult, 26H); $^{13}$C NMR (75 MHz, $CDCl_3$) δ 174.5, 157.5, 135.6, 133.5, 129.1, 128.7, 127.0, 126.1, 125.8, 118.8, 105.4, 71.9, 70.8, 64.4, 60.3, 56.6, 55.2, 53.1, 42.3, 41.3, 40.8, 40.7, 28.2, 26.0, 25.6, 23.8, 23.6, 22.8, 22.5, 18.4; mass spectrum (API-TIS) m/z 572 (M+H).

10d. 5-(bis{[(Nitrosothio)cyclohexyl]methyl}amino)pentyl (2S)-2-(6-methoxy(2-naphthyl))propanoate t-BuONO (210 μL, 1.58 mmol) was added to a stirred solution of the product of Example 10c (0.4 g, 0.66 mmol) in $CH_2Cl_2$ (25 mL) at –78° C. under nitrogen. The cold bath was removed and the mixture was allowed to stir for 15 minutes. Satd $Na_2CO_3$ (1 mL) was added and the mixture was shaken. The organic layer was separated and washed with water (50 mL). The organic layer was dried over $Na_2SO_4$ and concentrated. The residue was chromatographed on silica gel eluting with 1:9 EtOAc:hexane to afford the title compound (0.273 g, 66%) as a viscous oil. TLC $R_f$ (0.27, EtOAc/hexane, 1:9). $^1$H NMR (300 MHz, $CDCl_3$) δ 7.64–7.75 (mult, 3H), 7.38 (d, J=8.4 Hz, 1H), 7.05–7.13 (mult, 2H), 3.99–4.03 (mult, 2H), 3.86 (s, 3H), 3.75–3.80 (mult, 1H), 3.24 (s, 4H), 2.42–2.49 (mult, 6H), 2.00 (t, J=7.2 Hz, 3H), 1.55 (d, J=7.1 Hz, 3H), 0.97–1.80 (mult, 18H); $^{13}$C NMR (75 MHz, $CDCl_3$) δ 174.0, 157.5, 135.6, 133.5, 129.1, 128.8, 126.9, 126.1, 125.8, 118.8, 105.4, 67.1, 64.4, 64.2, 56.6, 55.1, 45.3, 35.4, 28.3, 25.4, 24.1, 23.3, 22.3, 18.4; mass spectrum (API-TIS) m/z 570 (M-2NO).

Example 11

2-({3-[(2S)-2-(6-Methyl(2-naphthyl))propanoyloxy]propyl}{[(nitrosothio) cyclohexyl]methyl}amino)acetic acid 11a. 3-[({[({[(3-Hydroxypropyl)amino]methyl}cyclohexyl)disulfanyl]cyclohexyl}methyl)amino]propan-1-ol A mixture of the product of Example 2a (20 g, 69.8 mmol) and propanol amine (10.5 g, 140 mmol) in $CHCl_3$ (150 mL) were heated at 65° C. for 8 hours. The solvent was evaporated to obtain a viscous yellow liquid which was dissolved in MeOH (200 mL). $NaBH_4$ (5.3 g, 140 mmol) was added portionwise over 10 minutes and the resulting solution was stirred at room temperature for 1 hour. The solvent was evaporated and the residue was partitioned between water (200 mL) and EtOAc (100 mL). The organic layer was separated and the aqueous layer was extracted with EtOAc (2×50 mL). The combined organic layers were dried over $Na_2SO_4$ and concentrated to afford the title compound (27.5 g, 97%) as a colorless viscous oil. $^1$H NMR (300 MHz, $CDCl_3$) δ 3.84 (t, J=5.3 Hz, 4H), 2.91 (t, J=5.5 Hz, 4H), 2.66 (s, 4H), 1.20–1.80 (mult, 24H); $^{13}$C NMR (75 MHz, $CDCl_3$) δ 64.8, 57.1, 54.4, 50.6, 34.4, 30.4, 25.8, 22.2.

11b. tert-Butyl 2-({[({[({[(tert-butyl)oxycarbonyl]methyl}(3-hydroxypropyl) amino]methyl]cyclohexyl}disulfanyl)cyclohexyl]methyl}(3-hydroxypropyl) amino)acetate The product of Example 11a was dissolved in $CH_3CN$ (100 mL) and t-butyl bromoacetate (20 g, 15 mL, 102.5 mmol) and solid $K_2CO_3$ (10 g) were subsequently added. The resulting suspension was stirred at room temperature for 12 hours. The solid was removed by filtration and washed with $CH_3CN$ (50 mL). The filtrate was concentrated and the residue was chromatographed on silica gel eluting with 1:2 EtOAc:hexane to give the title compound (15.2 g, 88%). $^1$H NMR (300 MHz, $CDCl_3$) δ 3.49 (t, J=5.1 Hz, 2H), 3.38 (s, 2H), 2.82–2.85 (mult, 2H), 1.39 (s, 9H), 0.90–1.65 (mult, 10H); $^{13}$C NMR (75 MHz, $CDCl_3$) δ 172.4, 81.0, 71.4, 60.5, 60.1, 59.2, 52.4, 39.6, 28.4 (3C), 28.1 (3C), 26.0, 22.2 (2C); mass spectrum (API-TIS) m/z 304 (M+H).

11c. 3-({[({[({3-[(2S)-2-(6-Methyl(2-naphthyl))propanoyloxy]propyl}{[(tert-butyl)oxycarbonyl]methyl}amino)methyl]cyclohexyl}disulfanyl)cyclohexyl]methyl}{[(tert-butyl)oxycarbonyl]methyl}amino)propyl (2S)-2-(6-methyl(2-naphthyl))propanoate DCC (2.72 g, 13.2 mmol) in $CH_2Cl_2$ (20 mL) was added dropwise to a stirred solution of the product of Example 11b (3.4 g, 5.7 mmol), (2S)-2-(6-methoxy(2-naphthyl))propanoic acid (2.53 g, 11.0 mmol) and DMAP (0.2 g) in $CH_2Cl_2$ (30 mL) at 0° C. The resulting suspension was stirred for 1 hour at 0° C. The precipitate was removed by filtration and washed with $CH_2Cl_2$ (25 mL). The filtrate was concentrated to give a green oil which was chromatographed on silica gel eluting with 1:4 EtOAc:hexane to afford the title compound (2.8 g, 46.5%) as a white foam. $^1$H NMR (300 MHz, $CDCl_3$) δ 7.60 (t, J=8.1 Hz, 3H), 7.31(d, J=8.4 Hz, 1H), 7.03–7.06 (mult, 2H), 4.00–4.11 (mult, 2H), 3.82 (s, 3H), 3.73 (q, J=7.1 Hz, 1H), 3.22 (s, 2H), 2.68 (s, 2H), 2.61–2.68 (mult, 2H), 1.48 (d, J=7.2 Hz, 3H), 1.36 (s, 9H), 1.10–1.66 (mult, 12H); $^{13}$C NMR (75 MHz, $CDCl_3$) δ 174.6, 171.2, 157.5, 135.7, 133.6, 129.2, 128.8, 127.0, 126.2, 125.8, 118.9, 105.5, 80.7, 65.3, 62.1, 56.8, 56.0, 55.2, 52.8, 45.4, 28.1, 27.4, 25.6, 22.2, 18.5; mass spectrum (API-TIS) m/z 393 (M+H).

11d. 2-({3-[(2S)-2-(6-Methyl(2-naphthyl))propanoyloxy]propyl}{[({[({3-[(2S)-2-(6-methyl(2-naphthyl))propanoyloxy]propyl}(carboxymethyl)amino)methyl]cyclohexyl}disulfanyl)cyclohexyl]methyl}amino)acetic acid The product of Example 11c (2.2 g, 2.32 mmol) was dissolved in $CH_2Cl_2$ (10 mL) and TFA (10 mL) was added. The resulting solution was stirred at room temperature for 12 hours then poured onto crushed ice and the resulting mixture was made basic with conc $NH_4OH$ (10 mL). The mixture was extracted with EtOAc (3×50 mL). The combined organic extracts were dried over $Na_2SO_4$ and filtered. The solvent was evaporated and the residue was chromatographed on silica gel eluting with 1:19 MeOH:$CH_2Cl_2$ to afford the title compound (1.6 g, 73%) as a white foam. $^1$H NMR (300 MHz, $CDCl_3$) δ 7.63–7.70 (mult, 3H), 7.36 (d, J=8.0 Hz, 1H), 7.10–7.26 (mult, 2H), 4.08 (b rs, 2H), 3.89 (s, 3H), 3.80–3.82 (mult, 1H), 3.32 (br s, 2H), 2.67 (br s, 4H), 1.54 (d, J=6.8 Hz, 3H), 1.17–1.80 (mult, 12H); $^{13}$C NMR (75 MHz, $CDCl_3$) δ 174.5, 157.6, 135.6, 133.6, 129.2, 128.8, 127.2, 126.2, 125.9, 119.0, 105.5, 62.4, 55.2, 45.4, 33.0, 25.4, 22.0, 18.4; mass spectrum (API-TIS) m/z 945 (M+H).

11e. 2-({3-[(2S)-2-(6-Methyl(2-naphthyl))propanoyloxy]propyl}{[(nitrosothio) cyclohexyl]methyl}amino) acetic acid The product of Example 11d (1.60, 1.69 mmol) was dissolved in HOAc (10 mL) and powdered zinc (3.2 g) was added. The resulting suspension was stirred at room temperature for 12 hours. The inorganic solid was removed by filtration and washed with HOAc (25 mL). The filtrate was made basic with conc $NH_4OH$ in crushed ice and then extracted with EtOAc (4×25 mL). The combined organic extracts were dried over $Na_2SO_4$ and filtered. The solvent was evaporated to give a white foam (1.4 g). The white foam was subsequently dissolved in $CH_2Cl_2$ (15 mL) and conc HCl (2 mL) was added. 90% t-BuONO (0.41 mL, 3.43 mmol) was added via syringe. The resulting olive green solution was stirred at room temperature for 15 minutes and then poured onto crushed ice (~10 g). 10% $Na_2CO_3$ (10 mL) was added and the mixture was extracted with EtOAc (3×50 mL). The combined organic extracts were dried over $Na_2SO_4$ and concentrated. The residue was chromatographed on silica gel eluting with 2:1 EtOAc:hexane to afford the title compound (0.37 g, 22%) as a green oil (considerable decomposition occurred during the work up). $^1$H NMR (300 MHz, $CDCl_3$) δ 7.67 (t, J=10.7 Hz, 3H), 7.35 (dd, J=1.7 and 8.5 Hz, 1H), 7.10–7.26 (mult, 2H), 3.96–4.02 (mult, 2H), 3.90 (s, 3H), 3.82 (q, J=7.1 Hz, 1H), 3.32 (s, 2H), 3.27 (s, 2H), 2.58 (t, J=7.4 Hz, 2H), 2.33–2.58 (mult, 2H), 1.85 (t, J=13.3 Hz, 2H), 1.55 (d, J=7.1 Hz, 3H), 1.30–1.72 (mult, 12H); $^{13}$C NMR (75 MHz, $CDCl_3$) δ 175.1, 174.5, 157.5, 135.5, 133.6, 129.1, 128.8, 127.1, 126.1, 125.8, 118.9, 105.5, 66.8, 63.9, 62.2, 56.5, 55.2, 53.3, 45.3, 34.1, 26.5, 25.3, 21.9, 18.2; mass spectrum (API-TIS) m/z 503 (M+H).

Example 12

3-(Methyl{[1-methyl-4-(nitrosothio)(4-piperidyl)]methyl}amino)propyl 2-{2-[(2,6-dichlorophenyl)amino]pheny}acetate 12a. Ethyl 4-(methoxymethylene)piperidinecarboxylate A 1M solution of sodium hexamethyldisilazane (NaHMDS, 350 mL, 0.35 mol) in THF was added slowly to a suspension of (methoxymethyl)triphenyl phosphonium chloride (120 g, 0.35 mol,) in THF (100 mL) at −78° C. under $N_2$. The resulting brown solution was stirred at −78° C. for 20 minutes and then 1-carbethoxy-4-piperidone (50 g, 0.292 mol) in THF (50 mL) was added dropwise. The mixture was stirred at −78° C. for 5 minutes and then for 2 hours at room temperature. Water (200 mL) was added and the layers were separated. The aqueous layer was extracted with EtOAc and the combined organic extracts were dried over $Na_2SO_4$. The solvent was evaporated to give an orange solid which was suspended in $Et_2O$ (200 mL). The solid was removed by filtration and the filtrate was concentrated to give a yellow oil which was triturated with hexane (200 mL). The white solid which precipitated was removed by filtration. The filtrate was concentrated in vacuo and this was procedure repeated twice more to give the title compound (52 g, 89%) as a pale yellow oil. TLC $R_f$=0.72 (EtOAc:hexane, 1:2); $^1$H NMR (CDCl$_3$) δ 5.84 (s, 1H), 4.11 (q, J=7 Hz, 2H), 3.54 (s, 3 H), 3.37–3.42 (mult, 4 H), 2.24 (t, J=5.6 Hz, 2H), 1.99 (t, J=5.6 Hz, 2H), 1.24 (t, J=7 Hz, 3H); $^{13}$C NMR (CDCl$_3$) δ 155.6, 140.8, 113.4, 61.3, 59.5, 45.8, 44.6, 29.6, 25.2, 14.8; mass spectrum (API-TIS) m/z 200 (M+H). Anal Calcd for $C_{10}H_{17}N_1O_3$: C, 60.28; H, 8.60; 7.03. Found: C, 60.29; H, 8.63; N, 6.81.

12b. Ethyl 4-formylpiperidinecarboxylate

The product of Example 12a (52 g, 0.26 mol) in $CH_3CN$ (300 mL) and 1N HCl (75 mL) was stirred at room temperature for 24 hours. The solvent was evaporated and the residue was extracted with EtOAc (3×150 mL). The combined extracts were washed with brine (2×150 mL), dried over $Na_2SO_4$, and concentrated to afford the title compound which was used for the next step without further purification. $^1$H NMR (CDCl$_3$) δ 9.66 (s, 1H), 4.13 (q, J=7Hz, 2H), 3.90–3.99 (mult, 2H), 2.98 (mult, 2H), 2.42 (mult, 1H), 1.87–1.93 (mult, 2H), 1.63–1.49 (mult, 2H), 1.25 (t, J=7 Hz, 3H).

12c. Ethyl 4-{[1-ethoxycarbonyl)-4-formyl(4-piperidyl)] disulfanyl}-4-formylpiperidinecarboxylate.

To a stirred solution of the product of Example 12b in $CCl_4$ (120 mL) was added dropwise $S_2Cl_2$ (13.43 mL, 0.168 mol) over a period of 5 minutes at 50° C. After a short lag period (10–15 minutes), evolution of HCl gas was observed. After the gas evolution had ceased, the mixture was stirred at 55° C. for 1 hour and then cooled to room temperature. The solvent was evaporated to give a yellow oil which was purified by flash chromatography on silica gel eluting with 1:2 EtOAc:hexane to give a pale yellow oil which was dried in vacuo to give the title compound (76% based on 12a) as a sticky oil which solidified on standing at room temperature. $^1$H NMR (CDCl$_3$) δ 9.04, 1H), 4.11 (q, J=7 Hz, 2H), 3.65–3.85 (mult, 2H), 3.14–3.20 (mult, 2H), 2.01–2.07 (mult, 2H), 1.71–1.80 (mult, 2H), 1.25 (t, J=7 Hz, 3H); $^{13}$C NMR (CDCl$_3$) δ 193.2, 155.3, 61.8, 59.6, 40.8, 29.5, 14.7; mass spectrum (API-TIS) m/z 450 (M+NH$_4$).

12d. 3-(methyl{[1-methyl-4-(nitrosothio)(4-piperidyl)]methyl}amino)propan-1-ol

A mixture of product of Example 12c (7.0 g, 16.18 mmol) and propanol amine (2.91 g, 38.8 mmol) in dry CHCl$_3$ (50 mL) was heated at 65° C. for 8 hours. The solvent was evaporated to obtain a viscous yellow liquid which was dissolved in MeOH (30 mL). NaBH$_4$ (1.5 g, 38.83 mmol) was added portionwise over 10 minutes and the resulting solution was stirred at room temperature for 1 hour. Formaldehyde 38% (30 mL) was added and the resulting cloudy solution was stirred 2 hours at room temperature. The solvent was evaporated and the residue was partitioned with a mnixture of water (100 mL) and EtOAc (50 mL). The organic extracts were separated and the aqueous layer was extracted with EtOAc (2×50 mL). The combined organic layers were dried over $Na_2SO_4$ and evaporated to give a colorless viscous oil (9.2 g). The colorless oil (8.2 g) in THF (50 mL) was added to a stirred solution of lithium aluminum hydride (1M, 42 mL, 42 mmol) at room temperature under $N_2$. The resulting clear solution was stirred at room temperature for 3 hours and the excess lithium aluminum hydride was destroyed by portionwise addition of solid $Na_2SO_4 \cdot 10H_2O$ (~10 g). The precipitate was removed by filtration and washed with 10% MeOH in $CH_2Cl_2$ (2×50 mL). The combined filtrate was dried over $Na_2SO_4$ and concentrated to give a viscous liquid (5.1 g). The viscous liquid (5 g) was dissolved in MeOH (30 mL) and cooled to 0° C. and conc HCl (3 mL) was added. t-BuONO (3.2 mL, 26.8 mmol,) was then added via syringe and the resulting green solution was stirred for 20 minutes at room temperature. The solution was poured onto crushed ice (~10 g) and made basic with 10% $Na_2CO_3$ (10 mL). The green aqueous solution was extracted with EtOAc (3×50 mL). The combined organics were dried over $Na_2SO_4$ and concentrated. The residue was purified by chromatography on silica gel eluting with 1:4 MeOH:CH$_2$Cl$_2$ to afford the title compound (1.2 g). $^1$H NMR (CDCl$_3$): δ 3.70 (t, J=5.5 Hz, 2H), 3.23 (s, 2H), 2.74–2.80 (mult, 2H), 2.69 (t, J=6.1 Hz, 2H), 2.50–2.67 (mult, 2H), 2.34 (s, 3H), 2.31 (s, 3H), 2.25–2.45 (mult, 4H), 1.67 (p, J=5.9 Hz, 2H); $^{13}$C NMR (CDCl$_3$) δ 69.9, 62.9, 59.8, 51.4, 46.0, 44.3, 34.1, 29.0; mass spectrum (API-TIS) m/z 26 (M+H).

12e. 3-(Methyl{[1-methyl-4-(nitrosothio)(4-piperidyl)]methyl}amino)propyl 2-{2-[(2,6-dichlorophenyl)amino]pheny}acetate DCC (1.70 g, 8.26 mmol) in $CH_2Cl_2$ (25 mL) was added dropwise to a stirred solution of the product of Example 12d (1.2 g, 4.59 mmol), (2-((2,6-dichlorophenyl)amino) benzene)acetic acid (2.01 g, 6.88 mmol), and DMAP (0.075 g) in $CH_2Cl_2$ (25 mL) at room temperature. The resulting suspension was stirred for 2 hours at room temperature. The precipitate was removed by filtration and washed with $CH_2Cl_2$ (25 mL). The filtrate was concentrated to give a green oil which was chromatographed on silica gel eluting with 1:1 EtOAc:hexane followed by 1:9 MeOH:CH$_2$Cl$_2$ to afford a green solid (contamninated with dicyclohexyl urea). The solid was triturated with hexane (50 mL) and filtered. The filtrate was concentrated to give the title compound (1.4 g, 57%) as a viscous green oil. $^1$H NMR (300 MHz, CDCl$_3$) δ 7.35–7.40 (mult, 1H), 7.36 (d, J=8.0 Hz, 2H), 7.24–7.29 (mult, 1H), 7.14 (t, J=7.5 Hz, 1H), 6.90–7.05 (mult, 3H), 6.56 (d, J=7.9 Hz, 1H), 4.17 (t, J=6.3 Hz, 2H), 3.82 (s, 2H), 3.17 (s, 2H), 2.75–2.79 (mult, 2H), 2.31–2.60 (mult, 8H), 2.30 (s, 6H), 1.74–1.82 (mult, 2H); $^{13}$C NMR (75 MHz, CDCl$_3$) δ 172.3, 142.7, 137.8, 130.8, 129.4, 128.8, 127.9, 124.3, 123.9, 121.9, 118.2, 68.9, 63.2, 61.6, 56.5, 51.6, 46.1, 44.4, 38.6, 33.8, 26.7; mass spectrum (API-TIS) m/z 539 (M+H).

12f. 3-(Methyl{[1-methyl-4-(nitrosothio)(4-piperidyl)]methyl}amino)propyl 2-{2-[(2,6-dichlorophenyl)amino]pheny}acetate citrate Citric acid (0.43 g, 3.94 mmol) was dissolved in MeOH at 40° C. (1 mL) and the product of Example 12e (1.1 g, 2.03 mmol) was dissolved in EtOAc (2 mL). The solutions were mixed and left at −20° C. for 2 hours. The pale brown precipitate was removed by filtration and dried in vacuo for 3 hours to give the title compound (1.3 g, 88%) as a brown solid. mp. 118° C.; $^1$H NMR (300 MHz, d$_8$-THF) δ 7.57 d, J=8.0 Hz, 2H), 7.35–7.40 (mult, 1H), 7.05–7.25 (mult, 3H), 6.61 (d, J=7.9 Hz, 1H), 4.30 (t, J=6.3 Hz, 2H), 3.96 (s, 2H), 3.36 (s, 2H), 3.14–3.18 (mult, 2H), 2.93 (AB$_q$, 15.4 Hz, 4H), 2.64–2.85 (mult, 8H), 2.58 (s, 3H), 2.47 (s, 3H). Anal Calcd for $C_{31}H40N_4O_{10}S_1C_2$: C, 50.89; H, 5.51; N, 7.66; S, 4.38; Cl, 9.69. Found: C, 50.64; H, 5.62; N, 7.52; S, 4.28; Cl, 9.89.

Example 13

2-[1-Methyl-4-(nitrosothio)-4-piperidyl]ethyl 2-{2-[(2,6-dichlorophenyl) amino]phenyl}acetate citrate 13a. Ethyl 2-{1-methyl-4-piperidylidene}acetate A solution of n-BuLi (1.6M in hexane, 58.7 mL, 93.6 mmol) was added to a stirred solution of triethyl phosphonoacetate (17.5 g, 78.0 mmol) in THF (30 mL) at −78° C. under N$_2$. The resulting brownish solution was stirred for 30 minutes and then a solution of 1-N-methylpiperidone (8.8 g, 78.0 mmol) in THF (20 mL) was added. The cold bath was removed and the mixture was stirred at room temperature for 2 hours. Water (250 mL) was added and the mixture was extracted with EtOAc (3×100 mL). The combined organic extracts were dried over Na$_2$SO$_4$. The solvent was evaporated to afford the title compound (13.2 g, 92%). $^1$H NMR (300 MHz, CDCl$_3$) δ 5.64, 1H), 4.14 (q, J=7.1 Hz, 2H), 3.00 (t, J=5.1 Hz, 10H), 2.32–2.53 (mult, 5H), 2.29 (s, 3H), 1.27 (t, J=7.1 Hz, 3H); $^{13}$C NMR (75 MHz, CDCl$_3$) δ 166.4, 158.6, 114.2, 59.5, 56.7, 56.1, 45.7, 36.7, 29.3, 14.2.

13b. Ethyl 2-{1-methyl-4-(phenylmethylthio) piperidyl}acetate

The product of Example 13a (13.2 g, 72.01 mmol) and benzylmercaptan (8.4 mL, 72.01 mmol) in piperidine (35 mL) were heated at 100° C. for 12 h and then cooled to room temperature. Water (50 mL) was added and the aqueous layer was extracted with EtOAc (3×100 mL). The combined organic layers were dried over Na$_2$SO$_4$. The solvent was evaporated and the residue was purified by chromatography on silica gel eluting with 1:9 MeOH:CH$_2$Cl$_2$to afford the title compound (11.7 g, 53%) as a viscous liquid. $^1$H NMR (300 MHz, CDCl$_3$) δ 7.18–7.34 (mult, 5H), 4.17(q, J=7.1 Hz, 2H), 3.71 (s, 2H), 2.64 (s, 2H), 2.46–2.54 (mult, 4H), 2.29 (s, 3H), 1.83–1.95 (mult, 4H), 1.29 (t, J=7.1 Hz, 3H).

13c. 2-[1-Methyl-4-(phenylmethylthio)-4-piperidyl]ethan-1-ol

A solution of DIBAL in hexane (83 mL, 83 mmol) was added to a stirred solution of the product of Example 13b (11.7 g, 38.74 mmol) in THF (40 mL) at −78° C. under N$_2$. The cold bath was removed and the mixture was stirred 1.5 hours. Solid Na$_2$SO$_4$·10H$_2$O (3 g) was added portionwise with stirring until a thick precipitate was formed. 10% MeOH in CH$_2$Cl$_2$ (100 mL) was added and the mixture was filtered. The solid was washed with additional 10% MeOH in CH$_2$Cl$_2$ (100 mL) and the solvent was evaporated. The residue was chromatographed on silica gel eluting with 1:9 MeOH:CH$_2$Cl$_2$ to give the title compound (5.2 g, 50.6%) as a solid. $^1$H NMR (300 MHz, CDCl$_3$) δ 7.20–7.35 (mult, 5H), 3.86 (t, J=6.4 Hz, 2H), 3.66 (s, 2H), 2.50–2.57 (mult, 4H), 2.29 (s, 3H), 1.88 (t, J=6.5 Hz, 2H), 1.65–1.84 (mult, 4H).

13d. 2-[1-Methyl-4-(nitrosothio)-4-piperidyl]ethan-1-ol

The product of Example 13c (7.8 g, 29.38 mmol) was dissolved in THF (50 mL) and cooled to −78° C. and liquid NH$_3$ (100 mL) was added. Small pieces of Na (2 g) were added until the blue color persisted for 10 mninutes. Solid NH$_4$Cl (~5 g) was added to discharge the color and the cold bath was removed and NH$_3$ was evaporated (12 hours). Ether (100 mL) was added to the pale yellow solid and HCl in Et$_2$O (10 mL) was added until the solution became acidic. The mixture was left in a freezer for 30 minutes. The solid which formed was removed by filtration and washed with Et$_2$O (50 mL). The residue was triturated with MeOH (100 mL) and the undissolved solid was removed by filtration. The solvent was concentrated to 25 mL and conc HCl (2 mL) was added. 90% t-BuONO (3.1 mL, 23.7 mmol) was added via a syringe. The resulting olive green solution was stirred at room temperature for 20 minutes and then poured onto crushed ice (5 g). 10% Na$_2$CO$_3$ (10 mL) was added and the mixture was extracted with EtOAc (3×50 mL). The combined organics were dried over Na$_2$SO$_4$ and concentrated to give the title compound (3.6 g, 60%) as green oil. $^1$H NMR (300 MHz, CDCl$_3$) δ 3.88, J=6.9 Hz, 2H), 2.25–2.95 (mult, 13H), 2.30 (s, 3H); $^{13}$C NMR (75 MHz, CDCl$_3$) δ 62.5, 57.8, 51.5, 46.1, 36.4.

13e. 2-[1-Methyl-4-(nitrosothio)-4-piperidyl]ethyl 2-{2-[(2,6-dichlorophenyl) amino]phenyl}acetate DCC (1.33 g, 6.4 mmol) in CH$_2$Cl$_2$ (25 mL) was added dropwise to a stirred solution of the product of Example 13d (1.1 g, 5.38 mmol), (2-((2,6-dichlorophenyl)amino) benzene)acetic acid (1.6 g, 5.38 mmol), and DMAP (0.1 g) in CH$_2$Cl$_2$ (25 mL) at room temperature. The resulting suspension was stirred for 2 hours at room temperature. The precipitate was removed by filtration and washed with CH$_2$Cl$_2$ (25 mL). The filtrate was concentrated to give a green oil which was chromatographed on silica gel eluting with 1:1 EtOAc:hexane followed by 1:9 MeOH:CH$_2$Cl$_2$ to give a green solid (contaminated with dicyclohexyl urea). The solid was triturated with hexane (50 mL) and filtered. The filtrate was concentrated to afford the title compound (2.1 g, 81%) as a viscous green oil. $^1$H NMR (300 MHz, CDCl$_3$) δ 7.25, J=8.0 Hz, 2H), 7.21 (dd, J=1.3 and 7.4 Hz, 1H), 7.11–7.14 (mult, 1H), 6.94–7.00 (mult, 2H), 6.82 (s, 1H), 6.55 (d, J=7.9 Hz, 1H), 4.37 (t, J=6.9 Hz, 2H), 3.79 (s, 2H), 2.31 (s, 3H), 2.20–2.80 (mult, 10H); $^{13}$C NMR (75 MHz, CDCl$_3$) δ 142.6, 137.6, 130.9, 129.5, 128.8, 128.0, 124.0, 123.9, 122.0, 118.2, 61.5, 57.4, 51.4, 46.1, 38.6, 36.6; mass spectrum (API-TIS) m/z 483 (M+H).

13f. 2-[1-Methyl-4-(nitrosothio)-4-piperidyl]ethyl 2-{2-[(2, 6-dichlorophenyl) amino]phenyl}acetate citrate Citric acid (0.832 g, 3.94 mmol) was dissolved in MeOH at 40° C. (3 mL) and the product of Example 13e (1.9 g, 3.94 mmol) was dissolved in EtOAc (6 mL). The solutions were mixed and left at −20° C. for 2 hours. The pale brown precipitate was removed by filtration and dried in, vacuo for 6 hours to afford the title compound as a brown solid (2.3 g, 88%). mp 130° C.; $^1$H NMR (300 MHz, d$_8$-THF) δ 7.57 (d, J=8.1 Hz, 2H), 7.36 (d, J=7.4 Hz, 1H), 7.19–7.26 (mult, 3H), 7.05 (t, J=7.4 Hz, 1H), 6.60 (d, J=7.9 Hz, 1H), 4.53 (s, J=6.8 Hz, 2H), 3.93 (s, 2H), 3.25–3.40 (mult, 2H), 2.75–3.00 (mult, 12H), 2.69 (s, 3H). Anal Calcd for $C_{22}H_{25}N_3O_{10}S_1Cl_2$: C, 49.86; H, 4.93; N, 6.23; S, 4.75; Cl, 10.51. Found: C, 49.84; H, 4.98; N, 6.05; S, 4.73; Cl, 10.13.

Example 14

2-[1-Methyl-4-(nitrosothio)-4-piperidyl]ethyl 2-[4-(2-methylpropyl) phenyl]propanoate citrate 14a. 2-[1-Methyl-4-(nitrosothio)-4-piperidyl]ethyl 2-[4-(2-methylpropyl) phenyl]propanoate DCC (0.824 g, 3.98 mmol) in CH$_2$Cl$_2$ (25 mL) was added dropwise to a stirred solution of the product of Example 13d (0.74 g, 3.62 mmol), ibuprofen (0.75 g, 3.6 mmol), and DMAP (75 mg) in CH$_2$Cl$_2$ (25 mL) at room temperature. The resulting suspension was stirred for 1 hour at room temperature. The precipitate was removed by filtration and washed with CH$_2$Cl$_2$ (25 mL). The filtrate was concentrated to give a green oil which was chromatographed on silica gel eluting with 1:9 MeOH:CH$_2$Cl$_2$ to afford the title compound a green solid (contaminated with dicyclohexyl urea). The solid was triturated with hexane (50 mL) and filtered. The filtrate was concentrated to give the title compound (0.92 g, 65%) as a viscous green oil. 1H NMR (300 MHz, CDCl$_3$) δ 7.06–7.26 (mult, 4H), 4.25 (t, J=6.5 Hz, 2H), 3.62 (q, J=7.1 Hz, 1H), 2.28 (s, 3H), 2.21–2.67 (mult, 12H), 1.65–1.80 (mult, 1H), 1.45 (d, J=7.2 Hz, 3H), 0.88 (d, J=6.6 Hz, 6H); $^{13}$C NMR (75 MHz, CDCl$_3$) δ 174.6, 140.7, 137.6, 129.5, 127.3, 61.1, 57.7, 51.6(2C), 46.2, 45.3, 45.2, 36.7, 36.5, 30.3, 22.5, 18.5; mass spectrum (API-TIS) m/z 393 (M+H).

14b. 2-[1-Methyl-4-(nitrosothio)-4-piperidyl]ethyl 2-[4-(2-methylpropyl)phenyl]propanoate citrate Citric acid (0.44 g, 2.29 mmol) was dissolved in MeOH (3 mL) at 40° C. and the product of Example 14a (0.9 g, 2.29 mmol) was dissolved in EtOAc (5 mL). The solutions were mixed and left at −20° C. for 2 hours. The pale brown precipitate was removed by filtration and dried in vacuo for 6 hours to give the title compound as brown solid (0.76 g, 58%). mp 110° C. $^1$H NMR (300 MHz, d$_8$-THF) δ 7.32, J=8.1 Hz, 2H), 7.23 (d, J=8.0 Hz, 2H), 4.39 (t, J=6.5 Hz, 1H), 3.76–3.87 (mult, 1H), 2.55–3.30 (mult, 16H), 2.62 (s, 3H), 1.89–2.10 (mult, 1H), 1.55 (d, J=7.1 Hz, 3H), 1.04 (d, J=6.5 Hz, 6H). Anal Calcd for C$_{27}$H$_{40}$N$_2$O$_{10}$S$_1$: C, 55.47; H, 6.90; N, 4.79; S, 5.48. Found: C, 55.23; H, 7.01; N, 4.58; S, 5.37.

Example 15

2-[1-Methyl-4-(nitrosothio)-4-piperidyl]ethyl (2S) 2-(6-methoxy(2-naphthyl)) propanoate citrate 15a. 2-[1-Methyl-4-(nitrosothio)-4-piperidyl]ethyl (2S) 2-(6-methoxy(2-naphthyl)) propanoate DCC (0.56 g, 2.7 mmol) in CH$_2$Cl$_2$ (20 mL) was added dropwise to a stirred solution of the product of Example 13d (0.5 g, 2.45 mmol), (2S)-2-(6-methoxy(2-naphthyl)) propanoic acid (0.56 g, 2.45 mmol), and DMAP (0.05 g) in CH$_2$C$_2$ (20 mL) at room temperature. The resulting suspension was stirred for 1 hour at room temperature. The precipitate was removed by filtration and washed with CH$_2$Cl$_2$ (25 mL). The filtrate was concentrated to give a green oil which was chromatographed on silica gel eluting with 1:9 MeOH:CH$_2$Cl$_2$ to afford a green solid (contaminated with dicyclohexyl urea). The solid was triturated with hexane (50 mL) and filtered. The filtrate was concentrated to give the title compound (0.7 g, 69%) as a viscous green oil. $^1$H NMR (300 MHz, CDCl$_3$) δ 7.50–7.65 (mult, 3H), 7.01–7.29 (mult, 3H), 4.18 (t, J=6.5 Hz, 2H), 3.83 (s, 3H), 3.72 (q, J=7.0 Hz, 1H), 2.51 (t, J=6.6 Hz, 2H), 2.13 (s, 3H), 2.00–2.60 (mult, 8H), 1.45 (d, J=7.2 Hz, 3H), 1.47 (d, J=7.1 Hz, 3H); $^{13}$C NMR (75 MHz, CDCl$_3$) δ 174.4, 157.7, 135.4, 133.7, 129.2, 128.9, 127.2, 126.1, 126.0, 119.0, 105.6, 61.1, 57.6, 55.3, 51.4, 51.3, 46.0, 45.4, 40.8, 36.5, 36.4, 18.2; mass spectrum (API-TIS) m/z 415 (M+H).

15b. 2-[1-Methyl-4-(nitrosothio)-4-piperidyl]ethyl (2S) 2-(6-methoxy(2-naphthyl)) propanoate citrate Citric acid (0.33 g, 1.73 mmol) was dissolved in MeOH (3 mL) at 40° C. and the product of Example 15a (0.68 g, 1.73 mmol) was dissolved in EtOAc (5 mL). The solutions were mixed and left at −20° C. for 2 hours. The pale brown precipitate was removed by filtration and dried in vacuo for 6 hours to give the title compound as brown solid (0.72 g, 68%). mp 118° C.; $^1$H NMR (300 MHz, d$_8$-THF) δ 7.82–7.89 (mult, 3H), 7.50–7.54 (mult, 1H), 7.37–7.38 (mult, 1H), 7.27 (dd, J=2.3 and 8.9 Hz, 1H), 4.41 (t, J=6.5 Hz, 2H), 4.04 (s, 3H),), 3.99 (q, J=7.0 Hz, 1H), 2.94 (AB$_q$, J=15.3 Hz, Δv=27 Hz, 4H), 2.79 (t, J=6.4 Hz, 2H), 2.58 (s, 3H), 2.55–3.20 (mult, 8H), 1.67 (d, J=7.1 Hz, 3H). Anal Calcd for C$_{28}$H$_{36}$N$_2$O$_{11}$S$_1$: C, 55.25; H, 5.96; N, 4.60; S, 5.27. Found: C, 55.13; H, 5.88; N, 4.72; S, 5.23.

Example 16

2-[1-Methyl-4-(nitrosothio)-4-piperidyl]ethyl 2-[3-(phenylcarbonyl) phenyl]propanoate citrate 16a. 2-[1-Methyl-4-(nitrosothio)-4-piperidyl]ethyl 2-[3-(phenylcarbonyl) phenyl]propanoate DCC (0.33 g, 1.60 mmol) in CH$_2$Cl$_2$ (20 mL) was added dropwise to a stirred solution of the product of Example 13d (0.3 g, 1.47 mmol), 2-[3-(phenylcarbonyl)phenyl]propanoic acid 2-[3-(phenylcarbonyl)phenyl]propanoic acid (0.37 g, 1.47 mmol) and DMAP (0.05 g) in CH$_2$Cl$_2$ (20 mL) at room temperature. The resulting suspension was stirred for 1 hour at room temperature. The precipitate was removed by filtration and washed with CH$_2$Cl$_2$ (25 mL). The filtrate was concentrated to give a green oil which was chromatographed on silica gel eluting with 3:97 MeOH:CH$_2$Cl$_2$ to afford the title compound as a green solid (contaminated with dicyclohexyl urea). The solid was triturated with hexane (50 mL) and filtered. The filtrate was concentrated to give the title compound (0.41 g, 63%) as a viscous green oil. $^1$H NMR (300 MHz, CDCl$_3$) δ 7.35–7.73 (mult, 9H), 4.20 (t, J=6.6 Hz, 2H), 3.65 (q, J=7.1 Hz, 1H), 2.20 (s, 3H), 2.10–2.65 (mult, 10H), 1.44 (d, J=7.2 Hz, 3H); $^{13}$C NMR (75 MHz, CDCl$_3$) δ 196.3, 173.7, 140.6, 137.9, 137.4, 132.4, 131.4, 130.0, 129.1, 129.0, 128.5, 128.3, 61.2, 57.5, 51.4 (2C), 46.1, 45.3, 40.9, 36.6, 36.5, 18.2; mass spectrum (API-TIS) m/z 441 (M+H).

16b. 2-[1-Methyl-4-(nitrosothio)-4-piperidyl]ethyl 2-[3-(phenylcarbonyl) phenyl]propanoate citrate salt Citric acid (0.18 g, 0.93 mmol) was dissolved in MeOH (3 mL) at 40° C. and the product of Example 16a (0.41 g, 0.93 mmol) was dissolved in EtOAc (5 mL). The solutions were mixed and left at −20° C. for 12 hours. The pale brown precipitate was removed by filtration and dried in vacuo for 12 hours to give the title compound as brown solid (0.45 g, 76%). mp 98–104° C. $^1$H NMR (300 MHz, d$_8$-THF) δ 7.62–7.97 (mult, 9H), 4.40 (t, J=6.6 Hz, 2H), 3.97 (q, J=7.1 Hz, 1H), 2.64 (s, 3H), 2.60–3.30 (mult, 14H), 1.63 (d, J=7.1 Hz, 3H). Anal Calcd for C$_{30}$H$_{36}$N$_2$O$_{11}$S$_1$: C, 56.95; H, 5.74; N, 4.43; S, 5.07. Found: C, 56.77; H, 5.92; N, 4.25; S, 4.92.

Example 17

2-[1-Methyl-4-(nitrosothio)-4-piperidyl]ethyl 2{1-[(4-chlorophenyl) carbonyl]-5-methoxy-2-methylindol-3-yl}acetate citrate 17a. 2-[1-Methyl-4-(nitrosothio)-4-piperidyl]ethyl 2{1-[(4-chlorophenyl)carbonyl]-5-methoxy-2-methylindol-3-yl}acetate DCC (1.0 g, 4.84 mmol) was added to a stirred solution of the product of Example 13d (0.9 g, 4.40 mmol), 2-{1-[(4-chlorophenyl)carbonyl]-5-methoxy-2 methylindol-3-yl}acetic acid (1.57 g, 4.40 mmol), and DMAP (0.05 g) in CH$_2$Cl$_2$ (30 mL) at room temperature. The resulting suspension was stirred for 1 hour at room temperature. The precipitate was removed by filtration and washed with CH$_2$Cl$_2$ (25 mL). The filtrate was concentrated to give a green oil which was chromatographed on silica gel eluting with 5:95 MeOH:CH$_2$Cl$_2$ to afford a green solid (contaminated with dicyclohexyl urea). The solid was triturated with hexane (50 mL) and filtered. The filtrate was concentrated to give the title compound (1.85 g, 77%) as a viscous green oil. $^1$H NMR (300 MHz, CDCl$_3$) δ 7.47–7.65 (mult, 4H), 6.84–6.91 (mult, 2H), 6.65 (dd, J=2.5 and 9.0 Hz, 1H), 4.29 (t, J=6.7 Hz, 2H), 3.81 (s, 3H), 3.61 (s, 2H), 2.35 (s, 3H), 2.27 (s, 3H), 2.10–2.70 (mult, 10H); $^{13}$C NMR (75 MHz, CDCl$_3$) δ 170.5, 168.2, 156.1, 139.2, 135.9, 133.9, 131.1, 130.7, 130.6, 129.1, 114.9, 112.2, 111.6, 101.3, 61.3, 57.5, 55.7, 51.4 (2C), 46.1, 36.6, 30.3, 13.3; mass spectrum (API-TIS) m/z 544 (M+H).

17b. 2-[1-methyl-4-(nitrosothio)-4-piperidyl]ethyl 2{1-[(4-chlorophenyl)carbonyl]-5-methoxy-2-methylindol-3-yl}acetate citrate Citric acid (0.49 g, 2.57 mmol) was dissolved in MeOH (10 mL) at 40° C. and the product of Example 17a (1.4 g, 2.57 mmol) was dissolved in EtOAc (5 mL). The solutions were mixed and left at –20° C. for 12 hours. The pale brown precipitate was removed by filtration and dried in vacuo for 12 hours to give the title compound as a brown solid (1.8 g, 95%). m.p. 123° C. $^1$H NMR (300 MHz, d$_8$-THF) δ 7.86 d, J=8.4 Hz, 2H), 7.71 (d, J=8.4 Hz, 2H), 6.81 (dd, J=2.3 and 8.9 Hz, 1H), 4.45 (t, J=6.7 Hz, 2H), 3.95 (s, 3H), 3.84 (s, 2H), 2.57 (s, 3H), 2.57–3.20 (mult, 14H), 2.49 (s, 3H). Anal Calcd for C$_{33}$H$_{38}$N$_3$O$_{12}$S$_1$Cl: C, 53.84; H, 5.20; N, 5.71; S, 4.35; Cl, 4.82. Found: C, 53.69; H, 5.38; N, 5.57; S, 4.30; Cl, 4.61.

Example 18

2-{Methyl[2-methyl{[(nitrosothiol)cyclohexyl]methyl}amino)ethyl 2-{2-[(2,6-dichlorophenyl)amino]phenyl}acetate bis nitric acid salt 18a. 2,2,2-Trifluoro-N-{2-[(2-hyroxyethyl)amino]ethyl}acetamide 2-(2-aminoethylamino)ethanol (10 g, 96.01 mmol) was added via syringe to a stirred solution of ethyl trifluoroacetate (13.64 g, 96.01 mmol) in dry Et$_2$O (30 mL) at 0° C. The resulting solution was stirred at room temperature for 2 hours by which time a white precipitate had formed. The precipitate was removed by filtration, washed with Et$_2$O (100 mL), and dried in vacuo for 3 hours to afford the title compound (13.6 g, 100%). $^1$H NMR (300 MHz, CDCl$_3$) δ (t, J=5.1 Hz, 2H), 3.45 (t, J=5.6 Hz, 2H), 2.86 (t, J=5.6 Hz, 2H), 2.78 (t, J=4.9 Hz, 2H), 2.22 (br s, 2H); mass spectrum (API-TIS) m/z 201 (M+H).

18b. N-{2-[(tert-Butoxy)-N-(2-hydroxyethyl)carbonylamino]ethyl}-2,2,2-trifluoroacetamide BOC anhydride (14.83 g, 67.96 mmol) was added to a stirred solution of the product of Example 18a (13.6 g, 67.96 mmol) in THF (100 mL) and the mixture was stirred at room temperature for 2 hours. Water (200 mL) and EtOAc (100 mL) were added. The organic layer was isolated, dried over Na$_2$SO$_4$, and concentrated to give the title compound as a viscous oil (20 g, 98%). $^1$H NMR (300 MHz, CDCl$_3$) δ 2.35–3.75 (br mult, 8H), 1.45 (s, 9H); mass spectrum (API-TIS) m/z 301 (M+H).

18c. N-(2-Aminoethyl)(tert-butoxy)-N-(2-hydroxyethyl)carboxamide

A mixture of the product of Example 18b (20 g, 66.6 mmol) and solid K$_2$CO$_3$(5 g) in MeOH (50 mL) and water (10 mL) were heated at 60° C. for 18 hours. The solvent was evaporated to give a viscous oil which was extracted with EtOAc (5×50 mL). The combined organics were washed with water (50 mL). The organic phase was dried over Na$_2$SO$_4$ and the solvent was evaporated to afford the title compound (10 g, 66%) as an oil. $^1$H NMR (300 MHz, CDCl$_3$) δ 3.74 (mult, 2H), 3.30–3.50 (mult, 3H), 2.90–3.10 (mult, 3H), 1.46 (s, 9H); mass spectrum (API-TIS) m/z 205 (M+H).

18d. 2-{Methyl[methyl{[(nitrosothio)cyclohexyl]methyl}amino)ethyl]amino}ethan-1-ol.

A mixture of the product of Example 2a (5.84 g, 20.4 mmol) and the product of Example 18c (10 g, 49.01 mmol) in dry CHCl$_3$ (50 mL) were heated at 65° C. for 16 hours. The solvent was evaporated to obtain a viscous yellow liquid which was dissolved in MeOH (50 mL). NaBH$_4$ (1.8 g, 47.3 mmol) was added portionwise over 10 minutes and the resulting solution was stirred at room temperature for 1 hour. Formaldehyde 38% (20 mL) was added and the resulting cloudy solution was stirred for 2 hours at room temperature. The solvent was evaporated and the residue was partitioned between water (100 mL) and EtOAc (50 mL). The organic layer was separated and the aqueous layer was extracted with EtOAc (2×50 mL). The combined organic layers were dried over Na$_2$SO$_4$ and concentrated to give (16 g) a colorless viscous oil. This colorless oil in THF (50 mL) was added in a dropwise fashion to a stirred solution of lithium aluminum hydride (1M, 60 mL, 60 mmol) at room temperature under N$_2$. The resulting clear solution was stirred at room temperature for 4 hours. The excess lithium aluminum hydride was destroyed by portionwise addition of Na$_2$SO$_4$·10H$_2$O (10 g). The precipitate was removed by filtration and the solid was washed with 10% MeOH in CH$_2$Cl$_2$ (2×50 mL). The combined filtrate was dried over Na$_2$SO$_4$ and concentrated to give a viscous liquid (10 g). This viscous liquid (10 g) was dissolved in MeOH (30 mL) and cooled to 0° C. Concentrated HCl (5 mL) was added. 90% t-BuONO (5.4 mL, 38.4 mmol) was added via a syringe and the resulting green solution was stirred for 20 minutes at room temperature. The solution was poured onto crushed ice (10 g) and the resulting mixture was made basic with 10% Na$_2$CO$_3$ (10 mL). The green aqueous solution was extracted with EtOAc (3×50 mL). The organic layer was dried over Na$_2$SO$_4$ and concentrated. The residue was purified by chromatography on silica gel eluting with 1:9 MeOH:EtOAc to give the title compound (4.3 g). $^1$H NMR (CDCl$_3$) δ 3.57 (t, J=5.3 Hz, 2H), 3.19 (s, 2H), 3.05 (br s, 1H), 2.38 (s, 3H), 2.27 (s, 3H), 2.11–2.80 (mult, 8H), 1.40–1.85 (mult, 6H); $^{13}$C NMR (75 MHz, CDCl$_3$) δ 69.3, 64.4, 58.9, 58.5, 58.4, 55.3, 45.3, 42.2, 34.2, 25.5, 22.2.

18e. 2-{Methyl[2-methyl{[(nitrosothiol)cyclohexyl]methyl}amino)ethyl 2-{2-[(2,6-dichlorophenyl)amino]phenyl}acetate DCC (1.20 g, 5.80 mmol) in CH$_2$Cl$_2$ (25 mL) was added dropwise to a stirred solution of the product of Example 18d (1.3 g, 4.75 mmol (2-((2,6-dichlorophenyl) amino)benzene) acetic acid (1.4 g, 4.75 mmol), and DMAP (0.2 g) in CH$_2$Cl$_2$ (25 mL) at room temperature. The resulting suspension was stirred at room temperature for 3 hours. The precipitate was removed by filtration and washed with CH$_2$Cl$_2$ (25 mL). The filtrate was concentrated to give a green oil which was chromatographed on silica gel eluting with 1:1 EtOAc:hexane to give the title compound (0.82 g, 30.6%) as a viscous green oil. $^1$H NMR (300 MHz, CDCl$_3$) δ 7.32 (d, J=8.0 Hz, 2H), 7.21 (d, J=7.4 Hz, 1H), 7.11 (t, J=7.6 Hz, 1H), 6.90–6.99 (mult, 3H), 6.54 (d, J=8.0 Hz, 1H), 4.22 (t, J=5.8 Hz, 2H), 3.82 (s, 2H), 3.13 (s, 2H), 2.43–2.66 (mult, 4H), 2.33 (s, 3H), 2.24 (s, 3H), 2.0–2.15 (mult, 2H), 1.25–1.70 (mult, 6H); $^{13}$C NMR (75 MHz, CDCl$_3$) δ 172.3, 142.7, 137.8, 130.8, 129.5, 128.8, 127.9, 124.3, 123.9, 121.9, 118.2, 69.1, 64.5, 63.0, 58.2, 56.0, 55.9, 45.4, 42.9, 38.6, 34.2, 25.6, 22.3.

18f. 2-{Methyl[2-methyl{[(nitrosothiol)cyclohexyl] methyl}amino)ethyl 2-{2-[(2,6-dichlorophenyl)amino] phenyl}acetate bis nitrate salt Concentrated nitric acid (0.12 g, 1.9 mmol) in dry acetone (1 mL) was added to a stirred solution of the product of Example 18e (0.45 g, 0.792 mmol) in dry acetone (3 mL). The resulting solution was left at −20° C. for 12 hours. The pale brown precipitate was removed by filtration and dried in vacuo for 3 hours to give the title compound as a pale brown solid (0.406 g, 74%). mp 78° C.; $^1$H NMR (300 MHz, d$_8$-THF) δ 7.56, J=8.0 Hz, 2H), 7.49 (d, J=7.4 Hz, 1H), 7.16–7.26 (mult, 3H), 7.02 (t, J=7.4 Hz, 1H), 6.56 (d, J=7.9 Hz, 1H), 4.67 (t, J=4.6 Hz, 2H), 4.07 (s, 2H), 3.45–3.75 (mult, 6H), 3.07 (s, 3H), 2.76 (s, 3H), 2.65–2.79 (mult, 2H), 2.69–2.76 (mult, 2H), 1.60–2.00 (mult, 6H). Anal Calcd for $C_{27}H_{38}N_6O_9SCl_2$: C, 46.76; H, 5.52; N, 12.12; S, 4.62; Cl, 10.22. Found: C, 46.73; H, 5.57; N, 12.02; S, 4.90; Cl, 10.52.

Example 19

2-{Methyl[2-methyl{[(nitrosothiol)cyclohexyl] methyl}amino)ethyl 2-{1-[(4-chlorophenyl) carbonyl]-5-methoxy-2-methylindol-3-yl}acetate 19a. 2-{Methyl[2-methyl{[(nitrosothiol)cyclohexyl] methyl})ethyl 2-{1-[(4-chlorophenyl)carbonyl]-5-methoxy-2-methylindol-3-yl}acetate Solid DCC (2.86 g, 13.81 mmol) was added to a stirred solution of the product of Example 18d (3.0 g, 10.97 mmol), indomethacin (4.12 g, 11.52 mmol), and DMAP (0.2 g) in $CH_2Cl_2$ (30 mL) at room temperature. The resulting suspension was stirred for 2 hours at room temperature. The precipitate was removed by filtration and washed with $CH_2Cl_2$ (25 mL). The filtrate was concentrated to give a green oil which was chromatographed on silica gel eluting with 1:1 EtOAc:hexane to give the title compound (3.80 g, 56%) as a viscous green oil. $^1$H NMR (300 MHz, CDCl$_3$) δ 7.65, (J=8.4 Hz, 2H), 7.46 (d, J=8.4 Hz, 2H), 6.95 (d, J=2.4 Hz, 1H), 6.85 (d, J=8.4 Hz, 1H), 6.68 (d, J=2.4, Hz, 1H), 6.64 (d, J=2.4, Hz, 1H), 4.17 (t, J=9.7 Hz, 2H), 3.83 (mult, 3H), 3.68 (s, 2H), 3.14 (s, 2H), 2.28–2.70 (mult, 8H), 2.38 (s, 3H), 2.34 (s, 3H), 2.23 (s, 3H), 2.05–2.15 (mult, 2H), 1.45–1.85 (mult, 6H); $^{13}$C NMR (75 MHz, CDCl$_3$) δ 170.8, 168.3, 155.9, 139.2, 135.9, 133.8, 131.1, 130.7, 129.1, 114.9, 112.5, 111.5, 101.3, 69.1, 64.5, 62.8, 58.2, 56.0, 55.6, 45.4, 43.0, 34.2, 30.2, 25.5, 22.2, 13.4; mass spectrum (API-TIS) m/z 630 (M+H).

Example 20

2-([(Dimethylamino)ethyl]{[(nitrosothio)cyclohexyl] methyl}amino) ethyl 2-{2-[(2,6-dichlorophenyl) amino]phenyl}acetate 20a. 2,2,2-Trifluoro-N-[(methylamino)ethyl]acetamide N-Methyl ethylenediamine (15 g, 202.3 mmol) was added dropwise to a stirred solution of ethyl trifluoroacetate (28.7 g, 204.34 mmol) in dry Et$_2$O (50 mL) at 0° C. The resulting solution was stirred at room temperature for 2 hours. Hexane (75 mL) was added and the solution was left at −20° C. for 16 hours to produce a white precipitate which was removed by filtration, washed with Et$_2$O (100 mL) and dried in vacuo for 3 hours to afford the title compound (29.4 g, 85%). $^1$H NMR (300 MHz, CDCl$_3$) δ 3.42 (t, J=5.8 Hz, 2H), 2.80 (t, J=5.9 Hz, 2H), 2.43 (s, 3H); mass spectrum (API-TIS) 171 (M+H).

20b. N-{[(tert-Butoxy)-N-methylcarbonylamino]ethyl}-2,2,2-trifluoroacetamide

BOC anhydride (37.2 g, 170.4 mmol) was added to a stirred solution of the product of Example 20a (29.0 g, 170.45 mmol) in THF (100 mL) and the mixture was stirred at room temperature for 2 hours. Water (200 mL) and EtOAc (100 mL) were added. The organic layer was isolated and dried over Na$_2$SO$_4$. The solvent was evaporated to give the title compound as a viscous oil (45 g, 98%). $^1$H NMR (300 MHz, CDCl$_3$) δ 3.48 (br s, 4H), 2.90 (s, 3H), 1.45 (s, 9H); mass spectrum (API-TIS) m/z 271 (M+H).

20c. N-(2-Amninoethyl)(tert-butoxy)-N-(methyl) carboxamide

A mixture of the product of Example 20b (45.0 g, 166.5 mmol) and solid K$_2$CO$_3$(15 g) in MeOH (100 mL) and water (20 mL) were heated at 60° C. for 18 hours. The solvent was evaporated to give a viscous oil which was extracted with EtOAc (3×100 mL). The combined organics were washed with water (100 mL) and dried over Na$_2$SO$_4$. The solvent was evaporated to afford the title compound (7.8 g, 27%) as an oil. $^1$H NMR (300 MHz, CDCl$_3$) δ 3.30 (t, J=6.2 Hz, 2H), 2.91 (s, 3H), 2.88 (t, J=6.4 Hz, 2H), 1.49 (s, 9H); $^{13}$C NMR (75 MHz, CDCl$_3$) δ 79.4, 40.2, 34.6, 28.4 (3C); mass spectrum (API-TIS) m/z 175 (M+H).

20d. tert-Butyl 2-({[({[({[(tert-butyl)oxycarbonyl] methyl}{2-[(tert-butoxy)-N-methylcarbonylamino] ethyl}amino)methyl]cyclohexyl}disulfanyl)cyclohexyl] methyl}{2-[(tert-butoxy)-N-methylcarbonylamino] ethyl}amino)acetate A mixture of the product of Example 2a (5.34 g, 18.5 mmol) and the product of Example 20c (7.80 g, 44.76 mmol) in dry CHCl$_3$ (75 mL) were heated at 65° C. for 16 hours. The solvent was evaporated to obtain a viscous yellow liquid which was dissolved in MeOH (50 mL). NaBH$_4$ (3.4 g, 89.5 mmol) was added portionwise over 10 minutes and the resulting solution was stirred at room temperature for 1 hour. The solvent was evaporated and the residue was dissolved in water (100 mL). The mixture was extracted with EtOAc (3×75 mL). The combined organic extracts were dried over Na$_2$SO$_4$ and concentrated to give a colorless viscous oil. The colorless oil (10.2 g) was dissolved in CH$_3$CN (100 mL) and tert-butyl bromoacetate (20 g, 102.5 mmol) and solid K$_2$CO$_3$ (10 g) were subsequently added. The resulting suspension was stirred at room temperature for 12 hours. The solid was removed by filtration and washed with CH$_3$CN (50 mL). The filtrate was concentrated and the residue was chromatographed on silica gel eluting with 1:9 EtOAc:hexane to give the title compound (6.3 g, 41% based on cyclohexanecarboxaldehyde disulfide) and an unidentified lower Rf product (2.2 g). $^1$H NMR (300 MHz, CDCl$_3$) δ 3.38 (br s, 4H), 3.26 (br s, 4H), 2.87 (s, 10H), 2.84 (s,4H), 1.47 (s, 18H), 1.45 (s, 18H), 1.17–1.80 (mult, 20H); $^{13}$C NMR (75 MHz, CDCl$_3$) δ 171.3, 155.5, 80.8, 79.1, 65.6, 57.1, 56.1, 54.4, 47.7, 34.7, 32.7, 28.4 (3C), 28.2 (3C), 25.6, 22.3 (2C); mass spectrum (API-TIS) m/z 831 (M+H).

20e 2-([(Dimethylamino)methyl]{[(nitrosothio)cyclohexyl] methyl}amino)ethan-1-ol To a stirred solution of lithium aluminum hydride (1M, 23 mL, 23 mmol) was added the product of Example 20d (6.30 g, 7.58 mmol) in THF (50 mL) dropwise at room temperature under N$_2$. The resulting clear solution was stirred at room temperature for 1 hour and then heated at 70° C. for 12 hours and cooled to room temperature again. The excess lithium aluminum hydride was carefully destroyed by portionwise addition of solid Na$_2$SO$_4$·10H$_2$O (10 g). The precipitate was removed by filtration and washed with 10% MeOH in CH$_2$Cl$_2$ (2×50 mL). The combined filtrate was dried over Na$_2$SO$_4$ and concentrated to give a viscous liquid (3.2 g). The viscous liquid (3 g) was dissolved in MeOH (25 mL) and cooled to 0° C. Concentrated HCl (5 mL) was added. A solution of 90% t-BuONO (2.2 mL) was added via a syringe and the resulting green solution was stirred for 20 minutes at room temperature. The solution was then poured onto crushed ice (10 g) and the resulting mixture was made basic with 10% $Na_2CO_3$ (10 mL). The green aqueous solution was extracted with EtOAc (3×50 mL), dried over $Na_2SO_4$, and concentrated. The residue was purified by chromatography on silica gel eluting with 1:9 MeOH:$CH_2Cl_2$ to give the title compound (0.7 g) (substantial decomposition occurred during chromatography). $^1$H NMR ($CDCl_3$): δ 3.55, J=5.3 Hz, 2H), 3.35 (s, 2H), 2.70–2.82 (mult, 4H), 2.50–2.60 (mult, 2H), 2.22 (s, 6H), 2.10–2.40 (mult, 4H), 1.30–1.72 (mult, 6H); mass spectrum (API-TIS) m/z 290 (M+H).

20f. 2-([(Dimethylamino)methyl]{[(nitrosothio)cyclohexyl] methyl}amino)ethyl 2-{2-[2,6-dichlorophenyl)amino] phenyl}acetate DCC (0.59 g, 2.87 mmol) in $CH_2Cl_2$ (10 mL) was added dropwise to a stirred solution of the product of Example 20e (0.7 g, 2.41 mmol), (2-((2,6-dichlorophenyl)amino) benzene)acetic acid (0.71 g, 2.41 mmol), and DMAP (0.1 g) in $CH_2Cl_2$ (10 mL) at room temperature. The resulting suspension was stirred for 6 hours at room temperature. The precipitate was removed by filtration and washed with $CH_2Cl_2$ (25 mL). The filtrate was concentrated to afford a green oil which was chromatographed on silica gel eluting with 1:1 EtOAc:hexane followed by 1:9 MeOH:$CH_2Cl_2$ to afford the title compound (0.3 g, 22%) as a viscous green oil. $^1$H NMR (300 MHz, $CDCl_3$) δ 7.32 (d, J=8.0 Hz, 2H), 7.21 (d J=1.1 Hz, 1H), 7.18 (d J=1.1 Hz, 1H), 7.08–7.14 (mult, 1H), 6.91–6.99 (mult, 3H), 6.53 (d, J=7.9 Hz, 1H), 4.19 (t, J=6.2 Hz, 2H), 3.79 (s, 2H), 3.28 (s, 2H), 2.89 (t, J=6.2 Hz, 2H), 2.72–2.74 (mult, 2H), 2.31–2.47 (mult, 4H), 2.19 (s, 6H), 2.01–2.11 (mult, 2H), 1.45–1.68 (mult, 6H); $^{13}$C NMR (75 MHz, $CDCl_3$) δ 172.2, 142.6, 137.7, 130.8, 129.4, 128.8, 127.9, 124.1, 123.9, 121.9, 118.1, 67.3, 64.4, 62.9, 57.1, 54.5, 54.4, 45.7, 38.6, 34.2, 25.5, 22.2; mass spectrum (API-TIS) m/z 567 (M+H).

Example 21

2-[4-Methyl-4-(nitrosothio)piperidyl]ethyl (2S)-2-(6-methoxy(2-naphthyl))propanoate 21a. 2-(4-Methyl-4-sulfanylpiperidyl)ethyl (2S)-2-(6-methoxy(2-naphthyl)) propanoate To a mixture of the product of Example 1d (340 mg, 1.37 mmol) and, (2S)-2-(6-methoxy(2-naphthyl))propanoic acid (394 mg, 1.71 mmol) in $CH_2Cl_2$ (10 ml) was added DCC (353 mg, 1.71 mmol) all at once. A white precipitate started to form within five minutes. The reaction was stirred overnight. Ether was added to the mixture and the solid was removed by filtration. The solvent was evaporated. The residue was chromatographed on silica gel eluting with 1:3 EtOAc:hexane to afford the title compound (420 mg, 1.08 mmol, 79%) as a clear oil. $^1$H NMR (300 MHz, $CDCl_3$) δ 7.65 –7.70 (mult, 3H), 7.38–7.42 (mult, 1H), 7.10–7.15 (mult, 2H), 4.12–4.26 (mult, 2H), 3.91 (s, 3H), 3.85 (q, J=7.1 Hz, 1H), 2.57 (t, J=5.8 Hz, 2H), 2.44–2.51 (mult, 2H), 2.28–2.38 (mult, 2H), 1.52–1.63 (mult, 7H), 1.33 (s, 3H).

21b. 2-[4-Methyl-4-(nitrosothio)piperidyl]ethyl (2S)-2-(6-methoxy(2-naphthyl)) propanoate The product of Example 21a was dissolved in $Et_2O$ and HCl in $Et_2O$ was added dropwise. The white solid which formed was collected and washed thoroughly with $Et_2O$ and vacuum dried to give the HCl salt (400 mg, 0.94 mmol) as a white solid. The white solid (400 mg, 0.94 mmol) was dissolved in $CH_2Cl_2$ (4 ml) and cooled to 0° C. t-Butyl nitrite (187 μL, 1.42 mmol) was added. After 30 minutes, the solvent was evaporated to give a green solid which was partitioned between satd $K_2CO_3$ and EtOAc. The EtOAc extracts were combined and dried over $Na_2SO_4$. The solvent was evaporated and the residue was chromatographed on silica gel eluting with 1:1 EtOAc:hexane to give the title compound as green solid. mp 131° C.; $^1$H NMR (300 MHz, $CDCl_3$) δ 7.38–7.41 (mult, 1H), 7.09–7.15 (mult, 2H), 4.13–4.30 (mult, 2H), 3.91 (s, 3H), 3.85 (q, J=7.2 Hz, 1H), 2.54–2.63 (mult, 4H), 2.19–2.27 (mult, 4H), 1.96–2.04 (mult, 2H), 1.87 (s, 3H), 1.58 (d, J=7.1 Hz, 3H).

Example 22

2-(Methyl{[1-methyl-4-(nitrosothio)(4-piperidyl)] methyl}amino)ethyl (2S)-2-(6-methoxy(2-naphthyl)) propanoate hydrochloride 22a. tert-Butyl 6-aza-1-oxaspiro[2.5]octane-6-carboxylate To a suspension of NaH (3.13 g, 0.13 mol) in DMSO was added trimethylsulfoxonium iodide (28.7 g, 0.13 mol) in several portions. The mixture was stirred for 30 minutes. tert-Butyl-4-oxopiperidinecarboxyxlate (20.0 g, 0.10 mmol) was added at once and the mixture was heated at 60° C. for an hour. The reaction mixture was cooled to room temperature and poured into water. The mixture was extracted with EtOAc (2×). The combined organic layers were dried over $Na_2SO_4$ and then concentrated to give the title compound as a white solid (20.2 g, 9.46 mmol, 94%). $^1$H NMR (300 MHz, $CDCl_3$) δ 3.67–3.75 (mult, 2H), 3.37–3.46 (mult, 2H), 2.68 (s, 2H), 1.74–1.83 (mult, 2H), 1.46 (s, 9H), 1.39–1.45 (mult, 2H).

22b. tert-Butyl 6-aza-1-thiaspiro[2.5]octane-6-carboxylate

A mixture of the product of Example 22a (20.1 g, 9.44 mmol) and KSCN (27.5 g, 0.28 mol) in THF (94 ml) and water (94 ml) was stirred overnight. The reaction mixture was extracted with EtOAc. The combined organic extracts were dried over $Na_2SO_4$ and concentrated. The residue was chromatographed on silica gel eluting with 1:3 EtOAc:hexane to give the title compound (16.1 g, 70 mmol, 75%) as white crystals. $^1$H NMR (300 MHz, $CDCl_3$) δ 3.90–3.96 (mult, 2H), 3.08–3.21 (mult, 2H), 2.43 (s, 2H), 2.00–2.09 (mult, 2H), 1.43 (s, 9H), 1.35–1.43 (mult, 2H).

22c. tert-Butyl 4-{[(2-hydroxyethyl)methylamino]methyl}-4-sulfanyl piperidine carboxylate To a refluxing solution of 2-(methylamino)ethanol (17.5 ml) in benzene (35 ml) was added dropwise the product of Example 22b (5.0 g, 21.83 mmol) in benzene (20 ml) over 2.5 hours. The mixture was kept at reflux for another two hours then cooled to room temperature and poured into water. The mixture was extracted with EtOAc (2×). The combined organic extracts were dried over $Na_2SO_4$ and concentrated. The residue was chromatographed on silica gel eluting with 1:3 EtOAc:hexane to give the title compound (3.15 g, 10.36 mmol, 48%). $^1$H NMR (300 MHz, $CDCl_3$) δ 3.92–3.98 (mult, 2H), 3.64 (t, J=5.3 Hz, 2H), 3.13–3.19 (mult, 2H), 2.72 (t, J=5.3 Hz, 2H), 2.59 (s, 2H), 2.41 (s, 3H), 1.61–1.70 (mult, 4H), 1.47 (s, 9H).

22d. 2-{Methyl[(1-methyl-4-sulfanyl(4-piperidyl))methyl] amino}ethan-1-ol

To a solution of the product of Example 22c (3.92 g, 12.89 mmol) in THF (38 ml) was added lithium aluminum hydride (1M, 19.3 mL, 19.3 mmol) in THF. The mixture was refluxed overnight. The reaction was cooled to room temperature. Methanol was added to quench the reaction until no more bubbles were observed, followed by the addition of $H_2O$ until no more bubbles were formed. The mixture was filtered through celite and washed with 5:95 MeOH:$CH_2Cl_2$. The filtrate was concentrated to give the title compound (2.5 g, 11.46 mmol, 88%) which was used without further purification.

22e. 2-{Methyl[(1-methyl-4-sulfanyl(4-piperidyl))methyl]amino}ethyl (2S)-2-(6-methoxy(2-naphthyl))propanoate To a mixture of (2-((2,6-dichlorophenyl)amino)benzene) acetic acid (1.41 g, 4.76 mmol) and the product of Example 22d in CH$_2$Cl$_2$ (20 ml) was added DCC (1 g, 4.76 mmol) in CH$_2$Cl$_2$ (4.7 mL) at 0° C. The mixture was warmed to room temperature and filtered through celite. The filtrate was concentrated and the residue was chromatographed on silica gel eluting with 5:95 MeOH:CH$_2$C$_2$ to give the title compound (754 mg, 1.52 mmol, 32%) as a white foam. $^1$H NMR (300 MHz, CDCl$_3$) δ 7.33 (d, J=8.0, 2H), 7.20–7.23 (mult, 1H), 7.09–7.14 (mult, 1H), 6.93–6.99 (mult, 3H), 6.54 (d, J=8.0, 1H), 4.26 (t, J=5.8 Hz, 2H), 3.82 (s, 2H), 2.85 (t, J=5.8 Hz, 2H), 2.60–2.69 (mult, 2H), 2.52 (s, 2H), 2.41 (s, 3H), 2.33–2.37 (mult, 2H), 2.28 (s, 3H), 1.71–1.80 (mult, 2H), 1.57–1.61 (mult, 2H).

22f. 2-(Methyl{[1-methyl-4-(nitrosothio)(4-piperidyl)]methyl}amino)ethyl (2S)-2-(6-methoxy(2-naphthyl))propanoate hydrochloride To a stirred solution of the product of Example 22e (HCl salt, 683 mg, 1.2 mmol) in CH$_2$Cl$_2$ (10 ml) was added t-BuONO (138 mg, 1.2 nmmol) in CH$_2$Cl$_2$ (2 ml) over 5 minutes. The reaction mixture was stirred for 10 minutes. The reaction mixture was washed with satd Na$_2$CO$_3$, dried over Na$_2$SO$_4$, and concentrated. Chromatography on silica gel eluting with 2:98 MeOH:EtOAc afforded the title compound (612 mg, 1.02 mrnol, 85%) as a green oil. The HCl salt of the title compound was prepared using HCl/Et$_2$O. $^1$H NMR (300 MHz, CDCl$_3$) δ 7.36 (d, J=8.1 Hz, 2H), 7.23–7.27 (mult, 1H), 7.10–7.15 (mult, 1H), 6.91–7.05 (mult, 2H), 6.51 (d, J=8.0 Hz, 1H), 4.55–4.72 (mult, 2H), 3.90 (s, 2H), 2.36–3.75 (mult, 12 H), 2.84 (s, 3H), 2.81 (s, 3H).

Example 23

3-[4-methyl-4-(nitrosothio)piperidyl]propyl 2-{2-[(2,6-dichlorophenyl) amino]phenyl}acetate 23a. Methyl 3-(4-oxopiperidyl)propanoate To a suspension of 4-oxopiperidine hydrochloride monohydrate (10.0 g, 65.1 mmol) and methyl 3-bromopropanoate (7.8 ml, 71.6 mmol) in acetone (100 ml) was added K$_2$CO$_3$ (9.9 g, 71.6 mmol) and Et$_3$N (9.1 ml, 65.3 mmol). The mixture was refluxed for 24 hours. The solid was removed by filtration and the solvent was evaporated. The residue was partitioned between EtOAc and H$_2$O. The organic extracts were combined and dried over Na$_2$SO$_4$. The solvent was evaporated to give the title compound (15.0 g, 27.0 mmol, 42%) as an oil. $^1$H NMR (300 MHz, CDCl$_3$) δ 3.70 (s, 3H), 2.75–2.85 (mult, 6H), 2.52–2.57 (mult, 2H), 2.42–2.46 (mult, 4H).

23b. Methyl 3-(6-aza-1-oxaspiro[2.5]oct-6-yl)propanoate

To a suspension of NaH (2.11 g, 52.7 mmol) in DMSO (100 ml) was added trimethylsulfoxonium iodide (11.58 g, 52.62 mmol) in portions. The mixture was then stirred for 30 minutes. The product of Example 23a (7.49 g, 40.5 mmol) in DMSO (20 ml) was added and the mixture was heated at 60° C. for 1 hour. The reaction mixture was cooled to room temperature, poured into water, and extracted with EtOAc. The organic extracts were dried over Na$_2$SO$_4$. The solvent was evaporated to give the title compound (7.3 g, 36.7 mmol, 90.6%). $^1$H NMR (300 MHz, CDCl$_3$) δ 3.69 (s, 3H), 2.76 (t, J=5.3 Hz, 2H), 2.50–2.65 (mult, 7H), 1.80–1.85 (mult, 2H), 1.50–1.56 (mult, 2H).

23c. Methyl 3-(6-aza-1-thiaspiro[2.5]oct-6-yl)propanoate

To a solution of the product of Example 23b (6.2 g, 31.1 mmol) in MeOH (90 ml) was added thiourea (2.85 g, 37.4 mmol). The reaction mixture was heated at 45° C. for 3 hours. The solvent was evaporated and the residue was triturated with Et$_2$O and filtered. The filtrate was concentrated and again triturated with hexane and filtered. Evaporation of the solvent gave the title compound (5.06 g, 23.5 mmol, 76%) as a clear oil. $^1$H NMR (300 MHz, CDCl$_3$) δ 3.69 (s, 3H), 2.71–2.80 (mult, 4H), 2.34–2.56 (mult, 4H), 2.34 (s, 2H), 2.10–2.20 (mult, 2H), 1.52–1.60 (mult, 2H).

23d. 3-(4-Methyl-4-sulfanylpiperidyl)propan-1-ol

To a solution of lithium aluminum hydride (1M, 29.4 ml, 29.4 mmol) in THF at 0° C. was added the product of Example 23c (5.06 g, 23.5 mmol) dropwise over 20 minutes. The reaction was kept at 0° C. for 1 hour. Methanol (5 ml) was carefully added to destroy excess lithium aluminum hydride, followed by water (4 mnl). The solid which formed was removed by filtration and washed with 1:9 MeOH:CH$_2$Cl$_2$. The combined filtrates were concentrated to give the title compound (2.93 g, 15.5 mmol, 66%). $^1$H NMR (300 MHz, CDCl$_3$) δ 3.79 (t, J=5.2 Hz, 2H), 2.71–2.78 (mult, 2H), 2.65 (t, J=5.7 Hz, 2H), 2.40–2.46 (mult, 2H), 1.68–1.75 (mult, 6H), 1.62 (s, 1H), 1.44 (s, 3H).

23e. 3-[4-Methyl-4-(nitrosothio)piperidyl]propan-1-ol

To a mixture of the product of Example 23d (1.21 g, 6.40 mmol) in CH$_2$Cl$_2$ was added HCl in Et$_2$O. The solvent was evaporated to give a solid which was dissolved in EtOH (10 ml) and H$_2$O (2 ml). This homogeneous solution was added slowly to a stirred solution of t-BuONO (0.94 ml, 8.0 mmol) in EtOH (10 ml) over 10 minutes. The reaction mixture was stirred for 1 hour. The solvent was evaporated and the residue was dissolved in CH$_2$Cl$_2$ and washed with satd Na$_2$CO$_3$. The organic layer was dried over Na$_2$SO$_4$ and concentrated to give the title compound as a green oil (1.25 g, 5.73 mmol, 90%). $^1$H NMR (300 MHz, CDCl$_3$) δ 3.82 (t, J=5.2 Hz, 2H), 2.88–2.93 (mult, 2H), 2.65 (t, J=5.7 Hz, 2H), 2.47–2.53 (mult, 2H), 2.30–2.42 (mult, 2H), 2.21–2.28 (mult, 2H), 2.00 (s, 2H), 1.70–1.76 (mult, 2H).

23f. 3-[4-Methyl-4-(nitrosothio)piperidyl]propyl 2-{2-[(2,6-dichlorophenyl) amino]phenyl}acetate To a suspension of (2-((2,6-dichlorophenyl)amino)benzene)acetic acid (1.20 g, 4.05 mmol) and the product of Example 23e (0.68 g, 3.12 mmol) in CH$_2$Cl$_2$ (10 ml) was added DCC (1M solution in CH$_2$Cl$_2$, 4.05 ml, 4.05 mmol) over 15 minutes. DMAP (1 mg) was added and the reaction was stirred at room temperature for 1.5 hours. The solid which formed was removed by filtration. The solvent was evaporated and the residue was purified by chromatography on silica gel to give the title compound as a green oil (770 mg, 1.55 mmol, 50%). $^1$H NMR (300 MHz, CDCl$_3$) δ 7.33 (d, J=8.1 Hz, 2H), 7.21–7.26 (mult, 1H), 7.10–7.12 (mult, 1H), 6.91–7.00 (mult, 3H), 6.54 (d, J=8.0, 1H), 4.22 (t, J=6.5, 2H), 3.80 (s, 2H), 2.66–2.70 (mult, 2H), 2.18–2.48 (mult, 8H), 1.98 (s, 3H), 1.82–1.88 (mult, 2H); $^{13}$C NMR (75 MHz, CDCl) 172.3, 142.7, 137.8, 130.8, 129.5, 128.9, 127.9, 124.3, 124.0, 122.0, 118.2, 63.7, 55.9, 54.8, 49.9, 38.7, 38.3, 26.2.

Example 24

3-[4-Methyl-4-(nitrosothio)piperidyl]propyl (2S)-2-(6-methoxy (2-naphthyl))propanoate 24a. 3-[4-Methyl-4-(nitrosothio)piperidyl]propyl (2S)-2-(6-methoxy(2-naphthyl)) propanoate To a suspension of (2S)-2-(6-methoxy(2-naphthyl)) propanoic acid (901 mg, 3.91 mmol) and the product of Example 23e (0.57 g, 2.61 mmol) in CH$_2$Cl$_2$ (10 ml) was added DCC (800 mg, 3.9 mmol) in CH$_2$Cl$_2$ (3.9 mL) over 15 minutes. DMAP (3 mg) was added and the reaction was stirred at room temperature for 1.5 hours. The solid which formed was removed by filtration. The solvent was evaporated and the residue was purified by chromatography on silica gel to afford the title compound as a green solid. $^1$H NMR (300 MHz, CDCl$_3$) δ 7.65–7.69 (mult, 3H), 7.37–7.41

(mult, 1H), 7.09–7.14 (mult, 2H), 4.08–4.15 (mult, 2H), 3.90 (s, 3H), 3.79–3.86 (mult, 1H), 2.52–2.56 (mult, 2H), 2.35–2.39 (mult, 2H), 2.12–2.27 (mult, 6H), 1.93 (s, 3H), 1.70–1.77 (mult, 2H), 1.26 (d, J=2.8 Hz, 3H); $^{13}$C NMR (75 MHz, CDCl$_3$) δ 174.6, 157.6, 135.7, 133.7, 129.2, 128.9, 127.1, 126.2, 125.9, 119.0, 105.6, 63.0, 55.8, 55.3, 54.7, 49.8, 45.5, 38.2, 26.1, 18.3.

Example 25

2-[2-({N-[2-Methyl-2-(nitrosothio)propyl] carbamoyl}methoxy) acetylamino]ethyl 2-{2-[(2,6-dichlorophenyl)amino]phenyl}acetate 25a. 2-{[N-(2-Methyl-2-sulfanylpropyl)carbamoyl] methoxy}acetic acid To an ice-cooled suspension of 1-amino-2-methyl-2-propanethiol hydrochloride (4.21 g, 29.7 mmol) in CH$_2$Cl$_2$ (50 mL) was added Et$_3$N (4.56 mL, 32.7 mmol) followed by diglycolic anhydride (3.43 g, 29.6 mmol). After stirring at room temperature for 30 minutes the reaction was concentrated under vacuum. Cold 2N HCl (50 mL) was added to the residue. The mixture was extracted with EtOAc (5×30 mL). The combined organic extracts were washed with brine (30 mL) and dried over Na$_2$SO$_4$. Concentration and trituration with Et$_2$O:hexane gave the title compound as a white solid (5.50 g, 84.2%). mp 81–82° C.; $^1$H NMR (300 MHz, CDCl$_3$) δ 8.80 (br s, 1H), 7.48 (br s, 1H), 4.24 (s, 2H), 4.20 (s, 2H), 3.41 (d, J=6.4 Hz, 2H), 1.59 (s, 1H), 1.38 (s, 6H); $^{13}$C NMR (75 MHz, CDCl$_3$) δ 172.8, 170.4, 70.8, 68.4, 51.9, 44.9, 29.8; mass spectrum (API-TIS) m/z 239 (M+NH$_4$), 222 (M+H).

25b. 2-({N-[2-Methyl-2-(nitrosothio)propyl] carbamoyl}methoxy)acetic acid

To a solution of the product of Example 25a (5.76 g, 26.03 mmol) in CH$_2$Cl$_2$ (100 mL) at room temperature was added t-BuONO (3.2 mL, 27.37 mmol). After 30 minutes the reaction was concentrated and the residue solidified upon cooling. Washing with Et$_2$O:hexane gave the title compound (6.41 g, 98%) as a green crystal. mp 81–83° C.; $^1$H NMR (300 MHz, CDCl$_3$) δ 8.49 (br s, 1H), 7.28 (br s, 1H), 4.18 (s, 2H), 4.17 (s, 2H), 4.12 (d, J=6.5 Hz, 2H), 1.90 (s, 6H); $^{13}$C NMR (75 MHz, CDCl$_3$) δ 173.0, 170.7, 70.9, 68.4, 56.7, 49.0, 26.8; mass spectrum (API-TIS) m/z 268 (M+NH$_4$), 251 (M+H). Anal Calcd for C$_8$H$_{14}$N$_2$O$_5$S: C, 38.39; H, 5.64; N, 11.19; S,12.81. Found C, 38.56; H,5.76; N, 10.88; S, 12.96.

25c. 2-{[N-(2-Hydroxyethyl)carbamoyl]methoxy}-N-[2-methyl-2-(nitrosothio) propyl]acetamide To a solution of the product of Example 25b (1.0 g, 4.0 mmol) in CH$_2$Cl$_2$ (50 ml) was added ethanolamine (0.27 g, 4.42 mmol) followed by hydroxysuccinamide (509 mg, 4.4 mmol). DCC (824 mg, 4.0 mmol) in CH$_2$Cl$_2$ (4 mL) was then added and the reaction was stirred at room temperature for 0.5 hours. The reaction mixture was then poured into water (50 ml) and extracted with EtOAc (6×). The solvent was evaporated to give the title compound which was used for the next reaction without further purification.

25d. 2-[2-({N-[2-Methyl-2(nitrosothio)propyl] carbamoyl}methoxy)acetylamino]ethyl 2-{2-[(2,6-dichlorophenyl)amino]phenyl}acetate To a solution the product of Example 25c (4.0 mmol) and (2-((2,6-dichlorophenyl)amino)benzene)acetic acid (1.4 g, 4.8 mmol) in CH$_2$Cl$_2$ (50 ml) was added DCC (1 g, 4.8 mmol) in CH$_2$Cl$_2$ (4.8 mL) followed by DMAP (25 mg). The mixture was stirred at room temperature for 4 hours. The solid was removed by filtration. The filtrate was concentrated to give a residue which was chromatographed on silica gel eluting with EtOAc to give the title compound as a green foam (1.08 g, 1.89 mmol, 47% over two steps). $^1$H NMR (300 MHz, CDCl$_3$) δ 7.34 (d, J=8.1 Hz, 2H), 7.20 (dd, J=1.0 and 7.5 Hz, 1H), 7.13 (t, J=7.7 Hz, 1H), 6.92–7.02 (mult, 2H), 6.54 (d, J=7.0 Hz, 1H), 4.29 (t, J=5.1 Hz, 2H), 4.0 (d, J=7.5 Hz, 2H), 3.98 (s, 2H), 3.92 (s, 2H), 3.82 (s, 2H), 3.57–3.63 (mult, 2H), 1.87 (s, 6H); $^{13}$C NMR (75 MHz, CDCl$_3$) 172.7, 168.8, 168.4, 142.5, 137.5, 130.8, 129.4, 128.9, 128.1, 124.2, 123.8, 122.0, 118.2, 70.7, 63.7, 57.1, 49.1, 38.6, 38.3, 26.7.

Example 26

[2-({N-[2-Methyl-2-(nitrosothio)propyl] carbamoyl}methoxy) acetyloxy]methyl 2-{2-[(2,6-dichlorophenyl)amino]phenyl}acetate 26a. Chloromethyl 2-{2-[(2,6dichlorophenyl)amino] phenyl}acetate To a slurry of sodium (2-((2,6-dichlorophenyl)amino) benzene)acetic acid (10 g, 31 mmol), NaHCO$_3$ (9.9 g, 44 mmol), and n-Bu$_4$NOH (1 mL, 40% by wt in H$_2$O) in CH$_2$Cl$_2$ (90 mL) and H$_2$O (90 mL) was added chloromethylchlorosulfate (4.5 mL, 44 mmol) in CH$_2$Cl$_2$ (10 mL) over 15 minutes. After stirring for 1 hour the biphasic slurry became clear. The layers were separated and the aqueous phase was extracted with CH$_2$Cl$_2$. The combined organic layers were washed with 5% HaHCO$_3$, dried over Na$_2$SO$_4$, and concentrated. The residue was recrystallized from 5:1 hexane:EtOAc (25 mL) to give the title compound (12 g, 89%). mp 89–91° C.; $^1$H NMR (300 MHz, CDCl$_3$) δ 7.35 (d, J=8.0 Hz, 2H), 7.23 (d, J=7.8 Hz, 1H), 7.15 (dt, J=1.4 and 7.6 Hz, 1H), 6.99 (t, J=8.0 Hz, 1H), 6.99 (d, J=7.3 Hz, 1H), 6.58 (d, J=7.6 Hz, 1H),6.56 (s, 1H), 5.74 (s, 2H), 3.90 (s, 2H). Anal Calcd for C$_{15}$H$_{12}$Cl$_3$NO$_2$: C, 52.28; H, 3.51; N, 4.06; 30.86. Found C, 52.18; H, 3.64; N, 3.94; Cl, 30.67.

26b. Iodomethyl 2–12-[(2,6-dichlorophenyl)amino] phenyl}acetate

The product of Example 26a (710 mg, 2 mmol) and NaI (1.8 g, 12 mmol) were stirred overnight in acetone (6 mL) at room temperature. A 1:1 mixture of Et$_2$O:hexane (30 mL) was added to precipitate inorganic salts which were removed by filtration. Evaporation of the solvent and recrystallization of the residue from 10:1 hexane:EtOAc (2 mL) gave the title compound (450 mg, 50%). mp 66° C.; $^1$H NMR (300 MHz, CDCl$_3$) δ 7.34 (d, J=8.0 Hz, 2H), 7.22 (dd, J=1.4 and 7.8 Hz, 1H), 7.15 (dt, J=1.5 and 7.6 Hz, 1H), 6.96–7.02 (mult, 2H), 6.57 (d, J=7.6 Hz, 1H), 6.54 (s, 1H), 5.94 (s, 2H), 3.84 (s, 2H). Anal Calcd for C$_{15}$H$_{12}$Cl$_2$INO$_2$: C, 41.32; H, 2.77; N, 3.20; Cl, 16.26; I, 29.10. Found C, 41.59; H, 2.81; N, 3.20; Cl, 16.16; I, 28.99.

26c. [2-({N-[2-Methyl-2-(nitrosothio)propyl] carbamoyl}methoxy)acetyloxy]methyl 2-{2-[(2,6-dichlorophenyl)amino]phenyl}acetate To a solution of the product of Example 25b (0.39 g, 1.56 mmol) and the product of Example 26b (0.57 g, 1.31 mmol) in CH$_2$Cl$_2$ (10 ml) was added i-Pr$_2$NEt (0.27 ml, 1.56 mmol). The reaction was stirred at room temperature for 2 hours. The solvent was evaporated. The residue was chromatographed on silica gel eluting with 1:4 EtOAc:hexane to give the title compound (233 mg, 0.42 mmol, 32%) as a green oil. $^1$H NMR (300 MHz, CDCl$_3$) δ 7.33 (d, J=8.1 Hz, 2H), 7.22 (dd, J=1.3 and 7.5 Hz, 1H), 7.12–7.15 (mult, 2H), 7.00–7.02 (mult, 2H), 6.56 (d, J=8.1 Hz, 1H), 5.84 (s, 2H), 4.13 (s, 2H), 4.07 (d, J=6.8 Hz, 2H), 4.06 (s, 2H), 3.87 (s, 2H), 1.89 (s, 6H); $^{13}$C NMR (75 MHz, CDCl$_3$) δ 170.7, 169.0, 168.4, 142.5, 137.5, 130.9, 129.3, 128.8, 128.3, 124.1, 123.3, 122.3, 118.5, 79.6, 71.0, 68.0, 56.8, 48.8, 38.0, 31.5, 26.7, 22.6, 14.1, 14.0.

Example 27

2-[4-(Nitrosothio)-4-piperidyl]ethyl (2S)-2-(6-methoxy(2-naphthyl)) propanoate hydrochloride 27a. 2-{1-[(tert-Butyl)oxycarbonyl]-4-sulfanyl-4-piperidyl}ethyl (2S)-2-(6-methoxy(2-naphthyl)) propanoate The product of Example 6d (210 mg, 0.8 mmol) and pyridine were dissolved in $CH_2Cl_2$ (5 mL) and cooled to 0° C. The acid chloride of (2S)-2-(6-methoxy(2-naphthyl)) propanoic acid (200 mg, 0.8 mmol) in $CH_2Cl_2$ (2 mL) was added dropwise. The reaction was allowed to warm to room temperature with continued stirring over 1 hour. Additional acid chloride (150 mg, 0.6 mmol) was added and stirring continued for 1 hour. The reaction mixture was diluted with $CH_2Cl_2$ (25 mL); washed 1×15 with 1N HCl, satd $NaHCO_3$, and brine; and dried over $Na_2SO_4$. Evaporation of the solvent and chromatography on silica gel eluting with 5:1 hexane:EtOAc gave 210 mg (55%) of the title compound. $^1$H NMR (300 MHz, $CDCl_3$) δ 7.64–7.72 (mult, 3H), 7.37 (dd, J=1.8 and 8.5 Hz, 1H), 7.11–7.16 (mult, 2H), 4.35 (d, J=6.8 Hz, 2H), 3.91 (s, 3H), 3.82 q, J=7.1 Hz, 1H), 3.72–3.78 (mult, 2H), 3.13 (ddd; J=6.7, 10.8, and 15 Hz; 2H), 1.87 (dt, J=1.5 and 6.7 Hz, 2H), 1.57 (d, J=7.1 Hz, 3H), 1.44 (s, 9H), 1.48–1.53 (mult, 2H).

27b. 2-(4-Sulfanyl-4-piperidyl)ethyl (2S)-2-(6-methoxy(2-naphthyl))propanoate Hydrochloride The product of Example 27a (370 mg, 0.8 mmol) was dissolved in 4.9M HCl in $Et_2O$ (6 mL). The reaction was allowed to stir at room temperature for 2 hours during which time a precipitate formed. The solid was isolated by filtration, washed with fresh $Et_2O$, and dried in vacuo. This gave 230 mg (70%) of the title compound. mp 222–225° C.; $^1$H NMR (300 MHz, $d_6$-DMSO) δ 9.02 (br s, 1H), 8.88 (br s, 1H), 7.76–7.81 (mult, 2H), 7.70 (s, 1H), 7.37 (d, J=8.5 Hz, 1H), 7.28 (d, J=2.2 Hz, 1H), 7.14 (dd, J=2.4 and 9.0 Hz, 1H), 4.26 (d, J=6.4 Hz, 2H), 3.89 (q, J=6.8 Hz, 1H), 3.85 (s, 3H), 2.93–3.03 (mult, 5H), 1.87 (d, J=6.7 Hz, 2H), 1.55–1.81 (mult, 4H), 1.46 (d, J=7.1 Hz, 3H). Anal Calcd for $C_{21}H_{27}NO_3S·HCl$: C, 61.52; H, 6.88; N, 3.42; Cl, 8.65. Found C, 61.50; H, 6.92; N, 3.38; Cl, 8.67.

27c. 2-[4-(Nitrosothio)-4-piperidyl]ethyl (2S)-2-(6-methoxy(2-naphthyl))propanoate Hydrochloride The product of Example 27b (50 mg, 0.12 mmol) was dissolved in a mixture of HOAc (2 mL) and $CH_2Cl_2$ (6 mL) and cooled to 0° C. protected from light. t-BuONO (22 mL, 0.18 mmol) was added and the mnixture was stirred for 1 hour. The $CH_2Cl_2$ was removed on a rotary evaporator and the HOAc was removed via lyophilization. This gave the title compound as a light green powder. $^1$H NMR (300 MHz, $d_6$-DMSO) δ 11.91 (br s, 1H), 8.96 (br s, 1H), 7.75–7.80 (mult, 2H), 7.67 (s, 1H), 7.33 (dd, J=1.6 and 8.5 Hz, 1H), 7.28 (d, J=2.3 Hz, 1H), 7.14 (dd, J=2.5 and 8.9 Hz, 1H), 4.21 (d, J=6.2 Hz, 2H), 3.86 (q, J=7.0 Hz, 1H), 3.85 (s, 3H), 3.11–3.30 (mult, 2H), 2.82–3.02 (mult, 2H), 2.35–2.60 (mult, 6H), 1.43 (d, J=7.1 Hz, 3H).

Example 28

{[3-(Methyl{[(nitrosothio)cyclohexyl]methyl}amino)propyl]oxycarbonyl}methyl 2-{2-[(2,6-dichlorophenyl)amino]phenyl}acetate 28a. {[3(Methyl{[(nitrosothio)cyclohexyl]methyl}amino)propyl]oxycarbonyl}methyl 2-{2-[(2,6-dichlorophenyl)amino]phenyl}acetate 2-(2-{2-[(2,6-Dichlorophenyl)amino]phenyl}acetyloxy) acetic acid (115 mg, 0.32 mmol), the product of Example 4c (80 mg, 0.32 mmol), and DMAP (20 mg, 0.16 mmol) were dissolved in $CH_2Cl_2$ (4 mL). DCC (70 mg, 0.32 mmol) was added and the solution was stirred at room temperature for 1 hour. The solution was filtered to remove dicyclohexyl urea and the solvent was evaporated on a rotary evaporator. The residue was filtered through silica gel eluting with 3:1 hexane:EtOAc. $^1$H NMR (300 MHz, $CDCl_3$) δ 7.33 (d, J=8.1 Hz, 2H), 7.27 (mult, 1H), 7.13 (t, J=6.5 Hz, 1H), 6.94–7.00 (mult, 2H), 6.73 (s, 1H), 6.55 (d, J=8.0 Hz, 1H), 4.67 (s, 2H), 4.15 (t, J=6.5 Hz, 2H), 3.93 (s, 2H), 3.10 (s, 3H), 2.42–2.50 (mult, 4H), 2.28 (s, 3H), 2.02–2.11 (mult, 2H), 1.44–1.71 (mult, 8H).

Example 29

2-{4-[3-Methyl-3-(nitrosothio)butanoyl]piperazinyl}ethyl 2-{2-[(2,6-dichlorophenyl)methyl]phenyl}acetate 29a. 1-[4-(2-Hydroxyethyl)piperazinyl]-3-methyl-3-(phenylmethylthio)butan-1-one A mixture of 3-methyl-3-(phenylmethylthio)butanoic acid (1 g, 4.6 mmol) and hexachloroacetone were dissolved in $CH_2Cl_2$ (20 mL) and cooled to −78° C. Triphenyl phosphine was added and the mixture was stirred for 30 minutes. Hydroxyethyl piperazine (550 μL, 4.5 mmol) was added in $CH_2Cl_2$ (10 mL) dropwise. Triethylamine (630 μL, 4.5 mmol) was added in $CH_2Cl_2$ (10 mL) dropwise. The cold bath was removed and the solution was stirred for 24 hours. The solvent was evaporated. The crude mixture was poured into 1N HCl (100 mL) and washed with $Et_2O$ (2×50 mL). The aqueous layer was made basic with 10% $K_2CO_3$ in a brine solution. The product was extracted with EtOAc (3×100 mL), dried over $Na_2SO_4$, and concentrated. This gave the title compound which was used immediately in the next reaction. $^1$H NMR (300 MHz, $CDCl_3$) δ 7.18–7.37 (mult, 5H), 3.8 (s, 2H), 3.6 (t, J=5 Hz, 4H), 3.4 (t, J=5 Hz, 2H), 2.45–2.65 (mult, 8H), 1.5 (s, 6H).

29b. 1-[4-(2-Hydroxyethyl)piperazinyl]-3-methyl-3-sulfanylbutan-1-one

Ammonia (100 mL) was condensed into a 3 neck flask at −78° C. The product of Example 29a was added to the flask in a minimum amount of $Et_2O$. The solution was stirred for 20 mninutes. Sodium was added in pea sized chunks until the solution remained a blue color for greater than 10 minutes. The solution was stirred for an additional 30 minutes. The ice bath was removed and the ammonia was allowed to evaporate at room temperature. This gave the title compound (600 mg, 55% over 2 steps). $^1$H NMR (300 MHz, $CDCl_3$) δ 3.63 (t, J=5 Hz, 4H), 3.52 (t, J=5 Hz, 2H), 2.63 (s, 2H), 2.38–2.57 (mult, 6H), 1.51 (s, 6H).

29c. 1-[4-(2-Hydroxyethyl)piperazinyl]-3-methyl-3-(nitrosothio)butan-1-one

A solution of t-BuONO (270 μL, 2.25 mmol) was dissolved in $CH_2Cl_2$ (5 mL) and cooled to −78° C. The product of Example 29b (430 mg, 1.5 mmol) in MeOH (0.5 mL) and $CH_2Cl_2$ (10 mL) was added dropwise over 15 miinutes. The ice bath was removed and stirring was continued for 30 minutes. The solvent and excess reagent were evaporated. This gave the title compound (400 mg, 97%). $^1$H NMR (300 MHz, $CDCl_3$) δ 3.63 (t, J=5 Hz, 4H), 3.47 (t, J=5 Hz, 2H), 3.27 (s, 2H) 2.44–2.60 (mult, 6H), 2.04 (s, 6H).

29d. 2-{4-[3-Methyl-3-(nitrosothio)butanoyl]piperazinyl}ethyl 2-{2-[(2,6-dichlorophenyl)methyl]phenyl}acetate The product of Example 29c (400 mg, 1.45 mmol), (2-((2,6-dichlorophenyl)amino)benzene)acetic acid (520 mg, 1.7 mmol), DCC (350 mg, 1.7 mmol), and DMAP (50 mg, 0.3 mmol) were dissolved in $CH_2Cl_2$ (50 mL). The solution was stirred for 3 hours at room temperature. The precipitate was removed by filtration and the filtrate was concentrated. The residue was chromatographed on silica gel eluting with 1:1 hexane:EtOAc. This gave the title compound (400 mg, 50%) as a green oil. $^1$H NMR (300 MHz, CDCl$_3$) δ 7.34 (d, J=8 Hz, 2H), 7.22 (d, J=8 Hz, 1H), 7.1–7.05 (mult, 1H), 6.93–7.01 (mult, 2H), 6.84 (s, 1H), 6.53 (d, J=8 Hz, 1H), 4.27 (t, J=5 Hz, 2H), 3.81 (s, 2H), 3.46–3.54 (mult, 2H), 3.29–3.37 (mult, 2H), 3.22 (s, 2H), 2.63 (t, J=5 Hz, 2H), 2.31–2.42 (mult, 4H), 2.02 (s, 6H); $^{13}$C NMR (75 MHz, CDCl$_3$) δ 172.0, 167.6, 142.6, 137.6, 130.8, 129.5, 128.9, 128.0, 124.1, 121.9, 118.1, 62.2, 56.3, 54.8, 53.1, 52.9, 46.0, 44.5, 41.4, 38.6, 29.1.

Example 30

{4-[Dicyclopropyl(nitrosothio)methyl]-1-methyl-4-piperidyl}methyl (2S)-2-(6-methoxy(2-naphthyl)) propanoate 30a. tert-Butyl 4-(dicyclopropylsulfanylmethyl)-4-(ethoxycarbonyl)piperidine carboxylate To a stirred solution of ethyl N-(t-butoxycarbonyl) isonipecotate (1.06 g, 4.12 mmol) in THF (8 mL) at −78° C. was added LDA (1.5M, 2.75 mL, 4.12 mmol) dropwise, and the mixture was stirred for 30 minutes before addition of a solution of dicyclopropylthioketone (415 mg, 3.30 mmol) in THF (1 mL). After the addition, the reaction mixture was warmed to room temperature over 2 hours, quenched with satd aq NH$_4$Cl, and extracted with EtOAc. The combined organic extracts were dried over Na$_2$SO$_4$, filtered, and concentrated to afford the title compound as a viscous oil (1.53 g, 96%), which was used in the next step without further purification.

30b. [4-(Dicyclopropylsulfanylmethyl)-1-methyl-4-piperidyl]methan-1-ol

To a stirred solution of the product of Example 30a (1.20 g, 3.13 mmol) in THF (10 mL) was added lithium aluminum hydride (1M, 9.4 mL, 9.4 mmol) in THF dropwise. The mixture was heated to reflux for 15 hours. After cooling to room temperature, the mixture was poured onto Na$_2$SO$_4$·10H$_2$O, filtered, and concentrated. The residue was chromatographed on silica gel eluting with 1:9 MeOH:CHCl$_3$ to give the title compound (0.38 g, 48%) as a white solid. mp 66° C.; $^1$H NMR (300 MHz, CDCl$_3$) δ 4.00 (s, 2H), 2.7–2.8 (mult, 2H), 2.30 (s, 3H), 2.1–2.2 (mult, 3H), 1.7–1.8 (mult, 3H), 1.0–1.1 (mult, 2H), 0.4–0.7 (mult, 6H); $^{13}$C NMR (75 MHz, CDCl$_3$) δ 61.8, 58.9, 51.9, 46.1, 44.6, 27.9, 16.2, 3.0, 1.0.

30c. [4-(Dicyclopropylsulfanylmethyl)-1-methyl-4-piperidyl]methyl (2S)-2-(6-methoxy(2-naphthyl)) propanoate A solution of the acid chloride from (2S)-2-(6-methoxy (2-naphthyl))propanoic acid (0.341 g, 1.37 mmol), the product of Example 30b (0.293 g, 1.14 mmol), and pyridine (0.5 mL) in CH$_2$Cl$_2$ (8 mL) were stirred at room temperature overnight. After being diluted with CH$_2$Cl$_2$ (30 mL), the mixture was washed with 2M Na$_2$CO$_3$, dried over Na$_2$SO$_4$, filtered, and concentrated. The residue was chromatographed on silica gel eluting with 2% MeOH:CHCl$_3$ to afford the title compound (0.430 g, 81%) as a foam. $^1$H NMR (300 MHz, CDCl$_3$) δ 7.0–7.7 (mult, 6H), 4.40 (d, J=16.4 Hz, 1H), 4.22 (d, J=16.4 Hz, 1H), 3.89 (s, 3H), 3.77 (q, J=7.4 Hz, 1H), 2.7–1.8 (m 8H), 2.20 (s, 3H), 1.71 (d, J=7.4 Hz, 3H), 1.20 (s, 1H), 0.9–0.2 (mult, 10H).

30d. {4-[Dicyclopropyl(nitrosothio)methyl]-1-methyl-4-piperidyl{methyl (2S)-2-(6-methoxy(2-naphthyl)) propanoate To a stirred solution of the product of Example 30c (268 mg, 0.573 mmol) in CH$_2$Cl$_2$ (5 mL) at 0° C. were added pyridine (162 μL, 2 mmol) and nitrosonium tetrafluoroborate (81 mg, 0.69 mmol). After stirring for 15 minutes, the reaction mixture was quenched with water (2 mL) and partitioned between CH$_2$Cl$_2$ and 1M K$_2$CO$_3$. The organic layer was separated, dried over Na$_2$SO$_4$, filtered, and concentrated. The residue was chromatographed on silica gel eluting with EtOAc to give the title compound (259 mg, 91%) as a green solid. mp 88° C.; $^1$H NMR (300 MHz, CDCl$_3$) δ 7.07–7.70 (mult, 6H), 4.63 (d, J=12.8 Hz, 1H), 4.50 (d, J=12.8 Hz, 1H), 3.92 (s, 3H), 3.84 (q, J=7.2 Hz, 1H), 1.7–2.8 (mult, 8H), 2.21 (s, 3H), 1.57 (d, J=7.2 Hz, 3H), 0.15–0.75 (mult, 10 H)

Example 31

2-{2-[(2,6-Dichlorophenyl)amino]phenyl}-1-(2-{methyl[2-methyl-2-(nitrosothio)propyl] amino}ethylthio)ethan-1-one hydrochloride 31a. Di 1-methyl-1-(1,3-thiazolidin-2-yl)ethyl disulfide A stirred mixture of 2-[(1,1-dimethyl-2-oxoethyl) disulfanyl]-2-methylpropanal (0.54 g, 2.60 mmol), 2-aminoethanethiol hydrochloride (0.63 g, 5.5 mmol), and K$_2$CO$_3$ (1.0 g) in MeOH (15 mL) were heated to reflux for 1 hour. After cooling to room temperature, the mixture was filtered, and the filtrate was concentrated to give the title compound (a mixture of diastereomers) as a colorless liquid (0.85 g, 94%). $^1$H NMR (300 MHz, CDCl$_3$) δ 4.77 and 4.75 (2s, 2H), 3.7–3.4 (mult, 2H), 2.7–3.1 (mult, 6H), 1.99 (br s, 2H), 1.51 and 1.47 (2s, 12H).

31b. tert-Butyl 2-{1-[(1-{3-[(tert-butyl)oxycarbonyl](1,3-thiazolidin-2-yl)}-isopropyl)disulfanyl]-isopropyl}-1,3-thiazolidine-3-carboxylate A solution of the product of Example 31a (7.43 g, 28.6 mmol), di-t-butyl dicarbonate (15.6 g, 71.5 mmol), DMAP (12 mg), and Et$_3$N (20 mL, 143 mmol) in CH$_2$Cl$_2$ (100 mL) were stirred at room temperature for 15 hours. After being diluted with CH$_2$Cl$_2$ (200 mL), the mixture was washed with 1N HCl, dried over Na$_2$SO$_4$, filtered, and concentrated. This gave the title compound (12.5 g) as an oil which was used in the next step without further purification.

31c. 2-Methyl-1-[methyl(2-sulfanylethyl)amino]propane-2-thiol

To a stirred solution of the product of Example 31b (2.35 g, 4.48 mmol) in THF (50 mL) was added lithium aluminum hydride (1.0M, 20 mL, 20 mmol) in THF dropwise. The mixture was heated to reflux overnight. Upon cooling, the mixture was poured onto Na$_2$SO$_4$·10H$_2$O, filtered, and concentrated to give the title compound (0.98 g, 61%) as a colorless liquid. $^1$H NMR (300 MHz, CDCl$_3$) δ 2.74 (t, J=5.9 Hz, 2H), 2.63 (t, J=5.9 Hz, 2H), 2.48 (s, 2H), 2.37 (s, 3H), 1.43 and 1.42 (2s, 2H), 1.36 (s, 6H).

31d. 2-{2-[(2,6-dichlorophenyl)amino]phenyl}-1-{2-[methyl(2-methyl-2-sulfanylpropyl)amino] ethylthio}ethan-1-one hydrochloride A solution of the product of Example 31c (2.58 g, 14.3 mmol), (2-((2,6-dichlorophenyl)amino)benzene)acetic acid (5.09 g, 17.2 mmol), and DCC (3.55 g, 17.2 mmol) in CH$_2$Cl$_2$ (60 mL) were stirred at room temperature for 90 minutes. The solid formed during the reaction was removed by filtration and the filtrate was concentrated. The residue was chromatographed on silica gel eluting with 1:9 EtOAc:hexane. The free base was converted to its hydrochloride by treatment with an ether solution of HCl to give the title compound (8.8 g, 73%). $^1$H NMR (300 MHz, d$_6$-DMSO) δ 6.5–8.2 (mult, 8H), 4.02 (s, 2H), 3.06 (t, J=6.5

Hz, 2H), 2.74 (t, J=6.5 Hz, 2H), 2.63 (s, 2H), 2.40 (s, 3H), 1.38 (s, 6H); $^{13}$C NMR (75 MHz, d$_6$-DMSO) δ 198.5, 142.5, 137.6, 130.8, 129.4, 128.7, 128.0, 124.2, 123.9, 121.9, 118.0, 71.5, 58.7, 47.6, 46.3, 44.2, 30.2, 27.7.

31e. 2-{2-[(2,6-Dichlorophenyl)amino]phenyl}-1-(2-{methyl[2-methyl-2-(nitrosothio) propyl] amino}ethylthio)ethan-1-one hydrochloride To a stirred solution of the product of Example 31d (0.47 g, 0.951 mmol) in CH$_2$Cl$_2$ (20 mL) at −5° C. was added t-BuONO (0.132 mL, 1.00 mmol) and the mixture was stirred for 5 minutes. Evaporation of the solvent afforded the desired product as a green solid (0.48 g, 96%). $^1$H NMR (300 MHz, d$_6$-DMSO) δ 6.5–7.7 (mult, 8H), 4.01 (s, 2H), 3.09 (s, 2H), 3.00 (t, J=6.4 Hz, 2H), 2.72 (t, J=6.4 Hz, 2H), 2.39 (s, 3H), 1.85 (s, 6H); $^{13}$C NMR (75 MHz, d$_6$-DMSO) δ 198.6, 142.6, 137.6, 130.9, 129.5, 128.8, 128.1, 124.2, 124.0, 121.9, 118.1, 68.4, 58.8, 58.7, 47.6, 44.3, 27.4, 26.9.

Example 32

2-{2-[(2,6-Dichlorophenyl)amino]phenyl}-1-[2-(methyl{[(nitrosothio) cyclohexyl]methyl}amino) ethylthio]ethan-1-one 32a. 1-{[Methyl(2-sulfanylethyl)amino]methyl}cyclohexane-1-thiol The title compound was synthesized from the product of Example 2a in using a sequence analogous to the preparation of the product of Example 31c. $^1$H NMR (300 MHz, CDCl$_3$) δ 2.88 (t, J=6.6 Hz, 2H), 2.77 (t, J=7.7 Hz, 2H), 2.54 (s, 2H), 2.38 (s, 3H), 1.9–1.4 (mult, 12H).

32b. 2-{2-[(2,6-Dichlorophenyl)amino]phenyl}-1-(2-{methyl[(sulfanylcyclohexyl) methyl]amino}ethylthio) ethan-1-one A solution of the product of Example 32a (2.44 g, 11.1 mmol), (2-((2,6-dichlorophenyl)amino)benzene)acetic acid (3.29 g, 11.1 mmol), and DCC (2.29 g, 11.1 mmol) in CH$_2$Cl$_2$ (60 mL) were stirred at room temperature for 40 minutes. The solid formed during the reaction was removed by filtration and the filtrate was concentrated. The residue was chromatographed on silica gel eluting with 1:10 EtOAc:hexane to give the title compound (1.20 g, 30%) as a white solid. mp 55° C.; 1H NMR (300 MHz, CDCl$_3$) δ 6.5–7.4 (mult, 8H), 4.04 (s, 2H), 3.08 (t, J=7.3 Hz, 2H), 2.76 (t, J=7.3 Hz, 2H), 2.54 (s, 2H), 2.43 (s, 3H), 2.16 (s, 1H), 1.4–1.8 (mult, 10H); $^{13}$C NMR (75 MHz, CDCl$_3$)δ 198.7, 142.6, 137.6, 130.9, 129.4, 128.8, 128.0, 124.3, 123.9, 121.9, 118.1, 58.9, 52.2, 47.6, 44.6, 37.7, 27.6, 25.9, 22.3.

32c. $^2$-{2-[(2,6-Dichlorophenyl)amino]phenyl}-1-[2-(methyl{[(nitrosothio) cyclohexyl]methyl}amino) ethylthio]ethan-1-one To a stirred solution of the product of Example 32b (0.790 g, 1.48 mmol) in CH$_2$Cl$_2$ (25 mL) at 0° C. was added t-BuONO (200 μL, 1.50 mmol), and the mixture was stirred for 10 additional minutes. Evaporation of the solvent gave the title compound as a green solid (800 mg, 90%). mp 115–129° C.; $^1$H NMR (300 MHz, CDCl$_3$) δ 6.5–7.4 (mult, 8H), 4.00 (s, 2H), 3.19 (s, 2H), 2.96 (t, J=7.8 Hz, 2H), 2.70 (t, J=7.8 Hz, 2H), 2.37 (s, 3H), 1.4–1.7 (mult, 10H); $^{13}$C NMR (75 MHz, CDCl$_3$) δ 198.5, 142.4, 137.4, 130.7, 129.3, 128.6, 127.9, 124.1, 123.9, 121.8, 117.9, 68.3, 64.2, 58.8, 47.4, 44.3, 33.9, 27.1, 25.4, 22.0.

Example 33

4-({Methyl[2-methyl-2-(nitrosothio)propyl]amino}methyl)phenyl 2-{2-[(2,6-dichlorophenyl)amino]phenyl}acetate 33a. 4-{[Methyl(2-methyl-2-sulfanylpropyl)amino]methyl}phenyl 2-{2-[(2,6-dichlorophenyl)amino]phenyl}acetate A solution of the product of Example 5c (2.50 g, 11.0 mmol), (2-((2,6-dichlorophenyl)amino)benzene)acetic acid (3.26 g, 11.0 mmol), and DCC (2.24 g, 11.0 mmol) in CH$_2$Cl$_2$ (60 mL) were stirred at room temperature for 30 minutes. The solid formed during the reaction was removed by filtration and the filtrate was concentrated. The residue was chromatographed on silica gel eluting with 1:9 EtOAc:hexane) to give the title compound (5.0 g, 94%) as a colorless liquid. $^1$H NMR (300 MHz, CDCl$_3$) δ 6.5–7.4 (mult, 8H), 4.03 (s, 2H), 3.67 (s, 2H), 2.77 (s, 2H), 2.55 (s, 3H), 1.35 (s, 6H).

33b. 4-({Methyl[2-methyl-2-(nitrosothio)propyl]amino}methyl)phenyl 2-{2-[(2,6-dichlorophenyl)amino]phenyl}acetate To a stirred solution of the product of Example 33a (1.28 g, 2.37 mmol) in CH$_2$Cl$_2$ (45 mL) was added t-BuONO (330 μL, 2.49 mmol), and the mixture was stirred for 10 additional minutes. Evaporation of the solvent gave the title compound as a green solid (0.79 g, 90%). mp 126–130° C.; $^1$H NMR (300 MHz, CDCl$_3$) δ 6.5–7.4 (mult, 8H), 4.06 (s, 2H), 3.66 (s, 2H), 3.18 (s, 2H), 2.30 (s, 3H), 1.92 (s, 6H); $^{13}$C NMR (75 MHz, CDCl$_3$) δ 170.7, 149.5, 142.7, 137.7, 137.3, 131.0, 129.5, 129.5, 128.82, 128.2, 124.1, 123.9, 122.2, 121.2, 118.5, 68.2, 63.8, 59.1, 44.3, 38.6, 27.2.

Example 34

(2R,3R)-2,3-Dihydroxy-3-{N-[2-methyl-2-(nitrosothio)propyl]carbamoyl}propyl 2-{2-[(2,6-dichlorophenyl)amino]phenyl}acetate 34a. [(4R,5R)-5-(hydroxymethyl)-2,2-dimethyl(1,3-dioxolan-4-yl)]-N-(2-methyl-2-sulfanylpropyl) carboxamide A solution of 2,3-O-isopropylidene-D-erythoursonolactone (0.16 g, 1.0 mmol), 1-amino-2-methyl-2-propanethiol (0.160 g, 1.52 mmol), and 2-hydroxypyridine (9.5 mg, 0.1 mmol) in THF (15 mL) were refluxed for 2 hours. After evaporation of the solvent, the resulting solid was purified by recrystallization from EtOAc to afford the title compound as white needles (0.30 g, 96%). mp 82° C.; $^1$H NMR (300 MHz, CDCl$_3$) δ 7.32 (br, 1H), 4.67 (d, J=7.6 Hz, 1H), 4.59 (mult, 1H), 3.80 (td, J=4.6 and 12.0 Hz, 1H), 3.66–3.52 (mult, 3H), 3.21 (dd, J=5.3 and 13.6 Hz, 1H), 1.76 (br, 1H), 1.67 (s, 1H), 1.61 (s, 3H), 1.42 (s, 3H), 1.40 (s, 3H), 1.36 (s, 3H); $^{13}$C NMR (75 MHz, CDCl$_3$) δ 170.0, 109.4, 76.4, 76.1, 60.8, 51.1, 44.3, 29.7, 29.0, 26.4, 23.9.

34b. [(4R,5R)-5-(hydroxymethyl)-2,2-dimethyl(1,3-dioxolan-4-yl)]-N-[2-methyl-2-(nitrosothio)propyl] carboxamide To a stirred solution of the product of Example 34a (1.97 g, 7.48 mmol) in CHCl$_3$ (50 mL) was added t-BuONO (1.06 mL, 8.0 mmol). After being agitated for 10 minutes, the resultant green solution was concentrated to yield the title compound (1.95 g, 92%) as a red solid. mp 79° C. $^1$H NMR (300 MHz, CDCl$_3$) δ 6.92–7.35 (mult, 7H), 6.67 (mult, 1H), 6.53 (d, J=8.0 Hz, 1H), 4.51 (mult, 1H), 4.31 (mult, 1H), 3.95–4.28 (mult, 4H), 3.90 (s, 2H), 3.88 (s, 2H), 1.86 (s, 6H).

34c. ((4R,5R)-2,2-dimethyl-5-{N-[2-methyl-2-(nitrosothio) propyl]carbamoyl}-1,3-dioxolan-4-yl)methyl 2-{2-[(2,6-dichlorophenyl)amino]phenyl)acetate A mixture of the product of Example 34b (1.48 g, 5.06 mmol), (2-((2,6-dichlorophenyl)amino)benzene)acetic acid (1.55 g, 5.06 mmol), DCC (1.0 M in CH$_2$Cl$_2$, 5.06 mL), and DMAP (10 mg) in CH$_2$Cl$_2$ (40 mL) were stirred at room temperature for 5 hours. The solid which formed was removed by filtration. The filtrate was concentrated, and the resulting solid was chromatographed on silica gel eluting with 1:1 EtOAc:hexane to furnish the title compound as a green foam (2.1 g, 62%). $^1$H NMR (300 MHz, CDCl$_3$) δ 6.90–7.35 (mult, 6H), 6.87 (mult, 1H), 6.54 (d, J=8.0 Hz, 1H), 4.53–4.66 (mult, 4H), 4.00–4.06 (mult, 3H), 3.82 (mult, 2H), 1.88 (s, 3H), 1.86 (s, 3H), 1.45 (s, 3H), 1.35 (s, 3H); $^{13}$C NMR (75 MHz, CDCl$_3$) δ 171.7, 168.7, 142.7, 137.7, 130.8, 129.4, 128.7, 127.9, 124.0, 123.9, 121.8, 118.2, 110.3, 75.5, 74.9, 63.6, 56.6, 48.9, 38.2, 26.8, 26.7, 24.5.

34d. (2R,3R)-2,3-Dihydroxy-3-{N-[2-methyl-2-(nitrosothio)propyl]carbamoyl}propyl 2-{2-[(2,6-dichlorophenyl)amino]phenyl}acetate A solution of the product of Example 34c (0.57 g, 1.0 mmol) and 2N aq HCl (10 mL) in THF (20 mL) were stirred at room temperature for 20 hours. The mixture was poured into water (20 mL) and extracted with EtOAc (25×3). The combined organic layers were washed with aq NaHCO$_3$, dried over Na$_2$SO$_4$, filtered, and concentrated. The residue was chromatographed on silica gel to afford the title compound (0.31 g, 68%) as a green solid. mp 57–59° C.; $^1$H NMR (300 MHz, CDCl$_3$) δ 6.92–7.5 (mult, 7H), 6.67 (mult, 1H), 6.53 (d, J=8.0 Hz, 1H), 4.51 (mult, 1H), 4.31 (mult, 1H), 3.95–4.28 (mult, 4H), 3.90 (s, 2H), 3.88 (s, 2H), 1.86 (s, 6H); $^{13}$C NMR (75 MHz, CDCl$_3$) δ 174.1, 172.8, 142.6, 137.6, 130.9, 129.5, 128.9, 124.2, 123.7, 122.2, 118.3, 71.7, 69.8, 65.9, 56.6, 49.1, 38.3, 29.9, 26.7.

Example 35

2-{1-[2-Methyl-2-(nitrosothio)propyl]-4-piperidyl}ethyl 2-{2-[(2,6 dichlorophenyl)amino]phenyl}acetate 35a. 2-[1-(2-Methyl-2-sulfanylpropyl)-4-piperidyl]ethan-1-ol A solvent-free mixture of 4-piperidineethanol (5.00 g, 38.7 mnmol) and the product of Example 8a (3.41 g, 38.7 mmol) were stirred at 85° C. for 4 hours. Crystallization from EtOAc afforded the title compound as white needles (6.95 g, 83%). mp 42° C.; $^1$H NMR (300 MHz, CDCl$_3$) δ 3.66 (t, J=6.7 Hz, 2H), 2.86–2.91 (mult, 2H), 2.34 (s, 2H), 2.28 (mult, 2H), 2.03–2.25 (br, 1H), 1.60–1.63 (mult, 2H), 1.46–1.59 (mult, 2H), 1.32 (mult, 1H), 1.29 (s, 6H), 1.24–1.26 (mult, 2H); $^{13}$C NMR (75 MHz, CDCl$_3$) δ 71.3, 60.4, 56.3, 46.5, 39.4, 32.8, 31.9, 30.0.

35b. 2-{1-[2-Methyl-2-(nitrosothio)propyl]-4-piperidyl}ethan-1-ol

To a stirred solution of the product of Example 35a (7.28 g, 28.7 mmol) in MeOH (100 mL) was added t-BuONO (3.79 mL, 28.7 mmol). After being agitated for 15 minutes, the mixture was concentrated, and the residue was partitioned between aq Na$_2$CO$_3$ and EtOAc. The organic layer was dried over Na$_2$SO$_4$, filtered, and concentrated. Chromatography on silica gel eluting with 1:1 EtOAc:hexane furnished the title compound (5.50 g, 90%) as a green oil. $^1$H NMR (300 MHz, CDCl$_3$) δ 3.58 (t, J=6.6 Hz, 2H), 2.89 (s, 2H), 2.74–2.79 (mult, 2H), 2.54 (br, 1H), 2.26 (t, J=11.6 Hz, 2H), 1.81 (s, 6H), 1.56–1.51 (mult, 2H), 1.14–1.22 (mult, 5H); $^{13}$C NMR (75 MHz, CDCl$_3$) δ 68.3, 60.1, 59.0, 56.1, 39.1, 32.5, 31.7, 26.8.

35c. 2-{1-[2-Methyl-2-(nitrosothio)propyl]-4-piperidyl}ethyl 2-{2-[(2,6-dichlorophenyl)amino] phenyl}acetate A mixture of the product of Example 35b (2.37 g, 9.62 mmol), (2-((2,6-dichlorophenyl)amino)benzene)acetic acid (2.96 g, 10 mmol), and DCC (1.0M in CH$_2$Cl$_2$, 10 mL) in CH$_2$Cl$_2$ (100 mL) were stirred at room temperature for 1 hour before filtration. The filtrate was concentrated, and the residue was chromatographed on silica gel eluting with 1:1 EtOAc:hexane to give the title compound (4.0 g, 80%) as a green oil. $^1$H NMR (300 MHz, CDCl$_3$) δ 6.96–7.40 (mult, 7H), 6.60 (d, J=7.9 Hz, 1H), 4.23 (t, J=6.7 Hz, 2H), 3.86 (s, 2H), 2.97 (s, 2H), 2.83 (d, J=11.5 Hz, 2H), 2.30 (t, J=10.8 Hz, 2H), 1.91 (s, 6H), 1.57–1.66 (mult, 4H), 1.21–1.33 (mult, 4H); $^{13}$C NMR (75 MHz, CDCl$_3$) δ 172.2, 142.5, 137.6, 130.7, 129.3, 128.7, 127.8, 124.3, 123.9, 121.8, 118.1, 68.2, 63.2, 58.9, 56.0, 38.6, 34.9, 32.3, 32.1, 26.8.

Example 36

{(2S)-1-[2-Methyl-2-(nitrosothio)propyl]pyrrolidin-2yl}methyl 2-{2-[(2,6-dichlorophenyl)amino] phenyl}acetate 36a. [(2S)-1-(2-Methyl-2-sulfanylpropyl)pyrrolidin-2-yl] methan-1-ol A neat mixture of (S)-2-pyrrolidinemethanol (6.21 g, 61.4 mmol) and the product of Example 8a (5.41 g, 61.4 mmol) was stirred at 80° C. for 5 hours. The reaction mixture was chromatographed on silica gel eluting with 1:1 EtOAc:hexane to give the title compound (9.9 g, 85%) as a colorless liquid. $^1$H NMR (300 MHz, CDCl$_3$) δ 3.62 (dd, J=3.4 and 11.1, Hz, 1H), 3.43 (dd, J=3.3 and 11.1 Hz, 1H), 3.30–3.37 (mult, 1H), 2.73–2.79 (mult, 2H), 2.42–2.58 (mult, 2H), 1.67–1.85 (mult, 4H), 1.39 (s, 3H), 1.36 (s, 3H); $^{13}$C NMR (75 MHz, CDCl$_3$) δ 70.1, 67.1, 62.8, 57.6, 46.1, 31.3, 30.9, 26.7, 24.2.

36b. {(2S)-1-[2-Methyl-2-(nitrosothio)propyl]pyrrolidin-2-yl}methan-1-ol

To a stirred solution of the product of Example 36a (9.17 g, 40.6 mmol) in CH$_2$Cl$_2$ (200 mL) was added t-BuONO (5.42 mL, 41.0 mmol) dropwise. After being agitated for 10 minutes, the mixture was washed with aq Na$_2$CO$_3$, dried over Na$_2$SO$_4$, filtered, and concentrated. The residue was chromatographed on silica gel eluting with 1:1 EtOAc:hexane to provide the title compound (6.73 g, 78%) as a green oil. $^1$H NMR (300 MHz, CDCl$_3$) δ 3.25–3.48 (mult, 3H), 3.16 (d, J=14.0 Hz, 1H), 2.76–2.81 (mult, 1H), 2.46–2.55 (mult, 2H), 1.93 (s, 6H), 1.70–1.89 (mult, 5H); $^{13}$C NMR (75 MHz, CDCl$_3$) δ 67.3, 67.2, 62.2, 58.2, 57.65, 27.9, 27.7, 26.8, 24.5.

36c. {(2S)-1-[2-Methyl-2-(nitrosothio)propyl]pyrrolidin-2-yl}methyl 2-{2-[(2,6-dichlorophenyl)amino] phenyl}acetate A mixture of the product of Example 36b (6.70 g, 30.7 mmol), (2-((2,6-dichlorophenyl)amino)benzene)acetic acid (10.4 g, 35.0 mmol), and DCC (1.0 M in CH$_2$Cl$_2$, 35 mL) in CH$_2$Cl$_2$ were stirred at room temperature for 3 hours. The solid which formed was removed by filtration and the filtrate was concentrated. The residue was chromatographed on silica gel eluting with 1:2 EtOAc:hexane to afford the title compound (5.7 g, 32%) as a green oil. $^1$H NMR (300 MHz, CDCl$_3$) δ 6.89–7.33 (mult, 7H), 6.54 (d, J=7.9 Hz, 1H), 4.10 (dd, J=5.0 and 10.9 Hz, 1H), 3.97 (dd, J=6.5 and 10.7 Hz, 1H), 3.79 (s, 2H), 3.39 (d, J=14.0 Hz, 1H), 3.16–3.24 (mult, 2H), 2.92–2.97 (mult, 1H), 2.40–2.49 (q, J=7.8 Hz, 1H), 1.89 (s, 3H), 1.83 (s, 3H), 1.67–1.79 (mult, 2H); $^{13}$C NMR (75 MHz, CDCl$_3$) δ 172.3, 142.7, 137.8, 130.8, 129.4, 128.8, 127.9, 124.3, 124.0, 122.0, 118.2, 67.9, 67.7, 64.4, 58.3, 57.6, 38.6, 28.3, 27.9, 27.4, 24.0.

Example 37

2-({4-[2-Methyl-2-(nitrosothio)propyl]piperazinyl}ethoxy)ethyl 2-{1-[(4-chlorophenyl)carbonyl]-5-methoxy-2-methylindol-3-yl}acetate 37a. 2-{2-[4-(2-Methyl-2-sulfanylpropyl)piperazinyl]ethoxy}ethan-1-ol A neat mixture of 1-[4-(2-hydroxyethoxy)ethyl]piperazine (1.04 g, 5.97 mmol) and the product of Example 8a (0.526 g, 6.00 mmol) were stirred at 80° C. for 2 hours. Crystallization from EtOAc gave the title compound (1.45 g, 93%) as a yellow solid. mp 38° C.; $^1$H NMR (300 MHz, CDCl$_3$) δ 3.60–3.71 (mult, 6H), 2.71 (t, J=4.6 Hz, 4H), 2.55–2.60 (mult, 6H), 2.40 (s, 2H), 1.31 (s, 6H), 2.22 (br, 1H); $^{13}$C NMR (75 MHz, CDCl$_3$) δ 71.9, 70.4, 67.2, 60.9, 57.2, 54.4, 53.2, 45.7, 29.6.

37b. 2-(2-{4-[2-Methyl-2-(nitrosothio)propyl]piperazinyl}ethoxy)ethan-1-ol

To a stirred solution of the product of Example 37a (3.85 g, 14.7 mmol) in MeOH (50 mL) was added 12N aq HCl (2.45 mL, 29.4 mmol) followed by t-BuONO (1.99 mL, 15.0 mmol). After 15 minutes the mixture was concentrated and the residue was partitioned between EtOAc and aq Na$_2$CO$_3$. The organic layer was separated, dried over Na$_2$SO$_4$, filtered, and concentrated to afford the title compound (4.10 g, 95%) as a green oil. $^1$H NMR (300 MHz, CDCl$_3$) δ 3.59–3.70 (mult, 6H), 2.99(s, 2H), 2.50–2.70 (mult, 11H), 1.88 (s, 6H); $^{13}$C NMR (75 MHz, CDCl$_3$) δ 72.2, 67.9, 67.4, 61.7, 58.7, 57.7, 54.8, 53.4, 26.9.

37c. 2-({4-[2-Methyl-2-(nitrosothio)propyl]piperazinyl}ethoxy)ethyl 2-{1-[(4-chlorophenyl)carbonyl]-5-methoxy-2-methylindol-3-yl}acetate A mixture of the product of Example 37b (6.80 g, 23.4 mmol), 2-{1-[(4-chlorophenyl)carbonyl]-5-methoxy-2-methylindol-3-yl}acetic acid (9.20 g, 26 mmol), and DCC (5.30 g, 25.7 mmol) in CH$_2$Cl$_2$ (100 mL) were stirred at room temperature for 3 hours. The solid which formed was removed by filtration and the filtrate was concentrated. The residue was chromatographed on silica gel eluting with EtOAc to afford the title compound (12.0 g, 74%) as a green oil. $^1$H NMR (300 MHz, CDCl$_3$) δ 7.65 (d, J=8.4 Hz, 2H), 7.45 (d, J=8.4 Hz, 2H), 6.97 (d, J=2.1 Hz, 1H), 6.87 (d, J=9.0 Hz, 1H), 6.64 (mult, 1H), 4.25 (t, J=4.5 Hz, 2H), 3.82 (s, 3H), 3.62–3.69 (mult, 5H), 3.54 (t, J=5.8 Hz, 2H), 2.96 (s, 2H), 2.63 (t, J=4.5 Hz, 4H), 2.44–2.53 (mult, 8H), 2.37 (s, 2H), 1.86 (s, 6H); $^{13}$C NMR (75 MHz, CDCl$_3$)δ 170.6, 168.0, 155.9, 139.1, 135.8, 133.8, 131.0, 130.7, 130.5, 129.0, 114.8, 112.3, 111.4, 101.3, 68.7, 68.0, 63.9, 58.7, 57.5, 55.5, 55.2, 53.7, 30.1, 26.9, 13.3.

Example 38

2-(2-{4-[2-Methyl-2-(nitrosothio)propyl]piperazinyl}ethoxy)ethyl (2S)-2-(6-methoxy(2-naphthyl))propanoate 38a. 2-(2-{4-[2-Methyl-2-(nitrosothio)propyl]piperazinyl}ethoxy)ethyl (2S)-2-(6-methoxy(2-naphthyl))propanoate A mixture of the product of Example 37b (3.08 g, 10.6 mmol), (2S)-2-(6-methoxy(2-naphthyl))propanoic acid (2.70 g, 11.6 mmol), and DCC (2.40 g, 11.6 mmol) in CH$_2$Cl$_2$ (50 mL) were stirred at room temperature for 3 hours. The solid which formed was removed by filtration and the filtrate was concentrated. The residue was chromatographed on silica gel eluting with EtOAc to afford the title compound (5.4 g, 91%) as a green oil. $^1$H NMR (300 MHz, CDCl$_3$) δ 7.65–7.69 (mult, 3H), 7.38–7.41 (mult, 1H), 7.08–7.13 (mult, 2H), 4.22 (s, 2H), 3.88 (s, 3H), 3.41 (t, J=5.7 Hz, 2H), 3.56 (mult, 2H), 2.91 (s, 2H), 2.55 (mult, 4H), 2.33–2.40 (mult, 7H), 1.83 (s, 6H), 1.56 (d, J=7.1 Hz, 3H); $^{13}$C NMR (75 MHz, CDCl$_3$) δ 174.2, 157.3, 135.3, 133.4, 129.0, 128.6, 126.8, 125.9, 125.6, 118.7, 105.2, 68.5, 68.4, 67.8, 63.6, 58.6, 57.3, 54.9, 53.4, 45.0, 26.7, 18.3.

Example 39

4-({4-[2-Methyl-2-(nitrosothio)propyl]piperazinyl}methyl)phenyl 2-{1-[(4-chlorophenyl)carbonyl]-5-methoxy-2-methylindol-3-yl}acetate 39a. 2-Methyl-1-piperazinylpropane-2-thiol A solution of the product of Example 8a (15.5 g, 0.176 mol) and piperazine (30.0 g, 0.50 mol) in THF (200 mL) were stirred at reflux for 4 hours. The solvent was evaporated and the crude material was crystallized from 1:4 EtOAc:hexane to give the title compound (21 g, 82%) as white flakes. mp 55° C.; $^1$H NMR (300 MHz, CDCl$_3$) δ 2.85 (t, J=4.6 Hz, 4H), 2.58 (t, J=4.6 Hz, 4H), 2.34 (s, 2H), 1.29 (s, 6H).

39b. 4-{[4-(2-Methyl-2-sulfanylpropyl)piperazinyl]carbonyl}phenyl acetate

A mixture of the product of Example 39a (2.50 g, 14.4 mol), 4-acetoxybenzoic acid (2.60 g, 14.4 mmol), DCC (3.00 g, 14.4 mol), and 1-hydroxybenzotriazole (15 mg) in CH$_2$Cl$_2$ (100 mL) were stirred for 1 hour. The solid which formed was removed by filtration and the filtrate was concentrated. The residue was chromatographed on silica gel eluting with 1:1 EtOAc:hexane to afford the title compound (4.20 g, 88%) as white solid. mp 121° C.; $^1$H NMR (300 MHz, CDCl$_3$) δ 7.39–7.43 (mult, 2H), 7.10–7.14 (mult, 2H), 3.3–3.9 (mult, 4H), 2.6–2.8 (mult, 4H), 2.41 (s, 2H), 2.29 (s, 3H), 1.30 (s, 6H); $^{13}$C NMR (75 MHz, CDCl$_3$) δ 168.6, 168.2, 151.0, 132.7, 127.9, 121.1, 70.4, 54.7, 45.5, 29.6, 20.5.

39c. 4-{[4-(2-Methyl-2-sulfanylpropyl)piperazinyl]methyl}phenol

To a solution of the product of Example 39b (1.00 g, 29.7 mmol) in THF (20 mL) was added lithium aluminum hydride (1.0 M, 6.0 mL, 6 mmol) in THF dropwise. The mixture was heated to reflux for 1 hours. The mixture was poured onto Na$_2$SO$_4$·10H$_2$O, filtered, and concentrated. The resulting material was purified by crystallization from EtOAc to give the title compound (0.81 g, 98%) as white rods. mp 81° C.; $^1$H NMR (300 MHz, CDCl$_3$) δ 7.07 (d, J=5.5 Hz, 2H), 6.61 (d, J=5.5 Hz, 2H), 3.45 (s, 2H), 2.7–2.8 (br, 4H), 2.5–2.6 (br, 4H), 2.35 (s, 2H), 1.28 (s, 6H); $^{13}$C NMR (75 MHz, CDCl$_3$) δ 156.0, 131.1, 127.0, 115.7, 70.8, 62.4, 54.5, 53.1, 46.3, 30.1.

39d. 4-({4-[2-Methyl-2-(nitrosothio)propyl]piperazinyl}methyl)phenol

To a stirred solution of the product of Example 39c (0.37 g, 13 mmol) and 12N aq HCl (0.22 mL, 26 mmol) in MeOH (10 mL) at 0° C. was added t-BuONO (0.20 mL, 15 mmol). After 10 minutes, the mixture was partitioned between aq NaHCO$_3$ and CH$_2$Cl$_2$. The organic layer was separated, dried over Na$_2$SO$_4$, filtered, and concentrated. The residue was chromatographed on silica gel eluting with 1:9 MeOH:EtOAc to afford the title compound (0.38 g, 98%) as a green oil. $^1$H NMR (300 MHz, CDCl$_3$) δ 7.05 (d, J=8.4 Hz, 2H), 6.58 (d, J=8.4 Hz, 2H), 3.43 (s, 2H), 2.95 (s, 2H), 2.4–2.7 (mult, 8H), 1.85 (s, 6H); $^{13}$C NMR (75 MHz, CDCl$_3$) δ 155.8, 131.1, 127.1, 115.7, 67.9, 62.4, 58.7, 54.5, 53.0, 26.9.

39e. 4-({4-[2-Methyl-2-(nitrosothio)propyl] piperazinyl}methyl)phenyl 2-{1-[(4-chlorophenyl) carbonyl]-5-methoxy-2-methylindol-3-yl}acetate A solution of the product of Example 39d (0.38 g, 0.0013 mol), 2-{1-[(4-chlorophenyl)carbonyl]-5-methoxy-2-methylindol-3-yl}acetic acid (0.47 g, 13 mmol), and DCC (0.27 g, 13 mmol) in CHCl$_3$ (10 mL) was stirred at room temperature for 30 minutes. The solid which formed was removed by filtration and the filtrate was concentrated. The residue was chromatographed on silica gel eluting with 2:1 hexane:EtOAc to afford the title compound (0.49 g, 62%) as a green oil which solidified on standing. mp 90–92° C.; $^1$H NMR (300 MHz, CDCl$_3$) δ 7.65 (d, J=8.4 Hz, 2H), 7.44 (d, J=8.4 Hz, 2H), 7.28 (d, J=8.4 Hz, 2H), 7.1–6.8 (mult, 4H), 6.68 (dd, J=2.4 and 9.0 Hz, 1H), 3.88 (s, 2H), 3.81 (s, 3H), 3.45 (s, 2H), 2.96 (s, 3H), 2.6–2.7 (mult, 4H), 2.43 (s, 3H), 2.2–2.4 (mult, 4H), 1.85 (s, 6H); $^{13}$C NMR (75 MHz, CDCl$_3$) δ 169.1, 168.0, 156.0, 149.6, 139.1, 136.0, 135.4, 133.7, 131.0, 130.7, 130.4, 130.0, 128.9, 121.0, 114.8, 111.9, 111.6, 101.1, 67.9, 62.0, 58.7, 55.5, 55.1, 53.0, 30.3, 26.8, 13.3.

Example 40

5-({4-[2-Methyl-2-(nitrosothio)propyl] piperazinyl}carbonyl)-2 pyridyl 2-{1-[(4-chlorophenyl)carbonyl]-5-methoxy-2-methylindol-3-yl}acetate 40a. 6-Hydroxy(3-pyridyl) 4-(2-methyl-2-sulfanylpropyl) piperazinyl ketone To a stirred suspension of 6-hydroxypyridine-3-carboxylic acid (5.68 g, 40.86 mmol) and the product of Example 39a (7.82 g, 44.9 mmol) in CH$_2$Cl$_2$ (80 mL) was added HOBt (55 mg) then DCC (9.25 g, 44.90 mmol). The reaction mixture was stirred at room temperature overnight. The solid was removed by filtration, and the filtrate was evaporated to give a crude material, which was purified by a column chromatography eluting with 1:9 MeOH:CH$_2$Cl$_2$ to give the title compound (9.0 g, 30.51 mmol, 74.7%) as a white solid. $^1$H NMR (300 MHz, CDCl$_3$) δ 7.61 (d, J=2.2 Hz, 1H), 7.55 (dd, J=2.4 and 9.4, 1H), 6.56 (d, J=9.4 Hz, 1H), 3.56–3.60 (m, 4H), 2.64–2.68 (m, 4H), 2.42 (s, 2H), 1.31 (s, 6H); $^{13}$C NMR (75 MHz, CDCl$_3$) δ 166.5, 164.8, 141.0, 136.1, 119.8, 115.2, 71.0, 55.3, 46.1, 30.2.

40b. 6-Hydroxy(3-pyridyl)-4-[2-methyl-2-(nitrosothio) propyl]piperazinyl ketone

To a stirred ice cold solution of the product of Example 40a in CH$_2$Cl$_2$ (100 mL) was added trifluoroacetic acid (4.7 mL, 61.0 mmol) dropwise. t-BuONO (3.84 g, 33.51 mmol) was then added. The reaction mixture was kept cold for 1 hour, then poured into saturated Na$_2$CO$_3$. The aqueous layer was extracted twice with CH$_2$Cl$_2$. The combined organic extracts were dried over Na$_2$SO$_4$ and evaporated to give the title compound as a green solid, which was used for the next step without further purification. $^1$H NMR (300 MHz, CDCl$_3$) δ 7.58 (d, J=2.3 Hz, 1H), 7.48 (dd, J=2.5 and 9.4, 1H), 6.49 (d, J=9.4 Hz, 1H), 3.45–3.50 (m, 4H), 2.97 (s, 2H), 2.55–2.60 (m, 4H), 1.82 (s, 6H); $^{13}$C NMR (75 MHz, CDCl$_3$) δ 166.4, 164.5, 140.7, 136.2, 119.6, 114.9, 67.9, 58.4, 55.0, 45.5 (br), 26.8.

40c. 5-({4-[2-Methyl-2-(nitrosothio)propyl] piperazinyl}carbonyl)-2-pyridyl 2-{1-[(4-chlorophenyl) carbonyl]-5-methoxy-2-methylindol-3-yl}acetate To a stirred ice cold solution of the acid chloride of), 2-1-[(4-chlorophenyl) carbonyl]-5-methoxy-2-methylindol-3-yl}acetic acid (1.15 g, 3.07 mmol) in CH$_2$Cl$_2$ (20 mL) was added Et$_3$N (0.47 mL, 3.38 mmol), then the product of Example 40b (995 mg, 3.07 mmol). This was followed by the addition of DMAP (20 mg). The reaction was stirred at room temperature for 2 hours. The solvent was evaporated and the residue was passed through a short column of silica gel, eluting with 1:1 EtOAc:Hex to give the title compound (0.99 g, 1.49 mmol, 49%) as a sticky green solid. $^1$H NMR (300 MHz, CDCl$_3$) δ 8.41 (d, J=2.2, 1H), 7.88 (dd, J=2.4 and 8.3, 1H), 7.61–7.67 (m, 2H), 7.42–7.47 (m, 2H), 7.03–7.10 (m, 2H), 6.89 (d, J=9.1, 1H), 6.67 (dd, J=2.5 and 9.1, 1H), 3.95 (s, 2H), 3.82 (s, 3H), 3.30–3.79 (m, 4H), 3.02 (s, 2H), 2.55–2.66 (m, 4H), 2.42 (s, 3H), 1.87 (s, 6H); $^{13}$C NMR (75 MHz, CDCl$_3$) δ 168.5, 168.2, 166.7, 158.3, 156.1, 147.1, 139.28, 138.8, 136.3, 133.7, 131.1, 130.8, 130.3, 130.1, 129.1, 116.1, 114.9, 111.8, 111.5, 111.25, 101.1, 68.0, 58.4, 55.7, 55.0, 30.4, 26.9, 13.4.

Example 41

2-({2-[(2S)-2-(6-Methoxy(2-naphthyl)) propanoyloxy]ethyl}{[(nitrosothio) cyclohexyl] methyl}amino)acetic acid 41a. tert-Butyl 2-({[({[({[(tert-butyl)oxycarbonyl]methyl} (2-hydroxyethyl)amino) methyl]cyclohexyl}disulfanyl) cyclohexyl]methyl}(2-hydroxyethyl)amino) acetate The product of Example 2b (13.0 g, 34.57 mmol) was dissolved in CH$_3$CN (100 mL) and tert-butyl bromoacetate (10.2 mL, 69.03 mmol) and solid K$_2$CO$_3$ (23 g) were subsequently added. The resulting suspension was stirred at room temperature for 12 hours. The solid was removed by filtration and washed with CH$_3$CN (50 mL). The filtrate was concentrated and the residue was chromatographed on silica gel eluting with 1:2 EtOAc:Hex to give the title compound (18.2 g, 87.5%). $^1$H NMR (300 MHz, CDCl$_3$) δ 3.55–3.61 (m, 4 H), 3.40 (s, 4 H), 2.86–2.88 (m, 8 H), 1.47 (s, 18 H), 1.20–1.67 (m, 20 H); $^{13}$C-NMR (75 MHz, CDCl$_3$) δ 172.0, 81.3, 65.8, 59.8, 59.7, 58.0, 56.2, 33.2, 28.1, 25.7, 22.3; mass spectrum (API-TIS), m/z 605 (MH$^+$).

41b. 2-({[(tert-Butyl)oxycarbonyl]methyl}{[({[({[(tert-butyl)oxycarbonyl]methyl}(2-[(2S)-2-(6-methoxy(2-naphthyl))propanoyloxy]ethyl}amino)methyl] cyclohexyl}disulfanyl)cyclohexyl]methyl}amino)ethyl (2S)-2-(6-methoxy-2-naphthyl)propanoate DCC (4.9 g, 23.8 mmol) in CH$_2$Cl$_2$ (50 mL) was added dropwise to a stirred solution of the product of Example 41a (6.0 g, 9.92 mmol), (2S)-2-(6-methoxy(2-naphthyl)) propanoic acid (4.56 g, 19.8 mmol) and DMAP (0.35 g) in CH$_2$Cl$_2$ (50 mL) at 0° C. The resulting suspension was stirred at room temperature for 1 hour. The precipitate was removed by filtration and washed with CH$_2$Cl$_2$ (2×25 mL). The filtrate was concentrated to give a green oil which was chromatographed on silica gel eluting with 1:1 EtOAc:Hex to afford the title compound (9.8 g, 96%) as a white foam. $^1$H NMR (300 MHz, CDCl$_3$) δ 7.65–7.69 (mult, 6 H), 7.38 (dd, J=1.7 and 8.8 Hz, 2 H), 7.08–7.13 (mult, 4 H), 3.87 (s, 6 H), 3.81–4.06 (mult, 2 H), 3.40 (br s, 4 H), 2.91 (mult, 4 H), 2.69 (s, 4 H), 1.56 (d, J=7.1 Hz, 6 H), 1.03–1.57 (mult, 20 H); $^{13}$C NMR (75 MHz, CDCl$_3$) δ 174.5, 174.0, 157.6, 135.3, 133.7, 129.2, 128.9, 127.2, 126.1, 126.0, 119.0, 105.6, 66.4, 62.6, 58.5, 56.0, 55.7, 55.3, 45.4, 33.0, 25.4, 22.1, 18.4; mass spectrum (API-TIS), m/z 917 (MH$^+$).

41c. 2-({[({[(((Carboxymethyl){2-[(2S)-2-(6-methoxy(2-naphthyl))propanoyloxy]ethyl}amino)methyl]cyclohexyl}disulfanyl)cyclohexyl]methyl}{2-[(2S)-2-(6-methoxy(2-naphthyl))propanoyloxy]ethyl}amino)acetic acid The product of Example 41b (9.4 g, 9.13 mmol) was dissolved in CH$_2$Cl$_2$ (25 mL) and TFA (25 mL) was then added. The resulting solution was stirred at room temperature for 12 hours. The mixture was poured onto crushed ice made basic with concentrated NH$_4$OH (40 mL). The aqueous product was extracted with EtOAc (3×50 mL). The combined organic layers were dried over Na$_2$SO$_4$ and filtered. The solvent was evaporated and the residue was chromatographed on silica gel eluting with 1:19 MeOH:CH$_2$Cl$_2$ to afford the title compound (8.3 g, 88%) as a white foam. $^1$H NMR (300 MHz, CDCl$_3$) δ 7.64 (d, J=8.4 Hz, 4 H), 7.43 (d, J=8.4 Hz, 4 H), 6.94 (d, J=2.3 Hz, 2 H), 6.84 (d, J=9.0 Hz, 2 H), 6.63 (dd, J=2.4 and 9.0 Hz, 2 H), 4.16 (mult, 4 H), 3.79 (s, 6 H), 3.65 (br s, 4 H), 3.40 (br s, 4 H), 3.01 (mult, 4 H), 2.81 (s, 4 H), 2.34 (s, 6H), 1.18–1.57 (m, 20 H); $^{13}$C NMR (75 MHz, CDCl$_3$) δ 170.7 (2C), 168.2, 156.0, 139.2, 136.0, 133.8, 131.1, 130.8, 130.6, 129.1, 114.9, 112.2, 111.5, 101.4, 65.8, 63.1, 58.2, 56.0, 55.7 (2C), 33.1, 30.1, 25.6, 22.1, 13.3; mass spectrum (API-TIS), m/z 1173 (MH$^+$).

41d. 2-({2-[(2S)-2-(6-Methoxy(2-naphthyl))propanoyloxy]ethyl}{[(nitrosothio) cyclohexyl]methyl}amino)acetic acid The product of Example 41c (6.2 g, 6.76 mmol) was dissolved in HOAc(30 mL) and powdered zinc (12 g) was added. The resulting suspension was stirred at room temperature for 12 hours. The inorganic solid was removed by filtration and washed with HOAc (25 mL). The filtrate was made basic with concentrated NH$_4$OH in crushed ice (100 g) and extracted with EtOAc (3×50 mL). The combined organic extracts were dried over Na$_2$SO$_4$ and filtered. The solvent was evaporated to give a white foam (4 g), which was subsequently dissolved in a mixture of CH$_2$Cl$_2$ (20 mL) and MeOH (10 mL) and cooled to 0° C. Conc. HCl (1.5 mL) was added followed by 90% tert-butyl nitrite (1.1 mL, 8.7 mmol) via syringe. The resulting green solution was stirred at 0° C. for 15 min and then poured onto crushed ice (15 g). 10% Na$_2$CO$_3$ (10 mL) was added until the minxture became slightly basic. The mixture was extracted with EtOAc (3×50 mL). The combined organic extracts were dried over Na$_2$SO$_4$ and filtered. The solvent was evaporated and the residue was chromatographed on silica gel eluting with 1:1 EtOAc:Hex to afford the title compound (2.1 g, 32%) as a green oil. $^1$H NMR (300 MHz, CDCl$_3$) δ 7.74–7.70 (m, 3 H), 7.37 (dd, J=1.7 and 8.4 Hz, 1 H), 4.08–4.14 (mult, 2 H), 3.89 (s, 3 H), 3.81(q, J=7.1 Hz, 1 H), 3.38 (s, 2 H), 3.34 (s, 2 H), 2.90–2.97 (mult, 2 H), 2.30–2.34 (mult, 2 H), 1.55 (d, J=3.94 (t, J=5.2 Hz, 2 H), 1.15–1.82 (m, 8 H); $^{13}$C NMR (75 MHz, CDCl$_3$) δ 174.7, 174.4, 157.6, 135.3, 133.7, 129.3, 128.9, 127.2, 126.1, 126.0, 119.0, 105.6, 67.1, 63.9, 62.6, 57.7, 55.3, 55.2, 45.4, 34.2, 25.4, 21.9, 18.3; mass spectrum (API-TIS), m/z 489 (MH$^+$).

Example 42

2-{[2-(2-{1-[(4-Chlorophenyl)carbonyl]-5-methoxy-2-methylindol-3-yl}acetyloxy)ethyl]{[(nitrosothio) cyclohexyl]methyl}amino}acetic acid 42a. 2-{{[(tert-Butyl)oxycarbonyl]methyl}[({[({[(tert-butyl)oxycarbonyl]methyl}[2-(2-{1-[(4-chlorophenyl) carbonyl]-5-methoxy-2-methylindol-3-yl}acetyloxy)ethyl]amino}methyl)cyclohexyl]disulfanyl}cyclohexyl) methyl]amino}ethyl 2-{1-[(4-chlorophenyl)carbonyl]-5-methoxy-2-methylindol-3-yl}acetate DCC (8.8 g, 42.5 mmol) in CH$_2$Cl$_2$ (50 mL) was added dropwise to a stirred solution of the product of Example 41a (5.5 g, 9.1 mmol), 2-{1-[(4-chlorophenyl) carbonyl]-5-methoxy-2-methylindol-3-yl}acetic acid (6.5 g, 18.16 mmol) and DMAP (0.25 g) in CH$_2$Cl$_2$ (60 mL) at 0° C. The resulting suspension was stirred for 1 hour at room temperature. The precipitate was removed by filtration and washed with CH$_2$Cl$_2$ (2×25 mL). The filtrate was concentrated to give a green oil which was chromatographed on silica gel eluting with 1:1 EtOAc:Hex to afford the title compound (8.3 g, 71.5%) as a white foam. $^1$H NMR (300 MHz, CDCl$_3$) δ 7.66 (d, J=8.4 Hz, 4 H), 7.45 (d, J=8.4 Hz, 4 H), 6.96 (d, J=2.3 Hz, 2 H), 6.85 (1=9.0 Hz, 2 H), 6.65 (dd, J=2.5 and 9.0 Hz, 2 H), 4.18 (t, J=5.8 Hz, 4 H), 3.82 (s, 6 H), 3.66 (s, 4 H), 3.39 (s, 4 H), 3.03 (t, J=5.9 Hz, 4 H), 2.85 (s, 4 H), 2.37 (s, 3 H), 1.45 (s, 18 H), 1.38–1.65 (m, 20 H); $^{13}$C NMR (75 MHz, CDCl$_3$) δ 174.1, 170.7, 156.0, 139.1, 135.8, 133.9, 131.1, 130.7, 130.6, 129.0, 114.9, 112.5, 111.6, 101.3, 80.9, 65.4, 63.7, 57.5, 56.0, 55.6, 54.8, 32.8, 30.2, 28.2, 25.7, 22.3, 13.3; mass spectrum (API-TIS), m/z 1285 (MH$^+$).

42b. 2-{[({[({(Carboxymethyl)[2-(2-{1-[(4-chlorophenyl) carbonyl]-5-methoxy-2-methylindol-yl}acetyloxy)ethyl] amino}methyl)cyclohexyl]disulfanyl}cyclohexyl) methyl][2-(2-{1-[(4-chlorophenyl)carbonyl]-5-methoxy-2-methylindol-3-yl}acetyloxy)ethyl]amino}acetic acid The product of Example 42a (8.3 g, 6.46 mmol) was dissolved in CH$_2$Cl$_2$ (20 mL) and TFA (10 mL) was then added. The resulting solution was stirred at room temperature for 12 hours and then poured onto crushed ice made basic with concentrated NH$_4$OH (20 mL). The aqueous layer was extracted with EtOAc (3×50 mL). The combined organic layer extracts were dried over Na$_2$SO$_4$ and filtered. The solvent was evaporated and the residue was chromatographed on silica gel eluting with 1:9 MeOH:CH$_2$Cl$_2$ to afford the title compound (4.8 g, 64%) as a white foam. $^1$H NMR (300 MHz, CDCl$_3$) δ 7.64 (d, J=8.4 Hz, 4 H), 7.43 (d, J=8.4 Hz, 4 H), 6.94 (d, J=2.3 Hz, 2 H), 6.84 (d, J=9.0 Hz, 2 H), 6.63 (dd, J=2.4 and 9.0 Hz, 2 H), 4.16 (mult, 4 H), 3.79 (s, 6 H), 3.65 (br s, 4 H), 3.40 (br s, 4 H), 3.01 (mult, 4 H), 2.81 (s, 4 H), 2.34 (s, 6H), 1.18–1.57 (m, 20 H); $^{13}$C NMR (75 MHz, CDCl$_3$) δ 170.7 (2C), 168.2, 156.0, 139.2, 136.0, 133.8, 131.1, 130.8, 130.6, 129.1, 114.9, 112.2, 111.5, 101.4, 65.8, 63.1, 58.2, 56.0, 55.7 (2C), 33.1, 30.1, 25.6, 22.1, 13.3; mass spectrum (API-TIS), m/z 1173 (MH$^+$).

42c. 2-{[2-(2-{1-[(4-Chlorophenyl)carbonyl]-5-methoxy-2-methylindol-3-yl}acetyloxy)ethyl]{[(nitrosothio) cyclohexyl]methyl}amino}acetic acid The product of Example 42b (4.50 g, 3.83 mmol) was dissolved in HOAc (22 mL) and powdered zinc (9 g) was added. The resulting suspension was stirred at room temperature for 12 hours. The solid was removed by filtration and washed with HOAc (25 mL). The filtrate was made basic with concentrated NH$_4$OH in crushed ice (100 g) and extracted with EtOAc (3×50 mL). The combined organic layers were dried over Na$_2$SO$_4$ and filtered. The solvent was evaporated to give a white foam (4 g), which was The product of Example 42b (4.50 g, 3.83 mmol) was dissolved in HOAc (22 mL) and powdered zinc (9 g) was added. The resulting suspension was stirred at room temperature for 12 hours. The solid was removed by filtration and washed with HOAc (25 mL). The filtrate was made basic with concentrated NH$_4$OH in crushed ice (100 g) and extracted with EtOAc (3×50 mL). The combined organic layers were dried over Na$_2$SO$_4$ and filtered. The solvent was evaporated to give a white foam (4 g), which was subsequently dissolved in a mixture of $CH_2Cl_2$ (10 mL) and MeOH (35 mL) and cooled to 0° C. Conc. HCl (5 mL) was added followed by 90% tert-butyl nitrite (1 mL, 8.2 mmol). The resulting green solution was stirred at room temperature for 15 min and then poured onto crushed ice (~10 g). 10% $Na_2CO_3$ (10 mL) was added until the mixture became basic and the aqeuous mixture was extracted with EtOAc (3×50 mL). The combined organic extracts were dried over $Na_2SO_4$, filtered, and concentrated. The residue was chromatographed on silica gel eluting 1:1 EtOAc:Hex to afford the title compound (2.5 g, 53%,) as a green oil. $^1$H NMR (MHz, $CDCl_3$) δ 7.68 (d, J=8.4 Hz, 2 H), 7.48 (d,J=8.4 Hz, 2 H), 6.96 (d,J=2.3 Hz, 1 H), 6.87 (d,J=9.0 Hz, 1 H), 6.67 (dd,J=2.5 and 9.0 Hz, 1 H), 4.08 (t,J=5.3 Hz, 2 H), 3.85 (s, 3 H), 3.67 (s, 2 H), 3.43 (s, 2 H), 3.94 (t,J=5.2 Hz, 2 H), 2.38–2.47 (mult, 2 H), 2.38 (s, 3H), 1.37–1.96 (m, 8 H); $^{13}$C NMR (75 MHz, $CDCl_3$) δ 173.7, 170.6, 168.4, 156.1, 139.3, 136.1, 133.9, 131.2, 130.8, 130.6, 129.1, 115.1, 112.2, 111.7, 101.3, 67.4, 63.9, 62.8, 58.2, 55.7, 34.5, 30.1, 25.5, 22.0, 13.4; mass spectrum (API-TIS), m/z 616 (MH$^+$).

Example 43

2-(Methyl{1-[2-methyl-2-(nitrosothio)propyl](4-piperidyl)}amino)ethyl (2S)-2-(6-methoxy(2-naphthyl))propanoate 43a. 1-(2-Methyl-2-sulfanylpropyl)piperidin-4-one To a stirred solution of the 1-(8-aza-1,4-dioxaspiro[4.5]dec-8-yl)-2-methylpropane-2-thiol (Synthesis, 1999, 7, 1106) (1.15 g, 4.98 mmol) in THF (12 mL) was added 6 N HCl (12 mL). The mixture was heated at 70° C. overnight, then poured into saturated $Na_2CO_3$. The mixture was extracted with EtOAc. The combined organic extracts were dried over $Na_2SO_4$ and evaporated. The residue was dissolved in EtOAc and acidified by adding HCl/EtOAc until no more solid formed. The solvent was decanted and the solid was then partitioned between EtOAc and satd $Na_2CO_3$. The aqueous layer was extracted with EtOAc and the combined organic extracts were dried over $Na_2SO_4$ and evaporated to give the title compound (0.90 g, 4.81 mmol, 97%) as a green oil. $^1$H NMR (300 MHz, $CDCl_3$) δ 2.96 (t, J=6.0, 4H), 2.52 (s, 2H), 2.41 (t, J=6.0, 4H), 1.34 (s, 6H).

43b. 2-{Methyl[1-(2-methyl-2-sulfanylpropyl)(4-piperidyl)]amino}ethan-1-ol

To a solution of the product of Example 43a (931 mg, 4.98 mmol) in $CH_2Cl_2$ (20 mL) was added 2-(methylamino)ethanol (748 mg, 9.96 mmol). Sodium triacetoxyborohydride (3.17 g, 14.96 mmol) was then added. The mixture was poured into water and extracted with $CH_2Cl_2$. The combined organic extracts were dried over $Na_2SO_4$ and evaporated. The residue was purified by a column chromatography eluting with 1:9 MeOH:$CH_2Cl_2$ to give the title compound as an oil. $^1$H NMR (300 MHz, $CDCl_3$) δ 3.53 (t, J=5.4, 2H), 2.90–2.98 (m, 2H), 2.59 (t, J=5.4, 2H), 2.19–2.40 (m, 4H), 2.32 (s, 2H), 2.25 (s, 3H), 1.49–1.66 (m, 4H), 1.26 (s, 6H); $^{13}$C NMR (75 MHz, $CDCl_3$) δ 61.4, 58.0, 55.7, 54.6, 46.4, 36.9, 30.0, 28.2.

43c. 2-(Methyl{1-[2-methyl-2-(nitrosothio)propyl](4-piperidyl)}amino)ethan-1-ol

To an ice cold solution of the product of Example 43b (250 mg, 1.02 mmol) in $CH_2Cl_2$ (10 mL) was added trifluoroacetic acid (233 mg, 2.04 mmol) dropwise. t-BuONO was then added and the reaction was kept cold for 30 min. The reaction mixture was then washed with saturated $Na_2CO_3$. The organic layer was dried over $Na_2SO_4$ and evaporated to give the title compound as a green oil. The product was used without further purification for the next step. $^1$H NMR (300 MHz, $CDCl_3$) δ 3.52 (t, J=5.4, 2H), 2.94 (s, 2H), 2.83–2.90 (m, 2H), 2.57 (t, J=5.4, 2H), 2.29–2.36 (m, 3H), 2.22 (s, 2H), 1.85 (s, 6H), 1.49–1.62 (m, 4H); $^{13}$C NMR (75 MHz, $CDCl_3$) δ 67.9, 61.2, 58.9, 58.1, 55.8, 54.5, 36.9, 28.2, 26.8.

43d. 2-(Methyl{1-[2-methyl-2-(nitrosothio)propyl](4-piperidyl)}amino)ethyl (2S)-2-(6-methoxy(2-naphthyl))propanoate To a solution of the product of Example 43c (275 mg, 1.02 mmol) in $CH_2Cl_2$ (10 mL) was added (2S)-2-(6-methoxy(2-naphthyl))propanoic acid (258 mg, 1.12 mmol) and DCC (232 mg, 1.12 mmol). The mixture was stirred at room temperature for 2 hours. The solid was removed by filtration and the solvent evaporated. The residue was purified by column chromatography eluting with 1:4 EtOAc:Hex to give the title compound as a green oil. $^1$H NMR (300 MHz, $CDCl_3$) δ 7.94–7.98 (m, 3H), 7.67–7.70 (m, 1H), 7.38–7.43 (m, 2H), 4.40–4.45 (m, 2H), 4.18 (s, 3H), 4.09–4.17 (m, 1H), 3.15 (s, 2H), 3.01–3.07 (m, 2H), 2.89 (t, J=5.9, 2H), 2.50 (s, 3H), 2.43–2.53 (m, 2H), 2.11 (s, 6H), 1.84 (d, J=7.1, 3H), 1.62–1.82 (m, 4H); $^{13}$C NMR (75 MHz, $CDCl_3$) δ 174.4, 157.5, 133.6, 133.5, 129.1, 128.8, 127.0, 126.1, 125.8, 118.8, 105.4, 67.7, 63.1, 60.7, 58.8, 55.4, 55.1, 51.6, 45.3, 38.4, 28.1, 27.9, 26.7, 18.5.

Example 44

3-{(4S)-4-[1-Methyl-1-(nitrosothio)ethyl]-2-oxo-1,3-oxazolidin-3-yl}propyl (2S)-2-(6-methoxy(2-naphthyl))propanoate 44a. (2S)-2-Amino-3-methyl-3-[(2,4,6-trimethoxyphenyl)methylthio]butanoic acid A suspension of (2S)-2-amino-3-methyl-3-sulfanylbutanoic acid (5.0 g, 703 mnuol) in $CH_2Cl_2$ (150 mL) was cooled to 0° C. Trifluoroacetic acid (54 mL, 703 mmol) was added dropwise over a period of 5 min. 2,4,6-trimethoxybenzyl alcohol (6.64 g, 34 mmol) in $CH_2Cl_2$ (137 mL) was added dropwise at 0° C. with stirring. The stirring was continued for 1 hour at 0° C. and 2 hours at room temperature, the solvent removed in vacuo and the residue was dried under high vacuum for 3 hours. The crude red solid was recrystallized from 1:1:1 $CH_2Cl_2$:MeOH:EtOAc to give the title compound 10.5 g (95%) as a white solid which was used for the next step without further purification. $^1$H NMR (300 MHz, $CDCl_3$) δ 6.10 (s, 2H), 3.84 (s, 6H), 3.76 (s, 3H), 3.40—4.10 (mult, 3H), 1.69 (s, 3H), 1.23 (s, 3H); mass spectrum (API-TIS) m/z 330 (M+H).

44b. (2S)-2-Amino-3-methyl-3-[(2,4,6-trimethoxyphenyl)methylthio]butan-1-ol

To a stirred solution of the product of Example 44a (10.5 g, 32 mmol) in THF (80 mL) was added dropwise lithium aluminum hydride (1 M in THF, 64 mL, 64 mmol) at 0° C. under nitrogen. The resulting solution was stirred at 0° C. for 1 hour and then at room temperature for 2 hours. The excess reducing agent was destroyed carefully by portionwise addition of $Na_2SO_4 \cdot 10H_2O$ at 0° C. The granular white precipitate was removed by filtration and washed with 30% MeOH in $CH_2Cl_2$. The combined filtrate was dried over $Na_2SO_4$, filtered and evaporated to give the title compound 7.6 g (76%) as a yellow oil which was used for the next step without further purification. $^1$H NMR (300 MHz, $CDCl_3$) δ 6.10 (s, 2H), 3.80 (s, 6 H), 3.77 (s, 3H), 3.74 (s, 2H), 3.60–3.40 (mult, 2H), 3.36–3.43 (mult, 1H), 2.93–2.97 (m, 1H), 1.45 (s, 3H), 1.30 (s, 3H); mass spectrum (API-TIS) m/z 316 (M+H).

44c. (4S)-4-[1-Methyl-1-(2,4,6-trimethoxyphenylthio)ethyl]-1,3-oxazolidin-2-one A mixture of $K_2CO_3$ (0.33 g, 2.4 mmol), diethylcarbonate (50 mL) and the product of Example 44b (7.6 g, 24 mmol) were heated at 100° C. for 24 hours. The solvent was evaporated and the resultant light brown slurry was cooled to room temperature, diluted with $CH_2Cl_2$ and filtered to remove most of the remaining $K_2CO_3$. The filtrate was evaporated in vacuo and the residue was chromatographed on silica gel eluting with 1:1 EtOAc:Hex to give the title compound 2.6 g (32%) as a viscous yellow oil. Unreacted product 44b can be recovered by eluting with 20% MeOH in $CH_2Cl_2$. $^1$H NMR (300 MHz, $CDCl_3$) δ 5.86 (s, 2H), 5.75 (br s, 1H), 4.36–4.43 (mult, 1H), 4.23–4.29 (mult, 1H), 4.04–4.10 (mult, 1H), 3.86 (s, 6H), 3.83 (s, 2H), 3.81 (s, 3H), 1.30 (s, 6H); $^{13}$C NMR (75 MHz, $CDCl_3$) δ 160.7, 159.4, 158.7, 106.1, 90.8, 66.4, 59.4, 56.0, 55.5, 47.1, 23.9, 22.3, 20.3, 14.3; mass spectrum (API-TIS) m/z 342 (M+H), 359 (M+NH$_4$), 364 (M+Na).

44d. 3-Bromo-1-(1,1,2,2-tetramethyl-1-silapropoxy)propane

Imidazole (0.52 g, 7.6 mmol) and t-butyldimethylchlorosilane (5.80 g, 38 mmol) were added successively to a solution of 1-bromo-3-propanol (5.35 g, 38 mmol) in dry THF (10 mL) at room temperature. The resulting suspension was stirred at room temperature for 20 hours. EtOAc (25 mL) was added. The solution was washed with water, dried over $Na_2SO_4$, filtered and concentrated in vacuo at room temperature. The residue was chromatographed on silica gel eluting with 1:10 EtOAc:Hex to give the title compound 2.1 g (22%) as a colorless volatile liquid. $^1$H NMR (300 MHz, $CDCl_3$) δ 3.74 (t, J=5.7 Hz, 2H), 3.52 (t, J=6.5 Hz, 2H), 2.02–2.06 (mult, 2H), 0.90 (s, 9H), 0.07 (s, 6H); $^{13}$C NMR (75 MHz, $CDCl_3$) δ 60.6, 35.7, 30.8, 26.1, −5.2.

44e. (4S)-4-{1-Methyl-1-[(2,4,6-trimethoxyphenyl)methylthio]ethyl}-3-[3-(1,1,2,2-tetramethyl-1-silapropoxy)propyl]-1,3-oxazolidin-2-one NaH (0.32 g, 12.8 mmol) was added portionwise to a solution of the product of Example 44c (2.18 g, 6.4 mmol) in dry DMF (40 mL) under nitrogen. The resulting suspension was stirred at room temperature for 20 min to give a brown red solution. The product of Example 44d (1.94 g, 7.7 mmol) in dry DMF (10 mL) was added dropwise at room temperature. The mnixture was stirred at room temperature for 2 hours and the solvent was evaporated. The residue was partitioned between EtOAc:$H_2O$ and the organic layer was separated. The aqueous layer was extracted with EtOAc. The combined organic layers were washed with water, dried over $Na_2SO_4$, and filtered. The residue after evaporation of the solvent was chromatographed on silica gel eluting with 1:19 to 1:3 EtOAc:Hex to give the title compound 1.66 g (51%) as a white foam. $^1$H NMR (300 MHz, $CDCl_3$) δ 6.11 (s, 2H), 4.38–4.42 (mult, 1H), 4.05–4.11 (mult, 1H), 3.93–3.96 (mult, 1H), 3.83 (s, 6H), 3.80 (s, 3H), 3.77 (s, 2H), 3.65 (t, J=6.1 Hz, 2H), 3.58–3.71 (mult, 1H), 3.34–3.44 (mult, 1H), 1.66–1.96 (mult, 2H), 1.56 (s, 3H), 1.24 (s, 3H), 0.89 (s, 9H), 0.04 (s, 6H); $^{13}$C NMR (75 MHz, $CDCl_3$) δ 160.7, 159.5, 158.7, 107.0, 90.8, 65.7, 61.7, 60.6, 55.9, 55.4, 48.3, 42.6, 30.3, 26.8, 26.0, 22.2, 20.4, 18.4, −5.3;mass spectrum (API-TIS) m/z 514 (M+H), 536 (M+Na).

44f. (4S)-3-(3-Hydroxypropyl)-4-{1-methyl-1-[(2,4,6-trimethoxyphenyl)methylthio]ethyl}-1,3-oxazolidin-2-one Tetrabutylammoniumfluoride (1 M solution in THF, 4.0 mL, 4 mmol) was added dropwise to a solution of the product of Example 44e (1.66 g, 3.2 mmol) in THF (20 mL) at 0° C. The resulting solution was stirred at 0° C. for 3 hours. The residue after evaporation of the solvent was chromatographed on silica gel eluting with 1:1 EtOAc:$CH_2Cl_2$ to give the title compound 1.05 g (81%) as a colorless viscous oil. $^1$H NMR (300 MHz, $CDCl_3$) δ 6.12 (s, 2H), 4.28–4.33 (mult, 1H), 4.12–4.19 (mult, 1H), 3.95–3.98 (mult, 1H), 3.83 (s, 6H), 3.80 (s, 3H), 3.78 (s, 2H), 3.54–3.70 (mult, 4H), 2.57 (br s, 1H), 1.78–1.85 (mult, 2H), 1.49 (s, 3H), 1.30 (s, 3H); $^{13}$C NMR (75 MHz, $CDCl_3$)δ 160.9, 160.8, 158.7, 106.8, 90.9, 65.7, 62.0, 59.1, 56.0, 55.5, 47.6, 41.7, 30.3, 25.6, 23.2, 20.6; mass spectrum (API-TIS) m/z 400 (M+H), 417 (M+NH$_4$), 422 (M+Na).

44g. 3-((4S)-4-{1-Methyl-1-[(2,4,6-trimethoxyphenyl)methylthio]ethyl}-2-oxo-1,3-oxazolidin-3-yl)propyl (2S)-2-(6-methoxy(2-naphthyl))propanoate DCC (0.39 g, 1.9 mmol) in $CH_2Cl_2$ (3 mL) was added dropwise to a stirred solution of the product of Example 44f (0.64 g, 1.60 mmol), (S)-6-methoxy-a-methyl-2-naphthalene acetic acid (0.37 g, 1.6 mmol) and DMAP (80 mg, 0.7 mmol) in $CH_2Cl_2$ (10 mL) at 0° C. The resulting suspension was stirred at 0° C. for 1 hour, then at room temperature for 16 hours. The DCU that precipitated was removed by filtration and washed with $CH_2Cl_2$ (10 mL). The combined organic phases were dried over $Na_2SO_4$, filtered, and concentrated in vacuo. The residue was chromatographed on silica gel eluting with 2%, 5% to 10% EtOAc:$CH_2C_2$ to give the title compound 0.75 g (77%) as a white foam. $^1$H NMR (300 MHz, $CDCl_3$) δ 7.66–7.71 (mult, 3H), 7.39–7.42 (mult, 1H), 7.08–7.14 (m, 2H), 6.09 (s, 2H), 4.27–4.32 (mult, 1H), 4.02–4.15 (mult, 3H), 3.89 (s, 3H), 3.80 (s, 3H), 3.78 (s, 6H), 3.70–3.91 (mult, 2H), 3.64–3.65 (d, J=1.9 Hz, 2H), 3.54–3.62 (mult, 1H), 3.26–3.36 (mult, 1H), 1.83–2.03 (mult, 2H), 1.58 (d, J=7.2 Hz, 3H), 1.33 (s, 3H), 1.19 (s, 3H); $^{13}$C NMR (75 MHz, $CDCl_3$)δ 174.7, 160.8, 159.4, 158.7, 157.8, 135.7, 133.9, 129.4, 129.1, 127.3, 126.3, 126.1, 119.2, 106.8, 105.7, 90.8, 65.6, 62.2, 61.6, 55.9, 55.5, 55.4, 48.0, 45.6, 42.2, 26.5, 25.8, 22.7, 20.5, 18.6; mass spectrum (API-TIS) m/z 612 (M+H), 629 (M+NH$_4$).

44h. 3-[(4S)-4-(1-Methyl-1-sulfanylethyl)-2-oxo-1,3-oxazolidin-3-yl]propyl (2S)-2-(6-methoxy(2-naphthyl))propanoate A mixture of the product of Example 44 g (0.75 g, 1.2 mmol) was treated with water (490 μL), phenol (490 mg), anisole (490 μL) and finally trifluoroacetic acid (6.0 mL). The solution was stirred at room temperature for 1 hour and evaporated in vacuo to give a yellow oil. The yellow oil was dissolved in $CH_2Cl_2$ and chromatographed on silica gel eluting with 1:9, 2:8 to 1:2 EtOAc:Hex to give the title compound 0.44 g (83%) as white needles. mp 118° C. $^1$H NMR (300 MHz, $CDCl_3$) δ 7.66–7.72 (mult, 3H), 7.39–7.42 (mult, 1H), 7.11–7.17 (m, 2H), 4.05–4.21 (mult, 4H), 3.92 (s, 3H), 3.86 (quart, J=3.1, 7.2 Hz, 1H), 3.48–3.58 (mult, 1H), 3.32–3.36 (mult, 1H), 3.19–3.22 (mult, 1H), 1.82–2.09 (mult, 2H), 1.58 (d, J=7.2 Hz, 3H), 1.45 (s, 1H), 1.18 (s, 3H), 1.13 (s, 3H); $^{13}$C NMR (75 MHz, $CDCl_3$) δ 174.7, 159.0, 157.9, 135.9, 133.9, 129.4, 129.0, 127.4, 126.3, 126.0, 119.3, 105.8, 65.6, 65.4, 61.8, 55.5, 47.2, 45.6, 42.5, 28.9, 27.2, 26.4, 18.6; Mass spectrum (API-TIS) m/z 432 (M+H), 449 (M+NH$_4$). Anal Calcd for $C_{23}H_{29}NO_5S$: C, 64.01; H, 6.77; N, 3.25; S, 7.43. Found: C, 63.95; H, 6.81; N, 3.07; S, 7.26.

44i. 3-{(4S)-4-[1-Methyl-1-(nitrosothio)ethyl]-2-oxo-1,3-oxazolidin-3-yl}propyl (2S)-2-(6-methoxy(2-naphthyl))propanoate To a solution of tert-butyl nitrite (0.17 mL, 0.15 g, 1.48 mmol) in $CH_2Cl_2$ (3 mL) was added dropwise a solution of the product of Example 44 g (0.32 g, 0.74 mmol) in CH$_2$Cl$_2$ at 0° C. The resulting green solution was stirred at 0° C. for 10 min and at room temperature for 20 min in the dark. The residue after evaporation of the solvent was chromatographed on silica gel eluting with 1:4 to 1:2 EtOAc:Hex to give the title compound 0.26 g (76%) as a green solid. mp 116–117° C. $^1$H NMR (300 MHz, CDCl$_3$) δ 7.66–7.71 (mult, 3H), 7.38–7.42 (mult, 1H), 7.09–7.16 (m, 2H), 4.28 (s, 3H), 4.05–4.18 (mult, 2H), 3.92 (s, 3H), 3.87 (quart, J=2.9, 7.1 Hz, 1H), 3.55–3.64 (mult, 1H), 3.09–3.19 (mult, 1H), 1.72–2.02 (mult, 2H), 1.77 (s, 3H), 1.72 (s, 3H), 1.58 (d, J=7.2 Hz, 3H); $^{13}$C NMR (75 MHz, CDCl$_3$) δ 174.7, 158.8, 157.9, 135.7, 133.9, 129.4, 129.1, 127.4, 126.3, 126.0, 119.2, 105.7, 65.1, 63.2, 61.7, 58.9, 55.4, 45.5, 42.5, 26.3, 25.2, 24.6, 18.6; mass spectrum (API-TIS) m/z 461 (M+H), 478 (M+NH$_4$). Anal Calcd for C$_{23}$H$_{28}$N$_2$O$_6$S: C, 59.98; H, 6.13; N, 6.08; S, 6.96. Found: C, 59.95; H, 6.08; N, 5.89; S, 6.89.

Example 45

{Ethoxy[3-methyl-3-(nitrosothio)butoxy] phosphonyl}methyl (2S)-2-(6 -methoxy (2-naphthyl))propanoate 45a. (Diethoxyphosphoryl)methyl (2S)-2-[6-methoxy(2-naphthyl)]propanoate A solution of (2S)-2-(6-methoxy(2-naphthyl))propanoic acid (4.8 g, 20.85 mmol), diethyl (hydroxymethyl) phosphonate (3.76 g, 22.36 mmol), 1-[3-(dimethylamino) propyl]-3-ethylcarbodiimide hydrochloride (4.29 g, 22.38 mmol) and 4-(dimethylamino)pyridine (catalytic amount) in CH$_2$Cl$_2$ (125 mL) were stirred at room temperature for 2 hours. The reaction was taken up with 0.3 N HCl (150 mL) and extracted with CH$_2$Cl$_2$ (3×50 mL). The combined extracts were washed with water (2×50 mL), dried over Na$_2$SO$_4$, and evaporated under reduced pressure. The product was purified by silica gel column chromatography eluting with 2:1 EtOAc:Hex to obtained the title compound as a viscous oil, 5.23 g (66%). $^1$H NMR (300 MHz, CDCl$_3$) δ 7.70–7.68 (mult, 3H), 7.43–7.37 (mult, 1H), 7.15–7.09 (mult, 2H), 4.38 (d, J$_{H-P}$=8.6 Hz, 2H), 4.05–3.85 (mult, 5H), 3.95 (s, 3H), 1.60 (d, J=7.2 Hz, 3H), 1.25–1.1 (mult, 6H); $^{13}$C NMR (75 MHz, CDCl$_3$) δ 173.5 (d, J$_{C-P}$=7.9 Hz), 157.7, 134.9, 133.7, 129.1, 128.8, 127.1, 126.1, 119.0, 105.5, 62.71, 62.62, 62.61, 62.52, 57.1 (d, J$_{C-P}$=167.0 Hz), 55.2, 45.1, 18.3, 16.20, 16.18, 16.12, 16.11; mass spectrum (API-TIS) m/z 381 (M+H). Anal Calcd for C$_{19}$H$_{25}$O$_6$P: C, 60.0; H, 6.62. Found: C, 59.83; H, 6.41.

45b. (Ethoxy(hydroxyphosphoryl))methyl (2S)-2-(6-methoxy(2-naphthyl)) propanoate A mixture of the product of Example 45a (3.25 g, 9.22 mmol) and LiCl (1.0 g, 23.6 mmol) in anhydrous DMF (80 mL) was heated to 80° C. under argon for 24 hours. DMF was removed under vacuum. The resulting viscous oil was dissolved in methanol (100 mL) and treated with DOWEX-50W—H$^+$ resin (10 g). The mixture was stirred at room temperature for 1.5 hours. The resin was removed by filtration and the filtrate was concentrated. The residue was dissolved in EtOAc (200 mL). The solution was washed with water (3×50 mL), dried over Na$_2$SO$_4$ and concentrated. The residue was dried under vacuum to obtained the title compound as a clear oil, 2.61 g (80%). $^1$H NMR (300 MHz, CD$_3$OD) δ 7.74–7.70 (mult, 3H), 7.41–7.38 (mult, 1H), 7.20–7.09 (mult, 2H), 4.36 (d, J$_{H-P}$=8.6 Hz, 2H), 4.0–3.78 (mult, 5H), 3.89 (s, 3H), 1.57 (d, J=7.1 Hz, 3H), 1.05 (t, J=7.1 Hz, 3H); $^{13}$C NMR (75 MHz, CD$_3$OD) δ 175.0 (d, J$_{C-P}$=7.6 Hz), 159.0, 136.4, 135.1, 130.2, 130.0, 128.1, 126.9, 119.8, 106.4, 63.3 (d, J$_{C-P}$=6.1 Hz), 58.4 (d, J$_{C-P}$=164.9 Hz), 55.5, 46.1, 18.7, 16.4 (d, J$_{C-P}$=6.0 Hz); mass spectrum (API-TIS) m/z 351.2 (M–H)

45c. (Ethoxy{3-methyl-3-[(2,4,6-trimethoxyphenyl) methylthio]butoxy}phosphoryl) methyl (2S)-2-(6-methoxy(2-naphthyl))propanoate A mixture of the product of Example 45b (1.6417 g, 4.66 mmol), benzotriazol-1-yloxytris-(dimethylamino) phosphonium hexafluorophosphate (3.1168 g, 7.05 mmol), and diisopropyl ethylamine (3.2 mL, 18.37 mmol) in anhydrous DMF (40 mL) was stirred at room temperature for 10 mm. To the resultant brown solution was added 3-methyl-3-[(2,4,6-trimethoxyphenyl) methylthio]butan-1-ol (2.02 g, 6.73 mmol) and 4-(dimethylamino)-pyridine (0.26 g, 2.13 mmol). After 5.5 hours, the DMF was evaporated under reduced pressure. The resulting brown oil was taken up in EtOAc (100 mL). The solution was washed with 1 N HCl (2×75 mL), water (2×75 mL), brine (75 mL), and dried over Na$_2$SO$_4$, and concentrated under reduced pressure. The product was purified by silica gel column chromatography eluting with 2:1 EtOAc:Hex to obtained the title compound as a viscous oil, 2.08 g (70%). $^1$H NMR (300 MHz, CDCl$_3$) δ 7.87–7.83 (mult, 3H), 7.40–7.37 (mult, 1H), 7.14–7.07 (mult, 2H), 6.09 (s, 2H), 4.40–4.37 (mult, 2H), 4.35–4.10 (mult, 2H), 3.98–3.90 (mult, 3H), 3.89 (s, 3H), 3.80 (s, 6H), 3.78 (s, 3H), 3.66 (s, 2H), 1.9–1.86 (mult, 2H), 1.59 (d, J=7.2 Hz), 1.28 (s, 3H), 1.27 (s, 3H), 1.17–1.11 (mult, 3H); $^{13}$C NMR (75 MHz, CDCl$_3$) δ 173.4 (d, J$_{C-P}$=7.7 Hz), 160.2, 158.5, 157.5, 134.7, 133.6, 129.0, 128.7, 127.0, 125.95, 125.93, 125.9, 125.88, 118.9, 106.8, 105.4, 90.5, 64.19, 64.12, 64.05, 60.1, 57.96, 57.89, 55.73, 55.67, 55.6, 55.09, 55.04, 44.9, 43.7, 41.3, 41.2, 28.9, 20.2, 18.2, 16.1, 16.0; mass spectrum (API-TIS) m/z 652 (M+NH$_4$).

45d. [Ethoxy(3-methyl-3-sulfanylbutoxy)phosphonyl] methyl(2S)-2-(6-methoxy(2-naphthyl))propanoate Trifluoroacetic acid (10 mL) was added to a mixture of the product of Example 45c (1.04 g, 1.64 mmol) and L-cysteine (2.0 g, 16.5 mmol) and stirred at room temperature for 45 min. The TFA was evaporated under reduced pressure. The residue was taken up with EtOAc (125 mL). The solution was washed with water (5×125 mL), dried over Na$_2$SO$_4$, and concentrated under reduced pressure. The product was purified by silica gel column chromatography eluting with 3:2 EtOAc:Hex to obtained the title compound as a viscous oil, 0.61 g (82%). $^1$H NMR (300 MHz, CDCl$_3$) δ 7.7–7.67 (mult, 3H), 7.40–7.37 (mult, 1H), 7.14–7.07 (mult, 2H), 4.43–4.38 (mult, 2H), 4.2–3.85 (mult, 5H), 3.87 (s, 3H), 1.8–1.7 (mult, 2H), 1.65–1.55 (mult, 4H), 1.28 (s, 3H), 1.27 (s, 3H), 1.2–1.05 (mult, 3H); $^{13}$C NMR (75 MHz, CDCl$_3$) δ 173.2 (d, J$_{C-P}$=7.0 Hz), 157.5, 134.7, 134.6, 133.5, 129.0, 128.6, 126.9, 125.9, 125.8, 118.8, 105.3, 63.8, 63.7, 63.6, 62.7, 62.6, 62.5, 57.8, 55.5, 55.0, 45.7, 45.6, 44.84, 44.80, 42.3, 32.6, 18.15, 18.07, 16.02, 15.95; mass spectrum (API-TIS) m/z 455 (M+H).

45e. {Ethoxy[3-methyl-3-(nitrosothio)butoxy] phosphonyl}methyl (2S)-2-(6-methoxy(2-naphthyl)) propanoate tert-Butyl nitrite (0.45 mL, 3.4 mmol) was added to a solution of the product of Example 45d in CH$_2$Cl$_2$ (20 mL) and stirred at room temperature for 2 hours under argon in the dark. The resultant green solution was concentrated to dryness under reduced pressure. The product was purified by silica gel column chromatography eluting with 5:4 EtOAc:Hex to obtained the title compound as an oil, 237 mg (44%). $^1$H NMR (300 MHz, CDCl$_3$) δ 7.68–7.65 (mult, 3H), 7.40–7.36 (mult, 1H), 7.14–7.07 (mult, 2H), 4.44–4.36 (mult, 2H), 4.2–3.85 (mult, 5H), 3.87 (s, 3H), 2.37–2.33

(mult, 2H), 1.76 (s, 3H), 1.74 (s, 3H), 1.6–1.57 (mult, 3H), 1.2–1.12 (mult, 3H); $^{13}$C NMR (75 MHz, CDCl$_3$) δ 173.2 (d, J$_{C-P}$=7.0 Hz), 157.5, 134.7, 134.6, 133.5, 129.0, 128.6, 126.9, 125.9, 125.8, 118.8, 105.3, 63.8, 63.7, 63.6, 62.7, 62.6, 62.5, 57.8, 55.5, 55.0, 45.7, 45.6, 44.84, 44.80, 42.3, 32.6, 18.15, 18.07, 16.02, 15.95; mass spectrum (API-TIS) m/z 455 (M+H).

Example 46

6-(4-{[2-Methyl-2-(nitrosothio)propyl] amino}pyrimidin-2-ylthio)hexyl (2S)-2-(6-methoxy (2-naphthyl))propanoate 46a. 4-Chloro-2-(methylsulfonyl)pyrimidine m-Chloroperoxybenzoic acid (57–86%, 24.24 g, 80–121 mmol) was added to an ice-cooled solution of 4-chloro-2-methylthiopyrimidine (6.41 g, 39.9 mmol) in CH$_2$Cl$_2$ (120 mL). The reaction was stirred in the ice-bath for 10 min and at room temperature for 3 hours. The reaction was quenched with 6% Na$_2$S$_2$O$_3$ (50 mL). To the resulting mixture was carefully added saturated NaHCO$_3$ (100 mL). The organic layer was separated and the aqueous layer was extracted with CH$_2$Cl$_2$ (3×50 mL). The combined organic extracts were washed with saturated NaHCO$_3$ (50 mL), water, brine, dried over Na$_2$SO$_4$, concentrated under reduced pressure. The crude product was dissolved in CH$_2$Cl$_2$ (20 mL) and triturated with hexane (about 120 mL) to precipitate the title compound. The white solid was collected on a sintered glass funnel and washed with hexane (50 mL). The filtrate was concentrated and the residue was treated as above to yield a second crop. The solid was dried under vacuum to give the title compound as a white powder, 5.8 g (86%). $^1$H NMR (300 MHz, CDCl$_3$) δ 8.87 (d, J=5.4 Hz, 1H), 7.56 (d, J=5.4 Hz, 1H), 3.39 (s, 3H); $^{13}$C NMR (75 MHz, CDCl$_3$) δ 166.1, 163.3, 159.4, 124.7, 97.15, 39.1; mass spectrum (API-TIS) m/z 193 (M+H). Anal Calcd for C$_5$H$_5$ClN$_2$O$_2$S: C, 31.18; H, 2.62; N, 14.54. Found: C, 31.21; H, 2.63; N, 14.55.

46b. 6-(4-Chloropyrimidin-2-ylthio)hexan-1-ol

6-Mercapto-1-hexanol (1.4 mL, 10.2 mmol) was added to a suspension of NaH (60% in mineral oil, 0.42 g, 10.5 mmol) in THF (20 mL) and stirred at room temperature for 10 min then cooled down to −78° C. in dry ice bath. A suspension of the product Example 46a (1.74 g, 9.03 mmol) was added to the above mixture and stirred at −78° C. for 2.5 hours. The reaction was quenched with water (20 mL) and extracted with Et$_2$O (100 mL). The extract was washed with water (2×100 mL) and brine (100 mL), dried over Na$_2$SO$_4$, filtered, and concentrated under reduced pressure. The product was purified by silica gel column chromatography eluting with 1:2 EtOAc:Hex to obtained the title compound as a viscous oil, 1.8 g (81%). $^1$H NMR (300 MHz, CDCl$_3$) δ 8.67 (d, J=5.3 Hz, 1H), 7.00 (d, J=5.3 Hz, 1H), 3.63 (t, J=6.6 Hz, 2H), 3.14 (t, J=7.4 Hz, 2H), 2.60 (S, 1H), 1.8–1.4(mult, 8H); $^{13}$C NMR (75 MHz, CDCl$_3$) δ 173.4, 160.7, 157.8, 116.2, 62.3, 32.3, 30.8, 28.6, 28.3, 25.1; mass spectrum (API-TIS) m/z 247 (M+H).

46c. 1-Amino-2-methylpropane-2-thiol

To a suspension of 2-mercapto-2-methyl-1-propylamine hydrochloride (8 g, 56.7 mmol) in anhydrous Et$_2$O (100 mL) was added triethylamine (20 mL, 143.5 mmol). The reaction mixture was stirred at room temperature overnight and filtered. The filtrate was evaporated to give the title compound as a volatile solid (3.95 g, 91%). $^1$H NMR (300 MHz, CDCl$_3$) δ 2.77 (s, 2H), 1.72 (s, 3H), 1.34 (s, 6H); $^{13}$C NMR (75 MHz, CDCl$_3$) δ 56.2, 46.9, 29.6.

46d. 6-{4-[(2-Methyl-2-sulfanylpropyl)amino]pyrimidin-2-ylthio}hexan-1-ol

A solution of the product of Example 46b (1.65 g, 6.69 mmnol) and the product of Example 46c (1.91 g, 18.2 mmol) in anhydrous pyridine (40 mL) was degassed by two freeze-pump-thaw cycles and covered with argon. The reaction was heated to 70° C. overnight and then the pyridine was evaporated. The residue was chromatographed on silica gel eluting with 1:1 EtOAc:Hex to give the title compound 0.57 g (27%). $^1$H NMR (300 MHz, CDCl$_3$) δ 7.91 (d, J=5.8 Hz, 1H), 6.06 (d, J=5.8 Hz, 1H), 5.78 (br, 1H), 3.63 (t, J=6.6 Hz, 2H), 3.50 (br, 2H), 3.06 (t, J=7.4 Hz, 2H), 2.94 (S, 1H), 1.79 (s, 1H), 1.8–1.2 (mult, 8H), 1.38 (s, 6H); $^{13}$C NMR (75 MHz, CDCl$_3$) δ 170.9, 161.8, 154.8, 100.0, 62.2, 53.3, 45.4, 32.4, 30.3, 29.9, 29.3, 28.5, 25.2; mass spectrum (API-TIS) m/z 316 (M+H).

46e. 6-(4-{[2-Methyl-2-(nitrosothio)propyl] amino}pyrimidin-2-ylthio)hexan-1-ol tert-Butyl nitrite (90%, 0.3 mL, 2.27 mmol) was added to a solution of the product of Example 46d (0.55 g, 1.74 mmol) in CH$_2$Cl$_2$ (25 mL) and HCl (1N, 2 mL). The mixture was stirred at room temperature for 3 hours in the dark. The reaction mixture was partitioned and made basic with satd NaHCO$_3$ (20 mL) and water (20 mL). The aqueous layer was separated and extracted with CH$_2$Cl$_2$ (2×30 mL). The combined organic extracts were dried over Na$_2$SO$_4$, filtered, and concentrated. The product was purified by silica gel column chromatography 3:2 EtOAc:Hex to give the title compound as a green oil, 0.43 g (71%). $^1$H NMR (300 MHz, CDCl$_3$) δ 7.98 (d, J=5.9 Hz, 1H), 5.95 (d, J=5.9 Hz, 1H), 5.10 (br, 1H), 4.21 (br, 2H), 3.65 (t, J=6.5 Hz, 2H), 3.09 (t, J=7.4 Hz, 2H), 1.92 (s, 6H), 1.8–1.4 (mult, 8H); $^{13}$C NMR (75 MHz, CDCl$_3$) δ 171.0, 161.9, 154.8, 100.6, 62.3, 57.3, 50.4, 32.4, 30.4, 29.3, 28.6, 26.7, 25.2; mass spectrum (API-TIS) m/z 345 (M+H).

46f. 6-(4-{[2-Methyl-2-(nitrosothio)propyl] amino}pyrimidin-2-ylthio)hexyl (2S)-2-(6-methoxy(2-naphthyl))propanoate A solution of the product of Example 46e (0.355 g, 1.03 g), (2S)-2-(6-methoxy(2-naphthyl))propanoic acid (0.2517 g, 1.09 mmol), 1-[3-(dimethylamino)propyl]-3-ethylcarbodiimide hydrochloride (0.2411 g, 1.26 mmol) and 4-(dimethylamino)-pyridine (5 mg) in CH$_2$Cl$_2$ (25 mL) were stirred at room temperature for 2.5 hours. The reaction was washed with water (50 mL) and satd NaHCO$_3$ (1 mL). The aqueous washes were back extracted with CH$_2$Cl$_2$ (2×30 mL). The combined organic extracts were dried over Na$_2$SO$_4$, filtered, and concentrated. The product was purified by silica gel column chromatography 3:5 EtOAc:Hex to give the title compound as a green oil, 0.46 g (76%). $^1$H NMR (300 MHz, CDCl$_3$) δ 7.87 (d, J=5.9 Hz, 1H), 7.69–7.65 (mult, 3H), 7.41–7.37 (mult, 1H), 7.13–7.09 (mult, 2H), 5.99 (d, J=5.9 Hz, 1H), 5.64 (br, 1H), 4.15 (br, 2H), 4.06 (t, J=6.6 Hz, 2H), 3.88–3.83 (mult, 1H), 3.86 (s, 3H), 2.97 (t, J=7.4 Hz, 2H), 1.85 (s, 6H), 1.65–1.53 (mult, 7H), 1.37–1.24 (mult, 4H); mass spectrum (API-TIS) m/z 557.0 (M+H). Anal Calcd for C$_{28}$H$_{36}$N$_4$O$_4$S$_2$: C, 60.41; H, 6.52; N, 10.06. Found: C, 60.14; H, 6.37; N, 9.78.

Example 47

{(2S,5S)-5-[1-Methyl-1-(nitrosothio)ethyl]-3,6-dioxopiperazin-2-yl}methyl (2S)-2-(6-methoxy(2-naphthyl))propanoate 47a. (2S)-2-Amino-3-[(4-methoxyphenyl)methylthio]-3-methylbutanoic acid A suspension of (2S)-amino-3-methyl-3-sulfanylbutanoic (11.5 g, 77.2 mmol) in CH$_2$Cl$_2$ (60 mL) was treated with trifluoroacetic acid (13.7 mL) and stirred to dissolve at room temperature. The mixture was then cooled to −10° C. under nitrogen. A solution of 4-methoxybenzyl chloride (10.5 mL, 77.25mmol) in $CH_2Cl_2$ (90 mL) was added dropwise through an additional funnel over a period of 1.5 hours. Stirring was continued for 1.5 hours at room temperature. Methanol (10 mL) was added to dissolve the precipitate. The crude reaction was concentrated in vacuo. The residue was dissolved in $CH_2Cl_2$ (40 mL) and extracted with water (7×50 mL). The combined aqueous extracts were frozen and lyophilized. The residue was dissolved in methanol/water (1:3, 200 mL) and brought to pH 6–7 with sodium bicarbonate. The white solid was isolated by filtration, rinsed with MeOH/water (1:3), and dried to give the title compound (6.92 g, 33%). $^1$H NMR (300 MHz, $CD_3OD$) δ 7.28 (d, J=7.0 Hz, 2H), 6.85 (d, J=8.4 Hz, 2H), 3.79–3.76 (m, 5H), 3.51 (s, 1H), 1.63 (s, 3H), 1.33 (s, 3H).

47b. (4S)-4-{1-[(4-methoxyphenyl)methylthio]-isopropyl}-1,3-oxazolidine-2,5-dione The product of Example 47a (3.0 g, 11.1 mmol) was suspended in THF (45 mL) at 0° C. under nitrogen. A solution of phosgene (17 mL, 33.4 mmol) was slowly added. The solution was allowed to stir at 0° C. for 30 min then warmed to room temperature for 22 hours. The solvent was removed in vacuo. The yellowish oil was dried under high vacuum overnight without further purification. $^1$H NMR (300 MHz, $CD_3OD$) δ 7.31 (d, J=9.0 Hz, 2H) 7.16 (d, J=8.9 Hz, 2H), 4.39 (s, 1H), 3.82–3.73 (m, 5H), 1.51 (s, 3H), 1.35 (s, 3H); mass spectrum (API-TIS) m/z 313. $(M+NH_4)$.

47c. Methyl (2S)-2-{(2S)-2-amino-3-[(4-methoxyphenyl)methylthio]-3-methylbutanoylamino}-3-hydroxypropanoate To a stirred suspension of methyl (2S)-2-amino-3-hydroxypropanoate hydrogen chloride (1.73 g, 11.1 mmol) in $CHCl_3$ (50 mL) at −78° C. under nitrogen was added a solution of triethylamine (3.9 mL, 27.8 mmol) and the product of Example 47b in THF (30 mL). The resulting solution was stirred at −78° C. for 4 hours and then warmed to room temperature overnight. The solvents were removed in vacuo. The residue was partitioned between $Et_2O$ and $H_2O$. The organic phase was washed with brine, dried over $MgSO_4$, filtered and concentrated to give the title compound (3.17 g), which was used for next step without further purification. Mass spectrum (API-TIS) m/z 371 (M+H).

47d. (3S,6S)-3-(Hydroxymethyl)-6-{1-[(4-methoxyphenyl)methylthio]-isopropyl}piperazine-2,5-dione The product of Example 47c was refluxed in toluene (50 mL) for 24 hours, cooled slowly to room temperature and stored at −4° C. for 24 h. The solid was isolated by filtration, rinsed with ether, and dried to give the title compound (0.8 g, 21% from 47b). $^1$H NMR (300 MHz, $CDCl_3$) δ 8.19 (br, 1H), 8.02 (br, 1H), 7.25 (d, J=8.57 Hz, 2H), 6.89 (d, J=8.59 Hz, 2H), 4.92–4.84 (m, 1H), 4.08–4.06 (m, 1H), 3.81–3.76 (m, 5H), 1.49 (s, 3H), 1.44 (s, 3H); mass spectrum (API-TIS) m/z 339.0 (M+H).

47e. ((2S,5S)-5-{1-[(4-methoxyphenyl)methylthio]-isopropyl}-3,6-dioxopiperazin-2-yl)methyl (2S)-2-(6-methoxy(2-naphthyl))propanoate A mixture of the product of Example 47d (620 mg, 1.8 mmol), (2S)-2-(6-methoxy(2-naphthyl))propanoic acid (421 mg, 1.8 mmol), 4-(dimethylamino)-pyridine (223 mg, 1.8 mmol) and 1-ethyl-3-(3-dimethylamino propyl) carbodiimide hydrogen chloride (421 mg, 2.20 mmol) in DMF (25 mL) were stirred at room temperature under nitrogen overnight. The precipitate was removed by filtration, and the mother liquor was triturated with $Et_2O:CH_2Cl_2$ (1:1, 10 mL). The solid which precipitated was isolated by filtration, rinsed with $Et_2O$, and dried to give the title compound (0.46 g, 46%). $^1$H NMR (300 MHz, DMSO-$d_6$) δ 8.36–8.39 (m, 2H), 7.72–7.83 (m, 3H), 7.15–7.42 (m, 5H), 6.83–6.88 (d, 2H), 4.41–4.45 (m, 2H), 4.28 (d, J=9.6 Hz, 1H), 3.87–3.97 (m, 4H), 3.66–3.77 (m, 5H), 3.56–3.57 (m, 1H), 1.48 (d, J=7.0 Hz, 3H), 1.41 (s, 3H), 1.35 (s, 3H); mass spectrum (API-TIS) m/z 551.0 (M+H).

47f. [(2S,5S)-5-(1-Methyl-1-sulfanylethyl)-3,6-dioxopiperazin-2-yl]methyl (2S)-2-(6-methoxy(2-naphthyl))propanoate A solution of the product of Example 47e (450 mg, 0.82 mmol), anisole (0.61 mL, 5.50 mmol), trifluoroacetic acid (0.32 mL) in $CH_2Cl_2$ (1.5 mL) was cooled to 0° C. and treated dropwise with trifluoromethanesulfonic acid (0.6 mL). The resulting solution was stirred at 0° C. for 30 min and then at room temperature for 2 hours. The mixture was diluted with $Et_2O$ (5 mL) and $H_2O$ (5 mL). The solid that precipitated was isolated by filtration, rinsed with $Et_2O$, and dried to give the title compound (160mg, 45%). $^1$ NMR (300 MHz, DMSO-$d_6$) δ 8.48 (br, 1H), 8.29 (br, 1H), 7.72–7.83 (m, 3H), 7.16–7.42 (m, 3H), 4.40–4.44 (m, 2H), 4.22–4.24 (m, 1H), 3.88–3.94 (m, 4H), 3.56 (br, 1H), 2.72 (s, 1H), 1.36–1.49 (m, 9H); $^{13}$C NMR (75 MHz, DMSO-$d_6$) δ 173.6, 165.7, 165.4, 157.3, 135.3, 133.3, 129.2, 128.4, 126.9, 126.3, 125.6, 118.7, 105.7, 64.8, 64.6, 55.2, 53.3, 49.6, 44.3, 30.5, 29.7, 18.5; mass spectrum (API-TIS) m/z 431 (M+H).

47g. {(2S,5S)-5-[1-methyl-1-(nitrosothio)ethyl]-3,6-dioxopiperazin-2-yl}methyl (2S)-2-(6-methoxy(2-naphthyl))propanoate The product of Example 47f (150 mg, 0.35 mmol) was dissolved in DMF (25 mL) with the aid of sonication. To this solution was added dropwise tert-butylnitrite (0.14 mL, 1.05 mmol) under nitrogen. The resulting solution was stirred at room temperature for 2 hours. The solvent was removed and the residue was triturated with $Et_2O$. The solid was isolated by filtration and dried to give the title compound (130 mg, 81%). mp >180° C. decomposed; $^1$H NMR (300 MHz, DMSO-$d_6$) δ 8.85 (s, 1H), 8.36 (s, 1H), 7.71–7.83 (m, 3H), 7.15–7.40 (m, 3H), 3.88–4.38 (m, 8H), 2.03 (s, 3H), 1.98 (s, 3H), 1.46 (d, J=6.8 Hz, 3H); $^{13}$C NMR(75 MHz, DMSO-$d_6$) δ 173.5, 165.4, 164.5, 157.2, 135.3, 133.3, 129.2, 128.3, 126.9, 126.3, 125.6, 118.7, 105.7, 63.8, 63.2, 61.9, 55.153.0, 44.3, 26.6, 25.9, 18.5; mass spectrum (API-TIS) m/z 477 $(M+NH_4)$.

Example 48

2-(N-Methyl{1-[2-methyl-2-(nitrosothio)propyl](4 piperidyl)}carbonylamino)ethyl (2S)-2-(6-methoxy (2-naphthyl))propanoate 48a. Ethyl 1-(2-methyl-2-sulfanylpropyl)piperidine-4-carboxylate Ethyl piperidine-4-carboxylate (3.6 g, 22.9 mmol) was dissolved in benzene (5 mL), and 2,2-dimethylthiirane (5.04 g, 57.3 mmol) was added. The reaction mixture was stirred at 80° C. for 20 hours, poured into water and extracted several times with EtOAc. The combined organic extracts were washed with brine and dried over anhydrous sodium sulfate. The volatiles were evaporated and the residue was dried under vacuum to afford 5.45 g (97%) of the title compound. $^1$H NMR (300 MHz, $CD_3OD$) δ 4.12 (q, J=7.1 Hz, 2H), 2.92–2.96 (d, J=11.9 Hz, 2H), 2.19–2.40 (m, 6H), 1.61–1.86 (m, 4H), 1.29 (s, 6H), 1.25 (t, J=7.1 Hz, 2H).

48b. 1-(2-methyl-2-sulfanylpropyl)piperidine-4-carboxylic acid

The product of Example 48a (5.3 g, 21.6 mmol) was dissolved in ethanol (25 mL) and a solution of sodium hydroxide (3.1 g, 77.9 mmol) in water (30 mL) was added.

The reaction mixture was stirred at room temperature for 5 hours. The reaction mixture was concentrated under reduced pressure and concentrated HCl was added to pH 5.6. Ethanol was added and the volatiles were evaporated. The residue was suspended in EtOAc and filtered. The filter cake was washed with $CH_2Cl_2$ and the filtrate was concentrated in vacuo to give 4.5 g (96%) of the title compound. $^1$H NMR (300 MHz, $CD_3OD$) δ 3.13 (d, 2H), 2.55–2.68 (m, 4H), 2.17–2.26 9m, 1H), 1.77–1.92 (m, 5H), 1.32 (s, 6H).

48c. 1-[2-Methyl-2-(nitrosothio)propyl]piperidine-4-carboxylic acid

The product of Example 48b (1.31 g, 6.04 mmol) was dissolved in anhydrous methanol (20 mL) and 2N HCl (12 mL, 24 mmol) was added. The resulting mixture was cooled to 0° C. and a solution of sodium nitrite (1.66 g, 24.1 mmol) in water (5 mL) was added. The reaction mixture was stirred at 0° C. for 40 min. Ethanol (30 mL) was added and the volatiles were evaporated. The residue was dissolved in ethanol and sodium chloride was removed by filtration. The filtrate was concentrated in vacuo and the residue was purified by flash chromatography on silica gel, eluting with 100:1 to 40:1 $CH_2Cl_2$:MeOH to give 0.73 g (49%) of the title compound as a green oil. $^1$H NMR (300 MHz, $CDCl_3$) δ 3.04 (s, 2H), 2.87–2.93 (m, 2H), 2.46 (t, 2H), 2.30–2.34 (m, 1H), 1.89 (s, 6H), 1.68–1.87 (m, 4H), 48d. (tert-Butoxy)-N-(2-hydroxyethyl)-N-methylcarboxamide N-Methylaminoethanol (5.1 g, 67.7 mmol) was dissolved in THF (70 mL) and di-tert-butyl dicarbonate (15.7 g, 72 mmol) was added. The resulting solution was stirred at room temperature for 18 hours. The volatiles were evaporated and the residue was dried under vacuum overnight to give 11.2 g (95%) of the title compound. $^1$H NMR (300 MHz, $CDCl_3$) δ 3.74 (t, 2H), 3.38 (t, 2H), 2.91 (s, 3H), 2.21 (s, 1H), 1.46 (s, 9H).

48e. 2-[(tert-Butoxy)-N-methylcarbonylamino]ethyl (2S)-2-(6-methoxy(2-naphthyl))propanoate Under a nitrogen atmosphere, (2S)-2-(6-methoxy(2-naphthyl))propanoic acid (5.0 g, 21.7 mmol) was dissolved in anhydrous $CH_2Cl_2$ (50 mL) and 4-dimethylaminopyridine (2.65 g, 21.7 mmol) was added. The product of Example 48d (3.8 g, 21.7 mmol) was then added, followed by a solution of 1,3-dicyclohexyl-carbodiimide 4.1 g, 21.7 mmol) in $CH_2Cl_2$ (50 mL). The resulting mixture was stirred at room temperature for 18 hours. The solvent was evaporated and the residue was purified by flash chromatography on silica gel, eluting with 9:1 Hex:EtOAc to give 6.04 g (72%) of the title compound. $^1$H NMR (300 MHz, $CDCl_3$) δ 7.68 (t, 3H), 7.39 (d, 1H), 7.10–7.18 (m, 2H), 4.12–4.20 (m, 2H), 3.91 (s, 3H), 3.86 (q, 1H), 3.34–3.40 (m, 2H), 2.71 (s, 3H), 1.57 (d, 3H), 1.43 (s, 9H).

48f. 2-(Methylamino)ethyl (2S)-2-(6-methoxy(2-naphthyl)) propanoate

The product of Example 48e (6.04 g, 15.6 mmol) was dissolved in $CH_2Cl_2$ (50 mL) and anisole (1.7mL, 15.6 mmol) was added, followed by TFA (50 mL). The resulting mixture was stirred at room temperature for 15 minutes. Toluene was added and the volatiles were evaporated. The residue was purified by flash chromatography on silica gel, eluting with methylene 30:1 $CH_2Cl_2$:MeOH to give 3.0 g (68%) of the title compound as a white solid. $^1$H NMR (300 MHz, $CDCl_3$) δ 7.60–7.73 (m, 3H), 7.33–7.38 (m, 1H), 7.10–7.17 (m, 2H), 3.98 (q, 1H), 3.91 (s, 3H), 3.73–3.82 (m, 2H), 3.56 (t, 2H), 2.97 (d, 3H), 1.50 (d, 3H).

48g. 2-(N-Methyl{1-[2-methyl-2-(nitrosothio)propyl](4-piperidyl)}carbonylamino) ethyl (2S)-2-(6-methoxy(2-naphthyl))propanoate Under a nitrogen atmosphere the product of Example 48f (0.852 g, 2.98 mmol) was dissolved in $CHCl_3$ (20 mL) and the product of Example 48c (0.730 g, 2.98 mmol) was added. The resulting mixture was cooled to 0° C. and 4-dimethylaminopyridine (0.145 g, 1.19 mmol) was added, followed by 1,3-dicyclohexylcarbodiimide (0.614 g, 2.98 mmol) in $CH_2Cl_2$ (10 mL). The resulting mixture was stirred at 0° C for 5 hours. The precipitate was filtered, the filtrate was concentrated in vacuo and the residue was purified by chromatography on silica gel, eluting with 3:1 Hex:EtOAc to give 1.1 g (72%) of the title compound as a green foam. $^1$H NMR (300 MHz, $CDCl_3$) δ 7.60–7.75 (m, 3H), 7.32–7.38 (m, 1H), 7.07–7.20 (m, 2H), 3.97–4.31 (m, 3H), 3.67–3.92 (m, 4H), 3.25–3.43 (m, 1H), 2.99 (s, 2H), 2.93 (s, 2H), 2.85 (s, 1H), 2.72 (d, 1H), 2.60 (d, 1H), 1.84–2.21 (m, 3H), 1.81 (s, 6H), 1.25–1.50 (m, 7H).

Example 49

4-({4-[2-Methyl-2-(nitrosothio)propyl] piperazinyl}carbonyl)phenyl 2-{2-[(2,6-dichlorophenyl)amino]phenyl}acetate 49a. 4-Hydroxyphenyl 4-(2-methyl-2-sulfanylpropyl) piperazinyl ketone A mixture of said $K_2CO_3$ (153 mg, 1.10 mmol) and the product of Example 39b (1.86 g, 5.52 mmol) in MeOH (25 mL) was stirred at room temperature for 15 min. The inorganic solid was removed by filtration and the filtrate was concentrated. The residue was crystallized from EtOAc to afford the title compound (1.50 g, 92%) as a white solid. mp 46° C.; $^1$H NMR (300 MHz, $CDCl_3$) δ 7.23 (d, J=8.5 Hz, 2H), 6.76 (d, J=8.5 Hz, 2H), 4.0–3.4 (br, 4H), 2.8–2.5 (br, 4H), 2.43 (s, 2H), 1.30 (s, 6H); $^{13}$C NMR (75 MHz, $CDCl_3$) δ 171.2, 158.7, 128.9, 125.3, 115.3, 70.8, 55.1, 46.0, 30.0.

49b. 4-Hydroxyphenyl 4-[2-methyl-2-(nitrosothio)propyl] piperazinyl ketone

To a stirred solution of the product of Example 49a (1.0 g, 3.4 mmol) in MeOH (15 mL) at 0° C. were added 12 N HCl (0.29 mL, 3.5 mmol) and t-BuONO (0.51 mL, 4.0 nmmol). After 10 min the mixture was partitioned between EtOAc and aqueous $Na_2CO_3$. The organic layer was separated, dried over $Na_2SO_4$, filtered, and concentrated to give the title compound (0.95 g, 91%) as a green foam. $^1$H NMR (300 MHz, $CDCl_3$) δ 9.2 (br, 1H), 7.19 (m, 2H), 6.71 (m, 2H), 3.8–3.4 (br, 4H), 3.03 (s, 2H), 2.7–2.5 (br, 4H), 1.88 (s, 6H); $^{13}$ C NMR (75 MHz, $CDCl_3$) δ 171.4, 158.8, 129.0, 125.5, 115.5, 68.0, 58.5, 55.2, 26.9.

49c. 4-({4-[2-Methyl-2-(nitrosothio)propyl] piperazinyl}carbonyl)phenyl 2-{2-[(2,6-dichlorophenyl) amino]phenyl}acetate A mixture of the product of Example 49b (1.20 g, 3.72 mmol), (2-((2,6-dichlorophenyl)amino)benzene)acetic acid (1.10 g, 3.72 mmol), and DCC (0.770 g, 3.72 mmol) in $CH_2Cl_2$ (30 mL) were stirred at room temperature for 2 hours. The solid that formed was removed by filtration and the filtrate was concentrated. The residue was chromatographed on silica gel eluting with 2:1 Hex:EtOAc to afford the title compound (2.0 g, 90%) as a green solid. mp 61–62° C. $^1$H NMR (300 MHz, $CDCl_3$) δ 7.4–6.4 (m, 12H), 3.96 (s, 2H), 3.8–3.3 (mult, 4H), 2.94 (s, 2H), 2.7–2.4 (mult, 4H), 1.79 (s, 6H); $^{13}$C NMR (75 MHz, $CDCl_3$) δ 170.2, 169.3, 151.4, 142.6, 137.6, 133.3, 130.9, 129.4, 128.8, 128.5, 128.3, 124.1, 123.6, 122.3, 121.6, 118.5, 68.0, 58.4, 55.1, 38.4, 26.9.

Example 50

3-[(2S)-2-(6-Methoxy (2-naphthyl)propanoyloxy]-2-oxopropyl-3-methyl-3-(nitrosothio) butanoate 50a. 3-Chloro-2-oxopropyl 3-methyl-3-[(2, 4, 6-trimethoxyphenyl)methylthio]butanoate To a mixture of 3-methyl-3-[(2,4,6-trimethoxyphenyl)methylthio]butanoic acid (3 g, 9.54 mmol) and sodium bicarbonate (975 mg, 11.6 mmol) in DMF (30 mL) was added a solution of 1,3-dichloroacetone (4.23 g, 33.4 mmol) in DMF (15 mL) at 0° C. under nitrogen. The reaction mixture was allowed to warm to room temperature, and stirred for 48 hours. The residue after evaporation of the solvent was partitioned between EtOAc and $H_2O$. The organic phase was washed with water and brine, dried over $MgSO_4$, filtered, and concentrated. The residue was chromatographed on silica gel eluting with EtOAc:Hex (20–30%) to give the title compound as a yellow oil (2.19 g, 57%). $^1$H NMR (300 MHz, $CDCl_3$) δ 6.12 (s, 2H), 4.87 (s, 2H), 4.21 (s, 2H), 3.86–3.80 (mult, 11H), 2.83 (s, 2H), 1.52 (s, 6H); $^{13}$C NMR (75 MHz, $CDCl_3$) δ 196.5, 170.1, 160.4, 158.6, 107.3, 90.7, 66.4, 55.8, 55.3, 46.3, 45.9, 43.8, 28.2, 20.9; mass spectrum (API-TIS) m/z 422 (M+$NH_4$).

50b. 3-[(2S)-2-(6-Methoxy(2-naphthyl)propanoyloxy]-2-oxopropyl3-methyl-3-[(2,4,6-trimethoxyphenyl) methylthio]butanoate To a stirred mixture of (2S)-2-(6-methoxy(2-naphthyl)) propanoic acid (1.25 g, 5.41 mmol) and sodium bicarbonate (545 mg, 6.49 mmol) in DMF (15 mL) was added a solution of the product of Example 50a (2.19 g, 5.41 mmol) in DMF (10 mL) at room temperature under nitrogen. The reaction mixture was stirred for 4.5 days. The residue, after evaporation of the solvent, was partitioned between EtOAc and $H_2O$. The organic phase was washed with brine, dried over $MgSO_4$, filtered, and concentrated. The residue was chromatographed on silica gel eluting with $CH_2Cl_2$:Hex (80%–100%) to give the title compound (700 mg, 21.6%). $^1$H NMR (300 MHz, $CDCl_3$) δ 7.70–7.73 (mult, 3H), 7.41–7.44 (mult, 1H), 7.12–7.17 (mult, 2H), 6.09 (s, 2H), 4.75 (d, J=3.8 Hz, 2H), 4.60 (d, J=4.3 Hz, 2H), 3.95–4.02 (mult, 1H), 3.91 (s, 3H), 3.78 (mult, 11H), 2.78 (s, 2H), 1.64 (d, J=7.2 Hz, 3H), 1.48 (s, 6H).

50c. 3-[(2S)-2-(6-Methoxy(2-naphthyl)propanoyloxy]-2-oxopropyl-3-methyl-3-sulfanylbutanoate A mixture of the product of Example 50b (700 mg, 1.17 mmol), phenol (132 mg, 1.40 mmol), anisole (0.14 mL, 1.51 mmol), water (0.03 mL) and trifluoroacetic acid (4.2 mL) were stirred at room temperature for 1 hour. The volatiles were removed in vacuo. The residue was dissolved with EtOAc. The solution was carefully neutralized with satd $NaHCO_3$. The organic phase was washed with water and brine, dried over $MgSO_4$, filtered, and concentrated. The residue was chromatographed on silica gel eluting with 2:8 EtOAc:Hex to give the title compound (250 mg, 51%). $^1$H NMR δ 7.69–7.74 (mult, 3H, 7.39–7.43 (mult, 1H), 7.16–7.11 (mult, 2H), 4.73 (d, J=0.9 Hz, 2H), 4.62 (d, J=6.3 Hz, 2H), 3.94–4.02 (mult, 1H), 3.91 (s, 3H), 2.70 (s, 2H), 2.32 (s, 1H), 1.63 (d, J=7.2 Hz, 3H), 1.49 (s, 6H); $^{13}$C NMR (75 MHz, $CDCl_3$) δ 197.8, 173.8, 169.7, 157.8, 134.8, 133.8, 129.3, 128.9, 127.3, 126.1, 119.1, 105.7, 66.6, 55.3, 49.9, 45.0, 41.5, 32.4, 18.4; mass spectrum (API-TIS) m/z 436 (M+$NH_4$).

50d. 3-[(2S)-2-(6-Methoxy(2-naphthyl)propanoyloxy]-2-oxopropyl-3-methyl-3-(nitrosothio) butanoate To a stirred solution of the product of Example 50c (240 mg, 0.57 mmol) in $CH_2Cl_2$ (12 mL) was added tert-butylnitrite (0.23 mL, 1.72 nmuol) at room temperature under nitrogen. The mixture was stirred for 1 hour. The solvent was evaporated in vacuo. The residue was chromatographed on silica gel eluting with 2:8 EtOAc:Hex to give the title compound (160 mg, 63%). mp 45–46° C. $^1$H NMR δ 7.69–7.73 (mult, 3H), 7.39–7.42 (mult, 1H), 7.11–7.16 (mult, 2H), 4.69 (s, 2H), 4.59 (d, J=6.9 Hz, 2H), 3.97–4.01 (mult, 1H), 3.91 (s, 3H), 3.32 (s, 2H), 1.98 (s, 6H), 1.63 (d, J=7.2 Hz, 3H); $^{13}$C NMR δ 197.5, 173.7, 169.0, 157.8, 134.8, 133.8, 129.3, 128.9, 127.3, 126.1, 119.1, 105.6, 66.6, 66.1, 55.2, 53.3, 46.6, 45.0, 28.7, 18.3; mass spectrum (API-TIS) m/z 465 (M+$NH_4$).

Example 51

Comparative In Vivo Analgesic, Antiinflammatory and Gastric Lesion Activities The phenylbenzoquinone-induced writhing test in mice was used to measure analgesic activity. The ability of the compounds to inhibit phenylbenzoquinone-induced writhing in mice was measured using the method of Siegmund et al, *Proc. Soc. Exp. Biol. Med.* 95: 729–731, 1957. Male CD-1 mice (Charles River Laboratories, Wilmington, Mass.) weighing 20–25 g were fasted overnight. Vehicle or compounds were administered by oral gavage 1 hour prior to i.p. injection of 2 mg/kg of phenylbenzoquinone. Five minutes after the i.p. injection of phenylbenzoquinone, the number of writhes in a 5 minute period was counted.

The rat paw edema test was used to measure antiinflammatory activity. The rat paw edema test was performed according to the method of Winter et al, *Proc. Soc. Exp. Biol. Med.* 111: 544–547, 1962. Male Sprague-Dawley rats (250–275 g) were fasted overnight and dosed by oral gavage with vehicle or suspensions of compound one hour prior to the subplantar injection of 50 μl of 1% suspension of carrageenan. Three hours later, the paw volume was measured and compared with the initial volume measured immediately after carrageenan injection.

The rat gastric lesion test, described by Kitagawa et al, *J. Phirmacol. Exp. Ther.*, 253:1133–1137 (1990), and Al-Ghamdi et al, *J. Int. Med. Res.*, 19:2242 (1991), was used to evaluate the activity of compounds to produce gastric lesion. Male Sprague Dawley rats (Charles River Laboratories, Wilmington, Mass.) weighing 230–250 g were used for the experiments. The rats were housed with laboratory chow and water ad libitum prior to the study. The rats were fasted for 24 hours with free access to water and then dosed by oral gavage with vehicle or with test compounds given at a volume of 0.5 mL/100 g. Food was withheld for 18 hours after the initial dosing. Rats were euthanized by $CO_2$ eighteen hours after dosing. The stomachs were dissected along the greater curvature, washed with a directed stream of 0.9% saline and pinned open on a sylgard based petri dish for examination of the hemorrhagic lesion. Gastric lesion score was expressed in mm and calculated by summning the length of each lesion.

Table 1 shows the relative activities of compounds in the analgesic, antiinflammatory and gastric lesion tests, and are expressed as the ratio of activity relative to the parent NSAID. The results show that the nitrosylated NSAIDs have either comparable or enhanced analgesic and antiinflammatory activities compared to their parent NSAID molecule. Table 1 also shows that the nitrosylated NSAIDs of the present invention have significantly and unexpectedly decreased gastric lesion activities.

TABLE 1

Relative Activity

| Compound | Analgesia | Antiinflammation | Gastric Lesion |
|---|---|---|---|
| Diclofenac | 1 | 1 | 1 |
| Example 1 | 1.5 | 1.2 | 0.1 |
| Example 2 | 1 | 1.2 | 0.02 |
| Example 4 | 0.9 | 1.3 | 0.01 |
| Example 6 | not determined | not determined | 0.02 |
| Example 8 | 1.2 | 1.4 | 0.04 |
| Example 12 | not determined | not determined | 0.06 |
| Example 13 | not determined | 1 | 0.1 (100 μmole/Kg) |
| Example 15 | 1 | 1 | 0.1 (100 μmole/Kg) |
| Example 17 | 1 | not determined | <0.07 (100 μmole/Kg) |
| Example 22 | 1 | 1 | 0.1 (100 μmole/Kg) |
| Example 31 | 1 | 1 | 0.02 (100 μmole/Kg) |
| Example 32 | 1 | not determined | not determined |
| Example 33 | 1 | 1 | not determined |
| Example 38 | not determined | not determined | 0.25 (100 μmole/Kg) |

The disclosure of each patent, patent application and publication cited or described in the specification is hereby incorporated by reference herein in its entirety.

Although the invention has been set forth in detail, one skilled in the art will appreciate that numerous changes and modifications can be made to the invention, and that such changes and modifications may be made without departing from the spirit and scope of the present invention.

What is claimed is:

1. A composition comprising at least one compound of formula (I), formula (II), formula (III), formula (IV), or a pharmaceutically acceptable salt thereof, and at least one compound that donates, transfers, or releases nitric oxide, induces the production of endogenous nitric oxide or endothelium-derived relaxing factor, stimulates endogenous synthesis of nitric oxide or is a substrate for nitric oxide synthase, or a pharmaceutically acceptable salt thereof, wherein the compound of formula (I) is:

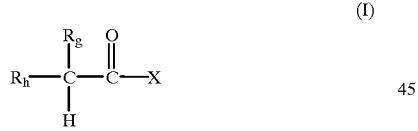

(I)

wherein
$R_g$ is a hydrogen atom or a lower alkyl group;
$R_h$ is:

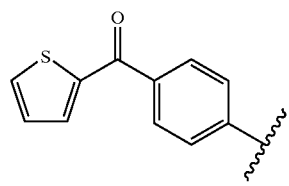

(1)

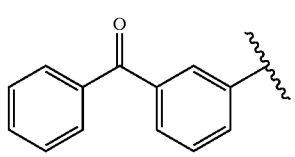

(2)

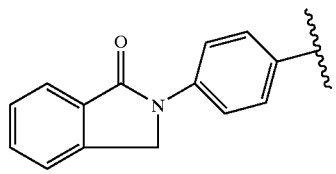

(3)

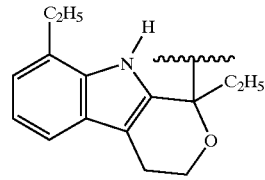

(4)

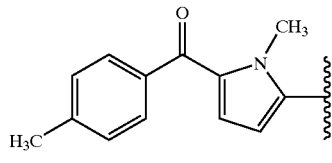

(5)

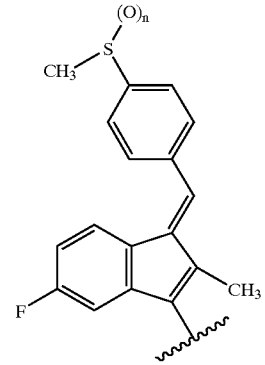

(6)

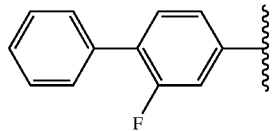

(7)

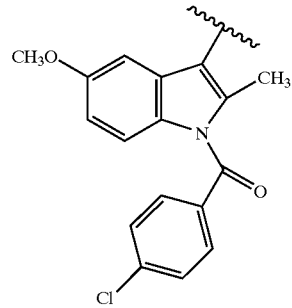

(8)

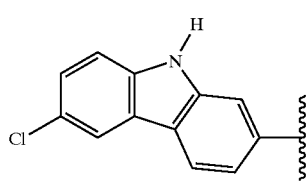

(9)

-continued (10)

(11)

(12)

(13)

(14)

(15)

(16)

(17)

(18)

-continued (19)

(20)

(21)

(22)

(23)

(24)

(25)

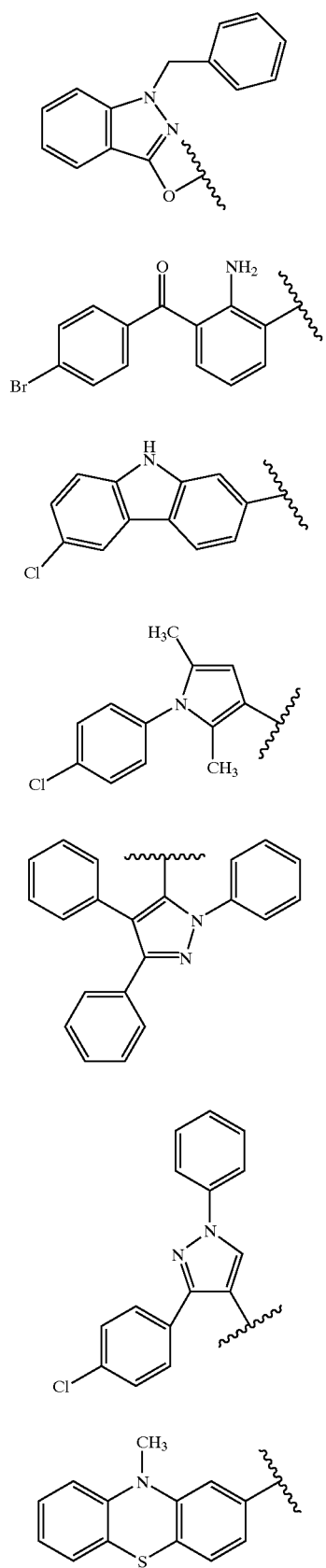
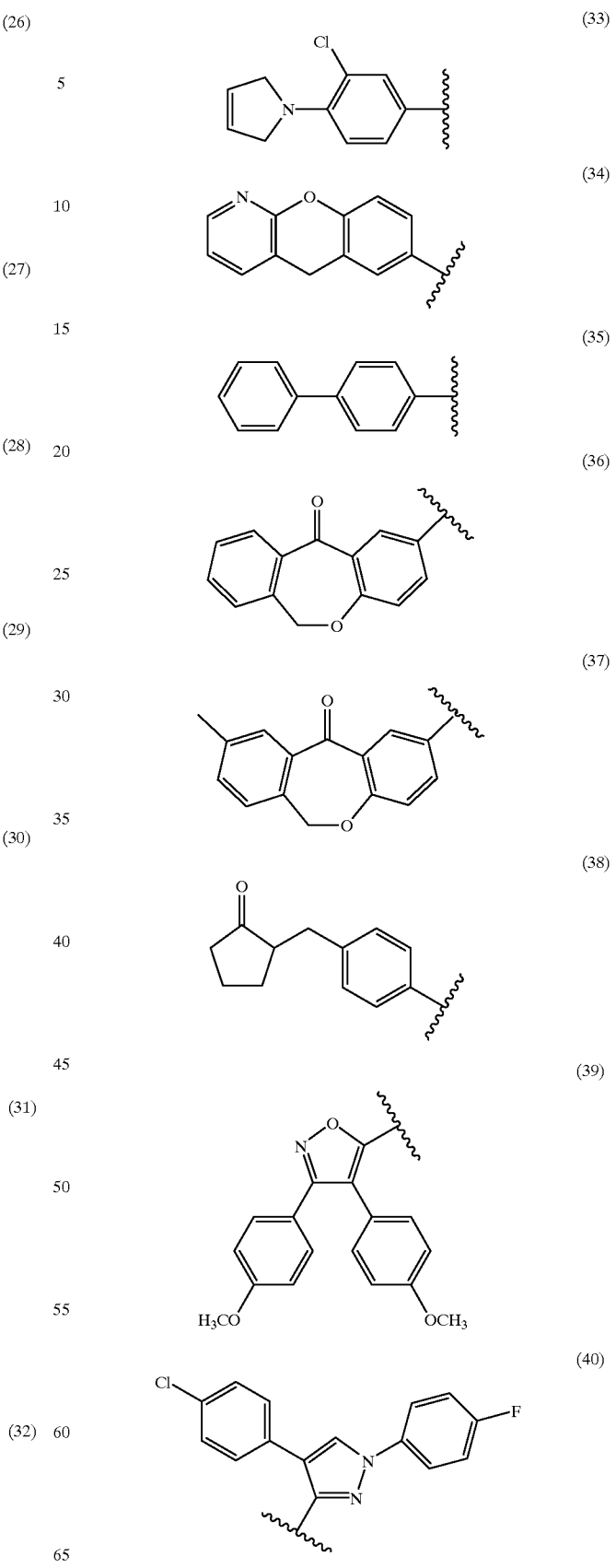

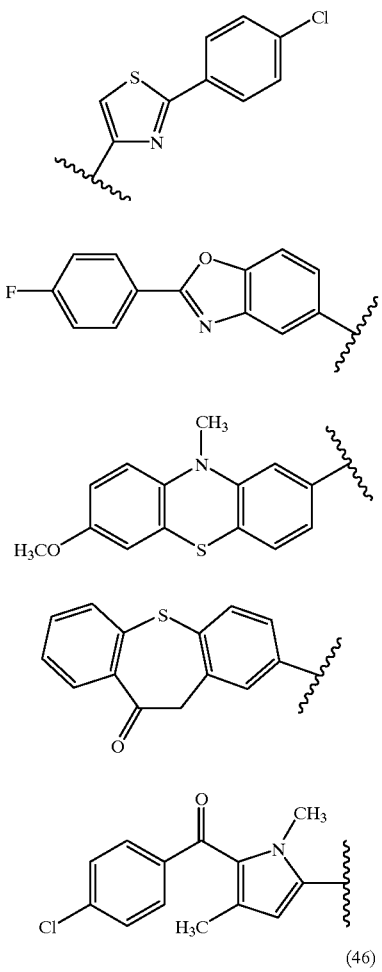
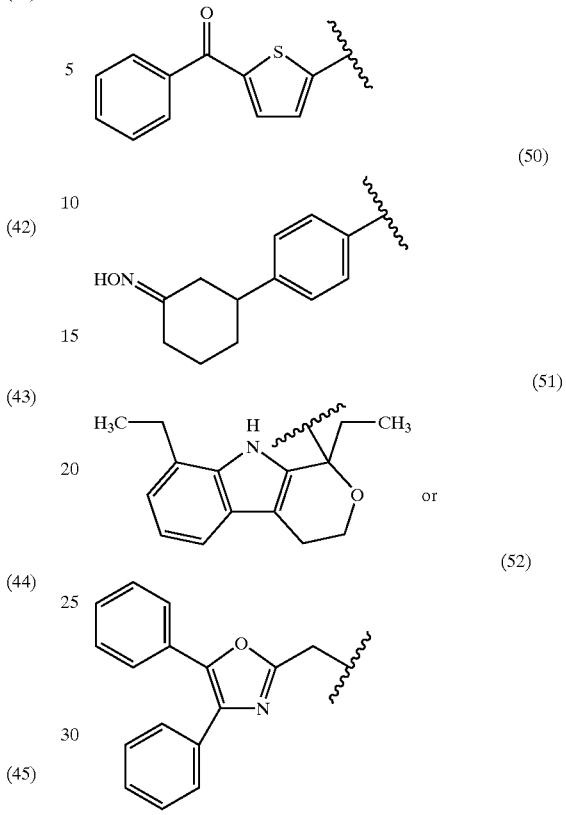

n is an integer of 0 or 1;
X is:
  (i) -T-$B_1$—W—$B_t$-T-$NO_s$;
  (ii) -T-$B_1$-$L_y$-$B_x$-T-$NO_s$;
  (iii) -T-$B_1$—W—$B_t$—$W_x$—$B_k$-T-$NO_s$;
  (iv) -T-$B_1$(C($R_b$)($R_c$))$_p$-$E_x$X-T-$NO_s$;
  (v) -T-$B_1$-G-$B_t$-$W_z$-$B_k$-$G_x$-$B_r$-T-$NO_s$;
  (vi) -T-$B_1$-J-$E_x$-T-$NO_s$; or
  (vii) -T-$B_1$-C($R_e$)=N-$E_z$-T-$NO_s$;
wherein
  s is an integer of 1 or 2;
  T at each occurrence is independently a covalent bond, a carbonyl, an oxygen, —S(O)$_o$— or —N($R_a$)($R_i$)—;
  o is an integer from 0 to 2;
  $R_a$ is a lone pair of electrons, a hydrogen or an alkyl group;
  $R_i$ is a hydrogen, an alkyl group, an aryl group, an alkylcarboxylic acid group, an aryl carboxylic acid group, an alkylcarboxylic ester group, an arylcarboxylic ester group, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester group, an amino alkyl, an amino aryl, —$CH_2$—C(T-Q)($R_e$)($R_f$), or —($N_2O_2^-$)·$M^+$, wherein $M^+$ is an organic or inorganic cation;
  L at each occurrence is independently —C(O)—, —C(S)—, -T-, a heterocyclic ring, an aryl group, an alkenyl group, an alkynyl group, an arylheterocyclic ring, or —($CH_2CH_2O$)$_q$;
  q is an integer from 1 to 5;
  B at each occurrence is independently an alkyl group, an aryl group, or —(C($R_e$)($R_f$))$_p$—, a heterocyclic ring, an aryl heterocyclic ring, or —($CH_2CH_2O$)$_q$;

p is an integer from 1 to 10;

$R_e$ and $R_f$ are each independently a hydrogen, an alkyl group, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, -T-NO$_s$, or (C(R$_e$)(R$_f$))$_k$-T-NO$_s$, or R$_e$ and R$_f$ taken together with the carbon atoms to which they are attached are a heterocyclic ring, a cycloalkyl group or a bridged cycloalkyl group;

$R_b$ and $R_c$ are each independently a haloalkyl, an alkenyl group, an alkynyl group, a bridged cycloalkyl group, a heterocyclic ring, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an arylalkyl, an alkylaryl, a carboxamido, an alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, -T-NO$_s$, or (C(R$_e$)(R$_f$))$_k$-T-NO$_s$, or R$_b$ and R$_c$ taken together with the carbon atoms to which they are attached are a carbonyl, a methanthial, a heterocyclic ring, a cycloalkyl group or a bridged cycloalkyl group;

G is a covalent bond, -T-C(O)—, —C(O)-T- or T; J is a carbonyl, a phosphoryl or a silyl;

k, l, t and z are each independently an integer from 1 to 3;

y is an integer from 1 to 3;

x and r are each independently an integer from 0 to 3;

E at each occurrence is independently —C(O)—, —C(S)—, -T-, —(C(R$_a$)(R$_f$))$_p$—, an alkyl group, an aryl group, a heterocyclic ring, arylheterocyclic ring, or (CH$_2$CH$_2$O)$_q$;

W is oxygen, —S(O)$_o$—, N(R$_a$)(R$_i$), carbonyl, or methanthial;

with the proviso that when R$_i$ is —CH$_2$—C(T-NO$_s$)(R$_e$)(R$_f$) or —(N$_2$O$_2$)$^-$·M$^+$, or R$_b$, R$_c$, R$_e$ or R$_f$ are T-NO$_s$ or (C(R$_e$)(R$_f$))$_k$-T-NO$_s$, then the "-T-NO$_s$" subgroup designated in X can be a hydrogen, an alkyl, an alkoxy, an alkoxyalkyl, an aminoalkyl, a hydroxy, a heterocyclic ring or an aryl group;

wherein the compound of formula (II) is:

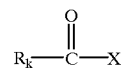

(II)

wherein

R$_k$ is:

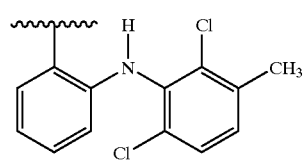

(1)

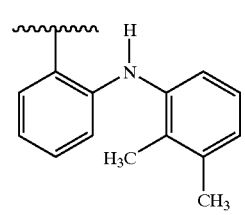

(2)

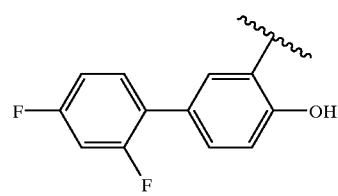

(3)

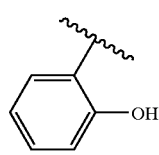

(4)

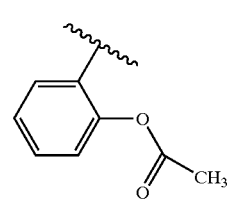

(5)

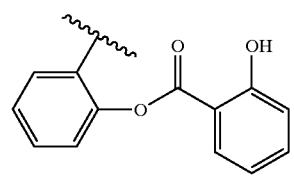

(6)

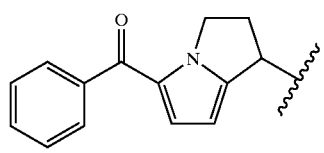

(7)

(8)
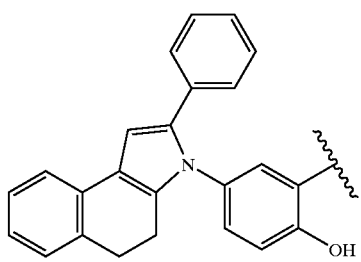
(9)
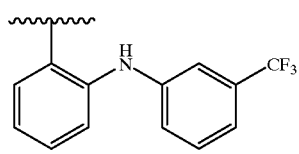
(10)
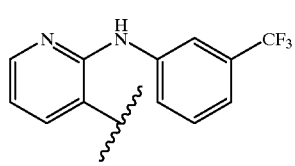
(11)
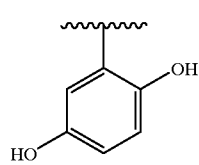
(12)
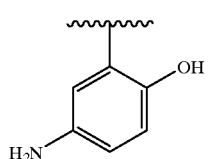
(13)
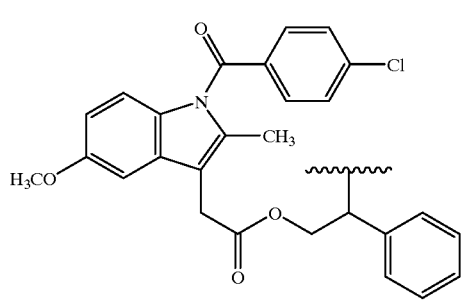
(14)
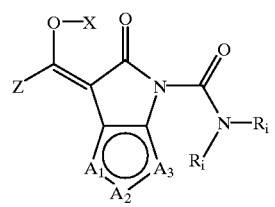
(15)
(16)
(17)
(18) or
(19)
and X is as defined as herein;
wherein the compound of formula (III) is:
(III)
wherein
  X is as defined herein;
  $R_i$ at each occurrence is independently $R_i$, wherein $R_i$ is as defined herein;
  Z is an aryl group; and
  $A_1$, $A_2$ and $A_3$ comprise the other subunits of a 5- or 6-membered monocyclic aromatic ring and each of $A_1$, $A_2$ and $A_3$ is independently:

(1) C—R$_o$, wherein R$_o$ at each occurrence is independently a hydrogen, an alkyl, an alkoxyalkyl, a halogen or a nitro group;
(2) N—R$_p$, wherein R$_p$ at each occurrence is independently a covalent bond to an adjacent ring atom in order to render the ring aromatic, a hydrogen, an alkyl, an arylalkyl, an aryl or a heteroaryl group;
(3) a sulfur atom;
(4) an oxygen atom; or
(5) B$_a$=B$_b$, wherein B$_a$ and B$_b$ are each independently a nitrogen atom or C—R$_o$ wherein R$_o$ is as defined herein;
wherein the compound of formula (IV) is:

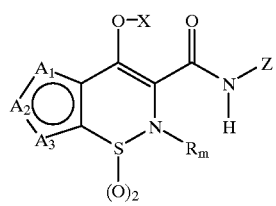

(IV)

wherein
R$_m$ is an alkyl group or an aryl group; and X, Z, A$_1$, A$_2$ and A$_3$ are as defined herein.

2. The composition of claim 1, further comprising a pharmaceutically acceptable carrier.

3. The composition of claim 1, wherein the compound of formula I is a nitrosated aryl propionic acid compound, a nitrosylated aryl propionic acid compound or a nitrosated and nitrosylated aryl propionic acid compound; the compound of formula II is a nitrosated aryl acetic acid compound, a nitrosylated aryl acetic acid compound or a nitrosated and nitrosylated aryl acetic acid compound; the compound of formula III is a nitrosated enolic anilide compound, a nitrosylated enolic anilide compound or a nitrosated and nitrosylated enolic anilide compound; and the compound of formula IV is a nitrosated oxicam compound, a nitrosylated oxicam compound, or a nitrosated and nitrosylated oxicam compound.

4. The composition of claim 3, herein the nitrosated aryl propionic acid compound, the nitrosylated aryl propionic acid compound or the nitrosated and nitrosylated aryl propionic acid compound is a nitrosated, nitrosylated or nitrosated and nitrosylated compound selected from aceclofenac, alcofenac, amfenac, brofenac, diclofenac, etodac, felbinac, flurbiprofen, fenoprofen, fenbufen, ibuprofen, indomethacin, indoprofen, ketoprofen, lonazolac, loxoprofen, mofezolac, miroprofen, naproxen, oxaprozin, pirprofen, sulindac, tiaprofen, or tolmetin; wherein the nitrosated aryl acetic acid compound, the nitrosylated aryl acetic acid compound, or the nitrosated and nitrosylated aryl acetic acid compound is a nitrosated, nitrosylated or nitrosated and nitrosylated compound selected from aspirin, acemetacin, carprofenac, diflunisal, etofenamate, flufenamic, flufenac, ketorolac, meclofenamic, mefenamic, or tolfenamic; wherein the nitrosated enolic anilide compound, the nitrosylated enolic anilide compound or the nitrosated and nitrosylated enolic anilide compound is a nitrosated tenidap, a nitrosylated tenidap or a nitrosated and nitrosylated tenidap; wherein the nitrosated oxicam compound, the nitrosylated oxicam compound or the nitrosated and nitrosylated compound is a nitrosated, nitrosylated or nitrosated and nitrosylated compound selected from droxicam, piroxicam, isoxicam, lomoxicam, or ampiroxicam.

5. The composition of claim 3, wherein the compound of formula I is a compound selected from 2-(4-methyl-4-(nitrosothio)piperidyl)ethyl 2-{2-((2,6-dichlorophenyl) amino) phenyl} acetate hydrochloride; 2-(methyl{((nitrosothio)cyclohexyl)methyl}amino)ethyl 2-{2-((2,6-dichlorophenyl)amino)phenyl}acetate hydrochloride; 2-(methyl{((nitrosothio) cyclohexyl)methyl}amino)ethyl (2S)-2-(6-methoxy(2-naphthyl))propanoate hydrochloride; 3{methyl{((nitrosothio)cyclohexyl)methyl}amino)propyl 2-{2-((2,6-dichlorophenyl)amino) phenyl}acetate; 4-({methyl(2-methyl-2-(nitrosothio)propyl)amino}methyl) phenyl (2S)-2-(6-methoxy(2-naphthyl))propanoate hydrochloride; 2-(4-(nitrosothio)-4-piperdyl)ethyl 2-{2-((2,6-dichlorophenyl) amino)phenyl}acetate hydrochloride; 2-(2-(2-{2-((2,6-dichlorophenyl)amino) phenyl}acetoxy)ethoxy) ethyl 3-(N-{((nitrosothio)cyclohexyl)methyl}-N-benzylcarbamoyl) propanoate; 2-{4-(2-methyl-2-(nitrosothio)propyl) piperazinyl}ethyl 2-{2-((2,6-dichlorophenyl) amino)phenyl}acetate citrate; 2-(2-(tert-butyl)-5-(nitrosothio)-1,3-dioxan-5-yl)ethyl (2S)-2-(6-methoxy(2-naphthyl)) propanoate; 5-(bis{((nitrosothio) cyclohexyl)methyl}amino)pentyl (2S)-2-(6-methoxy(2-naphthyl))propanoate; 2-({3-((2S)-2-(6-methyl(2-naphthyl))propanoyloxy)propyl}{((nitrosothio)cyclohexyl) methyl}amino)acetic acid; 3-(methyl{(1-methyl-4-(nitrosothio)(4-piperidyl))methyl}amino)propyl 2-{2-((2,6-dichlorophenyl)amino) phenyl}acetate; 2-(1-methyl-4-(nitrosothio)-4-piperidyl)ethyl 2-{2-((2,6-dichlorophenyl) amino) phenyl}acetate citrate; 2-(1-methyl-4-(nitrosothio)-4-piperidyl)ethyl 2-(4-(2-methylpropyl) phenyl)propanoate citrate; 2-(1-methyl-4-(nitrosothio)-4-piperidyl)ethyl (2S) 2-(6-methoxy(2-naphthyl)) propanoate citrate; 2-(1-methyl-4-(nitrosothio)-4-piperidyl)ethyl 2-(3 (phenylcarbonyl) phenyl)propanoate citrate; 2-(1-methyl-4-(nitrosothio)-4-piperidyl)ethyl 2{1-((4-chlorophenyl) carbonyl)-5-methoxy-2-methylindol-3-yl}acetate citrate; 2-{methyl(2-methyl{((nitrosothiol) cyclohexyl)methyl}amino)ethyl 2-{2-((2,6 dichlorophenyl)amino) phenyl} acetate bis nitric acid salt; 2-{methyl(2 methyl{((nitrosothiol)cyclohexyl) methyl}amino)ethyl 2-{1-((4-chlorophenyl)carbonyl)-5-methoxy-2-methylindol-3-yl}acetate; 2-(((dimethylamino) ethyl){((nitrosothio)cyclohexyl) methyl}amino)ethyl 2-{2-((2,6-dichorophenyl) amino)phenyl}acetate; 2-(4-methyl-4 (nitrosothio)piperidyl)ethyl (2S)-2-(6-methoxy(2-naphthyl))propanoate; 2-(methyl{(1-methyl-4-(nitrosothio) (4-piperidyl))methyl}amino)ethyl (2S)-2-(6-methoxy(2-naphthyl))propanoate hydrochloride; 3-(4-methyl-4-(nitrosothio)piperidyl)propyl 2-{2-((2,6-dichlorophenyl) amino)phenyl}acetate; 3-(4-methyl-4-(nitrosothio) piperidyl)propyl (2S)-2-(6-methoxy (2-naphthyl)) propanoate; 2-(2-({N-(2-methyl-2-(nitrosothio)propyl) carbamoyl} methoxy) acetylamino)ethyl 2-{2-((2,6-dichlorophenyl)amino) phenyl}acetate; (2-({N-(2-methyl-2-(nitrosothio)propyl) carbamoyl}methoxy)acetyloxy) methyl 2-{2-((2,6-dichlorophenyl) amino)phenyl}acetate; 2-(4-(nitrosothio)-4-piperidyl)ethyl (2S)-2-(6-methoxy(2-naphthyl)) propanoate hydrochloride; {(3-(methyl{((nitrosothio) cyclohexyl)methyl}amino)propyl) oxycarbonyl}methyl 2-{2-((2,6 dichlorophenyl) amino) phenyl}acetate; 2-{4-(3-methyl-3-(nitrosothio)butanoyl) piperazinyl} ethyl 2-{2-((2,6-dichlorophenyl)methyl) phenyl}acetate; {4-(dicyclopropyl(nitrosothio)methyl)-1-methyl-4-piperidyl}methyl (2S)-2-(6-methoxy(2-naphthyl)) propanoate; 2-{2-((2,6-dichlorophenyl)amino)phenyl}-1-(2-{methyl(2-methyl-2-(nitrosothio) propyl) amino}ethylthio)ethan-1-one hydrochloride; 2-{2-((2,6-dichlorophenyl) amino)phenyl}-1-(2-(methyl{((nitrosothio)

cyclohexyl)methyl}amino) ethylthio)ethan-1-one; 4-({diethyl(2-methyl-2-(nitrosothio)propyl)amino}methyl) phenyl 2-{2-((2,6-dichlorophenyl) amino)phenyl}acetate; (2R,3R)-2,3-dihydroxy-3-{N-(2-methyl-2 (nitrosothio) propyl)carbamoyl}propyl 2-{2-((2,6-dichlorophenyl) amino)phenyl} acetate; 2-{1-(2-methyl-2-(nitrosothio) propyl)-4-piperidyl}ethyl 2-{2-((2,6-dichlorophenyl) amino)phenyl}acetate; {(2S)-1-(2-methyl-2-(nitrosothio) propyl) pyrrolidin-2yl} methyl 2-{2-((2,6-dichlorophenyl) amino)phenyl}acetate; 2-({4-(2-methyl-2-(nitrosothio) propyl)piperazinyl} ethoxy)ethyl 2-{1-((4-chlorophenyl) carbonyl)-5-methoxy-2-methylindol-3-yl}acetate; 2-(2-{4-(2-methyl-2-(nitrosothio) propyl)piperazinyl}ethoxy)ethyl (2S)-2-(6-methoxy(2-naphthyl)) propanoate; 4-({4-(2-methyl-2-(nitrosothio) propyl)piperazinyl}methyl)phenyl 2-{1-((4-chlorophenyl)carbonyl)-5-methoxy-2-methylindol-3-yl}acetate; 5-({4-(2-methyl-2-(nitrosothio) propyl0piperazinyl}carbonyl)-2 pyridyl 2-{1-((4-chlorophenyl)carbonyl)-5-methoxy-2-methylindol-3-yl}acetate; 5-({4-(2-methyl-2-(nitrosothio)propyl) piperazinyl} carbonyl)-2pyridyl 2-{1-((4-chlorophenyl) carbonyl)-5-methoxy-2-methylindol-3-yl}acetate; 2-{(2-(2-{1-((4-chlorophenyl)carbonyl)-5-methoxy-2-methylindol-3-yl}acetyloxy)ethyl){((nitrosothio)cyclohexyl) methyl}amino}acetic acid; 2-(methyl{1-(2-methyl-2-(nitrosothio)propyl)(4-piperidyl)}amino)ethyl (2S)-2-(6-methoxy(2-naphthyl))propanoate; 3-{(4S)-4-(1-methyl-1-(nitrosothio)ethyl)-2-oxo-1,3-oxazolidin-3-yl}propyl (2S)-2-(6-methoxy(2-naphthyl))propanoate; {ethoxy(3-methyl-3-(nitrosothio) butoxy)phosphonyl}methyl (2S)-2-(6-methoxy (2-naphthyl)) propanoate; 6-(4-{(2-methyl-2-(nitrosothio)propyl)amino}pyrimidin-2-ylthio)hexyl (2S)-2-(6-methoxy(2-naphthyl))propanoate; {(2S,5S)-5-(1-methyl-1-(nitrosothio)ethyl)-3,6-dioxopiperazin-2-yl}methyl (2S)-2-(6-methoxy(2-naphthyl))propanoate; 2-(N-methyl {1-(2-methyl-2-(nitrosothio)propyl)(4 piperidyl)}carbonylamino)ethyl (2S)-2-(6-methoxy(2-naphthyl))propanoate; 4-({4-(2-methyl-2-(nitrosothio) propyl)piperazinyl} carbonyl)phenyl 2-{2-((2,6-dichlorophenyl)amino) phenyl}acetate; and 3-((2S)-2-(6-methoxy (2-naphthyl)propanoyloxy)-2-oxopropyl-3-methyl-3-(nitrosothio) butanoate, or a pharmaceutically acceptable salt thereof.

6. The composition of claim 1, wherein the at least one compound that donates, transfers, or releases nitric oxide, induces the production of endogenous nitric oxide or endothelium-derived relaxing factor, stimulates endogenous synthesis of nitric oxide or is a substrate for nitric oxide synthase is an S-nitrosothiol.

7. The composition of claim 6, wherein the S-nitrosothiol is S-nitroso-N-acetylcysteine, S-nitroso-captopril, S-nitroso-N-acetylpenicillamine, S-nitroso-homocysteine, S-nitroso-cysteine or S-nitroso-glutathione.

8. The composition of claim 6, wherein the S-nitrosothiol is:

(i) $HS(C(R_e)(R_f))_mSNO$;

(ii) $ONS(C(R_e)(R_f))_mR_e$; and (iii) $H_2N$—$CH(CO_2H)$—$(CH_2)_m$—$C(O)NH$—$CH(CH_2SNO)$—$(O)NH$—$CH_2$—$CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino an alkoxyhaloalkyl, a haloalkoxy, a sulfonic acid, an alkylsulfonic acid, an arylsulfonic acid, an arylalkoxy, an alkylthio, an arylthio, a cyano, an aminoalkyl, an aminoaryl, an alkoxy, an aryl, an arylalkyl, an alkylaryl, a carboxamido, a alkyl carboxamido, an aryl carboxamido, an amidyl, a carboxyl, a carbamoyl, an alkylcarboxylic acid, an arylcarboxylic acid, an ester, a carboxylic ester, an alkylcarboxylic ester, an arylcarboxylic ester, a haloalkoxy, a sulfonamido, an alkylsulfonamido, an arylsulfonamido, a urea, a nitro, or -T-Q; or $R_e$ and $R_f$ taken together with the carbon atoms to which they are attached are a carbonyl, a methanthial, a heterocyclic ring, a cycloalkyl group or a bridged cycloalkyl group; Q is —NO or —$NO_2$; and T is independently a covalent bond, a carbonyl, an oxygen, —$S(O)_o$— or —$N(R_a)R_1$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —$CH_2$—$C(T-Q)(R_e)(R_f)$, or —$(N_2O_2$—$)^-·M^+$, wherein $M^+$ is an organic or inorganic cation; with the proviso that when $R_i$ is —$CH_2$—$C(T-Q)(R_e)(R_f)$ or —$(N_2O_2$—$)·M^+$; then "-T-Q" can be a hydrogen, an alkyl group, an alkoxyalkyl group, an aminoalkyl group, a hydroxy group or an aryl goup.

9. The composition of claim 1, wherein the at least one compound that donates, transfers, or releases nitric oxide, induces the production of endogenous nitric oxide or endothelium-derived relaxing factor, stimulates endogenous synthesis of nitric oxide or is a substrate for nitric oxide synthase is L-arginine, L-homoarginine, N-hydroxy-L-arginine, nitrosated L-arginine, nitrosylated L-arginine, nitrosated N-hydroxy-L-arginine, nitrosylated N-hydroxy-L-arginine, citrulline, omithine or glutamine.

10. The composition of claim 1, wherein at least one compound that donates, transfers, or releases nitric oxide, induces the production of endogenous nitric oxide or endothelium-derived relaxing factor, stimulates endogenous synthesis of nitric oxide or is a substrate for nitric oxide synthase is:

(i) a compound that comprises at least one ON—C—, ON—N— or ON—C— group;

(ii) a compound that comprises at least one $O_2N$—O—, $O_2N$—N—, $O_2N$—S— or —$O_2N$—C— group;

(iii) a N-oxo-N-nitrosoamine having the formula: $R^1R^2$—$N(O$—$M^+)$—$NO$, wherein $R^1$ and $R^2$ are each independently a polypeptide, an amino acid, a sugar, an oligonucleotide, a straight or branched, saturated or unsaturated, aliphatic or aromatic, substituted or unsubstituted hydrocarbon, or a heterocyclic group, and $M^+$ is an organic or inorganic cation; or (iv) a thionitrate having the formula: $R^1$—(S)—$NO_2$, wherein $R^1$ is a polypeptide, an amino acid, a sugar, an oligonucleotide, a straight or branched, saturated or unsaturated, aliphatic or aromatic, substituted or unsubstituted hydrocarbon, or a heterocyclic group.

11. The composition of claim 10, wherein the compound comprising at least one ON—O—, ON—N— or ON—C— group is an ON—O-polypeptide, an ON—N-polypepetide, an ON—C-polypeptide, an ON—O-amino acid, an ON—N-amino acid, an ON—C-amino acid, an ON—O-sugar, an ON—N-sugar, an ON—C-sugar, an ON—O-oligonucleotide, an ON—N-oligonucleotide, an ON—C-oligonucleotide, a straight or branched, saturated or unsaturated, substituted or unsubstituted, aliphatic or aromatic ON—O-hydrocarbon, a straight or branched, saturated or unsaturated, substituted or unsubstituted, aliphatic or aromatic ON—N-hydrocarbon, a straight or branched, saturated or unsaturated, substituted or unsubstituted, aliphatic or aromatic ON—C-hydrocarbon, an ON—O-heterocyclic compound, an ON—N-heterocyclic compound or a ON—C-heterocyclic compound.

12. The composition of claim 10, wherein compound comprising at least one $O_2N$—O—, $O_2N$—N—, $O_2N$—S— or $O_2N$—C— group is an $O_2N$—O-polypeptide, an $O_2N$—N-polypeptide, an $O_2N$—S-polypeptide, an $O_2N$—C-polypeptide, an $O_2N$—O-amino acid, $O_2N$—N-amino acid, $O_2N$—S-amino acid, an $O_2N$—C-amino acid, an $O_2N$—O-sugar, an $O_2N$—N-sugar, $O_2N$—S-sugar, an $O_2N$—C-sugar, an $O_2N$—O-oligonucleotide, an $O_2N$—N-oligonucleotide, an $O_2N$—S-oligonucleotide, an $O_2N$—C-oligonucleotide, a straight or branched, saturated or unsaturated, aliphatic or aromatic, substituted or unsubstituted $O_2N$—O-hydrocarbon, a straight or branched, saturated or unsaturated, aliphatic or aromatic, substituted or unsubstituted $O_2N$—N-hydrocarbon, a straight or branched, saturated or unsaturated, aliphatic or aromatic, substituted or unsubstituted $O_2N$—S-hydrocarbon, a straight or branched, saturated or unsaturated, aliphatic or aromatic, substituted or unsubstituted $O_2N$—C-hydrocarbon, an $O_2N$—O-heterocyclic compound, an $O_2N$—N-heterocyclic compound, an $O_2N$—S-heferocyclic compound or an $O_2N$—C-heterocyclic compound.

13. A kit comprising a least one compound of formula (I), formula (II), formula (III), formula (IV), as defined in claim 1, or a pharmaceutically acceptable salt thereof, and at least one compound that donates, transfers, or releases nitric oxide, induces the production of endogenous nitric oxide or endothelium-derived relaxing factor, stimulates endogenous synthesis of nitric oxide or is a substrate for nitric oxide synthase.

14. The kit of claim 13, wherein the at least one compound of formula (I), formula (II), formula (III), formula (IV), or a pharmaceutically acceptable salt thereof, and at least one compound that donates, transfers, or releases nitric oxide, induces the production of endogenous nitric oxide or endothelium-derived relaxing factor, stimulates endogenous synthesis of nitric oxide or is a substrate for nitric oxide synthase are separate components in the kit or in the form of a composition in the kit.

15. The kit of claim 13 further comprising a pharmaceutically acceptable carrier.

16. A method for treating, preventing or reducing inflammation, pain and fever in a patient in need thereof comprising administering to the patient the composition of claim 2.

17. A method for treating or reversing the gastrointestinal, renal or other toxicities resulting from the use of a nonsteroidal antiinflammatory compound by a patient comprising administering to the patient the composition of claim 2.

18. A method for treating or preventing a gastrointestinal disorder in a patient n need thereof comprising administering to the patient the composition of claim 2.

19. New The method of claim 18, wherein the gastrointestinal disorder is a peptic ulcer, gastric hyperacidity, dyspepsia, gastroparesis, Zollinger-Ellison syndrome, gastroesophageal reflux disease, a stress ulcer, a bleeding peptic ulcer, short bowel syndrome, or a hypersecretory state associated with systemic mastocytosis or basophilic leukemia and hyperhistaminemia.

20. A method for treating an inflammatory disease or disorder in a patient in need thereof comprising administering to the patient the composition of claim 2.

21. The method of claim 20, wherein the inflammatory disease or disorder is reperfusion injury to an ischemic organ, myocardial infarction, inflammatory bowel disease, rheumatoid arthritis, osteoarthritis, hypertension, psoriasis, organ transplant rejection, organ preservation, a female or male sexual dysfunction, radiation-induced injury, asthma, atherosclerosis, thrombosis, platelet aggregation, restenosis, metastasis, influenza, incontinence, stroke, bum, trauma, acute pancreatitis, pyelonephritis, hepatitis, an autoimmune disease, an immunological disorder, senile dementia, insulin-dependent diabetes mellitus, disseminated intravascular coagulation, fatty embolism, Alzheimer's disease, adult or infantile respiratory disease, carcinogenesis or a hemorrhage in a neonate.

22. A method for treating or preventing an ophthalmic disease or disorder in a patient in need thereof comprising administering to the patient the composition of claim 2.

23. The method of claim 22, wherein the opthalmic disease or disorder is glucoma, inflammation of the eye or elevation of intraocular pressure.

24. The method of claim 16, wherein the composition is administered orally, topically, bucally, parentally, by inhalation, or by injection.

25. The method of claim 17, wherein the composition is administered orally, topically, bucally, parentally, by inhalation, or by injection.

26. The method of claim 18, wherein the composition is administered orally, topically, bucally, parentally, by inhalation, or by injection.

27. The method of claim 20, wherein the composition is administered orally, topically, bucally, parentally, by inhalation, or by injection.

28. The method of claim 22, wherein the composition is administered topically.

* * * * *